US006803457B1

(12) United States Patent
DeNinno et al.

(10) Patent No.: US 6,803,457 B1
(45) Date of Patent: Oct. 12, 2004

(54) COMPOUNDS FOR THE TREATMENT OF ISCHEMIA

(75) Inventors: Michael P. DeNinno, Gales Ferry, CT (US); Hiroko Masamune, Noank, CT (US); Robert W. Scott, Mystic, CT (US)

(73) Assignee: Pfizer, Inc., New York, NY (US)

( * ) Notice: Subject to any disclaimer, the term of this patent is extended or adjusted under 35 U.S.C. 154(b) by 622 days.

(21) Appl. No.: 09/640,530

(22) Filed: Aug. 17, 2000

Related U.S. Application Data

(60) Provisional application No. 60/156,828, filed on Sep. 30, 1999.

(51) Int. Cl.$^7$ .............................................. C07H 19/16
(52) U.S. Cl. ................ 536/27.21; 536/27.22; 536/27.23; 536/27.63; 514/46
(58) Field of Search .................... 536/27.21, 27.22, 536/27.23, 27.63, 27.11; 514/46

(56) References Cited

U.S. PATENT DOCUMENTS

| | | | | |
|---|---|---|---|---|
| 2,852,505 | A | * 9/1958 | Baker et al. | 536/27.21 |
| 2,852,506 | A | * 9/1958 | Goldman et al. | 536/27.11 |
| 5,604,210 | A | 2/1997 | Nagaoka et al. | 514/46 |
| 5,688,774 | A | 11/1997 | Jacobson et al. | 514/46 |
| 5,773,423 | A | 6/1998 | Jacobson et al. | 514/45 |
| 5,817,760 | A | 10/1998 | Jacobson et al. | 530/350 |

FOREIGN PATENT DOCUMENTS

| | | |
|---|---|---|
| WO | 9323418 | 11/1993 |
| WO | 9502604 | 1/1995 |
| WO | WO 01/23399 A1 * | 4/2001 |

OTHER PUBLICATIONS

Goldman et al., Synthesis and Reactions of 3'–Amino–3'–deoxyribosides of 6–Chloropurine, *Journal of Medicinal Chemistry*, 6(4), 413–423 (Jul., 1963).*

Jacobson et al., "Neoceptor Concept Based on Molecular Complementarity in GPCRs: A Mutant Adensoine $A_3$ Receptor with Selectively Enhanced Affinity for Amine–modified Nucleosides," *Journal of Medicinal Chemistry*, 44(24), 4125–4136 (Nov. 22, 2001): ACS WEB published on Oct. 16, 2001.*

Crane et al., "Isonucleosides from Glucosamine," *Journal of Carbohydrates Nucleosides Nucleotides*, 7(5), 281–296 (1980).*

Carola Gall–Rodriguez, et al, J. Med. Chem. 1994, 37, 636–646, "Structure–Activity Relationships of $N^6$–Benzyladenosine–5'–uronamides as $A_3$ Selective Adenosine Agonists" (Issue No. 5).

Suhaib M. Siddiqi et al. J. Med. Chem. 1995, 38, 1174–1188, "Search for New Purine– and Ribose–Modified Adenosine Analogues as Selective Agonists and Antagonists at Adenosine Receptors" (Issue No. 7).

Kenneth A. Jacobson, et al, J. Med. Chem. 1995, 38, 1720–1735, "Structure–Activity Relationships of 9–Alkyladenine and Ribose–Modified Adenosine Derivatives at Rat $A_3$ Adenosine Receptors" (Issue No. 10).

M. Yamashita et al., *Tetrahederon Letters*, vol. 25, No. 41, 1984, pp 4689–4692, *Structure and total synthesis of chryscandin, a new antifuangal antibiotic.* XP–002157271.

* cited by examiner

*Primary Examiner*—L. E. Crane
(74) *Attorney, Agent, or Firm*—Scully, Scott, Murphy & Presser

(57) ABSTRACT

$A_3$ agonists, methods of using such $A_3$ agonists and pharmaceutical compositions containing such $A_3$ agonists. The $A_3$ agonists are useful for the reduction of tissue damage resulting from tissue ischemia or hypoxia.

8 Claims, No Drawings

COMPOUNDS FOR THE TREATMENT OF ISCHEMIA

This application claims priority from provision application U.S. Ser. No. 60/156,828 filed Sep. 30, 1999, the benefit of which is hereby claimed under 37 C.F.R.§1.78(a)(3).

BACKGROUND OF INVENTION

This invention relates to adenosine A-3 receptor agonists, pharmaceutical compositions containing such inhibitors and the use of such inhibitors to treat for example, ischemia particularly, perioperative myocardial ischemic injury in mammals, including humans.

Mycardial ischemic injury can occur in out-patient as well as in perioperative settings and can lead to the development of sudden death, myocardial infarction or congestive heart failure. There is an unmet medical need to prevent or minimize myocardial ischemic injury, particularly perioperative myocardial infarction. Such a therapy is anticipated to be life-saving and reduce hospitalizations, enhance quality of life and reduce overall health care costs of high risk patients.

Pharmacological cardioprotection would reduce the incidence and progression of myocardial infarction and dysfunction occurring in these surgical settings (perioperatively). In addition to reducing myocardial damage and improving post-ischemic myocardial function in patients with ischemic heart disease, cardioprotection would also decrease the incidence of cardiac morbidity and mortality due to myocardial infarction and dysfunction in patients "at risk" (such as greater than 65 years, exercise intolerant, coronary artery disease, diabetes mellitus, hypertension) that require non-cardiac surgery.

U.S. Pat. No. 5,604,210 discloses the use of certain adenosine type compounds for the prevention or treatment of a brain edema, an intracranial hemorrhage and a cerebral infarction.

U.S. Pat. No. 5,688,774 discloses $A_3$ selective agonists, particularly, adenine compounds having selected substituents at the 2, 6 and 9 positions, and related substituted compounds, particularly those containing substituents on the benzyl and/or uronamide groups as agents which activate the $A_3$ receptor.

U.S. Pat. No. 5,773,423 discloses $N^6$-benzyladenosine-5'-N-uronamide and related substituted compounds, particularly those containing substituents on the benzyl and/or uronamide groups, and modified xanthine ribosides for the activation of the $A_3$ adenosine receptor.

J. Med. Chem. 1994, 37, 636–646, "Structure-Activity Relationships of $N^6$-Benzyladenosine-5'-uronamides as $A_3$-Selective Agonists" discloses the synthesis of adenosine analogues modified at the 5'-position as uronamides and/or as $N^6$-benzyl derivatives which are potentially useful as pharmacological and biochemical probes for $A_3$ receptors.

J. Med. Chem. 1995, 38, 1174–1188, "Search for New Purine- and Ribose-Modified Adenosine Analogues as Selective Agonists and Antagonists at Adenosine Receptors", discloses that the binding affinities at rat $A_1$, $A_{2a}$, and $A_3$ adenosine receptors of a wide range of derivatives of adenosine have been determined. In particular, 3'-β-amino compounds were found to have no activity.

J. Med. Chem. 1995, 38, 1720–1735, "Structure-Activity Relationships of 9-Alkyladenine and Ribose-Modified Adenosine Derivatives at Rat $A_3$ Adenosine Receptors" discloses the synthesis of 9-alkyladenine derivatives and ribose-modified N-benzyladenosine derivatives as leads for the development of antagonists for the rat $A_3$ adenosine receptor.

U.S. Pat. No. 5,817,760 discloses recombinant human adenosine receptors A1, A2a, A2b, and A3 which were prepared by cDNA cloning and polymerase chain reaction techniques. The recombinant adenosine receptors can be utilized in an assay to identify and evaluate entities that bind to or enhance binding to adenosine receptors.

Thus, while there has been some progress in this field of art, there is clearly a need and a continuing search in this field of art for treatments for perioperative myocardial ischemia.

SUMMARY OF THE INVENTION

This invention is directed to compounds of Formula I

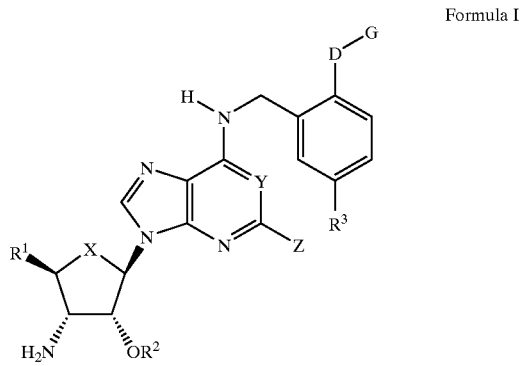

Formula I prodrugs thereof and pharmaceutically acceptable salts of said compounds and of said prodrug, wherein X is oxy, methylene or thio;

Y is CH or N;

Z is H, $(C_1-C_4)$alkyl, $(C_1-C_4)$alkyloxy, trifluoromethyl or halo;

$R^1$ is hydroxymethyl, $(C_1-C_3)$alkoxymethyl, $(C_3-C_5)$ cycloalkoxymethyl, carboxy, $(C_1-C_3)$alkoxycarbonyl, $(C_3-C_5)$cycloalkoxycarbonyl, 1,1-aminoiminomethyl, 1,1-(mono-N- or di-N,N-$(C_1-C_4)$alkylamino) iminomethyl, 1,1-(mono-N- or di-N,N-$(C_3-C_5)$ cycloalkylamino)iminomethyl, carbamoyl, mono-N- or di-N,N-$(C_1-C_4)$alkylaminocarbonyl, mono-N- or di-N, N-$(C_3-C_5)$cycloalkylaminocarbonyl or N-$(C_1-C_4)$ alkyl-N-$(C_3-C_5)$cycloalkylaminocarbonyl;

$R^2$ is H, $(C_1-C_3)$alkyl or $(C_3-C_5)$cycloalkyl;

$R^3$ is halo, trifluoromethyl, cyano, $(C_1-C_3)$alkyl, $(C_1-C_3)$ alkyloxy, ethenyl or ethynyl;

D is oxy, thio, NH, $(C_1-C_6)$alkyloxy, $(C_1-C_6)$alkylthio or $(C_1-C_6)$alkylamino;

G is a partially saturated, fully saturated or fully unsaturated five to eight membered ring optionally having one to three heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen; wherein said G is optionally mono-, di- or tri-substituted independently with halo, $(C_1-C_3)$alkyl, trifluoromethyl, trifluoromethoxy, nitro, cyano, $(C_3-C_6)$cycloalkyl, hydroxy or $(C_1-C_3)$alkoxy or G is cyano, $(C_1-C_4)$alkoxycarbonyl, $(C_3-C_5)$ cycloalkoxycarbonyl, $C(O)NR^4R^5$, $C(S)NR^4R^5$, C(NH)NR$^4$R$^5$, C(N(C$_1$-C$_3$)alkyl)NR$^4$R$^5$ or C(N(C$_3$-C$_{10}$)cycloalkyl)NR$^4$R$^5$;

R$^4$ is a bond, H, (C$_1$-C$_{10}$)alkyl, hydroxy, (C$_1$-C$_{10}$)alkoxy, (C$_3$-C$_{10}$)cycloalkoxy or a partially saturated, fully saturated or fully unsaturated five to eight membered ring, optionally linked through (C$_1$-C$_3$)alkyl, optionally having one to three heteroatoms selected independently from oxygen, sulfur and nitrogen, or, a bicyclic ring or a bicyclic ring with optional (C$_1$-C$_3$) bridge (e.g., adamantane) optionally linked through (C$_1$-C$_3$) alkyl, said bicyclic ring or bridged bicyclic ring optionally having one to four heteroatoms selected independently from nitrogen, sulfur and oxygen wherein said (C$_1$-C$_{10}$)alkyl, (C$_1$-C$_{10}$)alkoxy, (C$_3$-C$_{10}$)cycloalkoxy or R$^4$ ring(s) is optionally mono-, di- or tri-substituted independently with halo, (C$_1$-C$_3$)alkyl, trifluoromethyl, nitro, cyano, (C$_3$-C$_5$)cycloalkyl, hydroxy or (C$_1$-C$_3$)alkoxy;

R$^5$ is a bond, H, (C$_1$-C$_{10}$)alkyl or (C$_1$-C$_{10}$)cycloalkyl; or R$^4$ and R$^5$ taken together with the nitrogen to which they are attached form a fully saturated or partially unsaturated four to nine membered ring, said ring optionally bridged, optionally having one to three additional heteroatoms selected independently from oxygen, sulfur and nitrogen, said ring optionally mono- or di-substituted independently with oxo, hydroxy, (C$_1$-C$_6$)alkoxy, (C$_1$-C$_8$)alkyl, amino, mono-N- or di-N,N-(C$_1$-C$_4$)alkylaminocarbonyl, mono-N- or di-N,N-(C$_3$-C$_5$)cycloalkylaminocarbonyl, N-(C$_1$-C$_4$)alkyl-N-(C$_3$-C$_5$)cycloalkylaminocarbonyl, mono-N- or di-N,N-(C$_1$-C$_4$)alkylamino, mono-N- or di-N,N-(C$_3$-C$_5$)cycloalkylamino, N-(C$_1$-C$_4$)alkyl-N-(C$_3$-C$_5$)cycloalkylamino, formylamino, (C$_1$-C$_4$)alkylcarbonylamino, (C$_3$-C$_5$)cycloalkylcarbonylamino, (C$_1$-C$_4$)alkoxycarbonylamino, N-(C$_1$-C$_4$)alkoxycarbonyl-N-(C$_1$-C$_4$)alkylamino, (C$_1$-C$_4$)sulfamoyl, (C$_1$-C$_4$)alkylsulfonylamino, (C$_3$-C$_5$)cycloalkylsulfonylamino or a partially saturated, fully saturated or fully unsaturated five to eight membered ring, optionally linked through (C$_1$-C$_3$)alkyl, optionally having one to three heteroatoms selected independently from oxygen, sulfur and nitrogen, or a bicyclic ring consisting of two fused partially saturated, fully saturated or fully unsaturated three to six membered rings, taken independently, optionally linked through (C$_1$-C$_3$)alkyl, optionally having one to four heteroatoms selected independently from nitrogen, sulfur and oxygen, optionally mono or di-substituted with halo, trifluoromethyl, trifluoromethoxy (C$_1$-C$_3$)alkyl or (C$_1$-C$_3$)alkoxy.

A preferred group of compounds, designated the A Group, contains those compounds having the Formula I as shown above wherein X is oxy;
Y is N;
Z is H;
R$^1$ is (C$_1$-C$_8$)alkylcarbamoyl;
R$^2$ is H;
R$^3$ is halo, trifluoromethyl, cyano, (C$_1$-C$_3$)alkyl, (C$_1$-C$_3$) alkyloxy, ethenyl or ethynyl;
D is oxy, thio, (C$_1$-C$_6$)alkyloxy or (C$_1$-C$_6$)alkylthio;
G is phenyl, pyridyl, pyrimidinyl, pyrazinyl, thiazolyl, oxazolyl, isoxazolyl, pyridinazinyl, tetrazolyl, isothiazolyl, thiophenyl, furyl, 1,2,4-oxadiazolyl, 1,2,4-thiadiazolyl, pyrazolyl, pyrrolyl, indolyl, naphthalenyl, quinolinyl, isoquinolinyl, benzo[b]furanyl, benzo[b]thiophenyl, benzothiazolyl, tetrahydrofuranyl, pyrrolidinyl, piperidinyl, tetrahydropyranyl, morpholinyl wherein said G is optionally mono-, di- or tri-substituted independently with halo, (C$_1$-C$_3$)alkyl or (C$_1$-C$_3$)alkoxy; and pharmaceutically acceptable salts thereof.

A group of compounds which is preferred among the A Group of compounds, designated the B Group, contains those compounds wherein R$^1$ is methylcarbamoyl;
R$^3$ is halo;
D is (C$_1$-C$_6$)alkoxy;
G is phenyl, pyridyl, thiazolyl, oxazolyl, isoxazolyl, isothiazolyl, furanyl, 1,2,4-oxadiazolyl, 1,2,4-thiadiazolyl, pyrazolyl, pyrrolyl wherein said G is optionally mono-, di- or tri-substituted independently with halo, (C$_1$-C$_3$)alkyl, trifluoromethoxy or (C$_1$-C$_3$)alkoxy; and pharmaceutically acceptable salts thereof A group of compounds which is preferred among the B Group of compounds, designated the C Group, contains those compounds wherein D is (C$_1$-C$_2$)alkoxy;
G is phenyl, thiazolyl, oxazolyl, isoxazolyl, tetrahydrofuranyl, pyrrolidinyl, piperidinyl or morpholinyl wherein said G is optionally mono-, di- or tri-substituted independently with halo, (C$_1$-C$_3$)alkyl or (C$_1$-C$_3$)alkoxy; and pharmaceutically acceptable salts thereof.

Especially preferred compounds within the B Group of compounds are compounds wherein a. R$^3$ is chloro;
D is methyleneoxy; and
G is phenyl, b. R$^3$ is chloro;
D is methyleneoxy; and
G is 3-furanyl, c. R$^3$ is chloro;
D is methyleneoxy; and
G is 2-furanyl, d. R$^3$ is chloro,
D is methyleneoxy; and
G is 2-thiazolyl, e. R$^3$ is chloro;
D is methyleneoxy; and
G is 5-(3-methylisoxazolyl); and the pharmaceutically acceptable salts of said compounds.

Especially preferred compounds of this invention are the compounds (2S,3S,4R,5R)3-amino-5-[6-(2-benzyloxy-5-chloro-benzylamino)-purin-9-yl]-4-hydroxytetrahydrofuran-2-carboxylic acid methylamide, (2S,3S,4R,5R)3-amino-5-{6-[5-chloro-2-(furan-3-ylmethoxy)benzylamino]-purin-9-yl}-4-hydroxytetrahydrofuran-2-carboxylic acid methylamide, (2S,3S,4R,5R)3-amino-5-{6-[5-chloro-2-(furan-2-ylmethoxy)benzylamino] purin-9-yl}-4-hydroxytetrahydrofuran-2-carboxylic acid methylamide, (2S,3S,4R,5R)3-amino-5-{6-[5-chloro-2-(thiazol-2-ylmethoxy)-benzylamino]-purin-9yl}-4-hydroxy-tetrahydrofuran-2-carboxylic acid methylamide, (2S,3S,4R,5R)3-amino-5-{6-[5-chloro-2-(3-methylisoxazol-5-ylmethoxy)benzylamino]purin-9-yl}-4-hydroxytetrahydrofuran-2-carboxylic acid methylamide, and pharmaceutically acceptable salts of said compounds.

A preferred group of compounds, designated the D Group, contains those compounds having the Formula I as shown above wherein X is oxy;
Y is N;
Z is H;
$R^1$ is $(C_1-C_6)$alkylcarbamoyl;
$R^2$ is H;
$R^3$ is halo, trifluoromethyl, cyano, $(C_1-C_3)$alkyl, $(C_1-C_3)$alkyloxy, ethenyl or ethynyl;
D is $(C_1-C_6)$alkyloxy or $(C_1-C_6)$alkylthio;
G is $C(O)NR^4R^5$ or $C(S)NR^4R^5$
wherein $R^4$ and $R^5$ taken together with the nitrogen to which they are attached form a fully saturated four to nine membered ring, optionally having one to three additional heteroatoms selected independently from oxygen, sulfur and nitrogen, said ring optionally mono- or di-substituted independently with oxo, $(C_1-C_6)$alkoxy, $(C_1-C_8)$alkyl, amino, mono-N- or di-N,N-$(C_1-C_4)$alkylaminocarbonyl, mono-N- or di-N,N-$(C_3-C_5)$cycloalkylaminocarbonyl, N-$(C_1-C_4)$alkyl-N-$(C_3-C_5)$cycloalkylaminocarbonyl, mono-N- or di-N,N-$(C_1-C_4)$alkylamino, mono-N- or di-N,N-$(C_3-C_5)$cycloalkylamino or N-$(C_1-C_4)$alkyl-N-$(C_3-C_5)$cycloalkylamino, formylamino, $(C_1-C_4)$alkylformylamino, $(C_3-C_5)$cycloalkylformylamino, sulfamoyl, $(C_1-C_4)$alkylsulfonylamino, $(C_3-C_5)$cycloalkylsulfonylamino or a partially saturated, fully saturated or fully unsaturated five to eight membered ring, optionally linked through $(C_1-C_3)$alkyl, optionally having one to three heteroatoms selected independently from oxygen, sulfur and nitrogen, or, a bicyclic ring consisting of two fused partially saturated, fully saturated or fully unsaturated three to six membered rings, taken independently, optionally linked through $(C_1-C_3)$alkyl, optionally having one to four heteroatoms selected independently from nitrogen, sulfur and oxygen; and pharmaceutically acceptable salts thereof.

A preferred group of compounds which is preferred among the D Group of compounds, designated the E Group, contains those compounds wherein $R^1$ is methylcarbamoyl;
$R^3$ is halo;
D is $(C_1-C_2)$alkoxy;
G is $C(O)NR^4R^5$ or $C(S)NR^4R^5$;
wherein $R^4$ and $R^5$ taken together with the nitrogen to which they are attached form piperidinyl, piperazinyl, morpholinyl, azetidinyl or pyrrolidinyl said ring optionally mono- or di-substituted independently with oxo, hydroxy, $(C_1-C_6)$alkoxy, $(C_1-C_8)$alkyl, amino, carbamoyl, mono-N- or di-N,N-$(C_1-C_4)$alkylaminocarbonyl, mono-N- or di-N,N-$(C_3-C_5)$cycloalkylaminocarbonyl, N-$(C_1-C_4)$alkyl-N-$(C_3-C_5)$cycloalkylaminocarbonyl, mono-N- or di-N,N-$(C_1-C_4)$alkylamino, mono-N- or di-N,N-$(C_3-C_5)$cycloalkylamino or N-$(C_1-C_4)$alkyl-N-$(C_3-C_5)$cycloalkylamino, formylamino, $(C_1-C_4)$alkylformylamino, $(C_3-C_5)$cycloalkylformylamino, sulfamoyl, $(C_1-C_4)$alkylsulfonylamino, $(C_3-C_5)$cycloalkylsulfonylamino or
a partially saturated, fully saturated or fully unsaturated four to eight membered ring, optionally linked through $(C_1-C_3)$alkyl, optionally having one to two heteroatoms selected independently from oxygen, sulfur and nitrogen; and pharmaceutically acceptable salts thereof.

A preferred group of compounds which is preferred among the E Group of compounds, designated the F Group, contains those compounds wherein G is $C(O)NR^4R^5$;
wherein $R^4$ and $R^5$ taken together with the nitrogen to which they are attached form piperidinyl, piperazinyl, morpholinyl, azetidinyl, pyrrolidinyl said ring optionally mono- or di-substituted independently with hydroxy, oxo, $(C_1-C_6)$alkoxy, $(C_1-C_8)$alkyl, amino, carbamoyl, mono-N- or di-N,N-$(C_1-C_4)$alkylaminocarbonyl, mono-N- or di-N,N-$(C_1-C_4)$alkylamino, or a partially saturated, fully saturated or fully unsaturated four to eight membered ring, optionally linked through $(C_1-C_3)$alkyl, optionally having one to two heteroatoms selected independently from oxygen, sulfur and nitrogen; and pharmaceutically acceptable salts thereof.

Especially preferred compounds within the F Group of compounds are compounds wherein a. $R^3$ is chloro;
D is methyleneoxy;
G is $C(O)NR^4R^5$;
wherein $R^4$ and $R^5$ taken together with the nitrogen to which they are attached form piperazinyl substituted in the four position with methyl, b. $R^3$ is chloro;
D is methyleneoxy;
G is $C(O)NR^4R^5$;
wherein $R^4$ and $R^5$ taken together with the nitrogen to which they are attached form piperazinyl, c. $R^3$ is chloro;
D is methyleneoxy;
G is $C(O)NR^4R^5$;
wherein $R^4$ and $R^5$ taken together with the nitrogen to which they are attached form piperidinyl substituted in the four position with N,N-dimethylamino, d. $R^3$ is chloro;
D is methyleneoxy;
G is $C(O)NR^4R^5$;
wherein $R^4$ and $R^5$ taken together with the nitrogen to which they are attached form piperidinyl substituted in the four position with piperidin-1-yl, e. $R^3$ is chloro;
D is methyleneoxy;
G is $C(O)NR^4R^5$;
wherein $R^4$ and $R^5$ taken together with the nitrogen to which they are attached form piperidinyl substituted in the four position with methylamino, and pharmaceutically acceptable salts of said compounds.

A preferred group of compounds, designated the G Group, contains those compounds having the Formula I as shown above wherein X is oxy;
Y is N;
Z is H;
$R^1$ is $(C_1-C_6)$alkylcarbamoyl;
$R^2$ is H;
$R^3$ is halo, trifluoromethyl, cyano, $(C_1-C_3)$alkyl, $(C_1-C_3)$alkyloxy, ethenyl or ethynyl;
D is $(C_1-C_6)$alkyloxy or $(C_1-C_6)$alkylthio;
G is $C(O)NR^4R^5$ or $C(S)NR^4R^5$;

$R^4$ is H, $(C_1-C_{10})$alkyl, hydroxy, $(C_1-C_{10})$alkoxy, $(C_3-C_{10})$cycloalkoxy or a partially saturated, fully saturated or fully unsaturated five to eight membered ring, optionally linked through $(C_1-C_3)$alkyl, optionally having one to three heteroatoms selected independently from oxygen, sulfur and nitrogen, or a bicyclic ring consisting of two fused partially saturated, fully saturated or fully unsaturated three to six membered rings, taken independently, optionally linked through $(C_1-C_3)$alkyl, optionally having one to four heteroatoms selected independently from nitrogen, sulfur and oxygen;

$R^5$ is H, $(C_1-C_{10})$alkyl or $(C_1-C_{10})$cycloalkyl; and pharmaceutically acceptable salts thereof.

A group of compounds which is preferred among the G Group of compounds, designated the H Group, contains those compounds wherein $R^1$ is methylcarbamoyl;

$R^3$ is halo;

D is $(C_1-C_2)$alkoxy;

G is $C(O)NR^4R^5$ or $C(S)NR^4R^5$;

$R^4$ is H, $(C_1-C_{10})$alkyl, hydroxy, $(C_1-C_{10})$alkoxy, $(C_3-C_{10})$cycloalkoxy or a partially saturated, fully saturated or fully unsaturated five to eight membered ring, optionally linked through $(C_1-C_3)$alkyl, optionally having one to three heteroatoms selected independently from oxygen, sulfur and nitrogen;

$R^5$ is H, $(C_1-C_{10})$alkyl or $(C_1-C_{10})$cycloalkyl; and pharmaceutically acceptable salts thereof.

A group of compounds which is preferred among the H Group of compounds, designated the I Group, contains those compounds wherein G is $C(O)NR^4R^5$;

$R^4$ is H, $(C_1-C_{10})$alkyl, $(C_3-C_6)$cycloalkyl, hydroxy, $(C_1-C_{10})$alkoxy or $(C_3-C_{10})$cycloalkoxy;

$R^5$ is H, $(C_1-C_{10})$alkyl or $(C_3-C_{10})$cycloalkyl; and pharmaceutically acceptable salts thereof.

An especially preferred compound within the I Group of compounds is the compound wherein $R^3$ is chloro;

D is methyleneoxy;

G is $C(O)NR^4R^5$;

$R^4$ is H;

$R^5$ is H; and pharmaceutically acceptable salts thereof.

A preferred group of compounds, designated the J Group, contains those compounds having the Formula I as shown above wherein D is oxy, thio, $(C_1-C_6)$alkyloxy or $(C_1-C_6)$alkylthio;

G is phenyl, pyridyl, pyrimidinyl, pyrazinyl, thiazolyl, oxazolyl, isoxazolyl, pyridinazinyl, tetrazolyl, isothiazolyl, thiophenyl, furanyl, 1,2,4-oxadiazolyl, 1,2,4-thiadiazolyl, pyrazolyl, pyrrolyl, indolyl, naphthalenyl, quinolinyl, isoquinolinyl, benzo[b]furanyl, benzo[b]thiophenyl, benzothiazolyl, tetrahydrofuranyl, pyrrolidinyl, piperidinyl, tetrahydropyranyl, morpholinyl wherein said G is optionally mono-, di- or tri-substituted independently with halo, $(C_1-C_3)$alkyl or $(C_1-C_3)$alkoxy; and pharmaceutically acceptable salts thereof.

A group of compounds which is preferred among the J Group of compounds, designated the K Group, contains those compounds wherein D is $(C_1-C_6)$alkoxy;

G is phenyl, pyridyl, thiazolyl, oxazolyl, isoxazolyl, isothiazolyl, furanyl, 1,2,4-oxadiazolyl, 1,2,4-thiadiazolyl, pyrazolyl, pyrrolyl wherein said G is optionally mono-, di- or tri-substituted independently with halo, $(C_1-C_3)$alkyl or $(C_1-C_3)$alkoxy;

and pharmaceutically acceptable salts thereof.

A preferred group of compounds, designated the L Group, contains those compounds having the Formula I as shown above wherein D is $(C_1-C_6)$alkyloxy or $(C_1-C_6)$alkylthio;

G is $C(O)NR^4R^5$ or $C(S)NR^4R^5$ wherein $R^4$ and $R^5$ taken together with the nitrogen to which they are attached form a fully saturated four to nine membered ring, optionally having one to three additional heteroatoms selected independently from oxygen, sulfur and nitrogen, said ring optionally mono- or di-substituted independently with oxo, hydroxy, $(C_1-C_6)$alkoxy, $(C_1-C_8)$alkyl, amino, mono-N- or di-N,N-$(C_1-C_4)$alkylaminocarbonyl, mono-N- or di-N,N-$(C_3-C_5)$cycloalkylaminocarbonyl, N-$(C_1-C_4)$alkyl-N-$(C_3-C_5)$cycloalkylaminocarbonyl, mono-N- or di-N,N-$(C_1-C_4)$alkylamino, mono-N- or di-N, N-$(C_3-C_5)$cycloalkylamino or N-$(C_1-C_4)$alkyl-N-$(C_3-C_5)$ cycloalkylamino, formylamino, $(C_1-C_4)$alkylformylamino, $(C_3-C_5)$cycloalkylformylamino, sulfamoyl, $(C_1-C_4)$alkylsulfonylamino, $(C_3-C_5)$cycloalkylsulfonylamino or a partially saturated, fully saturated or fully unsaturated five to eight membered ring, optionally linked through $(C_1-C_3)$alkyl, optionally having one to three heteroatoms selected independently from oxygen, sulfur and nitrogen, or a bicyclic ring consisting of two fused partially saturated, fully saturated or fully unsaturated three to six membered rings, taken independently, optionally linked through $(C_1-C_3)$ alkyl, optionally having one to four heteroatoms selected independently from nitrogen, sulfur and oxygen; and pharmaceutically acceptable salts thereof.

A group of compounds which is preferred among the L Group of compounds, designated the M Group, contains those compounds wherein D is $(C_1-C_2)$alkoxy;

G is $C(O)NR^4R^5$ or $C(S)NR^4R^5$;

wherein $R^4$ and $R^5$ taken together with the nitrogen to which they are attached form piperidinyl, piperazinyl, morpholinyl, azetidinyl or pyrrolidinyl said ring optionally mono- or di-substituted independently with oxo, $(C_1-C_6)$alkoxy, $(C_1-C_8)$alkyl, amino, carbamoyl, mono-N- or di-N,N-$(C_1-C_4)$alkylaminocarbonyl, mono-N- or di-N,N-$(C_3-C_5)$cycloalkylaminocarbonyl, N-$(C_1-C_4)$alkyl-N-$(C_3-C_5)$cycloalkylaminocarbonyl, mono-N- or di-N,N-$(C_1-C_4)$alkylamino, mono-N- or di-N,N-$(C_3-C_5)$cycloalkylamino or N-$(C_1-C_4)$alkyl-N-$(C_3-C_5)$cycloalkylamino, formylamino, $(C_1-C_4)$alkylformylamino, $(C_3-C_5)$cycloalkylformylamino, sulfamoyl, $(C_1-C_4)$alkylsulfonylamino, $(C_3-C_5)$ cycloalkylsulfonylamino or a partially saturated, fully saturated or fully unsaturated four to eight membered ring, optionally linked through $(C_1-C_3)$alkyl, optionally having one to two heteroatoms selected independently from oxygen, sulfur and nitrogen; and pharmaceutically acceptable salts thereof.

A group of compounds which is preferred among the M Group of compounds, designated the N Group, contains those compounds wherein G is $C(O)NR^4R^5$;

wherein $R^4$ and $R^5$ taken together with the nitrogen to which they are attached form piperidinyl, piperazinyl, morpholinyl, azetidinyl, pyrrolidinyl said ring optionally mono- or di-substituted independently with oxo, hydroxy, $(C_1-C_6)$alkoxy, $(C_1-C_8)$alkyl, amino, carbamoyl, mono-N- or di-N,N-($C_1$-$C_4$) alkylaminocarbonyl, mono-N- or di-N,N-($C_1$-$C_4$) alkylamino, or a partially saturated, fully saturated or fully unsaturated four to eight membered ring, optionally linked through ($C_1$-$C_3$)alkyl, optionally having one to two heteroatoms selected independently from oxygen, sulfur and nitrogen; and pharmaceutically acceptable salts thereof.

A preferred group of compounds, designated the O Group, contains those compounds having the Formula I as shown above wherein D is ($C_1$-$C_6$)alkyloxy or ($C_1$-$C_6$)alkylthio;

G is C(O)NR$^4$R$^5$ or C(S)NR$^4$R$^5$;

R$^4$ is H, ($C_1$-$C_{10}$)alkyl, hydroxy, ($C_1$-$C_{10}$)alkoxy, ($C_3$-$C_{10}$)cycloalkoxy or a partially saturated, fully saturated or fully unsaturated five to eight membered ring, optionally linked through ($C_1$-$C_3$)alkyl, optionally having one to three heteroatoms selected independently from oxygen, sulfur and nitrogen, or a bicyclic ring consisting of two fused partially saturated, fully saturated or fully unsaturated three to six membered rings, taken independently, optionally linked through ($C_1$-$C_3$)alkyl, optionally having one to four heteroatoms selected independently from nitrogen, sulfur and oxygen;

R$^5$ is H, ($C_1$-$C_{10}$)alkyl or ($C_1$-$C_{10}$)cycloalkyl;

and pharmaceutically acceptable salts thereof.

A group of compounds which is preferred among the O Group of compounds, designated the P Group, contains those compounds wherein D is ($C_1$-$C_2$)alkoxy;

R$^4$ is H, ($C_1$-$C_{10}$)alkyl, hydroxy, ($C_1$-$C_{10}$)alkoxy, ($C_3$-$C_{10}$)cycloalkoxy or a partially saturated, fully saturated or fully unsaturated five to eight membered ring, optionally linked through ($C_1$-$C_3$)alkyl, optionally having one to three heteroatoms selected independently from oxygen, sulfur and nitrogen;

R$^5$ is H, ($C_1$-$C_{10}$)alkyl or ($C_1$-$C_{10}$)cycloalkyl; and pharmaceutically acceptable salts thereof.

A group of compounds which is preferred among the P Group of compounds, designated the Q Group, contains those compounds wherein G is C(O)NR$^4$R$^5$;

R$^4$ is H, ($C_1$-$C_{10}$)alkyl, ($C_3$-$C_6$)cycloalkyl, hydroxy, ($C_1$-$C_{10}$)alkoxy or ($C_3$-$C_{10}$)cycloalkoxy;

R$^5$ is H, ($C_1$-$C_{10}$)alkyl or ($C_3$-$C_{10}$)cycloalkyl; and pharmaceutically acceptable salts thereof.

Another aspect of this invention is directed to compounds having the Formula C

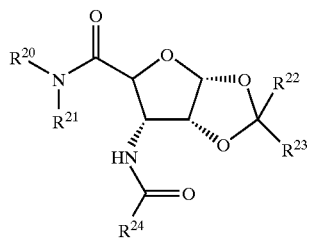

wherein R$^{20}$ and R$^{21}$ are each independently ($C_1$-$C_4$)alkyl, H, phenyl, phenyl($C_1$-$C_4$)alkyl or are joined together to form a piperidinyl, pyrrolidinyl or morpholinyl ring;

R$^{22}$ and R$^{23}$ are each independently ($C_1$-$C_4$)alkyl or are joined together to form a 5–6 membered carbocyclic ring; and R$^{24}$ is ($C_1$-$C_4$)alkyl, phenyl or phenyl($C_1$-$C_4$)alkyl, said phenyl or phenyl($C_1$-$C_4$)alkyl optionally mono-, di, or tri-substituted independently on the phenyl moiety with nitro, halo or trifluoromethyl.

Another aspect of this invention is directed to compounds having the Formula CI

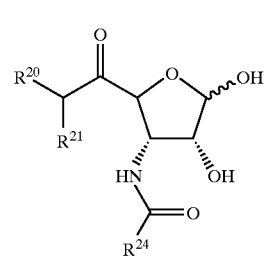

wherein R$^{20}$ and R$^{21}$ are each independently ($C_1$-$C_4$)alkyl, H, phenyl, phenyl($C_1$-$C_4$)alkyl or are joined together to form a piperidinyl, pyrrolidinyl or morpholinyl ring; and R$^{24}$ is ($C_1$-$C_4$)alkyl, phenyl or phenyl ($C_1$-$C_4$)alkyl, said phenyl or phenyl($C_1$-$C_4$)alkyl optionally mono-, di, or tri-substituted independently on the phenyl moiety with nitro, halo or trifluoromethyl.

Another aspect of this invention is directed to compounds having the Formula CII

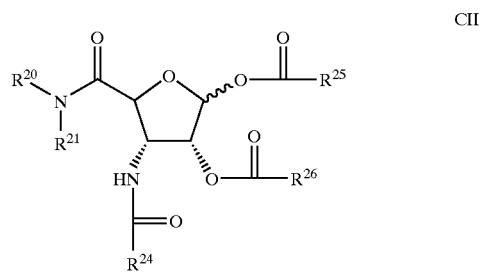

wherein R$^{20}$ and R$^{21}$ are each independently ($C_1$-$C_4$)alkyl, H, phenyl, phenyl($C_1$-$C_4$)alkyl or are joined together to form a piperidinyl, pyrrolidinyl or morpholinyl ring;

R$^{24}$ is ($C_1$-$C_4$)alkyl, phenyl or phenyl ($C_1$-$C_4$)alkyl, said phenyl or phenyl($C_1$-$C_4$)alkyl optionally mono-, di, or tri-substituted independently on the phenyl moiety with nitro, halo or trifluoromethyl; and R$^{25}$ and R$^{26}$ are each independently ($C_1$-$C_4$)alkyl or phenyl.

Another aspect of this invention is directed to compounds having the Formula CIII

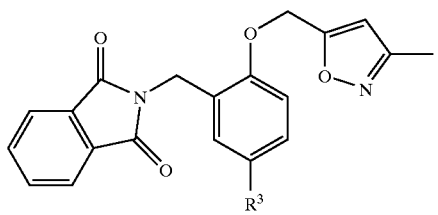

wherein R$^3$ is halo, trifluoromethyl, cyano, ($C_1$-$C_3$)alkyl, ($C_1$-$C_3$)alkyloxy, ethenyl or ethynyl.

Especially preferred compounds having Formula CIII as shown above are compounds wherein a. $R^3$ is trifluoromethyl;
b. $R^3$ is fluoro; and
c. $R^3$ is chloro.

Another aspect of this invention is directed to compounds having Formula CIV

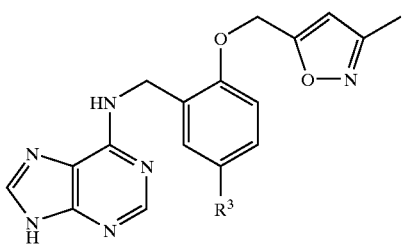

CIV wherein $R^3$ is halo, trifluoromethyl, cyano, $(C_1-C_3)$alkyl, $(C_1-C_3)$alkyloxy, ethenyl or ethynyl.

Especially preferred compounds having Formula CIV as shown above are compounds wherein a. $R^3$ is trifluoromethyl;
b. $R^3$ is fluoro; and
c. $R^3$ is chloro.

Another aspect of this invention is directed to compounds having the Formula CV

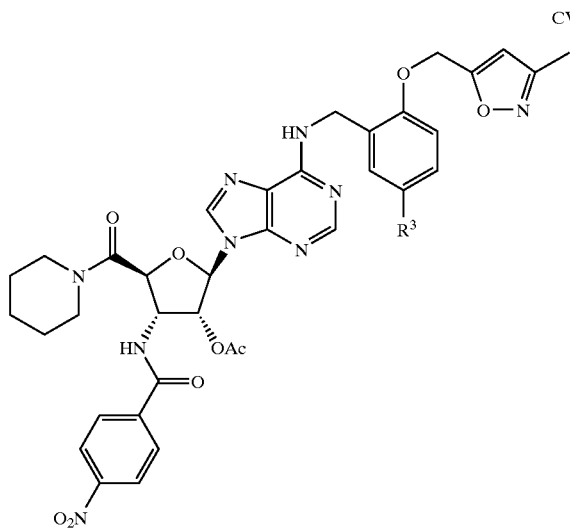

CV wherein $R^3$ is halo, trifluoromethyl, cyano, $(C_1-C_3)$alkyl, $(C_1-C_3)$alkyloxy, ethenyl or ethynyl.

Especially preferred compounds having Formula CV as shown above are compounds wherein a. $R^3$ is trifluoromethyl;
b. $R^3$ is fluoro; and
c. $R^3$ is chloro.

Another aspect of this invention is directed to compounds having the Formula CVI

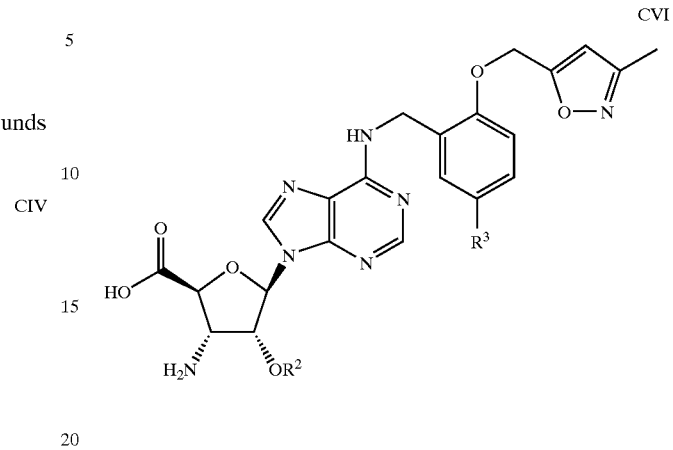

CVI wherein $R^2$ is H, $(C_1-C_3)$alkyl or $(C_3-C_5)$cycloalkyl; and $R^3$ is halo, trifluoromethyl, cyano, $(C_1-C_3)$alkyl, $(C_1-C_3)$alkyloxy, ethenyl or ethynyl.

Especially preferred compounds having Formula CVI as shown above are compounds wherein a. $R^2$ is H; and
$R^3$ is chloro,
b. $R^2$ is H; and
$R^3$ is fluoro,
c. $R^2$ is cyclopropyl; and
$R^3$ is fluoro.

Another aspect of this invention is directed to a method of making a compound of Formula CVII

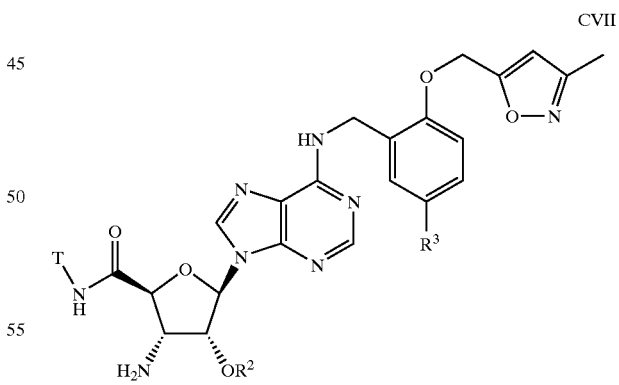

CVII wherein T is $(C_1-C_4)$alkyl;

$R^2$ is H, $(C_1-C_3)$alkyl or $(C_3-C_5)$cycloalkyl; and $R^3$ is halo, trifluoromethyl, cyano, $(C_1-C_3)$alkyl, $(C_1-C_3)$alkyloxy, ethenyl or ethynyl;

comprising acylating a (C₁–C₄alkyl)amine with a Formula CVI compound.

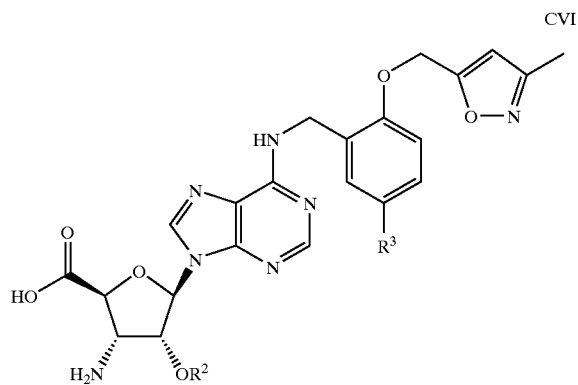

CVI wherein
R² is H, (C₁–C₃)alkyl or (C₃–C₅)cycloalkyl; and
R³ is halo, trifluoromethyl, cyano, (C₁–C₃)alkyl, (C₁–C₃) alkyloxy, ethenyl or ethynyl.

A preferred aspect of the above method is wherein
R² is H or cyclopropyl;
R³ is fluoro, chloro or trifluoromethyl;
and the Formula CVI acid is esterified to a (C₁–C₆)alkyl ester prior to acylation with the (C₁–C₄)alkylamine.

An especially preferred aspect of the immediately preceding method is wherein the Formula CVI acid is esterified with an alcohol in the presence of acid at a temperature of ambient to reflux for a period of about 1 hour to about 12 hours.

An especially preferred aspect of the immediately preceding method, is wherein the ester is reacted with the amine at a temperature of about ambient to reflux for about one to about 12 hours in an alcohol solvent.

An especially preferred aspect of the immediately preceding method designated the X method is, wherein the esterification occurs at a temperature of about 50° C. and the acylation occurs at a temperature of about 50° C.

An especially preferred aspect of the X method is wherein
the alcohol is methanol;
the acid is HCl;
the amine is methylamine;
R² is H; and
R³ is chloro.

An especially preferred aspect of the X method is wherein
the alcohol is methanol;
the acid is HCl;
the amine is methylamine;
R² is cyclopropyl; and
R³ is fluoro.

An especially preferred aspect of the X method is wherein
the alcohol is methanol;
the acid is HCl;
the amine is methylamine;
R² is H; and
R³ is trifluoromethyl.

Another aspect of this invention are methods of treating a mammal (e.g., human) having a disease or condition mediated by an A₃ adenosine receptor by administering a therapeutically effective amount of a compound of Formula I, a prodrug thereof, or a pharmaceutically acceptable salt of said compound or of said prodrug to the mammal.

Another aspect of this invention is directed to methods of reducing tissue damage (e.g., substantially preventing tissue damage, inducing tissue protection) resulting from ischemia or hypoxia comprising administering to a mammal (e.g., a female or male human) in need of such treatment a therapeutically effective amount of a compound of Formula I, a prodrug thereof, or a pharmaceutically acceptable salt of said compound or of said prodrug.

Preferred ischemic/hypoxic tissues taken individually or as a group are wherein the ischemic/hypoxic tissue is cardiac, brain, liver, kidney, lung, gut, skeletal muscle, spleen, pancreas, nerve, spinal cord, retina tissue, the vasculature, or intestinal tissue.

An especially preferred ischemic/hypoxic tissue is cardiac tissue.

It is especially preferred that the compounds are administered to prevent perioperative myocardial ischemic injury.

Preferably, the compounds of this invention are administered prophylactically.

The ischemic/hypoxic damage may occur during organ transplantation.

Preferably, the compounds of this invention are administered prior to, during or shortly after, cardiac surgery or non-cardiac surgery (e.g., a three to four day infusion).

In one aspect of this invention a compound of Formula I is administered locally.

A preferred dosage is about 0.001 to 100 mg/kg/day of the Formula I compound, a prodrug thereof or a pharmaceutically acceptable salt of said compound or of said prodrug. An especially preferred dosage is about 0.01 to 50 mg/kg/day of a compound of Formula I, a prodrug thereof, or a pharmaceutically acceptable salt of said compound or of said prodrug.

Another aspect of this invention is directed to methods of reducing myocardial tissue damage (e.g., substantially preventing tissue damage, inducing tissue protection) during surgery (e.g., coronary artery bypass grafting (CABG) surgeries, vascular surgeries, percutaneous transluminal coronary angioplasty (PTCA) or any percutaneous transluminal coronary intervention (PTCI), organ transplantation, or other non-cardiac surgeries) comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to methods of reducing myocardial tissue damage (e.g., substantially preventing tissue damage, inducing tissue protection) in patients presenting with ongoing cardiac (acute coronary syndromes, e.g., myocardial infarction or unstable angina) or cerebral ischemic events (e.g., stroke) comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to chronic methods of reducing myocardial tissue damage (e.g., substantially preventing tissue damage, inducing tissue protection) in a patient with diagnosed coronary heart disease (e.g., previous myocardial infarction or unstable angina) or patients who are at high risk for myocardial infarction (e.g., age >65 and two or more risk factors for coronary heart disease) comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to methods of preventing ischemic/hypoxic damage comprising the chronic oral administration to a mammal in need of such treatment of a therapeutically effective amount of a compound of Formula I, a prodrug of said compound, or a pharmaceutically acceptable salt of said compound or of said prodrug.

Another aspect of this invention is directed to methods for treating cardiovascular diseases comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to methods for treating arteriosclerosis comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to methods for treating arrhythmia comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to methods for treating angina pectoris comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to methods for treating cardiac hypertrophy comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to methods for treating renal diseases comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to methods for treating diabetic complications comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to methods for treating restenosis comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to methods for treating organ hypertrophies or hyperplasias comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to methods for treating septic shock and other inflammatory diseases (septicemia, endotoxcemia) comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to methods for treating cerebro ischemic disorders comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to methods for treating myocardial stunning comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to methods for treating myocardial dysfunction comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to methods for treating cerebrovascular diseases comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to methods for treating organ hypertrophies or hyperplasias comprising administering to a mammal (e.g., a female or male human) a therapeutically effective amount of a compound of Formula I, a prodrug thereof, or a pharmaceutically acceptable salt of said compound or of said prodrug.

This invention is also directed to pharmaceutical compositions which comprise a therapeutically effective amount of a compound of Formula I, a prodrug thereof, or a pharmaceutically acceptable salt of said compound or of said prodrug and a pharmaceutically acceptable carrier, vehicle or diluent.

This invention is also directed to pharmaceutical compositions for the reduction of tissue damage resulting from ischemia or hypoxia which comprise a therapeutically effective amount of a compound of Formula I, a prodrug thereof, or a pharmaceutically acceptable salt of said compound or of said prodrug and a pharmaceutically acceptable carrier, vehicle or diluent.

This invention is also directed to a kit for use by a consumer having or at risk of having a disease or condition resulting from, for example, ischemia or hypoxia which may be ameliorated by an $A_3$ agonist. The kit comprises a) a suitable dosage form such as an injectable parenteral solution particularly adapted for intravenous or intramuscular injection comprising a compound of Formula I; and b) instructions describing a method of using the dosage form to reduce tissue damage resulting from ischemia or hypoxia.

In the above pharmaceutical compositions and methods, preferred Formula I compounds include the preferred groups of compounds described above labeled as Group A-to Group Q.

Yet another aspect of this invention are combinations of a compound of Formula I, a prodrug thereof, or a pharmaceutically acceptable salt of said compound or of said prodrug and other compounds as described below.

This invention is also directed to a pharmaceutical combination composition comprising: a therapeutically effective amount of a composition comprising
 a first compound, said first compound being a compound Formula I of a prodrug thereof, or a pharmaceutically acceptable salt of said compound or of said prodrug;
 a second compound, said second compound being a cardiovascular agent; and, optionally,
 a pharmaceutical carrier, vehicle or diluent.

Another aspect of this invention are methods of reducing tissue damage (e.g., substantially preventing tissue damage, inducing tissue protection) resulting from or which could result from ischemia or hypoxia comprising administering to a mammal (e.g., a female or male human)
  a. a first compound, said first compound being a compound of Formula I, a prodrug thereof, or a pharmaceutically acceptable salt of said compound or of said prodrug; and
  b. a second compound, said second compound being a cardiovascular agent
wherein the amounts of the first and second compounds result in a therapeutic effect.

Another aspect of this invention are kits comprising:
  a. a compound of Formula I, a prodrug thereof, or a pharmaceutically acceptable salt of said compound or of said prodrug and a pharmaceutically acceptable carrier, vehicle or diluent in a first unit dosage form;
  b. a cardiovascular agent and a pharmaceutically acceptable carrier, vehicle or diluent in a second unit dosage form; and
  c. means for containing said first and second dosage forms wherein the amounts of the first and second compounds result in a therapeutic effect.

In the above combination compositions, combination methods and kits, preferably the cardiovascular agents and salts thereof (e.g., agents having a cardiovascular effect) are, for example, β-blockers (e.g., acebutolol, atenolol, bopindolol, labetolol, mepindolol, nadolol, oxprenol, pindolol, propranolol, sotalol), calcium channel blockers (e.g., amlodipine, nifedipine, nisoldipine, nitrendipine, verapamil), potassium channel openers, adenosine, adenosine agonists, sodium-hydrogen exchanger type 1 (NHE-1) inhibitors, ACE inhibitors (e.g., captopril, enalapril), nitrates (e.g., isosorbide dinitrate, isosorbide 5-mononitrate, glyceryl trinitrate), diuretics (e.g., hydrochlorothiazide, indapamide, piretanide, xipamide), glycosides (e.g., digoxin, metildigoxin), thrombolytics (e.g. tPA), platelet inhibitors (e.g., reopro), aspirin, dipyridamol, potassium chloride, clonidine, prazosin, pyruvate dehydrogenase kinase inhibitors (e.g., dichloroacetate), pyruvate dehydrogenase complex activators, biguanides (e.g., metformin) or other adenosine $A_3$ receptor agonists. Other cardiovascular agents include angiotensin II (AII) receptor antagonists, C5a inhibitors, soluble complement receptor type 1 (sCR1) or analogues, partial fatty acid oxidation (PFOX) inhibitors (specifically, ranolazine), acetyl CoA carboxylase activators, malonyl CoA decarboxylase inhibitors, 5'AMP-activated protein kinase (AMPK) inhibitors, adenosine nucleoside inhibitors, anti-apoptotic agents (e.g., caspase inhibitors), monophosphoryl lipid A or analogues, nitric oxide synthase activators/inhibitors, protein kinase C activators (specifically, protein kinase ε), protein kinase delta inhibitor, poly (ADP ribose) synthetase (PARS, PARP) inhibitors, metformin (gluconeogenesis inhibitors, insulin sensitizers), endothelin converting enzyme (ECE) inhibitors, endothelin ETA receptor antagonists, (thrombin activated fibrinolytic inhibitor) TAFI inhibitors and Na/Ca exchanger modulators.

Especially preferred NHE-1 inhibitors are [1-(8-bromoquinolin-5-yl)-5-cyclopropyl-1H-pyrazole-4-carbonyl]guanidine;
[1-(6-chloroquinolin-5-yl)-5-cyclopropyl-1H-pyrazole-4-carbonyl]guanidine;
[1-(indazol-7-yl)-5-cyclopropyl-1H-pyrazolecarbonyl]guanidine;
[1-(benzimidazol-5-yl)-5-cyclopropyl-1H-pyrazole-4-carbonyl]guanidine;
[1-(1-isoquinolyl)-5-cyclopropyl-1H-pyrazole-4-carbonyl]guanidine;
[5-cyclopropyl-1-(4-quinolinyl)-1H-pyrazole-4-carbonyl]guanidine;
[5-cyclopropyl-1-(quinolin-5-yl)-1H-pyrazole-4-carbonyl]guanidine;
[5-cyclopropyl-1-(quinolin-8-yl)-1H-pyrazole-4-carbonyl]guanidine;
[1-(indazol-6-yl)-5-ethyl-1H-pyrazole-4-carbonyl]guanidine;
[1-(indazol-5-yl)-5-ethyl-1H-pyrazole-4-carbonyl]guanidine;
[1-(benzimidazol-5-yl)-5-ethyl-1H-pyrazole-4-carbonyl]guanidine;
[1-(1-methylbenzimidazol-6-yl)-5-ethyl-1H-pyrazole-4-carbonyl]guanidine;
[1-(5-quinolinyl)-5-n-propyl-1H-pyrazole-4-carbonyl]guanidine;
[1-(5-quinolinyl)-5-isopropyl-1H-pyrazole-4-carbonyl]guanidine;
[5-ethyl-1-(6-quinolinyl)-1H-pyrazole-4-carbonyl]guanidine;
[1-(2-methylbenzimidazol-5-yl)-5-ethyl-1H-pyrazole-4-carbonyl]guanidine;
[1-(1,4-benzodioxan-6-yl)-5-ethyl-1H-pyrazole-4-carbonyl]guanidine;
[1-(benzotriazol-5-yl)-ethyl-1H-pyrazole-4-carbonyl]guanidine;
[1-(3-chloroindazol-5-yl)-5-ethyl-1H-pyrazole-4-carbonyl]guanidine;
[1-(5-quinolinyl)-5-butyl-1H-pyrazole-4-carbonyl]guanidine;
[5-propyl-1-(6-quinolinyl)-1H-pyrazole-4-carbonyl]guanidine;
[5-isopropyl-1-(6-quinolinyl)-1H-pyrazole-4-carbonyl]guanidine;
[1-(2-chloro-4-methylsulfonylphenyl)-5-cyclopropyl-1H-pyrazole-4-carbonyl]guanidine;
[1-(2-chlorophenyl)-5-cyclopropyl-1H-pyrazole-4-carbonyl]guanidine;
[1-(2-trifluoromethyl-4-fluorophenyl)-5-cyclopropyl-1H-pyrazole-4-carbonyl]guanidine;
[1-(2-bromophenyl)-5-cyclopropyl-1H-pyrazole-4-carbonyl]guanidine;
[1-(2-fluorophenyl)-5-cyclopropyl-1H-pyrazole-4-carbonyl]guanidine;
[1-(2-chloro-5-methoxyphenyl)-5-cyclopropyl-1H-pyrazole-4-carbonyl]guanidine;
[1-(2-chloro-4-methylaminosulfonylphenyl)-5-cyclopropyl-1H-pyrazole-4-carbonyl]guanidine;
[1-(2,5-dichlorophenyl)-5-cyclopropyl-1H-pyrazole-4-carbonyl]guanidine;
[1-(2,3-dichlorophenyl)-5-cyclopropyl-1H-pyrazole-4-carbonyl]guanidine;
[1-(2-chloro-5-aminocarbonylphenyl)-5-cyclopropyl-1H-pyrazole-4-carbonyl]guanidine;
[1-(2-chloro-5-aminosulfonylphenyl)-5-cyclopropyl-1H-pyrazole-4-carbonyl]guanidine;
[1-(2-fluoro-6-trifluoromethylphenyl)-5-cyclopropyl-1H-pyrazole-4-carbonyl]guanidine;
[1-(2-chloro-5-methylsulfonylphenyl)-5-cyclopropyl-1H-pyrazole-4-carbonyl]guanidine;
[1-(2-chloro-5-dimethylaminosulfonylphenyl)-5-cyclopropyl-1H-pyrazole-4-carbonyl]guanidine;
[1-(2-trifluoromethyl-4-chlorophenyl)-5-cyclopropyl-1H-pyrazole-4-carbonyl]guanidine;
[1-(2-chlorophenyl)-5-methyl-1H-pyrazole-4-carbonyl]guanidine;

[5-methyl-1-(2-trifluoromethylphenyl)-1H-pyrazole-4-carbonyl]guanidine;
[5-ethyl-1-phenyl-1H-pyrazole-4-carbonyl]guanidine;
[5-cyclopropyl-1-(2-trifluoromethylphenyl)-1H-pyrazole-4-carbonyl]guanidine;
[5-cyclopropyl-1-phenyl-1H-pyrazole-4-carbonyl]guanidine;
[5-cyclopropyl-1-(2,6-dichlorophenyl)-1H-pyrazole-4-carbonyl]guanidine; and
pharmaceutically acceptable salts thereof.

In the above combination compositions, combination methods and kits preferred Formula I compounds include the preferred groups of compounds described above labeled as Group A to Group Q.

This invention is also directed to a pharmaceutical combination composition comprising: a therapeutically effective amount of a composition comprising a first compound, said first compound being a Formula I compound, a prodrug thereof, or a pharmaceutically acceptable salt of said compound or of said prodrug;

a second compound, said second compound being a glycogen phosphorylase inhibitor; and, optionally, a pharmaceutical carrier, vehicle or diluent.

Another aspect of this invention are methods of reducing tissue damage (e.g., substantially preventing tissue damage, inducing tissue protection) resulting from or which could result from ischemia or hypoxia comprising administering to a mammal (e.g., a female or male human)

a. a first compound, said first compound being a Formula I compound, a prodrug thereof, or a pharmaceutically acceptable salt of said compound or of said prodrug; and b. a second compound, said second compound being a glycogen phosphorylase inhibitor wherein the amounts of the first and second compounds result in a therapeutic effect.

Another aspect of this invention are kits comprising:

a. a Formula I compound, a prodrug thereof, or a pharmaceutically acceptable salt of said compound or of said prodrug and a pharmaceutically acceptable carrier, vehicle or diluent in a first unit dosage form;

b. a glycogen phosphorylase inhibitor and a pharmaceutically acceptable carrier, vehicle or diluent in a second unit dosage form; and c. means for containing said first and second dosage forms wherein the amounts of the first and second compounds result in a therapeutic effect.

In the above combination compositions, combination methods and kits preferred Formula I compounds include the preferred groups of compounds described above labeled as Group A to Group Q.

In the above combination compositions, combination methods and kits preferred glycogen phosphorylase inhibitors are 5-chloro-1H-indole-2-carboxylic acid [(1S)((R)hydroxy-dimethylcarbamoyl-methyl)-2-phenyl-ethyl]-amide, 5,6-dichloro-1H-indole-2-carboxylic acid {(1S)-[(R)-hydroxy-(methoxy-methyl-carbamoyl)-methyl]-2-phenyl-ethyl}-amide, 5-chloro-1H-indole-2-carboxylic acid {(1S)[(R)-hydroxy-(methoxy-methyl-carbamoyl)-methyl]-2-phenyl-ethyl}-amide, 5-chloro-1H-indole-2-carboxylic acid {(1S)((R)-hydroxy-[(2-hydroxy-ethyl)-methyl-carbamoyl]-methyl}-2-phenyl-ethyl)-amide, 5-chloro-1H-indole-2-carboxylic acid {(1S)[(R)-hydroxy-(methyl-pyridin-2-yl-carbamoyl)-methyl]-2-phenyl-ethyl}-amide, 5-chloro-1H-indole-2-carboxylic acid ((1S)-{(R)-hydroxy-[methyl-(2-pyridin-2-yl-ethyl)carbamoyl]-methyl}-2-phenyl-ethyl)-amide, 5-chloro-1H-indole-2-carboxylic acid [(1S)-benzyl-(2R)-hydroxy-3-(4-methyl-piperazin-1-yl)-3-oxo-propyl]-3-amide hydrochloride, 5-chloro-1H-indole-2-carboxylic acid [(1S)-benzyl-(2R)-hydroxy-3-(3-hydroxy-azetidin-1-yl)-3-oxo-propyl]-amide, 5-chloro-1H-indole-2-carboxylic acid ((1S)-benzyl-(2R)-hydroxy-3-isoxazolidin-2-yl-3-oxo-propyl)-amide, 5-chloro-1H-indole-2-carboxylic acid ((1S)-benzyl-(2R)-hydroxy-3-[1,2]oxazinan-2-yl-3-oxo-propyl)-amide, 5-chloro-1H-indole-2-carboxylic acid [(1S)-benzyl-(2R)-hydroxy-3-((3S)-hydroxy-pyrrolidin-1-yl)-3-oxo-propyl]-amide, 5-chloro-1H-indole-2-carboxylic acid [(1S)benzyl-3-((3S,4S)-dihydroxy-pyrrolidin-1-yl)-(2R)-hydroxy-3-oxo-propyl]-amide, 5-chloro-1H-indole-2-carboxylic acid [(1S)-benzyl-3-((3R,4S)-dihydroxy-pyrrolidin-1-yl)-(2R)-hydroxy-3-oxo-propyl]-amide, 5-chloro-1H-indole-2-carboxylic acid ((1S)benzyl-(2R)-hydroxy-3-morpholin-4-yl-3-oxo-propyl)-amide, 5-chloro-1H-indole-2-carboxylic acid [(1S)-benzyl-2-(3-hydroxyimino-pyrrolidin-1-yl)-2-oxo-ethyl]-amide, 5-chloro-1H-indole-2-carboxylic acid [2-(cis-3,4-dihydroxy-pyrrolidin-1-yl)-2-oxo-ethyl]-amide, 5-chloro-1H-indole-2-carboxylic acid [2-((3S,4S)-dihydroxy-pyrrolidin-1-yl)-2-oxo-ethyl]-amide, 5-chloro-1H-indole-2-carboxylic acid [(1S)-benzyl-2-(cis-3,4-dihydroxy-pyrrolidin-1-yl)-2-oxo-ethyl]-amide, 5-chloro-1H-indole-2-carboxylic acid [2-(1,1-dioxo-thiazolidin-3-yl)-2-oxo-ethyl]-amide, 5-chloro-1H-indole-2-carboxylic acid (2-oxo-2-thiazolidin-3-yl-ethyl)-amide, 5-chloro-1H-indole-2-carboxylic acid [(1S)-(4-fluoro-benzyl)-2-(4-hydroxy-piperidin-1-yl)-2-oxo-ethyl]-amide, 5-chloro-1H-indole-2-carboxylic acid [(1S)-benzyl-2-((3RS)-hydroxy-piperidin-1-yl)-2-oxo-ethyl]-amide, 5-chloro-1H-indole-2-carboxylic acid [2-oxo-2-((1RS)-oxo-1-thiazolidin-3-yl)-ethyl]-amide, 5-chloro-1H-indole-2-carboxylic acid [(1S)-(2-fluoro-benzyl)-2-(4-hydroxy-piperidin-1-yl)-2-oxo-ethyl]-amide, 5-chloro-1H-indole-2-carboxylic acid [(1S)-benzyl-2-((3S,4S)-dihydroxy-pyrrolidin-1-yl)-2-oxo-ethyl]-amide, 5-chloro-1H-indole-2-carboxylic acid [(1S)-benzyl-2-(3-hydroxy-azetidin-1-yl)-2-oxo-ethyl]-amide, 5-Chloro-1H-indole-2-carboxylic acid [(1S)-benzyl-2-(3-hydroxyimino-azetidin-1-yl)-2-oxo-ethyl]-amide or 5-chloro-1H-indole-2-carboxylic acid [(1S)benzyl-2-(4-hydroxyimino-piperidin-1-yl)-2-oxo-ethyl]-amide.

This invention is also directed to a pharmaceutical combination composition comprising: a therapeutically effective amount of a composition comprising a first compound, said first compound being a Formula I compound, a prodrug thereof, or a pharmaceutically acceptable salt of said compound or of said prodrug;

a second compound, said second compound being an aldose reductase inhibitor; and, optionally, a pharmaceutical carrier, vehicle or diluent.

Another aspect of this invention are methods of reducing tissue damage (e.g., substantially preventing tissue damage, inducing tissue protection) resulting from or which could result from ischemia or hypoxia comprising administering to a mammal (e.g., a female or male human)

a. a first compound, said first compound being a Formula I compound, a prodrug thereof, or a pharmaceutically acceptable salt of said compound or of said prodrug; and b. a second compound, said second compound being an aldose reductase inhibitor wherein the amounts of the first and second compounds result in a therapeutic effect.

Another aspect of this invention are kits comprising:

a. a Formula I compound, a prodrug thereof, or a pharmaceutically acceptable salt of said compound or of said prodrug and a pharmaceutically acceptable carrier, vehicle or diluent in a first unit dosage form;

b. an aldose reductase inhibitor and a pharmaceutically acceptable carrier, vehicle or diluent in a second unit dosage form; and c. means for containing said first and second dosage forms wherein the amounts of the first and second compounds result in a therapeutic effect.

In the above combination compositions, combination methods and kits preferred Formula I compounds include the preferred groups of compounds described above labeled as Group A to Group Q.

In the above combination compositions, combination methods and kits a preferred aldose reductase inhibitor is zopolrestat: 1-phthalazineacetic acid, 3,4-dihydro-4-oxo-3-[[5-trifluoromethyl)-2-benzothiazolyl]methyl]-.

In the methods of treatment as applied to the combinations described above the following are preferred administration routes, modes, etc.

Preferred ischemic or hypoxic tissues taken individually or as a group are wherein the ischemic/hypoxic tissue is cardiac, brain, liver, kidney, lung, gut, skeletal muscle, spleen, pancreas, nerve, spinal cord, retina tissue, the vasculature, or intestinal tissue.

An especially preferred ischemic or hypoxic tissue is cardiac tissue.

It is especially preferred that the combinations are administered to prevent perioperative myocardial ischemic injury.

Preferably, the combinations of this invention are administered prophylactically.

The ischemic/hypoxic damage may occur during organ transplantation.

Preferably, the combinations of this invention are administered prior to, during and/or shortly after, cardiac surgery or non-cardiac surgery.

In one aspect of this invention the combinations are administered locally.

In one aspect of this inventor myocardial tissue damage is reduced during or after surgery.

In another aspect of this inventor myocardial tissue damage is reduced in patients presenting with ongoing cardiac or cerebral ischemic events.

In yet another aspect of this inventor myocardial tissue damage is reduced by chronic administration of the above combinations in a patient with diagnosed coronary heart disease.

The term "reduction" is intended to include partial prevention or prevention which, although greater than that which would result from taking no compound or from taking a placebo, is less than 100% in addition to substantially total prevention.

The term "damage resulting from ischemia or hypoxia" as employed herein refers to conditions directly associated with reduced blood flow or oxygen delivery to tissue, for example due to a clot or obstruction of blood vessels which supply blood to the subject tissue and which result, inter alia, in lowered oxygen transport to such tissue, impaired tissue performance, tissue dysfunction and/or necrosis and/or apoptosis. Alternatively, where blood flow or organ perfusion may be quantitatively adequate, the oxygen carrying capacity of the blood or organ perfusion medium may be reduced, e.g., in hypoxic environment, such that oxygen supply to the tissue is lowered, and impaired tissue performance, tissue dysfunction, and/or tissue necrosis and/or apoptosis ensues.

The term "treating", "treat" or "treatment" as used herein includes preventative (e.g., prophylactic) and palliative treatment.

By "pharmaceutically acceptable" it is meant the carrier, diluent, excipients, and/or salt must be compatible with the other ingredients of the formulation, and not deleterious to the recipient thereof.

The expression "prodrug" refers to compounds that are drug precursors which, following administration, release the drug in vivo via some chemical or physiological process (e.g., a prodrug on being brought to the physiological pH or through enzyme action is converted to the desired drug form).

Exemplary five to six membered aromatic rings optionally having one or two heteroatoms selected independently from oxygen, nitrogen and sulfur are phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl and pyrazinyl.

Exemplary partially saturated, fully saturated or fully unsaturated five to eight membered rings optionally having one to three heteroatoms selected independently from oxygen, sulfur and nitrogen are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4-oxadiazolyl, 1,2,3-triazolyl, 1,2,4-triazolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-oxathiazinyl and 1,4,2-oxadiazinyl.

Further exemplary seven membered rings are azepinyl, oxepinyl, thiepinyl and 1,2,4-diazepinyl.

Further exemplary eight membered rings are cyclooctyl, cyclooctenyl and cyclooctadienyl.

Exemplary bicyclic rings consisting of two fused partially saturated, fully saturated or fully unsaturated five and/or six membered rings, taken independently, optionally having one to four heteroatoms selected independently from nitrogen, sulfur and oxygen are indolizinyl, indolyl, isoindolyl, indolinyl, cyclopenta(b)pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)-pyridinyl, pyrido(3,2-b)-pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

By alkylene is meant saturated hydrocarbon (straight chain or branched) wherein a hydrogen atom is removed from each of the terminal carbons. Exemplary of such groups (assuming the designated length encompasses the particular example) are methylene, ethylene, propylene, butylene, pentylene, hexylene, heptylene). Of course, such linking moieties may also be referred to as the substituent without the "ene" suffix (e.g., methyl) as is commonly done by those skilled in the art, and still refer to a linking group.

By halo is meant chloro, bromo, iodo, or fluoro.

By alkyl is meant straight chain saturated hydrocarbon or branched saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, neopentyl, tertiary pentyl, 1-methylbutyl, 2-methylbutyl, 3-methylbutyl, hexyl, isohexyl, heptyl and octyl.

By alkoxy is meant straight chain saturated alkyl or branched saturated alkyl bonded through an oxygen. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy and octoxy.

As used herein the term mono-N- or di-N,N-$(C_1-C_x)$alkyl . . . refers to the $(C_1-C_x)$alkyl moiety taken independently when it is di-N,N-$(C_1-C_x)$alkyl . . . (x refers to integers).

It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3-, or 4-pyridyl, the term "thienyl" means 2-, or 3-thienyl, and so forth.

The expression "pharmaceutically-acceptable salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluenesulfonate. Where more than one basic moiety exists the expression includes multiple salts (e.g., di-salt). The expression also refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methylglucamine), benethamine (N-benzylphenethylamine), piperazine or tromethamine (2-amino-2-hydroxymethyl-1,3-propanediol).

As used herein, the expressions "reaction-inert solvent" and "inert solvent" refers to a solvent or mixture of solvents which does not interact with starting materials, reagents, intermediates or products in a manner which adversely affects the yield of the desired product.

The chemist of ordinary skill will recognize that certain compounds of this invention will contain one or more atoms which may be in a particular stereochemical or geometric configuration, giving rise to stereoisomers and configurational isomers. All such isomers and mixtures thereof are included in this invention. Hydrates of the compounds of this invention are also included.

DMF means N,N-dimethylformamide. DMSO means dimethyl sulfoxide. THF means tetrahydrofuran.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples below, by substituting a readily available isotopically labelled reagent for a non-isotopically labelled reagent.

Other features and advantages will be apparent from this description and claims which describe the invention.

DETAILED DESCRIPTION OF THE INVENTION

In general the compounds of this invention can be made by processes which include processes analogous to those known in the chemical arts, particularly in light of the description contained herein. Certain processes for the manufacture of the compounds of this invention are provided as further features of the invention and are illustrated by the following reaction schemes. Other processes are described in the experimental section.

SCHEME I
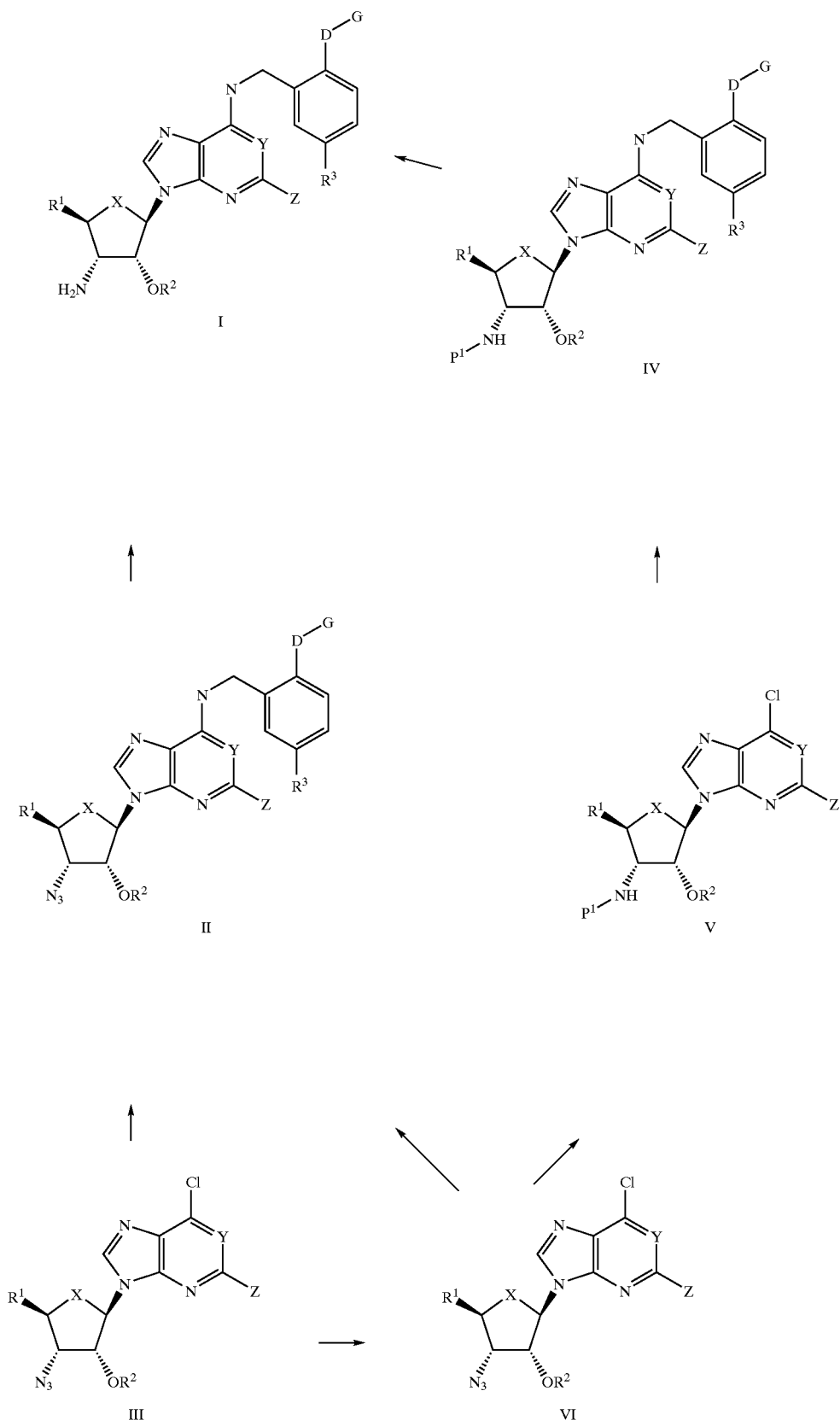

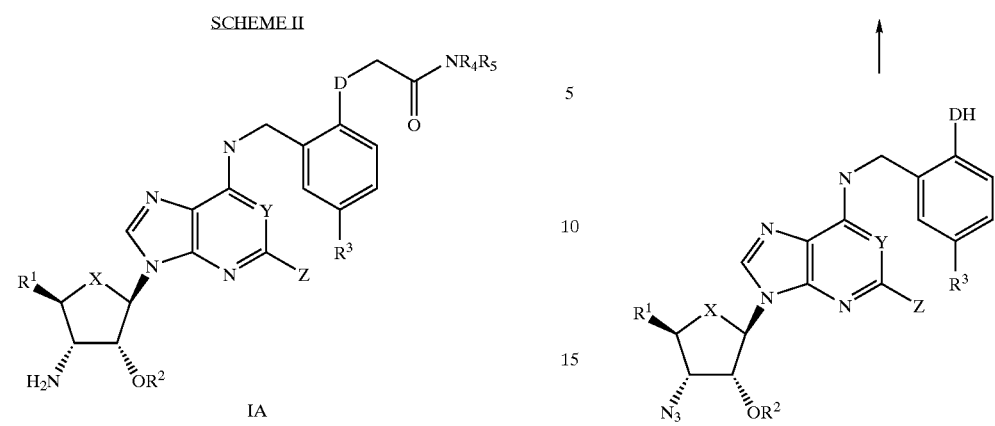
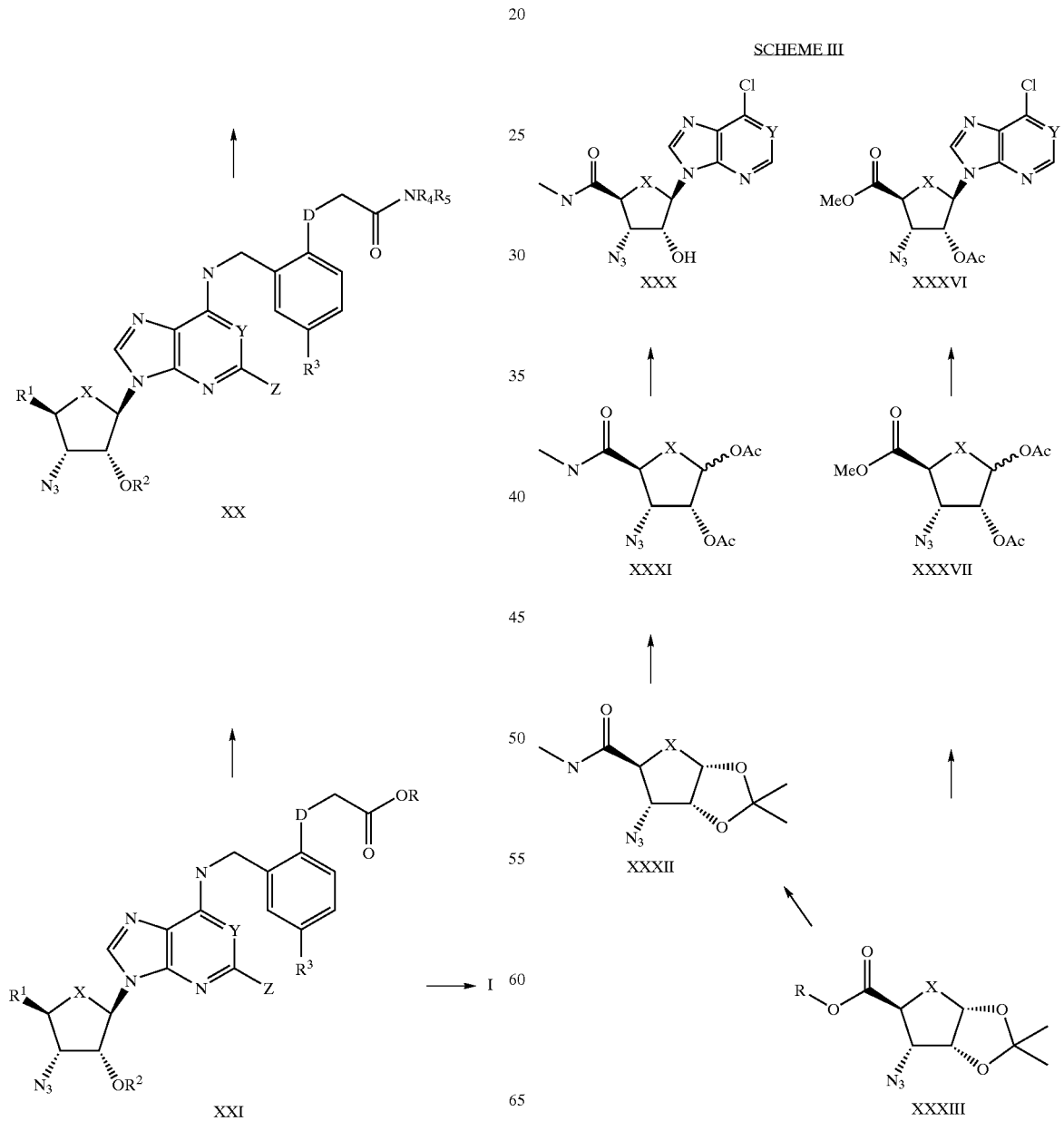

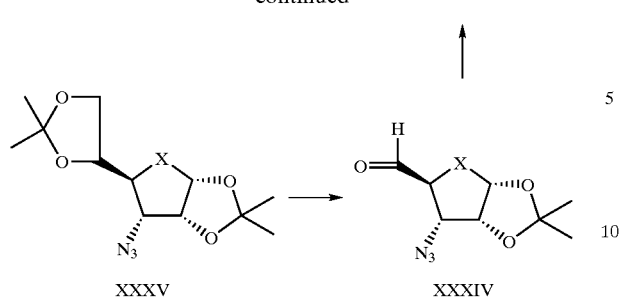

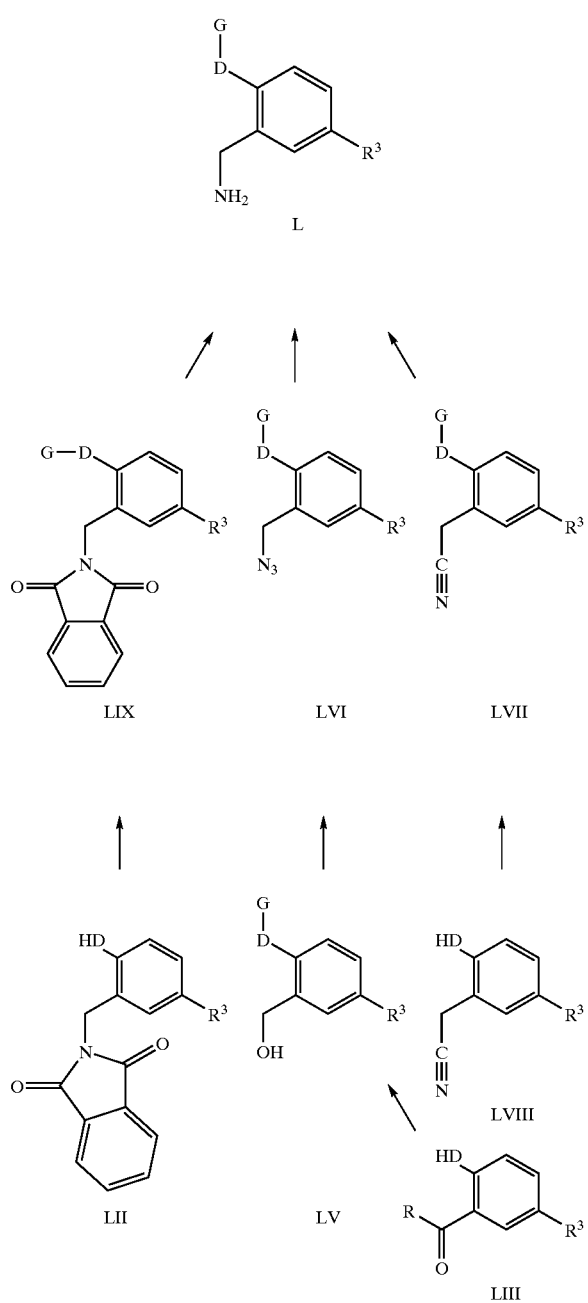

In general, the compounds of this invention can be made by coupling the desired chloropurine riboside and benzyl amine followed by azide reduction. The following text which is keyed to the above SCHEMES, provides a more detailed description.

According to reaction SCHEME I, the desired Formula I compounds wherein $R^1$, $R^2$, $R^3$, X, Y, Z, D and G are as defined above may be prepared by reduction of the azide in the corresponding Formula II compound. Typically the reduction is accomplished by combining the Formula II compound with a trialkyl or triaryl phosphine, preferably triphenyl phosphine, in a reaction inert solvent such as tetrahydrofuran, at temperatures of about 0° C. to about 65° C., typically at ambient temperature, for about thirty minutes to about two hours. The reaction is then treated with a base, preferably an amine base, most preferably ammonium hydroxide for about six hours to about forty-eight hours at a temperature of about 0° C. to about 65° C., preferably at ambient temperature.

The desired Formula II compound wherein $R^2$, $R^3$, X, Y, Z, D and G are as defined above and $R^1$ is an ester may be prepared from the appropriate Formula III compound and benzyl amine derivative (wherein $R^3$, D and G are as defined above). Typically, the condensation reaction is run in a polar solvent, such as ethanol, in the presence of a base, preferably an amine base, most preferably triethylamine at elevated temperatures of about 40° C. to about 75° C. for about two hours to about twenty-four hours.

Analogously, the desired Formula II compound wherein $R^2$, $R^3$, X, Y, Z, D and G are as defined above and $R^1$ is an amide may be prepared from the appropriate Formula VI compound and benzyl amine derivative (wherein $R^3$, D and G are as defined above). Typically, the condensation reaction is run in a polar solvent, such as ethanol, in the presence of a base, preferably an amine base, most preferably triethylamine at elevated temperatures of about 40° C. to about 75° C. for about two hours to about twenty-four hours.

The Formula VI amide may be prepared from the corresponding Formula III ester by amine addition. Typically, the appropriate amine is added to the Formula III ester at a temperature of about 15° C. to about 50° C. for about one hour to about twenty-four hours in a polar solvent such as methanol.

Some of the methods useful for the preparation of the compounds described herein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis*, John Wiley & Sons, New York, 1991.

Thus, for example, in an alternative reaction sequence the desired Formula I compound wherein $R^1$, $R^2$, $R^3$, X, Y, Z, D and G are as defined above may be prepared from the corresponding Formula VI compound by protection and amine addition followed by deprotection. Thus, the Formula VI compound wherein $R^1$, $R^2$, X, Y and Z are as defined above undergoes azide reduction. Typically the reduction is accomplished by combining the Formula VI compound with a trialkyl or triaryl phosphine, preferably triphenyl phosphine, in a reaction inert solvent such as tetrahydrofuran, at temperatures of about 0° C. to about 65° C., typically at ambient temperature, for about thirty minutes to about two hours. The reaction is then treated with a base, preferably an amine base, most preferably ammonium hydroxide for about six hours to about forty-eight hours at a temperature of about 0° C. to about 65° C. Following reduction, the amine moiety is protected ($P^1$).

Preferably the amine is protected with a tert-butoxycarbonyl group. The protection is accomplished by treating the amine with tert-butoxycarbonyl anhydride and a base, preferably an amine base, most preferably triethylamine, in an anhydrous solvent such as dichloromethane, at ambient temperature for about five hours to about twenty-four hours.

The desired Formula IV compound wherein $R^1$, $R^2$, $R^3$, X, Y, Z, D and G are as defined above are prepared from the appropriate Formula V compound and benzyl amine derivative (wherein $R^3$, D and G are as defined above). Typically, the condensation reaction is run in a polar solvent, such as ethanol, in the presence of a base, preferably an amine base, most preferably triethylamine at elevated temperatures of about 40° C. to about 75° C. for about two hours to about twenty-four hours.

Following amine addition the desired Formula I compound may be prepared from the corresponding protected Formula IV compound by an appropriate catalyzed deprotection reaction. Typically, the protected (e.g., tertiary butyl ester protected) compound is treated with a strong acid, preferably trifluoroacetic acid at 10° C. to 50° C., preferably at ambient temperature, for about one hour to about eight hours to remove the protecting moiety.

According to reaction SCHEME II the desired Formula IA compounds wherein $R^1$, $R^2$, $R^3$, X, Y, Z, $R^4$ and $R^5$ are as defined above and D is oxy, thio or NH may be prepared by reduction of the azide in the corresponding Formula XX compound. Typically, the reduction is accomplished by combining the Formula XX compound with a trialkyl or triaryl phosphine, preferably triphenyl phosphine, in a reaction inert solvent such as tetrahydrofuran, at temperatures of about 0° C. to about 65° C., typically at ambient temperature, for about thirty minutes to about two hours. The reaction is then treated with a base, preferably an amine base, most preferably ammonium hydroxide for about six hours to about forty-eight hours at a temperature of about 0° C. to about 65° C.

The Formula XXI ester (following conversion to the acid) is coupled with the appropriate amine in the presence of a suitable coupling agent to prepare the desired Formula XX compound. A suitable coupling agent is one which transforms a carboxylic acid into a reactive species which forms an amide linkage on reaction with an amine.

The coupling agent may be a reagent which effects this condensation in a one pot process when mixed together with the carboxylic acid and amine. Exemplary coupling reagents are 1-(3-dimethylaminopropyl)-3-ethylcarbodiimide hydrochloride-hydroxybenzotriazole (EDC/HOBT), dicyclohexylcarbodiimide/hydroxybenzotriazole(HOBT), 2-ethoxy-1-ethoxycarbonyl-1,2-dihydroquinoline (EEDQ), and diethylphosphorylcyanide. The coupling is performed in an inert solvent, preferably an aprotic solvent at a temperature of about −20° C. to about 50° C. for about one to about forty-eight hours, in the presence of excess amine as base. Exemplary solvents include acetonitrile, dichloromethane, dimethylformamide and chloroform or mixtures thereof.

The coupling agent may also be that agent which converts the carboxylic acid to an activated intermediate which is isolated and/or formed in a first step and allowed to react with the amine in a second step. Examples of such coupling agents and activated intermediates are thionyl chloride or oxalyl chloride to form the acid chloride, cyanuric fluoride to form an acid fluoride or an alkyl chloroformate such as isobutyl or isopropenyl chloroformate or propanephosphonic anhydride (propanephosphonic acid anhydride, PPA) (with a tertiary amine base) to form a mixed anhydride of the carboxylic acid, or carbonyldiimidazole to form an acylimidazole. If the coupling agent is oxalyl chloride, it is advantageous to employ a small amount of dimethylformamide as cosolvent with another solvent (such as dichloromethane) to catalyze the formation of the acid chloride. This activated acid derivative may be coupled by mixing with excess amine in an appropriate solvent together with an appropriate base. Appropriate solvent/base combinations are, for example, dichloromethane, dimethylformamide or acetonitrile or mixtures thereof in the presence of excess amine as base. Other appropriate solvent/base combinations include water or a ($C_1$–$C_5$)alcohol or a mixture thereof together with a cosolvent such as dichloromethane, tetrahydrofuran or dioxane and a base such as sodium, potassium or lithium hydroxide in sufficient quantity to consume the acid liberated in the reaction. Use of these coupling agents and appropriate selection of solvents and temperatures are known to those skilled in the art or can be readily determined from the literature. These and other exemplary conditions useful for coupling carboxylic acids are described in Houben-Weyl, Vol XV, part II, E. Wunsch, Ed., G. Theime Verlag, 1974, Stuttgart; M. Bodansky, Principles of Peptide Synthesis, Springer-Verlag, Berlin 1984; and *The Peptides, Analysis, Synthesis and Biology* (ed. E. Gross and J. Meienhofer), vols 1–5 (Academic Press, NY 1979–1983).

The Formula XXI compound may be converted to the corresponding acid by an acid catalyzed deprotection. Typically the protected (e.g., tertiary butyl ester protected) compound is treated with a strong acid, preferably trifluoroacetic acid at 10° C. to 50° C., preferably at ambient temperature for about one hour to about eight hours to form the corresponding acid.

The desired Formula XXI compound wherein $R^1$, $R^2$, $R^3$, X, Y, Z, D and R is a convenient ester moiety (alkyl) may be prepared from the appropriate Formula XXII compounds wherein $R^1$, $R^2$, $R^3$, X, Y, Z and D are as described above (typically DH represents D as oxy, thio or NH, i.e., prior to alkylation) by an alkylation reaction. Generally, the Formula XXII compound is combined with an alkylbromoacetate in the presence of a strong base such as sodium hydride in a polar aprotic solvent such as DMF at a temperature of about 0° C. to about 30° C. for a period of about one to about twenty-four hours.

The Formula XXII compound wherein $R^1$, $R^2$, $R^3$, X, Y, Z, D are as described above may be prepared from the appropriate Formula III compound and the appropriate benzyl amine derivative. Typically, the condensation reaction is performed in a polar solvent, such as ethanol, in the presence of a base, preferably an amine base, most preferably triethylamine at elevated temperatures of about 40° C. to about 75° C. for about two hours to about twenty-four hours.

According to SCHEME III the Formula XXX compounds wherein X and Y are as defined above are prepared from a glycosidation reaction between the appropriate Formula XXXI compound and a silylated 6-chloro purine. Typically, the reaction is catalyzed by a Lewis acid, preferably trimethylsilyltriflate, in a reaction inert solvent, such as dichloroethane or acetonitrile, at temperatures from about 30° C. to about 75° C., typically at 60° C. for about thirty minutes to about six hours.

The desired Formula XXXI compounds wherein X is defined above may be prepared by an acid catalyzed hydrolysis of the appropriate Formula XXXII compound. Typically the acid is a strong mineral acid, preferably sulfuric acid, in a protic solvent mixture of acetic acid and acetic anhydride at a temperature of about 5° C. to about 40° C. for about two hours to about twenty-four hours.

Analogously, the desired Formula XXXVI compounds wherein Y and X are as described above may be prepared from the appropriate Formula XXXIII compound using the glycosidation and hydrolysis reactions described above.

The desired Formula XXXII compound wherein X is defined above is prepared from the appropriate Formula XXXIII compound by activation of the carboxylic acid followed by reaction with an amine. Typically, the Formula XXXIII compound may be activated by conversion to an acid chloride by, for example, treatment with oxalyl chloride in a non-polar aprotic solvent, preferably dichloromethane with a catalytic amount of dimethyl formamide, at a temperature of about 0° C. with warming to ambient temperature for about two hours to about eight hours. The acid chloride is then treated with excess of the appropriate amine at a temperature of 0° C. to about 30° C.

The desired Formula XXXIII compound wherein X is defined above is prepared by oxidation of the appropriate Formula XXXIV compound. Generally the oxidant is ruthenium tetroxide, prepared using a catalytic amount of ruthenium trichloride and a stoichiometric amount of sodium periodate in a solvent mixture of chloroform, acetonitrile and water. The reaction is conveniently performed at ambient temperature for about four hours to about twenty-four hours.

The desired Formula XXXIV compound wherein X is defined above is prepared from the appropriate Formula XXXV compound by treatment with periodic acid which hydrolyzes the isopropylidene group and cleaves the glycol to furnish the aldehyde. The reaction is run in ethereal solvents, typically diethyl ether conveniently at ambient temperature for about two hours to about twenty-four hours.

The desired Formula XXXV compound is prepared from the corresponding hydroxyl compound by activation of the hydroxyl group and displacement with azide ion. Typically, activation is achieved by converting the hydroxyl group to the corresponding triflate derivative by reaction with triflic anhydride in the presence of an amine base, preferably pyridine at about –30° C. to about 0° C. for about thirty minutes to about two hours. The resulting triflate is treated with an alkali metal azide, preferably sodium azide, in a polar aprotic solvent, preferably dimethylformamide at about ambient temperature to about 50° C. for about six hours to about twenty-four hours.

SCHEME IV provides preparation methods for the benzylamine intermediates of this invention.

Thus, the Formula L benzyl amines wherein D, G and $R^3$ are as described above (typically DH represents D as oxy, thio or NH, i.e., prior to alkylation) are prepared for example by one of three methods. In the first method, the Formula LII imide is prepared from the corresponding Formula LI aromatic compound through an imidoalkylation reaction. Thus, the appropriate Formula LI compound is treated with N-chloromethylphthalimide and an acid or Lewis acid catalyst, such as zinc chloride in an aprotic reaction inert solvent such as THF at a temperature of ambient temperature to about 100° C., preferably about 50° C.

The resulting Formula LII compound is alkylated to prepare the corresponding Formula L compound by combination with the appropriate alkylation agent in a polar aprotic solvent such as DMF at a temperature of about 0° C. to about 50° C. for a period of about two to about twenty-four hours. Alternatively the alkylation can be accomplished under Mitsunobu conditions using an appropriate alcohol, triphenylphosphine, diethylazadicarboxylate in an ether solvent, preferably THF at ambient temperature for about four hours to about twenty-four hours.

The resulting Formula LIX phthalimide is deprotected by treatment with hydrazine hydrate in a protic solvent such as ethanol at a temperature of ambient temperature to about 100° C., preferably about 50° C. for about one to about six hours. Alternatively, the deprotection can be accomplished by first reducing the imide with a hydride reducing agent, preferably sodium borohydride, followed by heating with acetic acid at about 50° C. to about 100° C. for about ten to about twenty-four hours.

Alternatively, the Formula L benzyl amine can be prepared from a reaction sequence as follows. The Formula LV compounds are prepared from the corresponding Formula LIII compounds through a two step procedure of alkylation followed by metal hydride reduction. The Formula LV compounds can also be prepared from the corresponding Formula LIV compounds by treatment with a boronic acid, preferably phenylboronic acid, and formaldehye and an acid catalyst such as propionic acid in an aprotic solvent such as benzene at a temperature of about 30° C. to about 100° C. for about one to about twenty-four hours.

The Formula LVI compound wherein D, G and $R^3$ can be prepared from the corresponding Formula LV compound. Generally, the LV benzyl alcohol is treated with diphenylphosphoryl azide and a base, preferably a strong amine base such as diazobicycloundecane (DBU), in an aprotic solvent, preferably toluene, at temperatures from about 0° C. to about 50° C., most preferably at ambient temperature for about one to about twenty-four hours.

The resulting azide may be reduced to prepare the Formula L compound. In general, the reduction is accomplished by treating the appropriate Formula LVI azide with a hydrogenation catalyst, preferably a palladium catalyst, most preferably 10% Pd on carbon, in a reaction inert solvent such as an alcohol solvent, preferably ethanol. The reaction vessel is placed under an atmosphere of hydrogen gas, preferably at 15 to 50 psi conveniently at ambient temperature for about thirty minutes to about four hours. The azide reduction can also be accomplished by combining the azide with a trialkyl or triaryl phosphine, preferably triphenyl phosphine, in a reaction inert solvent such as tetrahydrofuran, at a temperature of about 0° C. to about 65° C., typically at ambient temperature, for about one-half hour to about two hours. The reaction is then treated with a base, preferably an amine base, most preferably ammonium hydroxide for about six hours to about forty-eight hours.

A third method for the synthesis of Formula L compounds is from the Formula LVII nitriles by either catalytic hydrogenation or metal hydride reduction. In general, the catalytic hydrogenation is accomplished by treating the appropriate formula LVII compound with a hydrogenation catalyst, preferably Raney nickel, in a reaction inert solvent such as an alcohol solvent, preferably ethanol containing about 1% aqueous ammonium hydroxide solution. The reaction vessel is placed under an atmosphere of hydrogen gas, preferably at 15 to 50 psi conveniently at ambient temperature for about 30 minutes to about four hours. Alternatively the reduction can be performed using a metal hydride reducing agent, preferably lithium aluminum hydride in an ethereal solvent, preferably tetrahydrofuran, at a temperature of about 0° C. to about 60° C., preferably at ambient temperature for about one to about six hours. The Formula LVII compounds are prepared by alkylation of the corresponding Formula LVIIII compounds by methods known to those skilled in the art, and as described for Formula LIX compounds.

The starting materials and reagents for the above described compounds are readily available or can be easily synthesized by those skilled in the art using conventional methods of organic synthesis. For example, many of the compounds used herein are related to, or are derived from compounds found in nature, in which there is a large scientific interest and commercial need, and accordingly many such compounds are commercially available or are reported in the literature or are easily prepared from other commonly available substances by methods which are reported in the literature.

Some of the compounds of this invention have asymmetric carbon atoms and can therefore exist as enantiomers or diastereomers. Diasteromeric mixtures can be separated into their individual diastereomers on the basis of their physical chemical differences by methods known per se., for example, by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers and mixtures thereof are considered as part of this invention. Also, some of the compounds of this invention are atropisomers (e.g., substituted biaryls) and are considered as part of this invention.

Those skilled in the art will recognize that the compounds of Formula I can exist in several tautomeric forms. All such tautomeric forms are considered as part of this invention. Also, for example all enol-keto forms of the compounds of Formula I are included in this invention.

Some of the compounds of this invention are acidic and they form a salt with a pharmaceutically acceptable cation. All of the compounds of this invention are basic and they form a salt with a pharmaceutically acceptable anion. All such salts, including di-salts are within the scope of this invention and they can be prepared by conventional methods. For example, they can be prepared simply by contacting the acidic and basic entities, in either an aqueous, non-aqueous or partially aqueous medium. The salts are recovered either by filtration, by precipitation with a non-solvent followed by filtration, by evaporation of the solvent, or, in the case of aqueous solutions, by lyophilization, as appropriate.

In addition, when the compounds of this invention form metabolites, hydrates or solvates they are also within the scope of the invention.

Other cardiovascular agents (e.g., agents having a cardiovascular effect) known to those skilled in the art such as those described above in the Summary may be used in conjunction with the compounds of this invention.

In combination therapy treatment, both the compounds of this invention and the other drug therapies are administered to mammals (e.g., humans, male or female) by conventional methods.

Any NHE-1 inhibitor may be used as the second compound (active agent) of this invention for combination therapies. The term NHE-1 inhibitor refers to compounds which inhibit the sodium/proton (Na+/H+) exchange transport system and hence are useful as a therapeutic or prophylactic agent for diseases caused or aggravated by the acceleration of the sodium/proton (Na+/H+) exchange transport system. Such inhibition is readily determined by those skilled in the art according to standard assays such as are described herein below and in conventional preclinical cardioprotection assays [see the in vivo assay in Klein, H. et al., Circulation 92:912–917 (1995); the isolated heart assay in Scholz, W. et al., Cardiovascular Research 29:260–268 (1995); the antiarrhythmic assay in Yasutake M. et al., Am. J. Physiol., 36:H2430–H2440 (1994); the NMR assay in Kolke et al., J. Thorac. Cardiovasc. Surg. 112: 765–775 (1996)]. A variety of NHE-1 inhibitors are described and referenced below, however, other NHE-1 inhibitors will be known to those skilled in the art such as are disclosed in WO99/43663 published Sep. 2, 1999. Accordingly, examples of NHE-1 inhibitors useful in the compositions and methods of this invention include, [1-(8-bromoquinolin-5-yl)-5-cyclopropyl-1H-pyrazole-4-carbonyl]guanidine;
[1-(6-chloroquinolin-5-yl)-5-cyclopropyl-1H-pyrazole-4-carbonyl]guanidine;
[1-(indazol-7-yl)-5-cyclopropyl-1H-pyrazole-4-carbonyl]guanidine;
[1-(benzimidazol-5-yl)-5-cyclopropyl-1H-pyrazole-4-carbonyl]guanidine;
[1-(1-isoquinolyl)-5-cyclopropyl-1H-pyrazole-4-carbonyl]guanidine;
[5-cyclopropyl-1-(4-quinolinyl)-1H-pyrazole-4-carbonyl]guanidine;
[5-cyclopropyl-1-(quinolin-5-yl)-1H-pyrazole-4-carbonyl]guanidine;
[5-cyclopropyl-1-(quinolin-8-yl)-1H-pyrazole-4-carbonyl]guanidine;
[1-(indazol-6-yl)-5-ethyl-1H-pyrazole-4-carbonyl]guanidine;
[1-(indazol-5-yl)-5-ethyl-1H-pyrazole-4-carbonyl]guanidine;
[1-(benzimidazol-5-yl)-5-ethyl-1H-pyrazole-4-carbonyl]guanidine;
[1-(1-methylbenzimidazol-6-yl)-5-ethyl-1H-pyrazole-4-carbonyl]guanidine;
1-(5-quinolinyl)-5-n-propyl-1H-pyrazole-4-carbonyl]guanidine;
[1-(5-quinolinyl)-5-isopropyl-1H-pyrazole-4-carbonyl]guanidine;
[1ethyl-1-(6-quinolinyl)-1H-pyrazole-4-carbonyl]guanidine;
[1-(2-methylbenzimidazol-5-yl)-5-ethyl-1H-pyrazole-4-carbonyl]guanidine;
[1-(1,4-benzodioxan-6-yl)-5-ethyl-1H-pyrazole-4-carbonyl]guanidine;
[1-(benzotriazol-5-yl)-5-ethyl-1H-pyrazole-4-carbonyl]guanidine;

[1-(3-chloroindazol-5-yl)-5-ethyl-1H-pyrazole-4-carbonyl] guanidine;
[1-(5-quinolinyl)-5-butyl-1H-pyrazole-4-carbonyl] guanidine;
[5-propyl-1-(6-quinolinyl)-1H-pyrazole-4-carbonyl] guanidine;
[5-isopropyl-1-(6-quinolinyl)-1H-pyrazole-4-carbonyl] guanidine;
[1-(2-chloro-4-methylsulfonylphenyl)-5-cyclopropyl-1H-pyrazole-4-carbonyl]guanidine;
[1-(2-chlorophenyl)-5-cyclopropyl-1H-pyrazole-4-carbonyl]guanidine;
[1-(2-trifluoromethyl-4-fluorophenyl)-5-cyclopropyl-1H-pyrazole-4-carbonyl]guanidine;
[1-(2-bromophenyl)-5-cyclopropyl-1H-pyrazole-4-carbonyl]guanidine;
[1-(2-fluorophenyl)-5-cyclopropyl-1H-pyrazole-4-carbonyl]guanidine;
[1-(2-chloro-5-methoxyphenyl)-5-cyclopropyl-1H-pyrazole-4-carbonyl]guanidine;
[1-(2-chloro-4-methylaminosulfonylphenyl)-5-cyclopropyl-1H-pyrazole-4-carbonyl]guanidine;
[1-(2,5-dichlorophenyl)-5-cyclopropyl-1H-pyrazole-4-carbonyl]guanidine;
[1-(2,3-dichlorophenyl)-5-cyclopropyl-1H-pyrazole-4-carbonyl]guanidine;
[1-(2-chloro-5-aminocarbonylphenyl)-5-cyclopropyl-1H-pyrazole-4-carbonyl]guanidine;
[1-(2-chloro-5-aminosulfonylphenyl)-5-cyclopropyl-1H-pyrazole-4-carbonyl]guanidine;
[1-(2-fluoro-6-trifluoromethylphenyl)-5-cyclopropyl-1H-pyrazole-4-carbonyl]guanidine;
[1-(2-chloro-5-methylsulfonylphenyl)-5-cyclopropyl-1H-pyrazole-4-carbonyl]guanidine;
[1-(2-chloro-5-dimethylaminosulfonylphenyl)-5-cyclopropyl-1H-pyrazole-4-carbonyl]guanidine;
[1-(2-trifluoromethyl-4-chlorophenyl)-5-cyclopropyl-1H-pyrazole-4-carbonyl]guanidine;
[1-(2-chlorophenyl)-5-methyl-1H-pyrazole-4-carbonyl] guanidine;
[5-methyl-1-(2-trifluoromethylphenyl)-1H-pyrazole-4-carbonyl]guanidine;
[5-ethyl-1-phenyl-1H-pyrazole-4-carbonyl]guanidine;
[5-cyclopropyl-1-(2-trifluoromethylphenyl)-1H-pyrazole-4-carbonyl]guanidine;
[5-cyclopropyl-1-phenyl-1H-pyrazole-4-carbonyl] guanidine;
[5-cyclopropyl-1-(2,6-dichlorophenyl)-1H-pyrazole-4-carbonyl]guanidine; and
pharmaceutically acceptable salts thereof.

Any aldose reductase inhibitor may be used as the second compound (active agent) of this invention for combination therapies. The term aldose reductase inhibitor refers to compounds which inhibit the bioconversion of glucose to sorbitol catalyzed by the enzyme aldose reductase. Such inhibition is readily determined by those skilled in the art according to standard assays (J. Malone, *Diabetes*, 29:861–864, 1980. "Red Cell Sorbitol, an Indicator of Diabetic Control"). A variety of aldose reductase inhibitors are described and referenced below, however, other aldose reductase inhibitors will be known to those skilled in the art. The disclosures of U.S. patents listed below are hereby incorporated by reference. Also, common chemical USAN names or other designation are in parentheses where applicable, together with reference to appropriate patent literature disclosing the compound.

The activity of an aldose reductase inhibitor in a tissue can be determined by testing the amount of aldose reductase inhibitor that is required to lower tissue sorbitol (i.e., by inhibiting the further production of sorbitol consequent to blocking aldose reductase) or lower tissue fructose (by inhibiting the production of sorbitol consequent to blocking aldose reductase and consequently the production of fructose). While not wishing to be bound by any particular theory or mechanism, it is believed that an aldose reductase inhibitor, by inhibiting aldose reductase, prevents or reduces ischemic or hypoxic damage as described hereinafter.

Accordingly, examples of aldose reductase inhibitors useful in the compositions and methods of this invention include:

1. 3-(4-bromo-2-fluorobenzyl)-3,4-dihydro-4-oxo-1-phthalazineacetic acid (ponalrestat, U.S. Pat. No. 4,251,528);
2. N[[(5-trifluoromethyl)-6-methoxy-1-naphthalenyl] thioxomethyl}-N-methylglycine (tolrestat, U.S. Pat. No. 4,600,724);
3. 5-[(Z,E)-β-methylcinnamylidene]-4-oxo-2-thioxo-3-thiazolideneacetic acid (epalrestat, U.S. Pat. No. 4,464,382, U.S. Pat. No. 4,791,126, U.S. Pat. No. 4,831,045);
4. 3-(4-bromo-2-fluorobenzyl)-7-chloro-3,4-dihydro-2,4-dioxo-1(2H)-quinazolineacetic acid (zenarestat, U.S. Pat. Nos. 4,734,419, and 4,883,800);
5. 2R,4R-6,7-dichloro-4-hydroxy-2-methylchroman-4-acetic acid (U.S. Pat. No. 4,883,410);
6. 2R,4R-6,7-dichloro-6-fluoro-4-hydroxy-2-methylchroman-4-acetic acid (U.S. Pat. No. 4,883,410);
7. 3,4-dihydro-2,8-diisopropyl-3-oxo-2H-1,4-benzoxazine-4-acetic acid (U.S. Pat. No. 4,771,050);
8. 3,4-dihydro-3-oxo-4-[(4,5,7-trifluoro-2-benzothiazolyl) methyl]-2H-1,4-benzothiazine-2-acetic acid (SPR-210, U.S. Pat. No. 5,252,572);
9. N-[3,5-dimethyl-4-[(nitromethyl)sulfonyl]phenyl]-2-methyl-benzeneacetamide (ZD5522, U.S. Pat. No. 5,270,342 and U.S. Pat. No. 5,430,060);
10. (S)-6-fluorospiro[chroman-4,4'-imidazolidine]-2,5'-dione (sorbinil, U.S. Pat. No. 4,130,714);
11. d-2-methyl-6-fluoro-spiro(chroman-4',4'-imidazolidine)-2',5'-dione (U.S. Pat. No. 4,540,704);
12. 2-fluoro-spiro(9H-fluorene-9,4'imidazolidine)2',5'-dione (U.S. Pat. No. 4,438,272);
13. 2,7-di-fluoro-spiro(9H-fluorene-9,4'imidazolidine)2',5'-dione (U.S. Pat. No. 4,436,745, U.S. Pat. No. 4,438,272);
14. 2,7-di-fluoro-5-methoxy-spiro(9H-fluorene-9,4'imidazolidine)2',5'-dione (U.S. Pat. No. 4,436,745, U.S. Pat. No. 4,438,272);
15. 7-fluoro-spiro(5H-indenol[1,2-b]pyridine-5,3'-pyrrolidine)2,5'-dione (U.S. Pat. No. 4,436,745, U.S. Pat. No. 4,438,272);
16. d-cis-6'-chloro-2',3'-dihydro-2'-methyl-spiro-(imidazolidine-4,4'-4'-H-pyrano(2,3-b)pyridine)-2,5-dione (U.S. Pat. No. 4,980,357);
17. spiro[imidazolidine-4,5'(6H)-quinoline]2,5-dione-3'-chloro-7',8'-dihydro-7'-methyl-(5'-cis) (U.S. Pat. No. 5,066,659);
18. (2S,4S)-6-fluoro-2',5'-dioxospiro(chroman-4,4'-imidazolidine)-2-carboxamide (U.S. Pat. No. 5,447,946); and
19. 2-[(4-bromo-2-fluorophenyl)methyl]-6-fluorospiro [isoquinoline-4(1H),3'-pyrrolidine]-1,2',3,5'(2H)-tetrone (ARI-509, U.S. Pat. No. 5,037,831).

Other aldose reductase inhibitors include compounds having formula IB

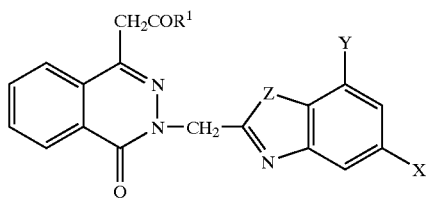

and pharmaceutically acceptable salts thereof, wherein
Z is O or S;
R¹ is hydroxy or a group capable of being removed in vivo to produce a compound of formula IB wherein R¹ is OH; and
X and Y are the same or different and are selected from hydrogen, trifluoromethyl, fluoro, and chloro.

A preferred subgroup within the above group of aldose reductase inhibitors includes numbered compounds 1, 2, 3, 4, 5, 6, 9, 10, and 17, and the following compounds of Formula IB:

20. 3,4-dihydro-3-(5-fluorobenzothiazol-2-ylmethyl)-4-oxophthalazin-1-yl-acetic acid [R¹=hydroxy; X=F; Y=H];
21. 3-(5,7-difluorobenzothiazol-2-ylmethyl)-3,4-dihydro-4-oxophthalazin-1-ylacetic acid [R¹=hydroxy; X=Y=F];
22. 3-(5-chlorobenzothiazol-2-ylmethyl)-3,4-dihydro-4-oxophthalazin-1-ylacetic acid [R¹=hydroxy; X=Cl; Y=H];
23. 3-(5,7-dichlorobenzothiazol-2-ylmethyl)-3,4-dihydro-4-oxophthalazin-1-ylacetic acid [R¹=hydroxy; X=Y=Cl];
24. 3,4-dihydro-4-oxo-3-(5-trifluoromethylbenzoxazol-2-ylmethyl)phthalazin-1-ylacetic acid [R¹=hydroxy; X=CF₃; Y=H];
25. 3,4-dihydro-3-(5-fluorobenzoxazol-2-ylmethyl)-4-oxophthalazin-1-yl-acetic acid [R¹=hydroxy; X=F; Y=H];
26. 3-(5,7-difluorobenzoxazol-2-ylmethyl)-3,4-dihydro-4-oxophthalazin-1-ylacetic acid [R¹=hydroxy; X=Y=F];
27. 3-(5-chlorobenzoxazol-2-ylmethyl)-3,4-dihydro-4-oxophthalazin-1-ylacetic acid [R¹=hydroxy; X=Cl; Y=H];
28. 3-(5,7-dichlorobenzoxazol-2-ylmethyl)-3,4-dihydro-4-oxophthalazin-1-ylacetic acid [R¹=hydroxy; X=Y=Cl]; and
29. zopolrestat; 1-phthalazineacetic acid, 3,4-dihydro-4-oxo-3-[[5-(trifluoromethyl)-2-benzothiazolyl]methyl]- [R¹=hydroxy; X=trifluoromethyl; Y=H].

In compounds 20–23, and 29 Z is S. In compounds 24–28, Z is O.

Of the above subgroup, compounds 20–29 are more preferred with 29 especially preferred.

An especially preferred aldose reductase inhibitor is 1-phthalazineacetic acid, 3,4-dihydro-4-oxo-3-[[5-trifluoromethyl)-2-benzothiazolyl]methyl]-.

The aldose reductase inhibitor compounds of this invention are readily available or can be easily synthesized by those skilled in the art using conventional methods of organic synthesis, particularly in view of the pertinent patent specification descriptions.

An amount of the aldose reductase inhibitor of this invention that is effective for the activities of this invention may be used. Typically, an effective dosage for the aldose reductase inhibitors for the combination compositions, methods and kits of this invention is in the range of about 0.1 mg/kg/day to 100 mg/kg/day in single or divided doses, preferably 0.1 mg/kg/day to 20 mg/kg/day in single or divided doses.

Any glycogen phosphorylase inhibitor may be used as the second compound of this invention. The term glycogen phosphorylase inhibitor refers to any substance or agent or any combination of substances and/or agents which reduces, retards, or eliminates the enzymatic action of glycogen phosphorylase. The currently known enzymatic action of glycogen phosphorylase is the degradation of glycogen by catalysis of the reversible reaction of a glycogen macromolecule and inorganic phosphate to glucose-1-phosphate and a glycogen macromolecule which is one glucosyl residue shorter than the original glycogen macromolecule (forward direction of glycogenolysis). Such actions are readily determined by those skilled in the art according to standard assays (e.g., as described hereinafter). A variety of these compounds are included in the following-published international patent applications: PCT application publication WO 96/39384 and WO96/39385. However, other glycogen phosphorylase inhibitors useful in the combinations, methods, and kits of this invention will be known to those skilled in the art.

Preferred glycogen phosphorylase inhibitors include compounds having the Formula IC

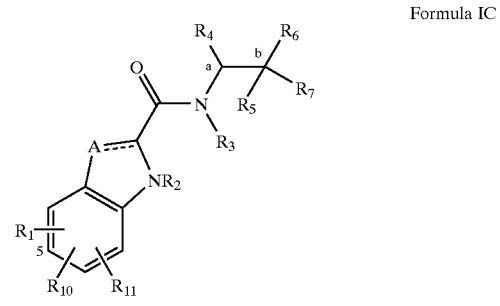

Formula IC and the pharmaceutically acceptable salts and prodrugs thereof
wherein
the dotted line (- - -) is an optional bond;
A is —C(H)=, —C(($C_1$–$C_4$)alkyl)= or —C(halo)= when the dotted line (- - -) is a bond, or A is methylene or —CH(($C_1$–$C_4$)alkyl)- when the dotted line (- - -) is not a bond;
$R_1$, $R_{10}$ or $R_{11}$ are each independently H, halo, 4-, 6 or 7-nitro, cyano, ($C_1$–$C_4$)alkyl, ($C_1$–$C_4$)alkoxy, fluoromethyl, difluoromethyl or trifluoromethyl;
$R_2$ is H;
$R_3$ is H or ($C_1$–$C_5$)alkyl;
$R_4$ is H, methyl, ethyl, n-propyl, hydroxyl($C_1$–$C_3$)alkyl, ($C_1$–$C_3$)alkoxy($C_1$–$C_3$)alkyl, phenyl($C_1$–$C_4$)alkyl, phenylhydroxy($C_1$–$C_4$)alkyl, phenyl($C_1$–$C_4$)alkoxy ($C_1$–$C_4$)alkyl, thien-2- or -3-yl($C_1$–$C_4$)alkyl or fur-2- or -3-yl($C_1$–$C_4$)alkyl wherein said $R_4$ rings are mono-, di- or tri-substituted independently on carbon with H, halo, ($C_1$–$C_4$)alkyl, ($C_1$–$C_4$)alkoxy, trifluoromethyl, hydroxy, amino or cyano; or
$R_4$ is pyrid-2-, -3- or 4-yl($C_1$–$C_4$)alkyl, thiazol-2-, -4- or -5-yl($C_1$–$C_4$)alkyl, imidazol-1-, -2-, -4- or -5-yl ($C_1$–$C_4$)alkyl, pyrrol-2- or -3-yl($C_1$–$C_4$)alkyl, oxazol-2-, -4- or -5-yl-($C_1$–$C_4$)alkyl, pyrazol-3-, 4- or -5yl ($C_1$–$C_4$)alkyl, isoxazol-3-, 4- or -5-yl($C_1$–$C_4$)alkyl, isothiazol-3-, -4- or -5-yl($C_1$–$C_4$)alkyl, pyridazin-3 or 4-yl-($C_1$–$C_4$)alkyl, pyrimidin-2-, -4-, -5- or -6-yl ($C_1$–$C_4$)alkyl, pyrazin-2- or -3-yl($C_1$–$C_4$)alkyl or 1,3, 5-triazin-2-yl($C_1$–$C_4$)alkyl, wherein said preceding $R_4$ heterocycles are optionally mono- or di-substituted independently with halo, trifluoromethyl, $(C_1-C_4)$ alkyl, $(C_1-C_4)$alkoxy, amino or hydroxy and said mono-or di-substituents are bonded to carbon;

$R_5$ is H, hydroxy, fluoro, $(C_1-C_5)$alkyl, $(C_1-C_5)$alkoxy, $(C_1-C_6)$alkanoyl, amino$(C_1-C_4)$alkoxy, mono-N- or di-N,N-$(C_1-C_4)$alkylamino$(C_1-C_4)$alkoxy, carboxy$(C_1-C_4)$alkoxy, $(C_1-C_5)$alkoxy-carbonyl$(C_1-C_4)$ alkoxy, benzyloxycarbonyl$(C_1-C_4)$alkoxy, or carbonyloxy wherein said carbonyloxy is carbon-carbon linked with phenyl, thiazolyl, imidazolyl, 1H-indolyl, furyl, pyrrolyl, oxazolyl, pyrazolyl, isoxazolyl, isothiazolyl, pyridazinyl, pyrimidinyl, pyrazinyl or 1,3,5-triazinyl and wherein said preceding $R_5$ rings are optionally mono-substituted with halo, $(C_1-C_4)$alkyl, $(C_1-C_4)$ alkoxy, hydroxy, amino or trifluoromethyl and said mono-substituents are bonded to carbon;

$R_7$ is H, fluoro or $(C_1-C_5)$alkyl; or $R_5$ and $R_7$ can be taken together to be oxo;

$R_6$ is carboxy, $(C_1-C_8)$alkoxycarbonyl, $C(O)NR_8R_9$ or $C(O)R_{12}$, wherein $R_8$ is H, $(C_1-C_3)$alkyl, hydroxy or $(C_1-C_3)$alkoxy; and $R_9$ is H, $(C_1-C_8)$alkyl, hydroxy, $(C_1-C_8)$alkoxy, methylene-perfluorinated$(C_1-C_8)$alkyl, phenyl, pyridyl, thienyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, piperidinyl, morpholinyl, pyridazinyl, pyrimidinyl, pyrazinyl, piperazinyl or 1,3,5-triazinyl wherein said preceding $R_9$ rings are carbon-nitrogen linked; or $R_9$ is mono-, di- or tri-substituted $(C_1-C_5)$alkyl, wherein said substituents are independently H, hydroxy, amino, mono-N- or di-N,N-$(C_1-C_5)$alkylamino; or $R_9$ is mono or di-substituted $(C_1-C_5)$alkyl, wherein said substituents are independently phenyl, pyridyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, pyridinyl, piperidinyl, morpholinyl, pyridazinyl, pyrimidinyl, pyrazinyl, piperazinyl or 1,3,5-triazinyl wherein the nonaromatic nitrogen-containing $R_9$ rings are optionally mono-substituted on nitrogen with $(C_1-C_6)$ alkyl, benzyl, benzoyl or $(C_1-C_6)$alkoxycarbonyl and wherein the $R_9$ rings are optionally mono-substituted on carbon with halo, $(C_1-C_4)$alkyl, $(C_1-C_4)$alkoxy, hydroxy, amino, or mono-N- and di-N,N$(C_1-C_5)$ alkylamino provided that no quaternized nitrogen is included and there are no nitrogen-oxygen, nitrogen-nitrogen or nitrogen-halo bonds;

$R_{12}$ is piperazin-1-yl, 4-$(C_1-C_4)$alkylpiperazin-1-yl, 4-formylpiperazin-1-yl, morpholino, thiomorpholino, 1-oxothiomorpholino, 1,1-dioxo-thiomorpholino, thiazolidin-3-yl, 1-oxo-thiazolidin-3-yl, 1,1-dioxo-thiazolidin-3-yl, 2-$(C_1-C_6)$alkoxycarbonylpyrrolidin-1-yl, oxazolidin-3-yl or 2(R)-hydroxymethylpyrrolidin-1-yl; or $R_{12}$ is 3- and/or 4-mono-or di-substituted oxazetidin-2-yl, 2-, 4-, and/or 5-mono- or di-substituted oxazolidin-3-yl, 2-, 4-, and/or 5- mono- or di- substituted thiazolidin-3-yl, 2-, 4-, and/or 5 mono- or di-substituted 1-oxothiazolidin-3-yl, 2-, 4-, and/or 5- mono- or di-substituted 1,1-dioxothiazolidin-3-yl, 3- and/or 4-, mono- or di-substituted pyrrolidin-1-yl, 3-, 4- and/or 5-, mono-, di- or tri-substituted piperidin-1-yl, 3-, 4-, and/or 5- mono-, di-, or tri-substituted piperazin-1-yl, 3-substituted azetidin-1-yl, 4- and/or 5-, mono- or di-substituted 1,2-oxazinan-2-yl, 3- and/or 4-mono- or di-substituted pyrazolidin-1-yl, 4- and/or 5-, mono- or di-substituted isoxazolidin-2-yl, 4 and/or 5-, mono- and/or di-substituted isothiazolidin-2-yl wherein said $R_{12}$ substituents are independently H, halo, $(C_1-C_5)$-alkyl, hydroxy, amino, mono-N- or di-N,N-$(C_1-C_5)$ alkylamino, formyl, oxo, hydroxyimino, $(C_1-C_5)$ alkoxy, carboxy, carbamoyl, mono-N- or di-N,N-$(C_1-C_4)$alkylcarbamoyl, $(C_1-C_4)$alkoxyimino, $(C_1-C_4)$alkoxymethoxy, $(C_1-C_6)$alkoxycarbonyl, carboxy$(C_1-C_5)$alkyl or hydroxy$(C_1-C_5)$alkyl;

with the proviso that if $R_4$ is H, methyl, ethyl or n-propyl $R_5$ is OH;

with the proviso that if $R_5$ and $R_7$ are H, then $R_4$ is not H, methyl, ethyl, n-propyl, hydroxy$(C_1-C_3)$alkyl or $(C_1-C_3)$alkoxy$(C_1-C_3)$alkyl and $R_8$ is $C(O)NR_8R_9$, $C(O)R_{12}$ or $(C_1-C_4)$alkoxycarbonyl.

Preferred glycogen phosphorylase inhibitors include compounds having the Formula ID

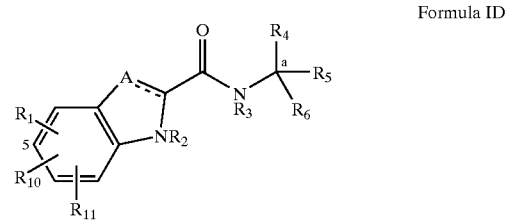

Formula ID and the pharmaceutically acceptable salts and prodrugs thereof wherein the dotted line (- - -) is an optional bond;

A is —C(H)=, —C(($C_1-C_4$)alkyl)=, —C(halo)= or —N=, when the dotted line (- - -) is a bond, or A is methylene or —CH(($C_1-C_4$)alkyl)-, when the dotted line (- - -) is not a bond;

$R_1$, $R_{10}$ or $R_{11}$ are each independently H, halo, cyano, 4-, 6-, or 7-nitro, $(C_1-C_4)$alkyl, $(C_1-C_4)$alkoxy, fluoromethyl, difluoromethyl or trifluoromethyl;

$R_2$ is H;

$R_3$ is H or $(C_1-C_5)$alkyl;

$R_4$ is H, methyl, ethyl, n-propyl, hydroxy$(C_1-C_3)$alkyl, $(C_1-C_3)$alkoxy$(C_1-C_3)$alkyl, phenyl$(C_1-C_4)$alkyl, phenylhydroxy$(C_1-C_4)$alkyl, (phenyl)(($C_1-C_4$)-alkoxy)$(C_1-C_4)$alkyl, thien-2- or -3-yl$(C_1-C_4)$alkyl or fur-2- or -3-yl$(C_1-C_4)$alkyl wherein said $R_4$ rings are mono-, di- or tri-substituted independently on carbon with H, halo, $(C_1-C_4)$alkyl, $(C_1-C_4)$alkoxy, trifluoromethyl, hydroxy, amino, cyano or 4,5-dihydro-1H-imidazol-2-yl; or $R_4$ is pyrid-2-, -3- or 4-yl$(C_1-C_4)$alkyl, thiazol-2-, 4- or -5-yl$(C_1-C_4)$alkyl, imidazol-2-, 4- or -5yl$(C_1-C_4)$alkyl, pyrrol-2- or -3-yl$(C_1-C_4)$alkyl, oxazol-2-, -4- or -5-yl $(C_1-C_4)$alkyl, pyrazol-3-, -4- or -5-yl$(C_1-C_4)$alkyl, isoxazol-3, 4- or -5-yl$(C_1-C_4)$alkyl, isothiazol-3, 4- or -5-yl$(C_1-C_4)$alkyl, pyridazin-3- or 4-yl$(C_1-C_4)$alkyl, pyrimidin-2-, 4-, -5- or -6-yl$(C_1-C_4)$alkyl, pyrazin-2- or -3-yl$(C_1-C_4)$alkyl, 1,3,5-triazin-2-yl$(C_1-C_4)$alkyl or indol-2-$(C_1-C_4)$alkyl, wherein said preceding $R_4$ heterocycles are optionally mono- or di-substituted independently with halo, trifluoromethyl, $(C_1-C_4)$alkyl, $(C_1-C_4)$alkoxy, amino, hydroxy or cyano and said substituents are bonded to carbon; or $R_4$ is $R_{15}$-carbonyloxymethyl, wherein said $R_{15}$ is phenyl, thiazolyl, imidazolyl, 1H-indolyl, furyl, pyrrolyl, oxazolyl, pyrazolyl, isoxazolyl, isothiazolyl, pyridyl, pyridazinyl, pyrimidinyl, pyrazinyl or 1,3,5-triazinyl and wherein said preceding $R_{15}$ rings are optionally mono- or di-substituted independently with halo, amino, hydroxy, $(C_1-C_4)$alkyl, $(C_1-C_4)$alkoxy or trifluoromethyl and said mono- or di-substituents are bonded to carbon;

$R_5$ is H;

$R_6$ is carboxy, $(C_1-C_8)$alkoxycarbonyl, benzyloxycarbonyl, $C(O)NR_8R_9$ or $C(O)R_{12}$ wherein $R_8$ is H, $(C_1-C_6)$alkyl, cyclo$(C_3-C_6)$alkyl, cyclo$(C_3-C_6)$alkyl$(C_1-C_5)$alkyl, hydroxy or $(C_1-C_8)$alkoxy; and $R_9$ is H, cyclo$(C_3-C_8)$alkyl, cyclo$(C_3-C_8)$alkyl$(C_1-C_5)$alkyl, cyclo$(C_4-C_7)$alkenyl, cyclo$(C_3-C_7)$alkyl$(C_1-C_5)$alkoxy, cyclo$(C_3-C_7)$alkyloxy, hydroxy, methylene-perfluorinated$(C_1-C_8)$alkyl, phenyl, or a heterocycle wherein said heterocycle is pyridyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, pyridinyl, piperidinyl, morpholinyl, pyridazinyl, pyrimidinyl, pyrazinyl, piperazinyl, 1,3,5-triazinyl, benzothiazolyl, benzoxazolyl, benzimidazolyl, thiochromanyl or tetrahydrobenzothiazolyl wherein said heterocycle rings are carbon-nitrogen linked; or $R_9$ is $(C_1-C_6)$alkyl or $(C_1-C_8)$alkoxy wherein said $(C_1-C_6)$alkyl or $(C_1-C_8)$alkoxy is optionally monosubstituted with cyclo$(C_4-C_7)$alken-1-yl, phenyl, thienyl, pyridyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, piperidinyl, morpholinyl, thiomorpholinyl, 1-oxothiomorpholinyl, 1,1-dioxothiomorpholinyl, pyridazinyl, pyrimidinyl, pyrazinyl, piperazinyl, 1,3,5-triazinyl or indolyl and wherein said $(C_1-C_6)$alkyl or $(C_1-C_8)$alkoxy are optionally additionally independently mono- or di-substituted with halo, hydroxy, $(C_1-C_5)$alkoxy, amino, mono-N- or di-N,N-$(C_1-C_5)$alkylamino, cyano, carboxy, or $(C_1-C_4)$alkoxycarbonyl; and wherein the $R_9$ rings are optionally mono- or di-substituted independently on carbon with halo, $(C_1-C_4)$alkyl, $(C_1-C_4)$alkoxy, hydroxy, hydroxy$(C_1-C_4)$alkyl, amino$(C_1-C_4)$alkyl, mono-N- or di-N,N-$(C_1-C_4)$alkylamino$(C_1-C_4)$alkyl, $(C_1-C_4)$alkoxy$(C_1-C_4)$alkyl, amino, mono-N- or di-N,N-$(C_1-C_4)$alkylamino, cyano, carboxy, $(C_1-C_5)$alkoxycarbonyl, carbamoyl, formyl or trifluoromethyl and said $R_9$ rings may optionally be additionally mono- or di-substituted independently with $(C_1-C_5)$alkyl or halo;

with the proviso that no quaternized nitrogen on any $R_9$ heterocycle is included;

$R_{12}$ is morpholino, thiomorpholino, 1-oxothiomorpholino, 1,1-dioxothiomorpholino, thiazolidin-3-yl, 1-oxothiazolidin-3yl, 1,1dioxothiazolidin-3-yl, pyrrolidin-1-yl, piperidin-1-yl, piperazin-1-yl, piperazin-4-yl, azetidin-1-yl, 1,2-oxazinan-2-yl, pyrazolidin-1-yl, isoxazolidin-2-yl, isothiazolidin-2-yl, 1,2-oxazetidin-2-yl, oxazolidin-3-yl, 3,4-dihydroisoquinolin-2-yl, 1,3-dihydroisoindol-2-yl, 3,4-dihydro-2H-quinol-1-yl, 2,3-dihydro-benzo[1,4]oxazin-4-yl, 2,3-dihydro-benzo[1,4]-thiazine4-yl, 3,4-dihydro-2H-quinoxalin-1-yl, 3,4-dihydro-benzo[c][1,2]oxazin-1-yl, 1,4-dihydro-benzo[d][1,2]oxazin-3-yl, 3,4-dihydro-benzo[e][1,2]-oxazin-2-yl, 3H-benzo[d]isoxazol-2-yl, 3H-benzo[c]isoxazol-1-yl or azepan-1-yl, wherein said $R_{12}$ rings are optionally mono-, di- or tri-substituted independently with halo, $(C_1-C_5)$alkyl, $(C_1-C_5)$alkoxy, hydroxy, amino, mono-N- or di-N,N-$(C_1-C_5)$alkylamino, formyl, carboxy, carbamoyl, mono-N- or di-N,N-$(C_1-C_5)$alkylcarbamoyl, $(C_1-C_6)$alkoxy$(C_1-C_3)$alkoxy, $(C_1-C_5)$alkoxycarbonyl, benzyloxycarbonyl, $(C_1-C_5)$alkoxycarbonyl$(C_1-C_5)$alkyl, $(C_1-C_4)$alkoxycarbonylamino, carboxy$(C_1-C_5)$alkyl, carbamoyl$(C_1-C_5)$alkyl, mono-N- or di-N,N-$(C_1-C_5)$alkylcarbamoyl$(C_1-C_5)$alkyl, hydroxy$(C_1-C_5)$alkyl, $(C_1-C_4)$alkoxy$(C_1-C_4)$alkyl, amino$(C_1-C_4)$alkyl, mono-N- or di-N,N-$(C_1-C_4)$alkylamino$(C_1-C_4)$alkyl, oxo, hydroxyimino or $(C_1-C_6)$alkoxyimino and wherein no more than two substituents are selected from oxo, hydroxyimino or $(C_1-C_6)$alkoxyimino and oxo, hydroxyimino or $(C_1-C_6)$alkoxyimino are on non-aromatic carbon; and wherein said $R_{12}$ rings are optionally additionally mono- or di-substituted independently with $(C_1-C_5)$alkyl or halo;

with the proviso that when $R_6$ is $(C_1-C_5)$alkoxycarbonyl or benzyloxycarbonyl then $R_1$ is 5-halo, 5-$(C_1-C_4)$alkyl or 5-cyano and $R_4$ is (phenyl)(hydroxy)$(C_1-C_4)$alkyl, (phenyl)($(C_1-C_4)$alkoxy)$(C_1-C_4)$alkyl, hydroxymethyl or Ar$(C_1-C_2)$alkyl, wherein Ar is thien-2- or -3-yl, fur-2- or -3-yl or phenyl wherein said Ar is optionally mono- or di-substituted independently with halo; with the provisos that when $R_4$ is benzyl and $R_5$ is methyl, $R_{12}$ is not 4-hydroxy-piperidin-1-yl or when $R_4$ is benzyl and $R_5$ is methyl $R_6$ is not $C(O)N(CH_3)_2$;

with the proviso that when $R_1$ and $R_{10}$ and $R_{11}$ are H, $R_4$ is not imidazol-4-ylmethyl, 2-phenylethyl or 2-hydroxy-2-phenylethyl;

with the proviso that when both $R_8$ and $R_9$ are n-pentyl, $R_1$ is 5-chloro, 5-bromo, 5-cyano, 5$(C_1-C_5)$alkyl, 5$(C_1-C_5)$alkoxy or trifluoromethyl;

with the proviso that when $R_{12}$ is 3,4-dihydroisoquinol-2-yl, said 3,4-dihydroisoquinol-2-yl is not substituted with carboxy($(C_1-C_4)$alkyl;

with the proviso that when $R_8$ is H and $R_9$ is $(C_1-C_6)$alkyl, $R_9$ is not substituted with carboxy or $(C_1-C_4)$alkoxycarbonyl on the carbon which is attached to the nitrogen atom N of $NHR_9$; and with the proviso that when $R_6$ is carboxy and $R_1$, $R_{10}$, $R_{11}$ and $R_5$ are all H, then $R_4$ is not benzyl, H, (phenyl)(hydroxy)methyl, methyl, ethyl or n-propyl.

In general an effective dosage for the pharmacological combination compositions of this invention, for example the ischemic damage reducing activities of combinations containing the glycogen phosphorylase inhibitor compounds of this invention, is in the range of 0.005 to 50 mg/kg/day, preferably 0.01 to 25 mg/kg/day and most preferably 0.1 to 15 mg/kg/day.

Any glycogen phosphorylase inhibitor may be used as the second compound of this invention. The term glycogen phosphorylase inhibitor refers to any substance or agent or any combination of substances and/or agents which reduces, retards, or eliminates the enzymatic action of glycogen phosphorylase. The currently known enzymatic action of glycogen phosphorylase is the degradation of glycogen by catalysis of the reversible reaction of a glycogen macromolecule and inorganic phosphate to glucose-1-phosphate and a glycogen macromolecule which is one glucosyl residue shorter than the original glycogen macromolecule (forward direction of glycogenolysis). Such actions are readily determined by those skilled in the art according to standard assays (e.g., as described hereinafter). A variety of these compounds are included in the following published international patent applications: PCT application publication WO 96/39384 and WO96139385. However, other glycogen phosphorylase inhibitors will be known to those skilled in the art.

Any sorbitol dehydrogenase inhibitor may be used as the second compound of this invention. Such compounds inhibit the formation of sorbitol dehydrogenase. Such actions are readily determined by those skilled in the art according to standard assays (e.g., as described hereinafter). A variety of these compounds will be known to those skilled in the art (e.g., U.S. Pat. No. 5,728,704).

The compounds of the present invention pharmacologically mimic the cardioprotective effects of ischemic preconditioning by activating adenosine A-3 receptors and hence are useful as therapeutic or prophylactic agents for diseases caused or aggravated by ischemia or hypoxia, or ischemia/reperfusion for example, cardiovascular diseases [e.g., arteriosclerosis, arrhythmia (e.g. ischemic arrhythmia, arrhythmia due to myocardial infarction, myocardial stunning, myocardial dysfunction, arrhythmia after PTCA or after thrombolysis, etc.), angina pectoris, cardiac hypertrophy, myocardial infarction, heart failure (e.g. congestive heart failure, acute heart failure, cardiac hypertrophy, etc.), restenosis after PTCA. PTCI, shock (e.g. hemorrhagic shock, endotoxin shock, etc.)], renal diseases (e.g. diabetes mellitus, diabetic nephropathy, ischemic acute renal failure, etc.) organ disorders associated with ischemia or ischemic reperfusion [(e.g. heart muscle ischemic reperfusion associated disorders, acute renal failure, or disorders induced by surgical treatment such as coronary artery bypass grafting (CABG) surgeries, vascular surgeries, organ transplantation, non-cardiac surgeries or percutaneous transluminal coronary angioplasty (PTCA)], cerebrovascular diseases (e.g., ischemic stroke, hemorrhagic stroke, etc.), cerebro ischemic disorders (e.g., disorders associated with cerebral infarction, disorders caused after cerebral apoplexy as sequelae, or cerebral edema. The compounds of this invention can also be used as an agent for myocardial protection during coronary artery bypass grafting (CABG) surgeries, vascular surgeries, percutaneous transluminal coronary angioplasty (PTCA), PTCI, organ transplantation, or non-cardiac surgeries.

Preferably, the compounds of this invention can be used as agents for myocardial protection before, during, or after coronary artery bypass grafting (CABG) surgeries, vascular surgeries, percutaneous transluminal coronary angioplasty (PTCA), organ transplantation, or non-cardiac surgeries.

Preferably, the compounds of this invention can be used as agents for myocardial protection in patients presenting with ongoing cardiac (acute coronary syndromes, e.g. myocardial infarction or unstable angina) or cerebral ischemic events (e.g., stroke).

Preferably, the compounds of this invention can be used as agents for chronic myocardial protection in patients with diagnosed coronary heart disease (e.g. previous myocardial infarction or unstable angina) or patients who are at high risk for myocardial infarction (e.g., age greater than 65 and two or more risk factors for coronary heart disease).

Accordingly, the compounds of this invention reduce mortality.

The utility of the compounds of the present invention as medical agents in the treatment of diseases, such as are detailed herein in mammals (e.g., humans), for example, myocardial protection during surgery or mycardial protection in patients presenting with ongoing cardiac or cerebral ischemic or hypoxic events or :chronic cardioprotection in patients with diagnosed coronary heart disease, or at risk for coronary heart disease, cardiac dysfunction or myocardial stunning is demonstrated by the activity of the compounds of this invention in conventional preclinical cardioprotection assays [see the in vivo assay in Klein, H. et al., Circulation 92:912–917 (1995); the isolated heart assay in Tracey, W. R. et al., Cardiovascular Research 33:410–415 (1997); the antiarrhythmic assay in Yasutake M. et al., Am. J. Physiol., 36:H2430–H2440 (1994); the NMR assay in Kolke et al., J. Thorac. Cardiovasc. Surg. 112: 765–775 (1996)] and the additional in vitro and in vivo assays described below. Such assays also provide a means whereby the activities of the compounds of this invention can be compared with the activities of other known compounds. The results of these comparisons are useful for determining dosage levels in mammals, including humans, for the treatment of such diseases.

Human Adenosine A1 and A3 Receptor Assays

Materials

Full-length human adenosine $A_1$ and $A_3$ receptor cDNA's subcloned into the eukaryotic expression vector pRcCMV (Invitrogen) were purchased from The Garvan Institute, Sydney, Australia. Chinese hamster ovary (CHO-K1) cells were obtained from the American Type Tissue Culture Collection (Rockville, Md., USA). DMEM and DMEM/F12 culture media and foetal calf serum were obtained from Gibco-BRL (Grand Island, N.Y., USA). The A1/A3 adenosine receptor agonist N6(4-amino-3-[125I]iodobenzyl) adenosine ($^{125}$I-ABA) was prepared by New England Nuclear (Boston, Mass., USA). Adenosine deaminase (ADA) was obtained from Boehringer Mannheim (Indianapolis, Ind., USA). The phosphodiesterase inhibitor RO-20-1724 was obtained from Research Biochemicals International (Matick, Mass., USA).

Expression of Human Adenosine A1 and A3 Receptors

For stable expression studies adenosine receptor $A_1$ and $A_3$ expression plasmids (20 µg) are transfected into CHO-K1 cells, or HEK 293s cells, respectively, grown in DMEM/F12 (CHO) or DMEM (HEK 293s), with 10% foetal calf serum media, using a calcium phosphate mammalian cell transfection kit (5 Prime-3 Prime). Stable transfectants are obtained by selection in complete media containing 500 µg/ml (CHO) or 700 µg/ml (HEK 293s) active neomycin (G418) and screened for expression by [$^{125}$I]-ABA binding.

Receptor Membrane Preparation

Cells stably expressing either human $A_1$ or human $A_3$ receptors are collected by centrifugation at 300×g for 5 minutes, the supernatant is discarded and the cell pellet is resuspended in cell buffer consisting of (mmoles/L): HEPES (10), $MgCl_2$ (5), PMSF (0.1), bacitracin (100 µg/ml), leupeptin (10 µg/ml), DNAse I (100 µg/ml), ADA (2 U/ml), pH 7.4. Crude cell membranes are prepared by repeated aspiration through a 21 gauge needle, collected by centrifugation at 60,000×g for 10 minutes and stored in cell buffer at −80° C.

Estimation of Compound Binding Affinity Constants ($K_i$)

Receptor membranes are resuspended in incubation buffer consisting of (mmoles/L): HEPES (10), EDTA (1), $MgCl_2$ (5), pH 7.4. Binding reactions (10–20 μg membrane protein) are carried out for one hour at room temperature in 250 μl incubation buffer containing 0.1 nM of $^{125}$I-ABA (2200 Ci/mmol) and increasing concentrations of compound (0.1 nM–30 μM). The reaction is stopped by rapid filtration with ice-cold PBS, through glass fibre filters (presoaked in 0.6% polyethylenimine) using a Tomtec 96-well harvester (Orange, Conn., USA). Filters are counted in a Wallac Microbeta liquid scintillation counter (Gaithersburg, Md., USA). Nonspecific binding is determined in the presence of 5 μM I-ABA. Compound inhibitory constants ($K_i$) are calculated by fitting binding data via nonlinear least squares regression analysis to the equation: % Inhibition=$100/[1+(10^C/10^X)^P]$, where X =log [drug concentration], C ($IC_{50}$)= log [drug concentration at 50% inhibition], and D=the Hill slope. At the concentration of radioligand used in the present study (10 fold<$K_D$), $IC_{50}$=$K_i$.

Assessment of Human Adenosine A3 Receptor Agonist Activity

Adenosine A3 agonist activity is assessed by compound inhibition of isoproternol-stimulated cAMP levels. HEK293s cells stably transfected with human A3 receptors (as described above) are washed with Phosphate Buffered Saline (PBS) (Ca/Mg-free) and detached with 1.0 mM EDTA/PBS. Cells are collected by centrifugation at 300×g for 5 minutes and the supernatant discarded. The cell pellet is dispersed and resuspended in cell buffer (DMEM/F12 containing 10 mM HEPES, 20 μM RO-20-1724 and 1 U/ml ADA). Following preincubation of cells (100,000/well) for 10 min at 37° C., 1 μM isoproterenol, with or without increasing concentrations (0.1 nM–300 nM) test compound, and the incubation is continued for 10 min. Reactions are terminated by the addition of 1.0 N HCl followed by centrifugation at 2000×g for 10 minutes. Sample supernatants (10 μl) are removed and cAMP levels determined by radioimmunoassay (New England Nuclear, Boston, Mass., USA). The basal and control isoproterenol-stimulated cAMP accumulation (pmol/ml/100,000 cells) are routinely 3 and 80, respectively. Smooth curves are fitted to the data via nonlinear least squares regression analysis to the equation: % isoproterenol-stimulated cAMP=$100/[1+(10^X/10^C)^P]$, where X =log [drug concentration], C ($IC_{50}$)=log [drug concentration at 50% inhibition], and D=the Hill slope.

As background information, it is noted that brief periods of myocardial ischemia followed by coronary artery reperfusion protects the heart from subsequent severe myocardial ischemia (Murry et al., Circulation 74:1124–1136, 1986).

The therapeutic effects of the compounds of this invention in preventing heart tissue damage resulting from an ischemic insult can be demonstrated in vitro along lines presented in Tracey et al. (Cardiovasc. Res., 33:410–415, 1997), as described specifically herein. Cardioprotection, as indicated by a reduction in infarcted myocardium, can be induced pharmacologically using adenosine receptor agonists in isolated, retrogradely perfused rabbit hearts as an in vitro model of myocardial ischemic preconditioning (Tracey et al. (Cardiovasc. Res., 33:410–415, 1997)). The in vitro test described below demonstrates that a test compound (i.e., a compound as claimed herein) can also pharmacologically induce cardioprotection, i.e., reduced myocardial infarct size, when administered to a rabbit isolated heart. The effects of the test compound are compared to ischemic preconditioning. The exact methodology is described below.

The protocol used for these experiments closely follows that described by Tracey et al. (Cardiovasc. Res., 33:410–415, 1997). Male New Zealand White rabbits (3–4 kg) are anesthetized with sodium pentobarbital (30 mg/kg, i.v.). After deep anesthesia is achieved (determined by the absence of an ocular blink reflex) the animal is intubated and ventilated with 100% $O_2$ using a positive pressure ventilator. A left thoracotomy is performed, the heart exposed, and a snare (2-0 silk) is placed loosely around a prominent branch of the left coronary artery, approximately ⅔ of the distance from the apex of the heart. The heart is removed from the chest and rapidly (<30 sec) mounted on a Langendorff apparatus. The heart is retrogradely perfused in a non-recirculating manner with a modified Krebs solution (NaCl 118.5 mM, KCl 4.7 mM, Mg $SO_4$ 1.2 mM, $KH_2PO_4$ 1.2 mM, $NaHCO_3$ 24.8 mM, $CaCl_2$ 2.5 mM, and glucose 10 mM), at a constant pressure of 80 mmHg and a temperature of 37° C. Perfusate pH is maintained at 7.4–7.5 by bubbling with 95% $O_2$/5% $CO_2$. Heart temperature is tightly controlled by using heated reservoirs for the physiological solution and water jacketing around both the perfusion tubing and the isolated heart. Heart rate and left ventricular pressures are determined via a latex balloon which is inserted in the left ventricle and connected by stainless steel tubing to a pressure transducer. The intraventricular balloon is inflated to provide a systolic pressure of 80–100 mmHg, and a diastolic pressure s 10 mmHg. Total coronary flow is also continuously monitored using an in-line flow probe and normalized for heart weight.

The heart is allowed to equilibrate for 30 min, over which time the heart must show stable left ventricular pressures within the parameters outlined above. If the heart rate falls below 180 bpm at any time prior to the 30 min period of regional ischemia, the heart is paced at about 200 bpm for the remainder of the experiment. ischemic preconditioning is induced by total cessation of cardiac perfusion (global ischemia) for 5 min, followed by reperfusion for 10 min. The regional ischemia is provided by tightening the snare around the coronary artery branch. Following the 30 min regional ischemia, the snare is released and the heart reperfused for an additional 120 min.

Pharmacological cardioprotection is induced by infusing the test compound at predetermined concentrations, for a 5 min period which ends 10 min before the 30 min regional ischemia. Hearts which receive test compounds do not undergo the period of ischemic preconditioning.

At the end of the 120 min reperfusion period, the coronary artery snare is tightened, and a 0.5% suspension of fluorescent zinc cadmium sulfate particles (1–10 μM) Duke Scientific Corp.(Palo Alto, Calif.) is perfused through the heart; this stains all of the myocardium, except that area-at-risk for infarct development (area-at-risk). The heart is removed from the Langendorff apparatus, blotted dry, wrapped in aluminum foil and stored overnight at −20° C. The next day, the heart is sliced into 2 mm transverse sections from the apex to the top of the ventricles. The slices are stained with 1% triphenyl tetrazolium chloride (TTC) in phosphate-buffered saline for 20 min at 37° C. Since TTC reacts with living tissue (containing NAD-dependent dehydrogenases), this stain differentiates between living (red stained) tissue, and dead tissue (unstained infarcted tissue). The infarcted area (no stain) and the area-at-risk (no fluorescent particles) are calculated for each slice of left ventricle using a precalibrated image analyzer. To normalize the ischemic injury for differences in the area-at-risk between hearts, the data is expressed as the ratio of infarct area vs. area-at-risk (% IA/MR). All data are expressed as mean ±SE and compared statistically using a Mann-Whitney non-parametric test with a Bonferroni correction for multiple comparisons. Significance is considered as $p<0.05$.

The results from the above in vitro test demonstrate that compounds of this invention induce significant cardioprotection relative to the control group.

The therapeutic effects of the compounds of this invention in preventing heart tissue damage resulting from an ischemic insult can also be demonstrated in vivo along lines presented in Liu et al. (Circulation, Vol. 84:350–356, 1991) as described specifically herein. The in vivo assay tests the cardioprotection of the test compound relative to the control group which receives saline vehicle. Cardioprotection, as indicated by a reduction in infarcted myocardium, can be induced pharmacologically using intravenously administered adenosine receptor agonists in intact, anesthetized rabbits studied as an in vivo model of myocardial ischemic preconditioning (Liu et al., Circulation 84:350–356, 1991). The in vivo assay tests whether compounds can pharmacologically induce cardioprotection, i.e., reduced myocardial infarct size, when parenterally administered to intact, anesthetized rabbits. The effects of the compounds of this invention can be compared to ischemic preconditioning. The methodology is described below.

Surgery: New Zealand White male rabbits (3–4 kg) are anesthetized with sodium pentobarbital as a bolus dose (30 mg/kg, i.v.) followed by an infusion (100 mg/kg/hr, i.v.) to maintain a surgical plane of anesthesia. A tracheotomy is performed via a ventral midline cervical incision and the rabbits are ventilated with 100% oxygen using a positive pressure ventilator. The ventilation is adjusted to maintain pH and $PCO_2$ within physiological ranges. Body temperature is held constant at 38° C. using a heating pad. Catheters are placed in the left jugular vein for drug administration and in the left carotid artery for blood pressure measurements. The hearts are then exposed through a left thoracotomy and a snare (00 silk) placed around a prominent branch of the left coronary artery approximately two-thirds of the distance from the apex of the heart. Ischemia is induced by pulling the snare tight. Releasing the snare allows the ischemic area to reperfuse. Myocardial ischemia is evidenced by regional cyanosis; reperfusion is evidenced by reactive hyperemia.

Protocol: Once arterial pressure and heart rate have been stable for at least 120 minutes the test is started. Ischemic preconditioning is induced by occluding the coronary artery for 5 min followed by a 10 min reperfusion. Pharmacological preconditioning is induced by infusing test compound over, for example, 5 minutes and allowing 10 minutes before further intervention. Following ischemic preconditioning, pharmacological preconditioning or no conditioning (unconditioned, vehicle control) the artery is occluded for 30 minutes and then reperfused for two hours to induce myocardial infarction.

At the end of the 2 hour reperfusion period, the hearts are quickly removed, placed on a Langendorff apparatus, and perfused for 1 minute with normal saline heated to body temperature (38° C.). The silk suture used as the snare is then tied tightly to reocclude the artery and a 0.5% suspension of fluorescent zinc cadmium sulphate particles (1–10 µm) Duke Scientific Corp. (Palo Alto, Calif.) is infused with the perfusate to stain all of the myocardium except for the area at risk (nonfluorescent ventricle). The hearts are then removed from the apparatus, blotted dry, wrapped in aluminum foil and stored overnight at −20° C. On the following day, the ventricles are sliced into 2 mm transverse slices sections from apex to base and stained with 1% triphenyl tetrazolium chloride (TTC) in phosphate buffered saline for 20 minutes at 38° C. Since TTC reacts with living tissue (NAD-dependent dehydrogenase present), this stain differentiates between living (red stained) tissue, and dead tissue (unstained infarcted tissue). The infarcted area (no stain) and the area at risk (no fluorescent particles) are calculated for each slice of left ventricle using a pre-calibrated image analyzer. To normalize the ischemic injury for differences in the area at risk between hearts, the data is expressed as the ratio of infarct area vs. area at risk (% IA/AAR). All data are expressed as Mean±SEM and compared statistically using single factor ANOVA or Mann Whitney non parametric test. Significance is considered as $p<0.05$.

The compounds of this invention can be tested for their utility in reducing or preventing ischemic or hypoxic injury in non-cardiac tissues, for example, the brain, or the liver, utilizing procedures reported in the scientific literature. The compounds of this invention in such tests can be administered by the preferred route and vehicle of administration and at the preferred time of administration either prior to the ischemic episode, during the ischemic or hypoxic episode, following the ischemic or hypoxic episode (reperfusion period) or during any of the below-mentioned experimental stages.

The benefit of the invention to reduce ischemic or hypoxic brain damage can be demonstrated, for example, in mammals using the method of Park, et al, (Ann. Neurol. 1988;24:543–551). According to the procedure of Park, et al., adult male Sprague Dawley rats are anesthetized initially with 2% halothane, and thereafter by mechanical ventilation with a nitrous oxide-oxygen mixture (70%:30%) containing 0.5–1% halothane. A tracheostomy is then performed. The stroke volume of the ventilator is adjusted to maintain arterial carbon dioxide tension at approximately 35 mm Hg and adequate arterial oxygenation ($PaO_2>90$ mm Hg). Body temperature can be monitored by a rectal thermometer, and the animals can be maintained normothermic, if necessary, by external heating. The animals next undergo subtemporal craniectomy to expose the main trunk of the left middle cerebral artery (MCA) under an operating microscope, and the exposed artery is occluded with microbipolar coagulation to generate large ischemic lesions in the cerebral cortex and basal ganglia. After three hours of MCA occlusion, the rats are deeply anesthetized with 2% halothane and a thoracotomy is performed to infuse heparinized saline into the left ventricle. The effluent is collected via an incision of the right atrium. The saline washout is followed by approximately 200 ml of a 40% formaldehyde, glacial acetic acid and absolute methanol solution (FAM; 1:1:8, v/v/v), then the animals are decapitated and the head is stored in fixative for 24 hours. The brain is then removed, dissected, embedded in paraffin wax, and sectioned (approximately 100 sections of 0.2 mm per brain). The sections are then stained with hematoxylin-eosin or with a combination of cresyl violet and Luxol® fast blue, and examined by light microscopy to identify and quantitate the ischemic damage using a precalibrated image analyzer. The ischemic volumes and areas are expressed in absolute units ($mm^3$ and $mm^2$) and as a percentage of the total region examined. The effect of the compounds, compositions and methods of this invention to reduce ischemic brain damage induced by MCA occlusion is noted based on a reduction in the area or volume of relative or absolute ischemic damage in the brain sections from the rats in the treatment group compared to brain sections from rats in a placebo-treated control group.

Other methods which could alternatively be utilized to demonstrate the benefit of the invention to reduce ischemic or hypoxic brain damage include those described by Nakayama, et al. in Neurology 1988,38:1667–1673; Memezawa, et al. in Stroke 1992,23:552–559; Folbergrova, et al. in Proc. Natl. Acad. Sci 1995,92:5057–5059; and Gotti, et al. in Brain Res. 1990,522:290–307.

The benefit of the compounds, compositions and methods of this invention to reduce ischemic or hypoxic liver damage can be demonstrated, for example, in mammals using the method of Yokoyama, et al. (Am. J. Physiol. 1990;258:G564–G570). According to the procedure of Yokoyama, et al., fasted adult male Sprague Dawley rats are anesthetized with sodium pentobarbital (40 mg/kg i.p.), then the animals are tracheotomized and mechanically ventilated with room air. The liver is extirpated and placed in an environmental chamber maintained at constant temperature (37° C.), then perfused through the portal vein at a constant pressure of 15 cm $H_2O$ with a modified, hemoglobin-free Krebs-Henseleit buffer (in mM: 118 NaCl, 4.7 KCl, 27 $NaHCO_3$, 2.5 $CaCl_2$, 1.2 $MgSO_4$, 1.2 $KH_2PO_4$, 0.05 EDTA, and 11 mM glucose, plus 300 U heparin). The pH of the perfusate is maintained at 7.4 by gassing the buffer with 95% $O_2$—5% $CO_2$. Each liver is perfused at a flow rate of 20 ml/min in a single-pass manner for a 30 min washout and equilibration period (preischemic period), followed by a 2 hour period of global ischemia, and then a 2 hour period of reperfusion under conditions identical to the preischemic period. Aliquots (20 ml) of the perfusate are collected during the preischemic period, immediately after the occlusive ischemic period, and every 30 min of the 2 hour reperfusion period. The perfusate samples are assayed for the appearance of hepatocellular enzymes, for example, aspartate amino-transferase (AST), alanine aminotransferase (ALT), and lactate dehydrogenase (LDH), which are taken to quantitatively reflect the degree of ischemic liver tissue damage during the procedure. AST, ALT, and LDH activities in the perfusate can be determined by several methods, for example, by the reflectometry method using an automatic Kodak Ektachem 500 analyzer reported by Nakano, et al. (Hepatology 1995;22:539–545). The effect of the compounds, compositions and methods of this invention in reducing ischemic liver damage induced by occlusion is noted based on a reduction in the release of hepatocellular enzymes immediately following the occlusive period and/or during the postischemic-reperfusion period in the perfused livers from the rats in the treatment group compared to perfused livers from rats in a placebo-treated control group.

Other methods and parameters which could alternatively be utilized to demonstrate the benefit of the compounds, compositions and methods of this invention in reducing ischemic or hypoxic liver damage include those described by Nakano, et al. (Hepatology 1995;22:539–545).

Measurement of Human NHE-1 Inhibitory Activity

Methodologies for measurement of human NHE-1 activity and inhibitor potency are based on those published by Watson et al., Am. J. Physiol., 24:G229-G238, 1991), where NHE-mediated recovery of intracellular pH is measured following intracellular acidification. Thus, fibroblasts stably expressing human NHE-1 (Counillon, L. et al., Mol. Pharmacol., 44:1041–1045 (1993) are plated onto collagen coated 96 well plates (50,000/well) and grown to confluence in growth media (DMEM high glucose, 10% fetal bovine serum, 50 u/ml penicillin and streptomycin). Confluent plates are incubated for 30 min at 37° C. with the pH sensitive fluorescent probe BCECF (5 $\mu$M; Molecular Probes, Eugene, Oreg.). BCECF loaded cells are incubated for 30 min at 37° C. in acid loading media (70 mM choline chloride, 50 mM $NHCl_4$, 5 mM KCl, 1 mM $MgCl_2$, 1.8 mM $CaCl_2$, 5 mM glucose, 10 mM HEPES, pH 7.5), and then placed in a Fluorescent Imaging Plate Reader (Molecular Devices, CA). BCECF fluorescence is monitored using excitation and emission wavelengths of 485 nM and 525 nM, respectively. Intracellular acidification is initiated via rapid replacement of acid loading media with recovery media (120 mM NaCl, 5 mM KCl, 1 mM $MgCl_2$, 1.8 mM $CaCl_2$, 5 mM glucose, 10 mM HEPES, pH 7.5)±test compound, and NHE-mediated recovery of intracellular pH is monitored as the subsequent time-dependent increase BCECF fluorescence. The potency of human NHE-1 inhibitors is calculated as the concentration that reduces recovery of intracellular pH by 50% ($IC_{50}$). Under these conditions reference NHE inhibitors amiloride and HOE-642 had $IC_{50}$ values for human NHE-1 of 50 $\mu$M and 0.5 $\mu$M, respectively.

Aldose Reductase Inhibitor Assays

Male Sprague-Dawley rats are rendered diabetic by injection of streptozocin at 55 mg/kg, i.v., in pH 4.5 citrate buffer. They are fed ad libitum in controlled conditions of housing, temperature and lighting. After five weeks of diabetes, the rats are anesthetized with an overdose of pentobarbital, and tissues are rapidly removed and analyzed for sorbitol and fructose.

Sorbitol levels are analyzed according to the method of Donald M. Eades et al., "Rapid Analysis of Sorbitol, Galactitol, Mannitol and Myoinositol Mixtures From Biological Sources", *Journal of Chromatography*, 490, 1–8, (1989).

Fructose in rat tissues is enzymatically measured using a modification of the method of Ameyama (*Methods in Enzymology*, 89:20–29, 1982), in which ferricyanide was replaced by resazurin, a dye that is reduced to the highly fluorescent resorufin. The amount of resorufin fluorescence is stoichiometric with the amount of fructose oxidized by fructose dehydrogenase. The assay contains 0.1 ml neutralized 6% perchloric acid nerve extract in a final volume of 1.5 ml. Following incubation for 60 minutes at room temperature in a closed drawer, sample fluorescence is determined at excitation=560 nm, emission=580 nm with slits of 5 mm each in a Perkin-Elmer model 650-40 fluorescence spectrophotometer. Fructose concentrations are calculated by comparison with a series of known fructose standards.

Measurement of SDH Activity

Male Sprague-Dawley rats (350–400 g) are used for these experiments. Diabetes is induced in some of the rats by a tail vein injection of streptozocin, 85 mg/kg. Twenty-four hours later, 4 groups of diabetic rats are given a single dose of the test compound of formula I of this invention (0.001 to 100 mg/kg) by oral gavage. Animals are sacrificed 4–6 hours after dosing and blood and sciatic nerves are harvested. Tissues and cells are extracted with 6% perchloric acid.

Sorbitol in erythrocytes and nerves is measured by a modification of the method of R. S. Clements et al. (Science, 166: 1007–8, 1969). Aliquots of tissue extracts are added to an assay system which has final concentrations of reagents of 0.033 M glycine, pH 9.4, 800 mM β-nicotine adenine dinucleotide, and 4 units/ml of sorbitol dehydrogenase. After incubation for 30 minutes at room temperature, sample fluorescence is determined on a fluorescence spectrophotometer with excitation at 366 nm and emission at 452 nm. After subtracting appropriate blanks, the amount of sorbitol in each sample is determined from a linear regression of sorbitol standards processed in the same manner as the tissue extracts.

Fructose is determined by a modification of the method described by M. Ameyama, *Methods in Enzymology*, 89: 20–25 (1982). Resazurin is substituted for ferricyanide. Aliquots of tissue extracts are added to the assay system, which has final concentrations of reagents of 1.2 M citric acid, pH 4.5, 13 mM resazurin, 3.3 units/ml of fructose dehydrogenase and 0.068% Triton X-100. After incubation for 60 minutes at room temperature, sample fluorescence is determined on a fluorescence spectrophotometer with excitation at 560 nm and emission at 580 nm. After subtracting appropriate blanks, the amount of fructose in each sample is determined from a linear regression of fructose standards processed in the same manner as the tissue extracts.

SDH activity is measured by a modification of the method described by U. Gerlach, *Methodology of Enzymatic Analyses*, edited by H. U. Bergmeyer, 3, 112–117 (1983). Aliquots of sera or urine are added to the assay system, which has final concentrations of reagents of 0.1 M potassium phosphate buffer, pH 7.4, 5 mM NAD, 20 mM sorbitol, and 0.7 units/ml of sorbitol dehydrogenase. After incubation for 10 minutes at room temperature, the average change in sample absorbance is determined at 340 nm. SDH activity was presented as milliOD$_{340}$ units/minute (OD$_{340}$=optical density at 340 nm).

Glycogen Phosphorylase Inhibitor Assays

The three different purified glycogen phosphorylase (GP) isoenzymes, wherein glycogen phosphorylase is in the activated "a" state (referred to as glycogen phosphorylase a, or the abbreviation GPa), and referred to here as human liver glycogen phosphorylase a (HLGPa), human muscle glycogen phosphorylase a (HMGPa), and human brain glycogen phosphorylase a (HBGPa), can be obtained by the following procedures.

Expression and Fermentation

The HLGP and HMGP cDNAs are expressed from plasmid pKK233-2 (Pharmacia Biotech. Inc., Piscataway, N.J.) in *E. coli* strain XL-1 Blue (Stratagene Cloning Systems, LaJolla, Calif.). The strain is inoculated into LB medium (consisting of 10 g tryptone, 5 g yeast extract, 5 g NaCl, and 1 ml 1 N NaOH per liter) plus 100 mg/L ampicillin, 100 mg/L pyridoxine and 600 mg/L MnCl$_2$ and grown at 37° C. to a cell density of OD$_{550}$=1.0. At this point, the cells are induced with 1 mM isopropyl-1-thio-β-D-galactoside (IPTG). Three hours after induction the cells are harvested by centrifugation and cell pellets are frozen at −70° C. until needed for purification.

The HBGP cDNA can be expressed by several methodologies, for example, by the method described by Crerar, et al. (J. Biol. Chem. 270:13748–13756). The method described by Crerar, et al. (J. Biol. Chem. 270:13748–13756) for the expression of HBGP is as follows: the HBGP cDNA can be expressed from plasmid pTACTAC in *E. Coli* strain 25A6. The strain is inoculated into LB medium (consisting of 10 g tryptone, 5 g yeast extract, 5 g NaCl, and 1 ml 1 N NaOH per liter) plus 50 mg/L ampicillin and grown overnight, then resuspended in fresh LB medium plus 50 mg/L ampicillin, and reinoculated into a 40× volume of LB/amp media containing 250 μM isopropyl-1-thio-β-D-galactoside (IPTG), 0.5 mM pyridoxine and 3 mM MgCl$_2$ and grown at 22° C. for 48–50 hours. The cells can then be harvested by centrifugation and cell pellets are frozen at −70° C. until needed for purification.

The HLGP cDNA is expressed from plasmid pBlueBac III (Invitrogen Corp., San Diego, Calif.) which is cotransfected with BaculoGold Linear Viral DNA (Pharmingen, San Diego, Calif.) into Sf9 cells. Recombinant virus is subsequently plaque-purified. For production of protein, Sf9 cells grown in serum-free medium are infected at a multiplicity of infection (moi) of 0.5 and at a cell density of 2×10$^6$ cells/ml. After growth for 72 hours at 27° C., cells are centrifuged, and the cell pellets frozen at −70° C. until needed for purification. Purification of Glycogen Phosphorylase expressed in *E. coli*

The *E. coli* cells in pellets described above are resuspended in 25 mM β-glycerophosphate (pH 7.0) with 0.2 mM DTT, 1 mM MgCl$_2$, plus the following protease inhibitors:

| | |
|---|---|
| 0.7 μg/mL | Pepstatin A |
| 0.5 μg/mL | Leupeptin |
| 0.2 mM | phenylmethylsulfonyl fluoride (PMSF), and |
| 0.5 mM | EDTA, | lysed by pretreatment with 200 μg/mL lysozyme and 3 μg/mL DNAase followed by sonication in 250 mL batches for 5×1.5 minutes on ice using a Branson Model 450 ultrasonic cell disrupter (Branson Sonic Power Co., Danbury Conn.). The *E. coli* cell lysates are then cleared by centrifugation at 35,000×g for one hour followed by filtration through 0.45 micron filters. GP in the soluble fraction of the lysates (estimated to be less than 1% of the total protein) is purified by monitoring the enzyme activity (as described in GPa Activity Assay section, below) from a series of chromatographic steps detailed below.

Immobilized Metal Affinity Chromatography (IMAC)

This step is based on the method of Luong et al (Luong et al. Journal of Chromatography (1992) 584, 77–84.). 500 mL of the filtered soluble fraction of cell lysates (prepared from approximately 160–250 g of original cell pellet) are loaded onto a 130 mL column of IMAC Chelating-Sepharose (Pharmacia LKB Biotechnology, Piscataway, N.J.) which has been charged with 50 mM CuCl$_2$ and 25 mM β-glycerophosphate, 250 mM NaCl and 1 mM imidazole at pH 7 equilibration buffer. The column is washed with equilibration buffer until the A$_{280}$ returns to baseline. The sample is then eluted from the column with the same buffer containing 100 mM imidazole to remove the bound GP and other bound proteins. Fractions containing the GP activity are pooled (approximately 600 mL), and ethylenediaminetetraacetic acid (EDTA), DL-dithiothreitol (DTT), phenylmethylsulfonyl fluoride (PMSF), leupeptin and pepstatin A are added to obtain 0.3 mM, 0.2 mM, 0.2 mM, 0.5 μg/mL and 0.7 μg/mL concentrations respectively. The pooled GP is desalted over a Sephadex G-25 column (Sigma Chemical Co., St. Louis, Mo.) equilibrated with 25 mM Tris-HCl (pH 7.3), 3 mM DTT buffer (Buffer A) to remove imidazole and is stored on ice until the second chromatographic step.

5'-AMP-Sepharose Chromatography

The desalted pooled GP sample (approximately 600 mL) is next mixed with 70 mL of 5'-AMP Sepharose (Pharmacia LKB Biotechnology, Piscataway, N.J.) which has been equilibrated with Buffer A (see above). The mixture is gently agitated for one hour at 22° C. then packed into a column and washed with Buffer A until the A$_{280}$ returns to baseline. GP and other proteins are eluted from the column with 25 mM Tris-HCl, 0.2 mM DTT and 10 mM adenosine 5'-monophosphate (AMP) at pH 7.3 (Buffer B). GP-containing fractions are pooled following identification by determining enzyme activity (described below) and visualizing the M$_r$ approximately 97 kdal GP protein band by sodium dodecyl sulfate polyacrylamide gel electrophoresis (SDS-PAGE) followed by silver staining (2D-silver Stain II "Daiichi Kit", Daiichi Pure Chemicals Co., LTD., Tokyo, Japan) and then pooled. The pooled GP is dialyzed into 25 mM β-glycerophosphate, 0.2 mM DTT, 0.3 mM EDTA, 200 mM NaCl, pH 7.0 buffer (Buffer C) and stored on ice until use.

Prior to use of the GP enzyme, the enzyme is converted from the inactive form as expressed in *E. coli* strain XL-1 Blue (designated GPb) (Stragene Cloning Systems, La Jolla, Calif.), to the active form (designated GPa) by the procedure described in Section (A) Activation of GP below.

Purification of Glycogen Phosphorylase Expressed in Sf9 Cells

The Sf9 cells in pellets described above are resuspended in 25 mM β-glycerophosphate (pH 7.0) with 0.2 mM DTT, 1 mM MgCl$_2$, plus the following protease inhibitors:

| | |
|---|---|
| 0.7 μg/mL | Pepstatin A |
| 0.5 μg/mL | Leupeptin |
| 0.2 mM | phenylmethylsulfonyl fluoride (PMSF), and |
| 0.5 mM | EDTA. | lysed by pretreatment with 3 μg/mL DNAase followed by sonication in batches for 3×1 minutes on ice using a Branson Model 450 ultrasonic cell disrupter (Branson Sonic Power Co., Danbury Conn.). The Sf9 cell lysates are then cleared by centrifugation at 35,000×g for one hour followed by filtration through 0.45 micron filters. GP in the soluble fraction of the lysates (estimated to be 1.5% of the total protein) is purified by monitoring the enzyme activity (as described in GPa Activity Assay section, below) from a series of chromatographic steps detailed below.

Immobilized Metal Affinity Chromatography (IMAC)

Immobilized Metal Affinity Chromatography is performed as described in the section above. The pooled, desalted GP is then stored on ice until further processed.

Activation of GP

Before further chromatography, the fraction of inactive enzyme as expressed in Sf9 cells (designated GPb) is converted to the active form (designated GPa) by the following procedure described in Section (A) Activation of GP below.

Anion Exchange Chromatography

Following activation of the IMAC purified GPb to GPa by reaction with the immobilized phosphorylase kinase, the pooled GPa fractions are dialyzed against 25 mM Tris-HCl, pH 7.5, containing 0.5 mM DTT, 0.2 mM EDTA, 1.0 mM phenylmethylsulfonyl fluoride (PMSF), 1.0 μg/mL leupeptin and 1.0 μg/mL pepstatin A. The sample is then loaded onto a MonoQ Anion Exchange Chromatography column (Pharmacia Biotech. Inc., Piscataway, N.J.). The column is washed with equilibration buffer until the A$_{280}$ returns to baseline. The sample is then eluted from the column with a linear gradient of 0–0.25 M NaCl to remove the bound GP and other bound proteins. GP-containing fractions elute between 0.1–0.2 M NaCl range, as detected by monitoring the eluant for peak protein absorbance at A$_{280}$. The GP protein is then identified by visualizing the M$_r$ approximately 97 kdal GP protein band by sodium dodecyl sulfate polyacrylamide gel electrophoresis (SDS-PAGE) followed by silver staining (2D-silver Stain II "Daiichi Kit", Daiichi Pure Chemicals Co., LTD., Tokyo, Japan) and then pooled. The pooled GP is dialyzed into 25 mM N,N-bis[2-Hydroxyethyl]-2-aminoethanesulfonic acid, 1.0 mM DTT, 0.5 mM EDTA, 5 mM NaCl, pH 6.8 buffer and stored on ice until use.

Determination of GP Enzyme Activity

A) Activation of GP: Conversion of GPb to GPa

Prior to the determination of GP enzyme activity, the enzyme is converted from the inactive form as expressed in *E. coli* strain XL-1 Blue (designated GPb) (Stragene Cloning Systems, La Jolla, Calif.), to the active form (designated GPa) by phosphorylation of GP using phosphorylase kinase as follows. The fraction of inactive enzyme as expressed in Sf9 cells (designated GPb) is also converted to the active form (designated GPa) by the following procedure.

GP Reaction with Immobilized Phosphorylase Kinase

Phosphorylase kinase (Sigma Chemical Company, St. Louis, Mo.) is immobilized on Affi-Gel 10 (BioRad Corp., Melvile, N.Y.) as per the manufacturer's instructions. In brief, the phosphorylase kinase enzyme (10 mg) is incubated with washed Affi-Gel beads (1 mL) in 2.5 mL of 100 mM HEPES and 80 mM CaCl$_2$ at pH 7.4 for 4 hours at 4° C. The Affi-Gel beads are then washed once with the same buffer prior to blocking with 50 mM HEPES and 1 M glycine methyl ester at pH 8.0 for one hour at room temperature. Blocking buffer is removed and replaced with 50 mM HEPES (pH 7.4), 1 mM β-mercaptoethanol and 0.2% NaN$_3$ for storage. Prior to use to convert GPb to GPa, the Affi-Gel immobilized phosphorylase kinase beads are equilibrated by washing in the buffer used to perform the kinase reaction, consisting of 25 mM β-glycerophosphate, 0.3 mM DTT, and 0.3mM EDTA at pH 7.8 (kinase assay buffer).

The partially purified, inactive GPb obtained from 5'-AMP-Sepharose chromatography above (from *E. coli*) or the mixture of GPa and GPb obtained from IMAC above (from Sf9 cells) is diluted 1:10 with the kinase assay buffer then mixed with the aforementioned phosphorylase kinase enzyme immobilized on the Affi-Gel beads. NaATP is added to 5 mM and MgCl$_2$ to 6 mM. The resulting mixture is mixed gently at 25° C. for 30 to 60 minutes. The sample is removed from the beads and the percent activation of GPb by conversion to GPa is estimated by determining GP enzyme activity in the presence and absence of 3.3 mM AMP. The percentage of total GP enzyme activity due to GPa enzyme activity (AMP-independent) is then calculated as follows:

$$\% \text{ of total } HLGPa = \frac{HLGP \text{ activity} - AMP}{HLGP \text{ activity} + AMP}$$

Alternately, the conversion of GPb to GPa can be monitored by isoelectric focusing, based on the shift in electrophoretic mobility that is noted following conversion of GPb to GPa. GP samples are analyzed by isoelectric focusing (IEF) utilizing the Pharmacia PfastGel System (Pharmacia Biotech. Inc., Piscataway, N.J.) using precast gels (pI range 4–6.5) and the manufacturer's recommended method. The resolved GPa and GPb bands are then visualized on the gels by silver staining (2D-silver Stain II "Daiichi Kit", Daiichi Pure Chemicals Co., LTD., Tokyo, Japan). Identification of GPa and GPb is made by comparison to E. coli derived GPa and GPb standards that are run in parallel on the same gels as the experimental samples.

B) GPa Activity Assay

The disease/condition treating/preventing activities described herein of the glycogen phosphorylase inhibitor compounds of this invention can be indirectly determined by assessing the effect of the compounds of this invention on the activity of the activated form of glycogen phosphorylase (GPa) by one of two methods; glycogen phosphorylase a activity is measured in the forward direction by monitoring the production of glucose-1-phosphate from glycogen or by following the reverse reaction, measuring glycogen synthesis from glucose-1-phosphate by the release of inorganic phosphate. All reactions can be run in triplicate in 96-well microtiter plates and the change in absorbance due to formation of the reaction product is measured at the wavelength specified below in a MCC/340 MKII Elisa Reader (Lab Systems, Finland), connected to a Titertech Microplate Stacker (ICN Biomedical Co, Huntsville, Ala.).

To measure the GPa enzyme activity in the forward direction, the production of glucose-1-phosphate from glycogen is monitored by the multienzyme coupled general method of Pesce et al. [Pesce, M. A., Bodourian, S. H., Harris, R. C. and Nicholson, J. F. (1977) Clinical Chemistry 23, 1711–1717] modified as follows: 1 to 100 µg GPa, 10 units phosphoglucomutase and 15 units glucose-6-phosphate dehydrogenase (Boehringer Mannheim Biochemicals, Indianapolis, Ind.) are diluted to 1 mL in Buffer A (described hereinafter). Buffer A is at pH 7.2 and contains 50 mM HEPES, 100 mM KCl, 2.5 mM ethyleneglycoltetraacetic acid (EGTA), 2.5 mM $MgCl_2$, 3.5 mM $KH_2PO_4$ and 0.5 mM dithiothreitol. 20 µl of this stock is added to 80 µl of Buffer A containing 0.47 mg/mL glycogen, 9.4 mM glucose, 0.63 mM of the oxidized form of nicotinamide adenine dinucleotide phosphate (NADP+). The compounds to be tested are added as 5 µL of solution in 14% dimethylsulfoxide (DMSO) prior to the addition of the enzymes. The basal rate of GPa enzyme activity in the absence of inhibitors is determined by adding 5 µL of 14% DMSO and a fully-inhibited rate of GPa enzyme activity is obtained by adding 20 µL of 50 mM of the positive control test substance, caffeine. The reaction is followed at room temperature by measuring the conversion of oxidized NADP+ to reduced NADPH at 340 nm.

To measure the GPa enzyme activity in the reverse direction, the conversion of glucose-1-phosphate into glycogen plus inorganic phosphate is measured by the general method described by Engers et al. [Engers, H. D., Shechosky, S. and Madsen, N. B. (1970) Can. J. Biochem. 48, 746–754] modified as follows: 1 to 100 µg GPa is diluted to 1 mL in Buffer B (described hereinafter). Buffer B is at pH 7.2 and contains 50 mM HEPES, 100 mM KCl, 2.5 mM EGTA, 2.5 mM $MgCl_2$ and 0.5 mM dithiothreitol. 20 µL of this stock is added to 80 µL of Buffer B with 1.25 mg/mL glycogen, 9.4 mM glucose, and 0.63 mM glucose-1-phosphate. The compounds to be tested are added as 5 µL of solution in 14% DMSO prior to the addition of the enzyme. The basal rate of GPa enzyme activity in the absence of added inhibitors is determined by adding 5 µL of 14% DMSO and a fully-inhibited rate of GPa enzyme activity is obtained by adding 20 µL of 50 mM caffeine. This mixture is incubated at room temperature for 1 hour and the inorganic phosphate released from the glucose-1-phosphate is measured by the general method of Lanzetta et al. [Lanzetta, P. A., Alvarez, L. J., Reinach, P. S. and Candia, O. A. (1979) Anal. Biochem. 100, 95–97] modified as follows: 150 µL of 10 mg/mL ammonium molybdate, 0.38 mg/mL malachite green in 1 N HCl is added to 100 µL of the enzyme mix. After a 20 minute incubation at room temperature, the absorbance is measured at 620 nm.

The above assays carried out with a range of concentrations of test compound allows the determination of an $IC_{50}$ value (concentration of test compound required for 50% inhibition) for the in vitro inhibition of GPa enzyme activity by that test compound.

Administration of the compounds of this invention can be via any method which delivers a compound of this invention preferentially to the desired tissue (e.g., liver and/or cardiac tissues). These methods include oral routes, parenteral, intraduodenal routes, etc. Generally, the compounds of the present invention are administered in single (e.g., once daily) or multiple doses or via constant infusion.

The compounds of this invention are useful, for example, in reducing or minimizing damage effected directly to any tissue that may be susceptible to either ischemia/reperfusion injury or injury resulting from hypoxia (e.g., heart, brain, lung, kidney, liver, gut, skeletal muscle, retina) as the result of an ischemic or hypoxic event (e.g., myocardial infarction). The active compound is therefore usefully employed prophylactically to prevent, i.e. (prospectively or prophylactically) to blunt or stem, tissue damage (e.g., myocardial tissue) in patients who are at risk for ischemia or hypoxia (e.g., myocardial ischemia).

Generally, the compounds of this invention are administered orally, or parenterally (e.g., intravenously, intramuscularly, subcutaneously or intramedullary). Topical administration may also be indicated, for example, where the patient is suffering from gastrointestinal disorders or whenever the medication is best applied to the surface of a tissue or organ as determined by the attending physician.

The amount and timing of compounds administered will, of course, be dependent on the subject being treated, on the severity of the affliction, on the manner of administration and on the judgment of the prescribing physician. Thus, because of patient to patient variability, the dosages given below are a guideline and the physician may titrate doses of the drug to achieve the treatment that the physician considers appropriate for the patient. In considering the degree of treatment desired, the physician must balance a variety of factors such as age of the patient, presence of preexisting disease, as well as presence of other diseases (e.g., cardiovascular disease).

Thus, for example, in one mode of administration the compounds of this invention may be administered just prior to surgery (e.g., within twenty-four hours before surgery, for example, cardiac surgery), during and/or subsequent to surgery (e.g., within twenty-four hours after surgery) where there is risk of ischemia (e.g., mycoardial ischemia). In another mode of administration, the compounds of this invention are administered with an initial loading dose (e.g., bolus injection or infusion) prior to surgery followed by a constant infusion prior to, during and post surgery. The compounds of this invention may also be administered in a chronic daily mode.

An amount of a compound of this invention is used that is effective for ischemic or hypoxic protection. A preferred dosage is about 0.001 to about 100 mg/kg/day of a compound of this invention. An especially preferred dosage is about 0.01 to about 50 mg/kg/day of a compound of this invention.

The compounds of the present invention are generally administered in the form of a pharmaceutical composition comprising at least one of the compounds of this invention together with a pharmaceutically acceptable vehicle or diluent. Thus, the compounds of this invention can be administered individually or together in any conventional oral, parenteral (e.g., intravenous, intramuscular injection), rectal or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions, for example, in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g., topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easter, Pa., 15th Edition (1975).

Pharmaceutical compositions according to the invention may contain, for example, 0.0001%–95% of the compound (s) of this invention. In any event, the composition or formulation to be administered will contain a quantity of a compound(s) according to the invention in an amount effective to treat the disease/condition of the subject being treated.

Advantageously, the present invention also provides kits for use by a consumer having, or at risk of having, a disease or condition resulting from, for example, ischemia or hypoxia, which can be ameliorated by an $A_3$ agonist. Such kits include a suitable dosage form such as an injectable parenteral solution particularly adapted for intravenous or intramuscular injection and instructions describing the method of using such dosage form to reduce the risk of tissue damage to the consumer. The instructions would direct the consumer or medical personnel to administer the parenteral solution according to administration modes known to those skilled in the art. Such kits could advantageously be packaged and sold in single or multiple parenteral kits units.

The two different compounds of the combination of this invention can be co-administered simultaneously or sequentially in any order, or as a single pharmaceutical composition comprising a compound of Formula I and an aldose reductase inhibitor as described above or a glycogen phosphorylase inhibitor as described above or a sorbitol dehydrogenase inhibitor or a cardiovascular agent.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of Formula I, a prodrug thereof or a salt of such compound or prodrug and a second compound as described above. The kit comprises a means for containing the separate compositions such as a container, a divided bottle or a divided foil packet. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . Second Week, Monday, Tuesday, . . . " etc. Other variations of memory aids will be readily apparent. A "daily dose" can be a single tablet or capsule or several pills or capsules to be taken on a given day. Also, a daily dose of Formula I compound can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory aid, so as to further facilitate compliance with the regimen. An example of such a memory aid is a mechanical counter which indicates the number of daily doses that has been dispensed. Another example of such a memory aid is a battery powered microchip memory coupled with a liquid crystal readout, or audible reminder signal which, for example, reads out the date that the last daily dose has been taken and/or reminds one when the next dose is to be taken.

The compounds of this invention generally will be administered in a convenient formulation. The following formulation examples are illustrative only and are not intended to limit the scope of the present invention.

In the formulations which follow, "active ingredient" means a compound(s) of this invention.

Formulation 1: Gelatin Capsules
Hard gelatin capsules are prepared using the following:

| Ingredient | Quantity (mg/capsule) |
|---|---|
| Active ingredient | 0.25–100 |
| Starch, NF | 0–650 |
| Starch flowable powder | 0–50 |
| Silicone fluid 350 centistokes | 0–15 |

A tablet formulation is prepared using the ingredients below:

Formulation 2: Tablets

| Ingredient | Quantity (mg/tablet) |
|---|---|
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–100 mg of active ingredients are made up as follows:

Formulation 3: Tablets

| Ingredient | Quantity (mg/tablet) |
|---|---|
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of active ingredient per 5 ml dose are made as follows:

Formulation 4: Suspensions

| Ingredient | Quantity (mg/5 ml) |
|---|---|
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The active ingredient is passed through a No. 45 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume. An aerosol solution is prepared containing the following ingredients:

Formulation 5: Aerosol

| Ingredient | Quantity (% by weight) |
|---|---|
| Active ingredient | 0.25 |
| Ethanol | 25.75 |
| Propellant 22 (Chlorodifluoromethane) | 74.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

Formulation 6: Suppositories

| Ingredient | Quantity (mg/suppository) |
|---|---|
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7: Intravenous Solution

| Ingredient | Quantity |
|---|---|
| Active ingredient | 25 mg–10,000 mg |
| Isotonic saline | 1,000 mL |

The solution of the above ingredients is intravenously administered to a patient.

The active ingredient above may also be a combination of agents.

General Experimental Procedures

NMR spectra were recorded on a Varian XL-300 (Varian Co., Palo Alto, Calif.), a Bruker AM-300 spectrometer (Bruker Co., Billerica, Mass.) or a Varian Unity 400 at about 23° C. at 300 or 400 MHz for proton. Chemical shifts are expressed in parts per million downfield from tetramethylsilane. The peak shapes are denoted as follows: s, singlet; d, doublet; t, triplet, q, quartet; m, multiplet; bs=broad singlet. Resonances designated as exchangeable did not appear in a separate NMR experiment where the sample was shaken with several drops of $D_2O$ in the same solvent. Atmospheric pressure chemical ionization mass spectra (APCIMS) were obtained on a Fisons Platform II Spectrometer. Chemical ionization mass spectra (CIMS) were obtained on a Hewlett-Packard 5989 instrument (Hewlett-Packard Co., Palo Alto, Calif.) (ammonia ionization, PBMS). Where the intensity of chlorine or bromine-containing ions are described the expected intensity ratio was observed (approximately 3:1 for $^{35}Cl/^{37}Cl$-containing ions and 1:1 for $^{79}Br/^{81}Br$-containing ions) and M is based on $^{35}Cl$ and $^{79}Br$. In some cases only representative $^1H$ NMR and APCIMS peaks are given.

Column chromatography was performed with either Baker Silica Gel (40 μm) (J.T. Baker, Phillipsburg, N.J.) or Silica Gel 60 (EM Sciences, Gibbstown, N.J.) in glass columns or in Flash 40™ or Flash 12™ (Biotage, Charlottesville, Va.) columns under nitrogen pressure. Radial Chromatography was performed using a Chromatron, (Harrison Research, Palo Alto, Calif.) Unless otherwise specified, reagents were used as obtained from commercial sources. Dimethylformamide, 2-propanol, tetrahydrofuran, and dichloromethane used as reaction solvents were the anhydrous grade supplied by Aldrich Chemical Company (Milwaukee, Wis.). Microanalyses were performed by Schwarzkopf Microanalytical Laboratory, Woodside, N.Y. The terms "concentrated" and "coevaporated" refer to removal of solvent at water aspirator pressure on a rotary evaporator with a bath temperature of less than 50° C. The abbreviation "min" and "h" stand for "minutes" and "hours" respectively and rt stands for room temperature.

Reference to the hydrochloride salt in the Example names below includes mono-or di-salts as appropriate in the particular Example.

EXAMPLE 1

BOC Cleavage (2S,3S,4R,5R)3-Amino-5-{6-[5-chloro-2-(3-methylisoxazol-5-ylmethoxy) benzylamino]purin-9-yl}-4-hydroxytetrahydrofuran-2-carboxylic acid methylamide.

(5-{6-[5-Chloro-2-(3-methylisoxazol-5-ylmethoxy) benzylamino]purin-9-yl}-4-hydroxy-2-methylcarbamoyltetrahydrofuran-3-yl)-carbamic add tert-butyl ester (1.0 mmol) was dissolved in anhydrous THF (10 mL). After adding $H_2O$ (10 mL) and then methanesulfonic add (1.5 mL, 15 mmol), the reaction was stirred for 6 h at 70° C. and then 15 h at room temperature. The organic solvent was removed by rotary evaporation and the remaining aqueous solution was neutralized to pH 7 with aqueous 1 N NaOH solution. The title compound then precipitated out and was recovered by filtration.

Mp 152.0–155.0° C.; $[\alpha]_{22}$=−30.5° (c=0.56, MeOH); $C_{23}H_{25}ClN_8O_5$. MW 528.96. MS 529.1 (M+H)$^+$.

$^1H$ NMR (400 MHz, DMSO-d$_6$) δ 8.57 (s, 1H); 8.45 (quart, 1H, J=4.6 Hz); 8.35 (bs, 1H); 8.19 (s, 1H); 7.23 (dd, 1H, J=8.5 Hz, J=2.4 Hz); 7.11 (d, 1H, J=8.5 Hz); 7.07 (bs, 1H); 6.48 (s, 1H); 5.99 (d, 1H, J=3.7 Hz); 5.87 (d, 1H, J=4.2 Hz); 5.29 (s, 2H); 4.62 (bs, 2H); 4.38–4.32 (mult, 1H); 4.08 (d, 1H, J=5.6 Hz); 3.58–3.51 (mult, 1H); 2.64 (d, 3H, J=4.6 Hz); 2.19 (s, 3H); 1.73 (bs, 2H).

EXAMPLE 2

Acetonide Cleavage (2S,3S,4R,5R)3-Amino-5-{6-[5-chloro-2-(3,4,5,6-tetrahydroxytetrahydropyran-2-ylmethoxy)benzylamino]purin-9-yl}-4-hydroxytetrahydrofuran-2-carboxylic acid methylamide:

To a solution of 3-amino-5-{6-[5-chloro-2-(2,2,7,7-tetramethyltetrahydro-bis[1,3]dioxolo[4,5-b;4',5'-d]pyran-5-ylmethoxy) benzylamino]purin-9-yl}-4-hydroxytetrahydrofuran-2-carboxylic acid methylamide (59 mg, 0.09 mmol) in chloroform (7 mL) was added trifluoroacetic acid (0.7 mL). This reaction was stirred under anhydrous conditions at room temperature for 2 h. After this time period water was added (10 mL) and the reaction was stirred at room temperature for 5 days. The solvent was removed with a rotary evaporator and the resulting solid was then triturated with $Et_2O$ to afford the title compound as a beige powder (60 mg). Mp 212.0–218.0° C. $C_{24}H_{30}ClN_7O_9$. MW 596.00. MS 596.1 (M+H)$^+$.

$^1H$ NMR (400 MHz, DMSO-d$_6$) δ 8.52–8.36 (mult, 5H): 8.35–8.24 (mult, 1H); 8.13 (s, 1H); 7.25–7.16 (mult, 1H); 7.10–6.90 (mult, 2H); 6.88–6.78 (mult, 1H); 6.21–6.16 (mult, 1H); 5.2–4.4 (mult, 2H); 5.02–4.88 (mult, 2H); 4.71–4.59 (mult, 2H); 4.53 (d, 1H, J=5.0 Hz); 4.30 (d, 1H, J=6.8 Hz); 4.26–4.20 (mult, 1H); 4.20–4.11 (mult, 1H); 4.10–3.99 (mult, 1H); 3.95–3.88 (mult, 1H); 3.84–3.76 (mult, 1H); 3.62–3.55 (mult, 1H); 3.34–3.25 (mult, 1H); 2.61 (d, 3H, J=4.4 Hz).

EXAMPLE 3

Reduction of Azide (2S,3S,4R,5R)3-Amino-5-[6-(2-benzyloxy-5-chlorobenzylamino)-purin-9-yl]-4-hydroxytetrahydrofuran-2-carboxylic acid methylamide.

(2S,3S,4R,6R)-3-Azido-5-[6-(2-benzyloxy-5-chlorobenzylamino)purin-9-yl-4-hydroxy tetrahydrofuran-2-carboxylic acid methyl amide (456 mg, 0.83 mmol) was dissolved in anhydrous THF (50 mL) and the reaction cooled to 0° C. After adding triphenylphosphine (304 mg, 1.2 mmol), the reaction was stirred for 30 minutes at 0° C. At the end of this time period, concentrated ammonium hydroxide (0.4 mL) and water (0.5 mL) were added and the reaction was allowed to slowly come to room temperature and stirred at room temperature for 15 h. The solvent was then removed by rotary evaporation and the product was preadsorbed onto silica gel and purified by flash chromatography ($SiO_2$, 5% then 18% methanol/$CH_2Cl_2$) to afford the title compound as a colorless solid.

Mp 114.2–115.2° C.

$[\alpha]_{22}$=−34.34° (c=0.265, MeOH);

$C_{25}H_{26}ClN_7O_4$. MW 523.98. MS 524.1 (M+H)$^+$.

$^1H$ NMR (400 MHz, DMSO) δ 8.58 (s, 1H); 8.47 (quart, 1H, J=4.6 Hz); 8.35 (bs, 1H); 8.22 (s, 1H); 7.48–7.46 (mult, 2H); 7.38–7.33 (mult, 2H); 7.33–7.25 (mult, 1H); 7.25–7.20 (mult, 1H); 7.10–7.05 (mult, 2H); 6.01 (d, 1H, J=3.9 Hz); 5.95–5.85 (mult, 1H); 5.17 (s, 2H); 4.85–4.75 (mult, 2H); 4.38–4.34 (mult, 1H); 4.11 (d, 1H, J=5.8 Hz); 3.56 (t, 1H, J=5.8 Hz); 2.66 (d, 3H, J=4.6 Hz); 1.9–1.7 (mult, 2H).

The following compounds, Examples 4–93 were prepared by analogous procedures to the immediately preceding Example 3.

EXAMPLE 4

(2S,3S,4R,5R)3-Amino-5-{6-[5-chloro-2-(2-morpholin-4-ylethoxy)benzylamino]-purin-9-yl}-4-hydroxytetrahydrofuran-2-carboxylic acid methylamide.

Mp 99.0–108.0° C.

$[\alpha]_{22}$=−29.64° (c=0.280, MeOH).

$C_{24}H_{31}ClN_8O_5$. MW 547.02. MS 547.2 (M+H)$^+$.

$^1$H NMR (400 MHz, DMSO-d$_6$) δ 8.57 (s, 1H); 8.45 (quart, 1H, J=4.6 Hz); 8.28 (bs, 1H); 8.21 (s, 1H); 7.22 (dd, 1H, J=8.7 Hz, J=2.4 Hz); 7.05 (bs, 1H); 7.01 (d, 1H, J=8.7 Hz); 6.02 (d, 1H, J=3.7 Hz), 6.05–5.80 (mult, 1H); 4.63 (bs, 2H); 4.40–4.30 (mult, 1H); 4.12 (t, 3H, J=5.5 Hz); 3.55–3.50 (mult, 5H); 2.70–2.60 (mult, 5H); 2.55–2.45 (mult, 4H); 2.25–1.95 (mult, 2H).

EXAMPLE 5

(2S,3S,4R,5R)-Amino-5-[6-(5-chloro-2-cyclobutylmethoxybenzylamino)-purin-9-yl]-4-hydroxytetrahydrofuran-2-carboxylic acid methylamide.

Mp 107.0–117.0° C.

$[\alpha]_{21.5}$=−31.28° (c=0.390, MeOH).

$C_{23}H_{28}ClN_7O_4$. MW 501.98. MS 501.9 (M+H)$^+$.

$^1$H NMR (400 MHz, DMSO-d$_6$) δ 8.55 (s, 1H); 8.45–8.40 (mult, 1H); 8.25 (bs, 1H); 8.19 (s, 1H); 7.18 (dd 1H, J=8.5 Hz, J=2.7 Hz); 7.05–7.00 (mult, 1H); 6.95 (d, 1H, J=8.5 Hz); 5.99 (d, 1H, J=3.7 Hz); 5.90–5.80 (mult, 1H); 4.65–4.60 (mult, 2H); 4.35–4.30 (mult, 1H); 4.09 (d, 1H, J=5.8 Hz); 3.95 (d, 2H, J=6.2 Hz); 3.53 (t, 1H, J=5.8 Hz); 2.75–2.65 (mult, 1H); 2.63 (d, 3H, J=4.6 Hz); 2.05–1.95 (mult, 2H); 1.90–1.80 (mult; 4H); 1.80–1.70 (mult, 2H).

EXAMPLE 6

(2S,3S,4R,5R)-3-Amino-5-{6-[5-chloro-2-(3-methoxy-benzyloxy)-benzylamino]-purin-9-yl}-4-hydroxytetrahydrofuran-2-carboxylic acid methylamide Mp 102.0–108.0° C.

$[\alpha]_{21.5}$=−28.89° (c=0.450, MeOH).

$C_{26}H_{28}ClN_7O_5$. MW 554.01. MS 553.8 (M+H)$^+$.

$^1$H NMR (400 MHz, DMSO-d$_6$) δ 8.56 (s, 1H); 8.46 (quart, 1H, J=4.4 Hz); 8.35 (bs, 1H); 8.20 (s, 1H); 7.26 (t, 1H, J=8.1 Hz); 7.25 (dd, 1H, J=8.8 Hz, J=2.6 Hz); 7.10–7.05 (mult, 1H); 7.05–7.00 (mult, 3H); 6.84 (d, 1H, J=7.3 Hz); 5.99 (d, 1H, J=3.7 Hz); 5.95–5.85 (mult, 1H); 5.13 (s, 2H); 4.75–4.65 (mult, 2H); 4.37–4.30 (mult, 1H); 4.09 (d, 1H, J=5.6 Hz); 3.71 (s, 3H); 3.54 (t, 1H, J=4.9 Hz); 2.64 (d, 3H, J=4.4 Hz); 1.80–1.75 (mult, 2H).

EXAMPLE 7

(2S,3S,4R,5R)3-Amino-5-{6-[5-chloro-2-(2,5-dimethoxy-benzyloxy)-benzylamino]-purin-9-yl}-4-hydroxytetrahydrofuran-2-carboxylic acid methylamide Mp 112.0–115.0° C.

$[\alpha]_{21.5}$=−30.48° (c=0.420, MeOH).

$C_{27}H_{30}ClN_7O_6$. MW 584.04. MS 583.8 (M+H)$^+$.

$^1$H NMR (400 MHz, DMSO-d$_6$) δ 8.59 (s, 1H); 8.50 (quart, 1H, J=3.7 Hz); 8.37 (bs, 1H); 8.22 (s, 1H); 7.22 (dd, 1H, J=8.9 Hz, J=2.7 Hz); 7.10–7.05 (mult, 1H); 7.05–7.00 (mult, 2H); 6.97 (d, 1H, J=8.9 Hz); 6.86 (dd, 1H, J=8.9 Hz, J=2.7 Hz); 6.02 (d, 1H, J=3.9 Hz); 5.95–5.90 (mult, 1H); 5.10 (s, 2H); 4.75–4.65 (mult, 2H); 4.40–4.35 (mult, 1H); 4.12 (d, 1H, J=5.4 Hz); 3.78 (s, 3H); 3.67 (s, 3H); 3.60–3.55 (mult, 1H); 2.67 (d, 3H, J=3.7 Hz); 1.85–1.75 (mult, 2H).

EXAMPLE 8

(2S,3S,4R,5R)3-Amino-5-{6-[5-chloro-2-(3-chloro-benzyloxy)-benzylamino]-purin-9-yl}-4-hydroxytetrahydrofuran-2-carboxylic acid methylamide Mp 85.0–90.0° C.

$C_{25}H_{25}Cl_2N_7O_4$. MW 558.43. MS 557.8 (M+H)$^+$.

$^1$H NMR (400 MHz, DMSO-d$_6$) δ 8.59 (s, 1H); 8.48 (quart, 1H, J=4.8 Hz); 8.40 (bs, 1H); 8.24 (s, 1H); 7.55 (s, 1H); 7.50–7.35 (mult, 3H); 7.24 (dd, 1H, J=8.7 Hz, J=2.7 Hz); 7.17–7.12 (bs, 1H); 7.05 (d, 1H, J=8.7 Hz); 6.02 (d, 1H, J=3.9 Hz); 5.95–5.85 (mult, 1H); 5.21 (s, 2H); 4.75–4.65 (mult, 2H); 4.40–4.35 (mult, 1H); 4.12 (d, 1H, J=5.8 Hz); 3.57 (t, 1H, J=5.8 Hz); 2.67 (d, 3H, J=4.8 Hz); 1.85–1.75 (mult, 2H).

EXAMPLE 9

(2S,3S,4R,5R)3Amino-5-{6-[5-chloro-2-(4-chloro-benzyloxy)-benzylamino]-purin-9-yl}-4-hydroxytetrahydrofuran-2-carboxylic acid methylamide Mp 88.0–92.0° C.

$[\alpha]_{24}$=−19.63° (c=0.275, DMSO).

$C_{25}H_{25}Cl_2N_7O_4$. MW 558.43. MS 558.1 (M+H)$^+$.

$^1$H NMR (300 MHz, DMSO-d$_6$) δ 8.61 (s, 1H); 8.49 (quart, 1H, J=4.4 Hz); 8.39 (bs, 1H); 8.24 (s, 1H); 7.53 (d, 2H, J=8.9 Hz); 7.45 (d, 2H J=8.9 Hz); 7.23 (dd, 1H, J=8.7 Hz, J=3.6 Hz); 7.09 (bs, 1H); 7.02 (d, 1H, J=8.7 Hz); 6.04 (d, 1H, J=6.3 Hz); 5.95–5.87 (mult, 1H); 5.19 (s, 2H); 4.75–4.68 (mult, 2H); 4.41–4.36 (mult, 1H); 4.13 (d, 1H, J=5.1 Hz); 3.58 (t, 1H, J=5.1 Hz); 2.68 (d, 3H, J=4.4 Hz); 1.91 to 1.77 (mult, 2H).

EXAMPLE 10

(2S,3S,4R,5R)3-Amino-5-{6-[5-chloro-2-(2-chloro-benzyloxy)-benzylamino]-purin-9-yl}-4-hydroxytetrahydrofuran-2-carboxylic acid methylamide Mp 88.0–92.0° C.

$[\alpha]_{24}$=−16.67° (c=0.36, DMSO).

$C_{25}H_{25}Cl_2N_7O_4$. MW 558.43. MS 558.1 (M+H)$^+$.

$^1$H NMR (300 MHz, DMSO-d$_6$) δ 8.60 (s, 1H); 8.49 (quart, 1H, J=4.6 Hz); 8.36 (bs, 1H); 8.23 (s, 1H); 7.70–7.65 (mult, 1H); 7.55–7.50 (mult, 1H); 7.42–7.36 (mult, 2H); 7.27 (dd, 1H, J=8.5 Hz, J=2.6 Hz); 7.17–7.09 (mult, 1H); 6.03 (d, 1H, J=4.4 Hz); 5.95–5.88 (mult, 1H); 5.24 (s, 2H); 4.79–4.67 (mult, 2H); 4.40–4.36 (mult, 1H); 4.15 (d, 1H, J=6.3 Hz); 3.58 (t, 1H, J=6.3 Hz); 2.67 (d, 3H, J=4.6 Hz); 1.87–1.77 (mult, 2H).

EXAMPLE 11

(2S,3S,4R,5R)3-Amino-5-{6-[5-chloro-2-(tetrahydrofuran-3-ylmethoxy)-benzylamino]-purin-9yl}-4-hydroxytetrahydrofuran-2-carboxylic acid methylamide Mp 114.0–118.0° C.

$C_{23}H_{28}ClN_7O_5$. MW 517.98. MS 518.0 (M+H)$^+$.

$^1$H NMR (400 MHz, DMSO-d$_6$) δ 8.58 (s, 1H); 8.47 (d, 1H, J=4.4 Hz); 8.31 (bs, 1H); 8.22 (s, 1H); 7.21 (dd, 1H, J=8.5 Hz, J=2.7 Hz); 7.06 (bs, 1H); 6.99 (d, 1H, J=8.7 Hz); 6.01 (d, 1H, J=3.9 Hz); 5.89 (bs, 1H); 4.64 (bs, 2H); 4.36 (bs, 1H); 4.11 (d, 1H, J=5.6 Hz); 4.00–3.87 (mult, 2H); 3.80–3.70 (mult, 2H); 3.67–3.60 (mult, 1H); 3.59–3.50 (mult, 2H); 2.66 (d, 3H, J=4.4 Hz); 2.60 (bs, 1H); 2.04–1.96 (mult, 1H); 1.78 (bs, 2H); 1.74–1.62 (mult, 1H).

EXAMPLE 12

(2S,3S,4R,5R)3-Amino-5-{6-[5-chloro-2-(4-methyl-benzyloxy)-benzylamino]-purin-9-yl}-4-hydroxytetrahydrofuran-2-carboxylic acid methylamide Mp 82.0–86.0° C.

$C_{26}H_{28}ClN_7O_4$. MW 538.01. MS 538.2 (M+H)$^+$.

¹H NMR (400 MHz, DMSO-d₆) δ 8.58 (bs, 1H); 8.48 (quart, 1H, J=4.8 Hz); 8.36 (bs, 1H); 8.20 (s, 1H); 7.45 (d, 1H, J=7.3 Hz); 7.27–7.15 (mult, 4H); 7.14 (d, 1H, J=8.7 Hz); 7.09 (bs, 1H); 6.01 (d, 1H, J=3.7 Hz); 5.90 (bs, 1H); 5.15 (s, 2H); 4.68 (bs, 2H); 4.38 (bs, 1H); 4.11 (d, 1H, J=5.8 Hz); 3.56 (t, 1H, J=5.8 Hz); 2.66 (d, 3H, J=4.8 Hz); 2.34 (s, 3H); 1.82 (bs, 2H).

EXAMPLE 13

(2S,3S,4R,5R)3-Amino-5-{6-[5-chloro-2-(2-methyl-benzyloxy)-benzylamino]-purin-9-yl}-4-hydroxytetrahydrofuran-2-carboxylic acid methylamide Mp 76.0–80.0° C.

$C_{26}H_{28}ClN_7O_4$. MW 538.01. MS 538.2 (M+H)⁺.

¹H NMR (400 MHz, DMSO-d₆) δ 8.59 (s, 1H); 8.48 (quart, 1H, J=4.6 Hz); 8.35 (bs, 1H); 8.22 (s, 1H); 7.35 (d, 2H, J=8.1 Hz); 7.21–7.15 (mult, 3H); 7.22–7.17 (mult, 2H); 6.01 (d, 1H, J=3.9 Hz); 5.88 (bs, 1H); 5.12 (s, 2H); 4.70 (bs, 2H); 4.37 (bs, 1H); 4.11 (d, 1H, J=5.8 Hz); 3.56 (t, 1H, J=5.8 Hz); 2.66 (d, 3H, J=4.6 Hz); 2.28 (s, 3H); 1.79 (bs, 2H).

EXAMPLE 14

(2S,3S,4R,5R)3-Amino-5-{6-[5-chloro-2-(3-methyl-benzyloxy)-benzylamino]-purin-9-yl}-4-hydroxytetrahydrofuran-2-carboxylic acid methylamide Mp 92.0–97.0° C.

$C_{26}H_{28}ClN_7O_4$. MW 538.01. MS 538.2 (M+H)⁺.

¹H NMR (400 MHz, DMSO-d₆) δ 8.56 (s, 1H); 8.45 (quart, 1H, J=4.6 Hz); 8.32 (bs, 1H); 8.19 (s, 1H); 7.25–7.21 (mult, 3H); 7.21–7.16 (mult, 1H); 7.11–7.00 (mult, 3H); 5.99 (d, 1H, J=3.9 Hz); 5.87 (bs, 1H); 5.10 (s, 2H); 4.67 (bs, 2H); 4.34 (bs, 1H); 4.09 (d, 1H, J=5.8 Hz); 3.54 (t, 1H, J=5.8 Hz); 2.63 (d, 3H, J=4.6 Hz); 2.25 (s, 3H); 1.84.

EXAMPLE 15

(2S,3S,4R,5R)3-Amino-5-{6-[5-chloro-2-(2-methoxybenzyloxy)benzylamino]-purin-9-yl}-4-hydroxytetrahydrofuran-2-carboxylic acid methylamide Mp 102.0–123.0° C.

$[\alpha]_{21}$=−49.39° (c=0.225, MeOH).

$C_{26}H_{28}ClN_7O_5$. MW 554.01. MS 554.1 (M+H)⁺.

¹H NMR (400 MHz, DMSO-d₆) δ 8.58 (s, 1H); 8.48 (quart, 1H, J=4.6 Hz); 8.34 (bs, 1H); 8.21 (s, 1H); 7.44 (dd, 1H, J=7.5 Hz, J=1.5 Hz); 7.30 (td, 1H, J=7.5 Hz, J=1.5 Hz); 7.22 (dd, 1H, J=8.7 Hz, J=2.7 Hz); 7.08–7.01 (mult, 3H); 6.94 (t, 1H, J=7.5 Hz); 6.02 (d, 1H, J=3.9 Hz); 5.91 (bs, 1H); 5.12 (s, 2H); 4.68 (bs, 2H); 4.37 (t, 1H, J=4.1 Hz); 4.11 (d, 1H, J=5.8 Hz); 3.82 (s, 3H); 3.57 (t, 1H, J=5.8 Hz); 2.66 (d, 3H, J=4.6 Hz); 1.91 (bs, 2H).

EXAMPLE 16

(2S,3S,4R,5R)3-Amino-5-{6-[5-chloro-2-(furan-3-ylmethoxy)benzylamino]-purin-9-yl}-4-hydroxytetrahydrofuran-2carboxylic acid methylamide Mp 93.0–97.0° C.

$C_{23}H_{24}ClN_7O_5$. MW 513.94. MS 513.8 (M+H)⁺.

¹H NMR (400 MHz, DMSO-d₆) δ 8.59 (s, 1H): 8.48 (quart, 1H, J=4.6 Hz); 8.34 (bs, 1H); 8.21 (s, 1H); 7.80 (s, 1H); 7.66 (s, 1H); 7.22 (dd, 1H, J=8.7 Hz, J=2.5 Hz); 7.10 (d, 1H, J=8.7 Hz); 7.06 (bs, 1H); 6.60 (s, 1H); 6.01 (d, 1H, J=3.7 Hz); 5.90 (bs, 1H); 5.03 (s, 2H); 4.64 (bs, 2H); 4.36 (bs, 1H); 3.56 (t, 1H, J=4.5 Hz); 3.14 (d, 1H, J=5.2 Hz); 2.66 (d, 3H, J=4.6 Hz); 1.77 (bs, 2H).

EXAMPLE 17

(2S,3S,4R,5R)3-Amino-5-{6-[5-chloro-2-(4-methoxy-benzyloxy)benzylamino]-purin-9-yl}-4-hydroxytetrahydrofuran-2-carboxylic acid methylamide $C_{26}H_{28}ClN_7O_5$. MW 554.01. MS 553.8 (M+H)⁺.

¹H NMR (400 MHz, DMSO-d₆) δ 8.55 (s, 1H); 8.44 (quart, 1H, J=4.4 Hz); 8.32 (bs, 1H); 8.19 (s, 1H); 7.37 (d, 2H, J=8.7 Hz); 7.18 (dd, 1H, J=8.7 Hz, J=2.7 Hz); 7.11–7.04 (mult, 2H); 6.89 (d, 2H, J=8.7 Hz); 6.00 (d, 1H, J=3.7 Hz); 6.95 (bs, 1H); 5.06 (s, 2H); 4.62–4.59 (mult, 2H); 4.37 (bs, 1H); 4.11 (d, 1H, J=5.4 Hz); 3.70 (s, 3H); 3.60–3.56 (mult, 1H); 2.63 (d, 3H, J=4.4 Hz).

EXAMPLE 18

(2S,3S,4R,5R)3-Amino-5-[6-(5-chloro-2-cyclopentylmethoxy-benzylamino)-purin-9-yl]-4-hydroxytetrahydrofuran-2-carboxylic acid methylamide Mp 110.6–116.2° C.

$[\alpha]_{22}$=−25.88° (c=0.255, MeOH).

$C_{24}H_{30}ClN_7O_4$. MW 516.00. MS 515.8 (M+H)⁺.

¹H NMR (400 MHz, DMSO-d₆) δ 8.58 (s, 1H); 8.47 (quart, 1H, J=4.2 Hz); 8.29 (bs, 1H); 8.21 (s, 1H); 7.19 (dd, 1H, J=8.5 Hz, J=2.3 Hz); 7.03 (bs, 1H); 6.97 (d, 1H, J=8.5 Hz); 6.01 (d, 1H, J=3.1 Hz); 5.91 (bs, 1H); 4.64 (bs, 2H); 4.37 (bs, 1H); 4.11 (d, 1H, J=5.6 Hz); 3.87 (d, 2H, J=6.4 Hz); 3.60–3.55 (mult, 1H); 2.65 (d, 3H, J=4.2 Hz); 2.36–2.22 (mult, 1H); 2.22–1.90 (mult, 2H); 1.80–1.70 (mutt, 2H); 1.62–1.44 (mult, 4H); 1.39–1.28 (mult, 2H).

EXAMPLE 19

(2S,3S,4R,5R)3-Amino-5-(6-{5-chloro-2-[3-(2-morpholin-4-yl-ethoxy)-benzyloxy]benzylamino}-purin-9-yl)-4-hydroxytetrahydrofuran-2-carboxylic acid methylamide $C_{31}H_{37}ClN_8O_6$. MW 653.14. MS 653.0 (M+H)⁺.

¹H NMR (400 MHz, DMSO-d₆) δ 8.57 (s, 1H); 8.45 (quart, 1H, J=4.4 Hz); 8.37 (bs, 1H); 8.22 (s, 1H); 7.26 (t, 1H, J=8.5 Hz); 7.21 (dd, 1H, J=8.5 Hz, J=2.5 Hz); 7.09 (bs, 1H); 7.06–7.00 (mult, 3H); 6.87 (d, 1H, J=8.5 Hz); 6.02 (d, 1H, J=3.7 Hz); 5.95 (bs, 1H); 5.14 (s, 2H); 4.70 (bs, 2H); 4.42–4.36 (mult, 1H); 4.14 (d, 1H, J=5.4 Hz); 4.06 (t, 2H, J=5.4 Hz); 3.62–3.57 (mult, 1H); 3.53 (mult, 4H); 2.67–2.61 (mult, 5H); 2.42–2.38 (mult, 4H).

EXAMPLE 20

(2S,3S,4R,5R)3-Amino-5-{6-[5-chloro-2-(tetrahydro-furan-3-ylmethoxy)-benzylamino]-purin-9-yl}-4-hydroxy-tetrahydro-furan-2-carboxylic acid methylamide Mp 132.0–161.0° C.

$[\alpha]_{21}$=−16.47° (c=0.170, MeOH).

$C_{23}H_{28}ClN_7O_5$. MW 517.98. MS 518.1 (M+H)⁺.

¹H NMR (400 MHz, DMSO-d₆) δ 8.53 (s, 1H); 8.42 (quart, 1H, J=4.4 Hz); 8.29 (bs, 1H); 8.19 (s, 1H); (dd, 1H, J=8.7 Hz, J=2.7 Hz); 7.04 (s, 1H); 6.97 (d, 1H, J=8.7 Hz); 6.11 (bs, 1H), 6.01 (d, 1H, J=3.9 Hz); 4.61 (bs, 2H); 4.44–4.40 (mult, 1H); 4.15 (d, 1H, J=5.0 Hz); 3.99–3.92 (mult, 1H); 3.91–3.85 (mult, 1H); 3.78–3.65 (mult, 2H); 3.64–3.58 (mult, 2H); 3.57–3.50 (mult, 1H); 2.95 (quart, 1H, J=7.3 Hz); 2.69–2.58 (mult, 5H); 2.02–1.93 (mult, H); 1.70–1.59 (mult, 1H).

EXAMPLE 21

(2S,3S,4R,5R)3-Amino-5-{6-[5-chloro-2-tetrahydro-furan-3-ylmethoxy)-benzylamino]-purin-9-yl}-4-hydroxy-tetrahydro-furan-2-carboxylic acid methylamide $C_{23}H_{28}ClN_7O_5$. MW 517.98. MS 518.0 (M+H)⁺.

¹H NMR (400 MHz, DMSO-d₆) δ 8.54 (s, 1H); 8.47–8.40 (mult, 1H); 8.29 (bs, 1H); 8.19 (s, 1H); 7.18 (dd, 1H, J=8.5 Hz, J=2.3 Hz); 7.03 (bs, 1H); 6.97 (d, 1H, J=8.5 Hz); 5.99

(d, 1H, J=3.7 Hz); 5.97 (bs, 1H); 4.61 (bs, 2H); 4.40–4.35 (mult, 1H); 4.11 (d, 1H, J=5.4 Hz); 3.98–3.92 (mult, 1H); 3.91–3.83 (mult, 1H); 3.78–3.68 (mult, 2H); 3.62–3.48 (mult, 3H); 2.87–2.82 (mutt, 1H); 2.65–2.57 (mult, 5H); 2.02–1.93 (mult, 1H); 1.69–1.59 (mutt, 1H).

EXAMPLE 22

(2S,3S,4R,5R)3-Amino-5-{6-(5-chloro-2-(furan-2-ylmethoxy)benzylamino]purin-9-yl}-4-hydroxytetrahydrofuran-2-carboxylic acid methylamide Mp 187.0–192.0° C.

$C_{23}H_{24}ClN_7O_5$. MW 513.95. MS 514.1 $(M+H)^+$.

$^1H$ NMR (400 MHz, DMSO-$d_6$) δ 8.55 (s, 1H); 8.44 (quart, 1H, J=4.4 Hz); 8.27 (bs, 1H); 8.20 (s, 1H); 7.67 (d, 1H, J=1.9 Hz); 7.21 (dd, 1H, J=8.9 Hz, J=2.7 Hz); 7.15 (d, 1H, J=8.9 Hz); 7.02 (bs, 1H); 6.57 (d, 1H, J=3.3 Hz); 6.44 (dd, 1H, J=3.3 Hz, J=1.9 Hz); 5.99 (d, 1H, J=4.0 Hz); 5.86 (bs, 1H); 5.11 (s, 2H); 4.58 (bs, 2H); 4.39–4.32 (mult, 1H); 4.09 (d, 1H, J=5.8 Hz); 3.59–3.53 (mult, 1H); 2.63 (d, 3H, J=4.4 Hz); 1.85 (bs, 2H).

EXAMPLE 23

(2S,3S,4R,5R)3-Amino-5-{6-[5-chloro-2-(2,2,7,7-tetramethyltetrahydro-bis[1,3]dioxolo[4,5-b;4',5'-d]pyran-5-ylmethoxy)benzylamino]purin-9-yl}-4-hydroxytetrahydrofuran-2-carboxylic acid methylamide $C_{30}H_{38}ClN_7O_9$. MW 676.13. MS 676.1 $(M+H)^+$.

$^1H$ NMR (400 MHz, DMSO-$d_6$) δ 8.55 (s, 1H); 8.47 (quart, 1H, J=4.4 Hz); 8.26 (bs, 1H); 8.22 (s, 1H); 7.22 (dd, 1H, J=8.7 Hz, J=2.3 Hz); 7.06 (bs, 1H); 7.02 (d, 1H, J=8.7 Hz); 6.02 (d, 1H, J=3.9 Hz); 5.48 (d, 1H, J=4.8 Hz); 4.65 (bs, 2H); 4.60 (dd, 1H, J=7.9 Hz, J=2.3 Hz); 4.42–4.39 (mult, 1H); 4.39–4.37 (mutt, 1H); 4.37–4.28 (mult, 2H); 4.20–4.13 (mult, 2H); 4.09–3.98 (mult, 2H); 3.62 (t, 1H, J=5.4 Hz); 2.65 (d, 3H, J=4.4 Hz); 1.37 (s, 3H); 1.34 (s, 3H); 1.25 (s, 6H).

EXAMPLE 24

(2S,3S,4R,5R)3-Amino-5-{6-[5-chloro-2-(2,5-dimethylfuran-3-ylmethoxy)benzylamino]purin-9-yl}-4-hydroxytetrahydrofuran-2-carboxylic acid methylamide Mp 85.0–88.0° C.

$C_{25}H_{28}ClN_7O_5$. MW 542.00. MS 542.1 $(M+H)^+$.

$^1H$ NMR (400 MHz, DMSO-$d_6$) δ 8.58 (s, 1H); 8.48 (quart, 1H, J=4.6 Hz); 8.29 (bs, 1H); 8.20 (s, 1H); 7.22 (dd, 1H, J=8.7 Hz, J=2.3 Hz); 7.07 (d, 1H, J=8.7 Hz); 7.05 (bs, 1H); 6.07 (s, 1H); 6.01 (d, 1H, J=3.7 Hz); 5.89 (bs, 1H); 4.88 (s, 2H); 4.60 (bs, 2H); 4.36 (bs, 1H); 4.10 (d, 1H, J=5.4 Hz); 3.55 (t, 1H, J=5.0 Hz); 2.66 (d, 3H, J=4.6 Hz); 2.23 (s, 3H); 2.16 (s, 3H); 1.77 (bs, 2H).

EXAMPLE 25

(2S,3S,4R,5R)3-Amino-5-{6-[5-chloro-2-(pyridin-3-ylmethoxy)benzylamino]purin-9-yl}-4-hydroxytetrahydrofuran-2-carboxylic acid methylamide Mp 200.0–218.0° C.

$C_{24}H_{25}ClN_8O_4$. MW 524.97. MS 525.0 $(M+H)^+$.

$^1H$ NMR (400 MHz, DMSO$_6$) δ 8.69 (s, 1H); 8.52 (quart, 1H, J=4.6 Hz); 8.45 (s, 1H); 8.45–8.39 (mult, 1H); 8.35 (d, 1H, J=5.0 Hz); 8.20 (s, 1H); 7.89 (d, 1H, J=7.7 Hz); 7.40 (dd, 1H, J=7.7 Hz, J=4.8 Hz); 7.24 (dd, 1H, J=8.5 Hz, J=2.3 Hz); 7.11 (d, 1H, J=8.5 Hz); 6.17 (d, 1H, J=4.4 Hz); 5.22 (s, 2H); 4.90–4.84 (mult, 1H); 4.76–4.63 (mult, 2H); 4.60–4.56 (mult, 1H); 4.55–4.51 (mult, 1H); 4.18–4.09 (mult, 2H); 2.61 (d, 3H, J=4.6 Hz).

EXAMPLE 26

(2S,3S,4R,5R)3-Amino-5-{6-[5-chloro-2-(5-dimethylaminomethylfuran-2-ylmethoxy)benzylamino]purin-9-yl}-4-hydroxytetrahydrofuran-2-carboxylic acid methylamide Mp 78.0–81.0° C.

$C_{26}H_{31}ClN_8O_5$. MW 571.04. MS 571.1 $(M+H)^+$.

$^1H$ NMR (400 MHz, $CD_3OD$) δ 8.35 (s, 1H); 8.25 (s, 1H); 7.24 (bs, 1H); 7.20 (dd, 1H, J=8.7 Hz, J=2.5 Hz); 7.10 (d, 1H, J=8.7 Hz); 6.43 (d, 1H, J=3.1 Hz); 6.26 (d, 1H, J=3.1 Hz); 6.06 (d, 1H, J=4.2 Hz); 5.08 (s, 2H); 4.73 (bs, 2H); 4.59 (t, 1H, J=4.8 Hz); 4.30 (d, 1H, J=5.6 Hz); 3.74 (t, 1H, J=5.4 Hz); 3.48 (s, 2H); 2.82 (s, 3H); 2.20 (s, 6H).

EXAMPLE 27

(2S,3S,4R,5R)3-Amino-5-{6-[5-chloro-2-(thiazol-2-ylmethoxy)-benzylamino]-purin-9-yl}-4-hydroxy-tetrahydro-furan-2-carboxylic acid methylamide Mp 208.0–209.0° C.

$[α]_{21}$=−32.08° (c=0.265, MeOH).

$C_{22}H_{23}ClN_8O_4S$. MW 531.00. MS 531.0 $(M+H)^+$.

$^1H$ NMR (400 MHz, DMSO-$d_6$) δ 8.57 (s, 1H); 8.45 (quart, 1H, J=4.2 Hz); 8.38 (bs, 1H); 8.20 (s, 1H); 7.82 (d, 1H, J=3.2 Hz); 7.75 (d, 1H, J=3.2 Hz); 7.23 (dd, 1H, J=8.7 Hz, J=2.3 Hz); 7.13 (d, 1H, J=8.7 Hz); 7.07 (s, 1H); 5.99 (d, 1H, J=3.5 Hz); 5.90–5.84 (mult, 1H); 5.49 (s, 2H); 4.69 (bs, 2H); 4.34 (bs, 1H); 4.09 (d, 1H, J=5.6 Hz); 3.59–3.50 (mult, 1H); 2.64 (d, 3H, J=4.2 Hz); 1.74 (bs, 2H).

EXAMPLE 28

(2S,3S,4R,5R)3-Amino-5-{6-[2-(benzothiazol-2-ylmethoxy)-5-chlorobenzylamino]purin-9-yl}-4-hydroxytetrahydrofuran-2-carboxylic acid methylamide Mp 127.0–129.0° C.

$C_{26}H_{25}ClN_8O_4S$. MW 581.06. MS 581.0 $(M+H)^+$.

$^1H$ NMR (400 MHz, DMSO-$d_6$) δ 8.58 (s, 1H); 8.51–8.39 (mult, 2H); 8.21 (s, 1H); 8.09 (d, 1H, J=8.1 Hz); 8.00 (d, 1H, J=8.1 Hz); 7.50 (t, 1H, J=8.1 Hz); 7.42 (t, 1H, J=8.1 Hz); 7.25 (dd, 1H, J=8.7 Hz, J=2.5 Hz); 7.16 (d, 1H, J=8.7 Hz); 7.09 (bs, 1H); 6.00 (d, 1H, J=3.7 Hz); 5.91–5.84 (mult, 1H); 5.65 (s, 2H); 4.78 (bs, 2H); 4.34 (bs, 1H); 4.09 (d, 1H, J=5.8 Hz); 3.59–3.50 (mult, 1H); 2.64 (d, 3H, J=4.8 Hz); 1.74 (bs, 2H).

EXAMPLE 29

(2S,3S,4R,5R)3-Amino-5-{6-[2-(benzofuran-2-ylmethoxy)-5-chlorobenzylamino]purin-9-yl}-4-hydroxytetrahydrofuran-2-carboxylic acid methylamide Mp 127.0–130.0° C.

$C_{27}H_{26}ClN_7O_5$. MW 564.01. MS 564.0 $(M+H)^+$.

$^1H$ NMR (400 MHz, DMSO-$d_6$) δ 8.57 (s, 1H); 8.46 (quart, 1H, J=4.4 Hz); 8.33 (bs, 1H); 8.16 (s, 1H); 7.61 (d, 1H, J=7.5 Hz); 7.56 (d, 1H, J=8.3 Hz); 7.32–7.24 (mult, 1H); 7.24–7.19 (mult, 3H); 7.08–7.01 (mult, 2H); 5.99 (d, 1H, J=3.5 Hz); 5.87 (d, 1H, J=4.8 Hz); 5.33 (s, 2H); 4.63 (mult, 2H); 4.38–4.30 (mult, 1H); 4.08 (d, 1H, J=5.6 Hz); 3.59–3.48 (mult, 1H); 2.63 (d, 3H, J=4.4 Hz); 1.73 (bs, 2H).

EXAMPLE 30

(2S,3S,4R,5R)3-Amino-5-{6-[5-chloro-2-(isothiazol-5-ylmethoxy)benzylamino]purin-9-yl}-4-hydroxytetrahydrofuran-2-carboxylic acid methylamide Mp 180.0–183.0° C.

$C_{22}H_{23}ClN_8O_4S$. MW 531.00. MS 531.1 $(M+H)^+$.

$^1H$ NMR (400 MHz, DMSO-$d_6$) δ 8.59 (s, 1H); 8.53 (d, 1H, J=1.5 Hz); 8.47 (quart, 1H, J=4.8 Hz); 8.39 (bs, 1H); 8.22 (s, 1H); 7.47 (d, 1H, J=1.5 Hz); 7.26 (dd, 1H, J=8.7 Hz, J=2.7 Hz); 7.15–7.08 (mult, 2H); 6.02 (d, 1H, J=3.7 Hz);

5.90 (bs, 1H); 5.59 (s, 2H); 4.69 (bs, 2H); 4.36 (bs, 1H); 4.11 (d, 1H, J=5.6 Hz); 3.56 (t, 1H, J=5.6 Hz); 2.66 (d, 3H, J=4.8 Hz); 1.79 (bs, 2H).

EXAMPLE 31

(2S,3S,4R,5R)3-Amino-5-{6-[5-chloro-2-(thiophen-2-ylmethoxy)benzylamino]purin-9-yl}-4-hydroxytetrahydrofuran-2-carboxylic acid methylamide
Mp 135.0–141.0° C.
$C_{23}H_{24}ClN_7O_4S$. MW 530.01. MS 530.1 (M+H)$^+$.
$^1$H NMR (400 MHz, DMSO-d$_6$) δ 8.58 (s, 1H); 8.47 (quart, 1H, J=4.6 Hz); 8.35 (bs, 1H); 8.21 (s, 1H); 7.55 (dd, 1H, J=5.0 Hz, J=1.2 Hz); 7.27–7.19 (mult, 2H); 7.15 (d, 1H, J=8.7 Hz); 7.09–7.00 (mult, 2H); 6.07–5.87 (mult, 1H); 6.02 (d, 1H, J=3.3 Hz); 5.36 (s, 2H); 4.64 (bs, 2H); 4.41 (bs, 1H); 4.14 (d, 1H, J=5.8 Hz); 3.66–3.56 (mult, 1H); 2.65 (d, 3H, J=4.6 Hz).

EXAMPLE 32

(2S,3S,4R,5R)3-Amino-5-{6-[5-chloro-2-(quinolin-2-ylmethoxy)benzylamino]purin-9-yl}-4-hydroxytetrahydrofuran-2-carboxylic acid methylamide
Mp 130.0–134.0° C.
$C_{28}H_{27}ClN_8O_4$. MW 575.03. MS 575.1 (M+H)$^+$.
$^1$H NMR (400 MHz, DMSO-d$_6$) δ 8.57(s, 1H); 8.50–8.36 (mult, 3H); 8.21 (s, 1H); 8.02–7.93 (mult, 2H); 7.78–7.67 (mult, 2H); 7.62–7.53 (mult, 1H); 7.18 (d, 1H, J=8.9 Hz); 7.13 (bs, 1H); 7.06 (d, 1H, J=8.9 Hz); 6.00 (d, 1H, J=3.7 Hz); 5.88 (d, 1H, J=4.6 Hz); 5.42 (s, 2H); 4.78 (bs, 2H); 4.34 (bs, 1H); 4.09 (d, 1H, J=5.6 Hz); 3.57–3.48 (mult, 1H); 2.64 (d, 3H, J=4.6 Hz); 1.73 (bs, 2H).

EXAMPLE 33

(2S,3S,4R,5R)3-Amino-5-{6-[5-chloro-2-(4-methyl-[1,2,3]thiadiazol-5-ylmethoxy)benzylamino]purin-9-yl}-4-hydroxytetrahydrofuran-2-carboxylic acid methylamide
Mp 107.0–110.0° C.
$C_{22}H_{24}ClN_9O_4S$. MW 546.01. MS 546.1 (M+H)$^+$.
$^1$H NMR (400 MHz, DMSO-d$_6$) δ 8.60 (s, 1H); 8.48 (bs, 1H); 8.39 (bs, 1H); 8.20 (s, 1H); 7.36–7.23 (mult, 1H); 7.18 (d, 1H, J=8.1 Hz); 7.13 (bs, 1H); 6.02 (bs, 1H); 5.92 (bs, 1H); 5.60 (s, 2H); 4.66 (bs, 2H); 4.36 (bs, 1H); 4.12 (bs, 1H); 3.57 (bs, 1H); 2.68 (bs, 6H); 1.78 (bs, 2H).

EXAMPLE 34

(2S,3S,4R,5R)3-Amino-5-{6-[5-chloro-2-(naphthalen-1-ylmethoxy)benzylamino]purin-9-yl)}-4-hydroxytetrahydrofuran-2-carboxylic acid methylamide
Mp 115.0–119.0° C.
$C_{29}H_{28}ClN_7O_4$. MW 574.04. MS 574.9 (M+H)$^+$.
$^1$H NMR (400 MHz, DMSO-d$_6$) δ 8.58 (s, 1H); 8.53–8.45 (mult, 1H); 8.34 (bs, 1H); 8.19 (s, 1H); 8.16 (d, 1H, J=7.9 Hz); 7.99–7.86 (mult, 2H); 7.72 (d, 1H, J=6.4 Hz); 7.63–7.45 (mult, 3H); 7.35–7.23 (mult, 2H); 7.09 (bs, 1H); 6.01 (bs, 1H); 5.90 (bs, 1H); 5.63 (s, 2H); 4.64 (bs, 2H); 4.36 (bs, 1H); 4.11 (d, 1H, J=5.0 Hz); 3.56 (bs, 1H); 2.66 (d, 3H, J=4.2 Hz); 1.77 (bs, 2H).

EXAMPLE 35

(2S,3S,4R,5R)3-Amino-5-{6-[5-chloro-2-(3,5-dimethylisoxazol-4-ylmethoxy)benzylamino]purin-9-yl}-4-hydroxytetrahydrofuran-2-carboxylic acid methylamide
$C_{24}H_{27}ClN_8O_5$. MW 542.99. MS 543.2 (M+H)$^+$.
$^1$H NMR (400 MHz, DMSO-d$_6$) δ 8.55 (bs, 1H); 8.44 (bs, 1H); 8.31 (bs, 1H); 8.16 (s, 1H); 7.25 (d, 1H, J=8.5 Hz); 7.11 (d, 1H, J=8.7 Hz); 7.08 (bs, 1H); 5.98 (bs, 1H); 5.83 (bs, 1H); 4.95 (s, 2H); 4.58 (bs, 2H); 4.37 (bs, 1H); 4.11 (d, 1H, J=4.9 Hz); 3.57 (bs, 1H); 2.64 (d, 3H, J=3.8 Hz); 2.39 (s, 3H); 2.22 (s, 3H), 1.15 (bs, 2H).

EXAMPLE 36

(2S,3S,4R,5R)3-Amino-5-{6-[5-chloro-2-(2-oxo-2-piperidin-1-ylethoxy)-benzylamino]-purin-9-yl}-4-hydroxy-tetrahydro-furan-2-carboxylic acid methylamide.
$C_{25}H_{31}ClN_8O_5$ M.W. 567.00. MS 567 (M+H)$^+$.
$^1$H NMR (400 MHz, CD$_3$OD) δ 8.34 (s, 1H); 8.29 (bs, 1H); 7.3 (bs, 1H); 7.18 (d, 1H, J=8.9 Hz); 6.89 (d, 1H, J=8.9 Hz); 6.07 (d, 1H, J=4.1 Hz); 4.91 (s, 2H); 4.82 (bs, 2H); 4.64 (t, 1H, J=4.3 Hz); 4.38 (d, 1H, J=5.6 Hz); 3.79 (t, 1H, J=5.4 Hz); 3.51 (m, 4H); 2.8 (s, 3H); 1.6 (m, 6H).

EXAMPLE 37

(2S,3S,4R,5R)3-Amino-5-[6-(5-chloro-2-phenylcarbamoylmethoxy-benzylamino)-purin-9-yl]-4-hydroxy-tetrahydro-furan-2-carboxylic acid methylamide.
$C_{26}H_{27}ClN_8O_5$ M.W. 567.00. MS 567 (M+H)$^+$.
$^1$H NMR (400 MHz, D6 DMSO) δ 8.6 (bs, 1H); 8.5 (bd, 1H, J=5.5 Hz); 8.4 (bs, 1H); 7.6 (d, 2H, J=8.2 Hz): 7.33 (t, 2H, J=8.2 Hz); 7.23 (d, 1H, J=8.8 Hz); 7.12 (bs, 1H); 7.03 (t, 1H, J=8.2 Hz); 6.96 (d, 1H, J=8.8 Hz); 6.0 (d, 1H, J=4.0 Hz); 5.9 (bs, 1H); 4.8 (s, 2H); 4.78 (bs, 2H); 4.39 (bs, 1H); 4.1 (d, 1H, J=5.5 Hz); 3.59 (m, 1H); 2.62 (d, 3H, J=4.0 Hz); 1.94 (bs, 2H).

EXAMPLE 38

(2S,3S,4R,5R)3-Amino-5-[6-(5-chloro-2-dimethylcarbamoylmethoxy-benzylamino)-purin-9-yl]-4-hydroxy-tetrahydro-furan-2-carboxylic acid methylamide.
$C_{22}H_{27}ClN_8O_5$ M.W. 518.96. MS 519 (M+H)$^+$.
$^1$H NMR (400 MHz, CD$_3$OD) δ 8.31 (s, 1H); 8.26 (bs, 1H); 7.28 (bs, 1H); 7.17 (dd, 1H, J=8.9, 2.5 Hz); 6.83 (d, 1H, J=8.9 Hz); 6.03 (d, 1H, J=4.0 Hz); 4.9 (s, 2H); 4.82 (bs, 2H); 4.6 (t, 1H, J=4.6 Hz); 4.26 (d, 1H, J=5.6 Hz); 3.7 (t, 1H, J=5.6 Hz); 3.02 (s, 3H); 2.9 (s, 3H); 2.8 (s, 3H).

EXAMPLE 39

(2S,3S,4R,5R)3-Amino-5-{6-[2-(benzylcarbamoyl-methoxy)-5-chlorobenzylamino]-purin-9-yl}-4-hydroxy-tetrahydro-furan-2-carboxylic acid methylamide.
$C_{27}H_{29}ClN_8O_5$ M.W. 581.04. MS 581 (M+H)$^+$.
$^1$H NMR (400 MHz, CD$_3$OD) δ 8.3 (s, 1H); 8.2 (s, 1H); 7.3 d, 1H, J=2.5 Hz); 7.19 (dd, 1H, J=8.8, 2.6 Hz); 6.9 (d, 1H, J=8.8 Hz); 6.02 (d, 1H, J=4.1 Hz); 4.82 (bs, 2H); 4.64 (s, 2H); 4.58 (t, 1H, J=4.5 Hz); 4.4 (s, 2H); 4.3 (d, 1H, J=5.6 Hz); 3.78 (t, 1H, J=4.8 Hz); 2.78 (s, 3H).

EXAMPLE 40

(2R,3R,4S,5S)(2-{[9-(4-Amino-3-hydroxy-5-methylcarbamoyl-tetrahydro-furan-2-yl)-9H-purin-6-ylamino]-methyl}-4-chloro-phenoxy)-acetic acid.
$C_{20}H_{22}ClN_7O_6$, M.W. 491.90. MS 492 (M+H)$^+$.

EXAMPLE 41

(2S,3S,4R,5R)3-Amino-5-(6-{5-chloro-2-[2-(4-methyl-piperazin-1-yl)-2-oxo-ethoxy]-benzylamino}-purin-9-yl)-4-hydroxy-tetrahydro-furan-2-carboxylic acid methylamide.
$C_{25}H_{32}ClN_9O_5$ M.W. 574.04. MS 574 (M+H)$^+$.
$^1$H NMR (400 MHz, CD$_3$OD) δ 8.34 (s, 1H); 8.29 (bs, 1H); 7.29 (bs, 1H); 7.19 (d, 1H, J=8.9 Hz); 6.92 (d, 1H, J=8.9 Hz); 6.06 (d, 1H, J=4.1 Hz); 4.91 (s, 2H); 4.82 (bs, 2H); 4.59 (t, 1H, J=5.3 Hz); 4.30 (d, 1H, J=5.6 Hz); 3.79 (t, 1H, J=5.6 Hz); 3.6 (m, 4H); 2.80 (m, 3H); 2.4 (m, 4H); 222 (s, 3H).

EXAMPLE 42

(2S,3S,4R,5R)3-Amino-5-[6-(5-chloro-2-propylcarbamoylmethoxy-benzylamino)-purin-9-yl]-4-hydroxy-tetrahydro-furan-2-carboxylic acid methylamide. $C_{23}H_{29}ClN_8O_5$ M.W. 532.99. MS 533 (M+H)$^+$.

$^1$H NMR (400 MHz, CD$_3$OD) δ 8.37 (s, 1H); 8.29 (s, 1H); 7.27 d, 1H, J=2.5 Hz); 7.2 (dd, 1H, J=8.8, 2.6 Hz); 6.95 (D, 1H, J=8.8 Hz); 6.07 (d, 1H, J=4.0 Hz); 4.82 (bs, 2H); 4.6 (m, 3H); 4.3 (d, 1H, J=5.6 Hz); 3.8 (t, 1H, J=5.6 Hz); 3.2 (t, 2H, J=7.1 Hz); 2.8 (s, 3H); 1.5 (m, 1H); 0.83 (t, 3H, J=7.1 Hz).

EXAMPLE 43

(2S,3S,4R,5R)3-Amino-5-{6-[5-chloro-2-(2-morpholin-4-yl-2-oxo-ethoxy)-benzylamino]-purin-9-yl}-4-hydroxy-tetrahydro-furan-2-carboxylic acid methylamide. $C_{24}H_{29}ClN_8O_6$ M.W. 561.00. MS 561 (M+H)$^+$.

$^1$H NMR (400 MHz, CD$_3$OD) δ 8.35 (s, 1H); 8.28 (bs, 1H); 7.3 (bs, 1H); 7.2 (d, 1H, J=8.9 Hz); 6.94 (d, 1H, J=8.9 Hz); 6.07 (d, 1H, J=4.1 Hz); 4.94 (s, 2H); 4.82 (bs, 2H); 4.63 (t, 1H, J=5.3 Hz); 4.35 (d, 1H, J=5.6 Hz); 3.92 (t, 1H, J=5.6 Hz); 3.65 (m, 4H); 3.58 (m, 4H); 2.8 (s, 3H).

EXAMPLE 44

(2S,3S,4R,5R)3-Amino-5-{6-[5-chloro-2-(2-oxo-2-pyrrolidin-1-yl-ethoxy)-benzylamino]-purin-9-yl}-4-hydroxy-tetrahydro-furan-2-carboxylic acid methylamide. $C_{24}H_{29}ClN_8O_5$ M.W. 545.00. MS 545 (M+H)$^+$.

$^1$H NMR (400 MHz, CD$_3$OD) δ 8.28 (s, 1H); 8.25 (s, 1H); 7.24 (bs, 1H); 7.18 (d, 1H, J=8.9 Hz); 6.89 (d, 1H, J=8.9 Hz); 6.07 (d, 1H, J=3.9 Hz); 4.82 (bs, 2H); 4.8 (s, 2H); 4.64 (t, 1H, J=5.3 Hz); 4.38 (d, 1H, J=5.6 Hz); 3.92 (t, 1H, J=5.6 Hz); 3.51 (t, 2H, J=6.7 Hz); 3.41 (t, 3H, J=6.7 Hz); 2.8 (s, 3H); 1.92 (m, 2H); 1.82 (m, 2H).

EXAMPLE 45

(2S,3S,4R,5R)3-Amino-5-[6-(5-chloro-2-dipropylcarbamoylmethoxy-benzylamino)-purin-9-yl]-4-hydroxy-tetrahydro-furan-2-carboxylic acid methylamide. $C_{26}H_{35}ClN_8O_5$ M.W. 575.07. MS 575 (M+H)$^+$.

$^1$H NMR (400 MHz, CD$_3$OD) δ 8.32 (s, 1H); 8.27 (bs, 1H); 7.28 (bs, 1H); 7.2 (d, 1H, J=8.9 Hz); 6.86 (d, 1H, J=8.9 Hz); 6.04 (d, 1H, J=3.8 Hz); 4.92 (s, 2H); 4.82 (bs, 2H); 4.6 (t, 1H, J=5.5 Hz); 4.3 (d, 1H, J=5.6 Hz); 3.8 (t, 1H, J=5.6 Hz); 3.3 (m, 4H); 2.8 (s, 3H); 1.65 (m, 1H); 1.48 (m, 1H); 0.97 (t, 3H, J=7.2 Hz); 0.88 (t, 3H, J=7.2 Hz).

EXAMPLE 46

(2S,3S,4R,5R)3-Amino-5-(6-{5-chloro-2-[(2-methoxyethylcarbamoyl)-methoxy]-benzylamino}-purin-9-yl)-4-hydroxy-tetrahydro-furan-2-carboxylic acid methylamide. $C_{23}H_{29}ClN_8O_6$ M.W. 548.99. MS 549 (M+H)$^+$.

$^1$H NMR (400 MHz, CD$_3$OD) δ 8.37 (s, 1H); 8.3 (s, 1H); 7.3 (d, 1H, J=2.5 Hz); 7.2 (dd, 1H, J=8.8, 2.5 Hz); 6.95 (d, 1H, J=8.8 Hz); 6.07 (d, 1H, J=4.0 Hz); 4.82 (bs, 2H); 4.6 (m, 3H); 4.3 (d, 1H, J=5.8 Hz); 3.8 (m, 1H); 3.41 (s, 3H); 3.3 (m, 4H); 2.8 (s, 3H).

EXAMPLE 47

(2S,3S,4R,5R)3-Amino-5-[6-(5-chloro-2-methylcarbamoylmethoxy-benzylamino)-purin-9-yl]-4-hydroxy-tetrahydro-furan-2-carboxylic acid methylamide. $C_{21}H_{25}ClN_8O_5$ M.W. 504.93. MS 505 (M+H)$^+$.

$^1$H NMR (400 MHz, CD$_3$OD) δ 8.32 (s, 1H); 8.26 (s, 1H); 7.24 (d, 1H, J=2.5 Hz); 7.2 (dd, 1H, J=8.9, 2.5 Hz); 6.83 (d, 1H, J=8.9 Hz); 6.04 (d, 1H, J=3.9 Hz); 4.82 (bs, 2H); 4.6 (t, 1H, J=5.5 Hz); 4.58 (s, 2H); 4.3 (d, 1H, J=5.6 Hz); 3.8 (t, 1H, J=5.6 Hz); 2.8 (s, 6H).

EXAMPLE 48

(2S,3S,4R,5R)3-Amino-5-[6-(5-chloro-2-cyclohexylcarbamoylmethoxy-benzylamino)-purin-9-yl]-4-hydroxy-tetrahydro-furan-2-carboxylic acid methylamide. $C_{26}H_{33}ClN_8O_5$ M.W. 573.05. MS 573 (M+H)$^+$. $^1$H NMR (400 MHz, D6 DMSO) d 8.6 (s, 1H); 8.43 (m, 1H); 8.4 (bs, 1H); 8.2 (s, 1H); 7.8 (bd, 1H, J=9 Hz); 7.2 (d, 1H, J=8.8 Hz); 7.1 (bs, 1H); 6.82 (d, 1H, J=8.8 Hz); 6.0 (d, 1H, J=4.0 Hz); 5.95 (bs, 1H); 4.7 (bs, 2H); 4.52 (s, 2H); 4.4 (m, 1H); 4.1 (d, 1H, J=5.7 Hz); 3.6 (m, 2H); 2.62 (d, 3H, J=4.2 Hz); 1.65 (m, 4H); 1.5 (m, 1H); 1.2 (m, 5H).

EXAMPLE 49

(2R,3R,4S,5S)4-[(2-{[9-(4-Amino-3-hydroxy-5-methylcarbamoyl-tetrahydro-furan-2-yl)-9H-purin-6-ylamino]-methyl}-4-chloro-phenoxy)-acetyl]-piperazine-1-carboxylic acid ethyl ester. $C_{27}H_{34}ClN_9O_7$ M.W. 632.07. MS 632 (M+H)$^+$. $^1$H NMR (400 MHz, CD$_3$OD) δ 8.33 (s, 1H); 8.28 (s, 1H); 7.3 (bs, 1H); 7.2 (d, 1H, J=8.7 Hz); 6.93 (d, 1H, J=8.7 Hz); 6.07 (d, 1H, J=3.9 Hz); 4.93 (s, 2H); 4.82 (bs, 2H); 4.6 (t, 1H, J=5.5 Hz); 4.3 (d, 1H, J=5.6 Hz); 4.1 (q, 2H, J=7.1 Hz); 3.79 (t, 1H, J=5.5 Hz); 3.6 (m, 4H); 3.42 (m, 4H); 2.8 (s, 3H); 1.22 (t, 3H, J=7.1 Hz).

EXAMPLE 50

(2S,3S,4R,5R)3-Amino-5-{6-[2-(2-azetidin-1-yl-2-oxo-ethoxy)-5-chloro-benzylamino]-purin-9-yl}-4-hydroxy-tetrahydro-furan-2-carboxylic acid methylamide. $C_{23}H_{27}ClN_8O_5$ M.W. 530.97. MS 531 (M+H)$^+$.

$^1$H NMR (400 MHz, CD$_3$OD) δ 8.33 (s, 1H); 8.27 (s, 1H); 7.3 (s, 1H); 7.2 (d, 1H, J=8.7 Hz); 6.85 (d, 1H, J=8.7 Hz); 6.07 (d, 1H, J=4.1 Hz); 4.82 (bs, 2H); 4.63 (s, 2H); 4.61 (t, 1H, J=5.3 Hz); 4.37 (m, 3H); 4.02 (m, 2H); 3.82 (t, 1H, J=5.6 Hz); 2.8 (s, 3H); 2.3 (m, 2H).

EXAMPLE 51

(2S,3S,4R,5R)3-Amino-5-(6-{5-chloro-2-[(2-morpholin-4-yl-ethylcarbamoyl)-methoxy]-benzylamino}-purin-9-yl)-4-hydroxy-tetrahydro-furan-2-carboxylic acid methylamide. $C_{26}H_{34}ClN_9O_6$ M.W. 604.07. MS 604 (M+H)$^+$.

$^1$H NMR (400 MHz, CD$_3$OD) δ 8.36 (s, 1H); 8.29 (s, 1H); 7.3 (s, 1H); 7.2 (d, 1H, J=8.7 Hz); 6.93 (d, 1H, J=8.7 Hz); 6.08 (d, 1H, J=3.7 Hz); 4.84 (bs, 2H); 4.63 (t, 1H, J=5.5 Hz); 4.6 (s, 2H); 4.38 (d, 1H, J=5.6 Hz); 3.9 (t, 1H, J=5.3 Hz); 3.55 (m, 4H); 3.4 (t, 2H, J=6.4 Hz); 2.8 (s, 3H); 2.42 (t, 2H, J=6.4 Hz); 2.4 (m, 4H).

EXAMPLE 52

(2S,3S,4R,5R)3-Amino-5-(6-{5-chloro-2-[2-oxo-2-(4-phenyl-piperazin-1-yl)-ethoxy]-benzylamino}-purin-9-yl)-4-hydroxy-tetrahydro-furan-2-carboxylic acid methylamide. $C_{30}H_{34}ClN_9O_5$ M.W. 636.12. MS 636 (M+H)$^+$.

$^1$H NMR (400 MHz, CD$_3$OD) δ 8.32 (s, 1H); 8.26 (s, 1H); 7.3 (s, 1H); 7.2 (m, 3H); 6.9 (m, 4H); 6.07 (d, 1H, J=3.9 Hz); 4.92 (s, 2H); 4.82 (bs, 2H); 4.59 (t, 1H, J=5.3 Hz); 4.3 (d, 1H, J=5.6 Hz); 3.72 (m, 5H); 3.11 (m, 4H); 2.8 (s, 3H).

EXAMPLE 53

(2S,3S,4R,5R)3-Amino-5-(6-{5-chloro-2-[2-(4-cyclohexyl-piperazin-1-yl)-2-oxo-ethoxy]-benzylamino}-purin-9-yl)-4-hydroxy-tetrahydro-furan-2-carboxylic acid methylamide. $C_{30}H_{40}ClN_9O_5$ M.W. 642.16. MS 642 (M+H)$^+$.

$^1$H NMR (400 MHz, CD$_3$OD) δ 8.33 (s, 1H); 8.29 (s, 1H); 7.3 (s, 1H); 7.2 (dd, 1H, J=8.8, 2.6 Hz); 6.93 (d, 1H, J=8.8 Hz); 6.08 (d, 1H, J=3.8 Hz); 4.93 (s, 2H); 4.52 (bs, 2H); 4.63 (t, 1H, J=5.5 Hz); 4.38 (d, 1H, J=5.6 Hz); 3.83(m, 1H); 3.6 (m, 4H); 2.8 (s, 3H); 2.6 (m, 4H); 2.32 (m, 1H); 1.8–1.2 (m, 10H).

EXAMPLE 54

(2S,3S,4R,5R)3-Amino-5-(6-{5-chloro-2-[2-(4-ethyl-piperazin-1-yl)-2-oxo-ethoxy]-benzylamino}-purin-9-yl)-4-hydroxy-tetrahydro-furan-2-carboxylic acid methylamide. $C_{26}H_{34}ClN_9O_5$ M.W. 588.07. MS 588 (M+H)$^+$.

$^1$H NMR (400 MHz, CD$_3$OD) 8.32 (s, 1H); 8.28 (s, 1H); 7.3 (bs, 1H); 7.2 (d, 1H, J=8.7 Hz); 6.93 (d, 1H, J=8.7 Hz); 6.07 (d, 1H, J=3.9 Hz); 4.93 (s, 2H); 4.82 (s, 2H); 4.64 (t, 1H, J=5.3 Hz); 4.38 (d, 1H, J=6.4 Hz); 3.9 (t, 1H, J=5.5 Hz); 3.6 (bs, 4H); 2.8 (s, 3H); 2.45 (m, 6H); 1.05 (t, 3H, J=7.3 Hz).

EXAMPLE 55

(2S,3S,4R,5R)3-Amino-5-[6-(5-chloro-2-cyclopropylcarbamoylmethoxy-benzylamino)-purin-9-yl]-4-hydroxy-tetrahydro-furan-2-carboxylic acid methylamide. $C_{23}H_{27}ClN_8O_5$ M.W. 530.98. MS 531 (M+H)$^+$. $^1$H NMR (400 MHz, CD$_3$OD) δ 8.37 (s, 1H); 8.31 (s, 1H); 7.3 (bs, 1H); 7.2 (dd, 1H, J=8.6, 2.6 Hz); 6.85 (d, 1H, J=8.6 Hz); 6.07 (d, 1H, J=3.9 Hz); 4.82 (bs, 2H); 4.58 (m, 3H); 4.3 (d, 1H, J=5.6 Hz); 3.75 (t, 1H, J=5.6 Hz); 2.8 (s, 3H); 2.63 (m, 1H); 0.7 (m, 2H); 0.5 (m, 2H).

EXAMPLE 56

(2S,3S,4R,5R)3-Amino-5-[6-(2-carbamoylmethoxy-5-chloro-benzylamino)-purin-9-yl]-4-hydroxy-tetrahydro-furan-2-carboxylic acid methylamide. $C_{20}H_{23}ClN_8O_5$ M.W. 490.91. MS 491 (M+H)$^+$.

$^1$H NMR (400 MHz, CD$_3$OD) δ 8.37 (s, 1H); 8.31 (s, 1H); 7.36 (d, 1H, 2.65 Hz); 7.25 (dd, 1H, J=8.6, 2.6 Hz); 6.96 (d, 1H, J=8.6 Hz); 6.09 (d, 1H, J=4.28 Hz); 4.88 (s, 2H); 4.62 (m, 3H); 4.33 (d, 1H, J=5.6 Hz); 3.77 (t, 1H, J=5.6 Hz); 2.84 (s, 3H).

EXAMPLE 57

(2S,3S,4R,5R)3-Amino-5-(6-{5-chloro-2-[2-(4-cyclopropyl-piperazin-1-yl)-2-oxo-ethoxy]-benzylamino}-purin-9-yl)-4-hydroxy-tetrahydro-furan-2-carboxylic acid methylamide. $C_{27}H_{34}ClN_9O_5$ M.W. 600.08. MS 600 (M+H)$^+$.

$^1$H NMR (400 MHz, CD$_3$OD) δ 8.32 (s, 1H); 8.28 (s, 1H); 7.3 (bs, 1H); 7.2 (dd, 1H, J=8.8, 2.8 Hz); 6.93 (d, 1H, J=8.8 Hz); 6.07 (d, 1H, J=4.06 Hz); 4.89 (s, 2H); 4.83 (bs, 2H); 4.64 (t, 1H, J=4.9 Hz); 4.35 (d, 1H, J=5.8 Hz); 3.86 (t, 1H, J=5.7 Hz); 3.53 (m, 4H); 2.80 (s, 3H); 2.60 (m, 4H); 1.63 (m, 1H); 0.47 (m, 2H); 0.42 (m, 2H).

EXAMPLE 58

(23,3S,4R,5R)3-Amino-5-(6-{5-chloro-2-[2-(4-isopropyl-piperazin-1-yl)-2-oxo-ethoxy]-benzylamino}-purin-9-yl)-4-hydroxy-tetrahydro-furan-2-carboxylic acid methylamide. $C_{27}H_{36}ClN_9O_5$ M.W. 602.1. MS 602 (M+H)$^+$.

$^1$H NMR (400 MHz, CD$_3$OD) δ 8.28 (s, 1H); 8.27 (s, 1H); 7.29 (bs, 1H); 7.2 (dd, 1H, J=8.8, 2.6 Hz); 6.9 (d, 1H, J=8.8 Hz); 6.11 (d, 1H, J=3.2 Hz); 4.93 (s, 2H); 4.9 (m, 1H); 4.82 (s, 2H); 4.53 (d, 1H, J=6.2 Hz); 4.28 (t, 1H, J=5.5 Hz); 3.74 (bs, 4H); 3.04 (m, 1H); 2.84 (m, 4H); 2.75 (s, 3H); 1.66 (d, 6H, J=6.4 Hz).

EXAMPLE 59

(2S,3S,4R,5R)3-Amino-5-(6-{5-chloro-2-[2-oxo-2-(4-propyl-piperazin-1-yl)-ethoxy]-benzylamino}-purin-9-yl)-4-hydroxy-tetrahydro-furan-2-carboxylic acid methylamide. $C_{27}H_{36}ClN_9O_5$ M.W. 602.1. MS 602 (M+H)$^+$.

$^1$H NMR (400 MHz, CD$_3$OD) δ 8.26 (s, 1H); 7.28 (bs, 1H); 7.2 (dd, 1H, J=8.4 2.2 Hz); 6.93 (d, 1H, J=8.4 Hz); 6.1 (d, 1H, J=3.2 Hz); 4.92 (s, 2H); 4.9 (m, 1H); 4.82 (s, 2H); 4.54 (d, 1H, J=6.4 Hz); 4.33 (d, 1H, J=6.19 Hz); 3.66 (bs, 4H); 2.74 (s, 3H); 2.66 (m, 4H); 2.49 (t, 2H, J=7.9 Hz); 1.57 (m, 2H); 0.93 (t, 3H, J=7.2 Hz).

EXAMPLE 60

(2S,3S,4R,5R)3-Amino-5-(6-{5-chloro-2-[2-(4-cyclopentyl-piperazin-1-yl)-2-oxo-ethoxy]-benzylamino}-purin-9-yl)-4-hydroxy-tetrahydro-furan-2-carboxylic acid methylamide. $C_{29}H_{38}ClN_9O_5$ M.W. 628.14. MS 628 (M+H)$^+$.

$^1$H NMR (400 MHz, CD$_3$OD) δ 8.31 (s, 1H); 8.28 (s, 1H); 7.3 (s, 1H); 7.2 (dd, 1H, J=8.6, 2.6 Hz); 6.93 (d, 1H, J=8.6 Hz); 6.08 (d, 1H, J=3.8 Hz); 4.89 (s, 2H); 4.82 (s, 2H); 4.70 (t, 1H, J=4.8 Hz); 4.4 (d, 1H, J=5.9 Hz); 3.98(t, 1H, J=5.6 Hz); 3.6 (m, 4H); 2.78 (s, 3H); 2.55 (m, 4H); 1.9–1.2 (m, 9H).

EXAMPLE 61

(2S,3S,4R,5R)3-Amino-5-(6-{2-[2-(4-benzyl-piperazin-1-yl)-2-oxo-ethoxyl-5-chloro-benzylamino}-purin-9-yl)-4-hydroxy-tetrahydro-furan-2-carboxylic acid methylamide. $C_{31}H_{36}ClN_9O_5$ M.W. 650.1. MS 650 (M+H)$^+$.

$^1$H NMR (400 MHz, CD$_3$OD) δ 8.30 (s, 1H); 8.27 (s, 1H); 7.27 (m, 7H); 6.90 (d, 1H, J=8.9 Hz); 6.06 (d, 1H, J=4.1 Hz); 4.85 (s, 2H); 4.81 (s, 2H); 4.61 (t, 1H, J=4.5 Hz); 4.32 (d, 1H, J=5.7 Hz); 3.79(t, 1H, J=5.6 Hz); 3.56 (m, 4H); 3.5 (s, 2H); 2.79 (s, 3H); 2.43 (m, 4H).

EXAMPLE 62

(2S,3S,4R,5R)3-Amino-5-(6-{5-chloro-2-[2-oxo-2-(3-oxo-piperazin-1-yl)-ethoxy]-benzylamino}-purin-9-yl)-4-hydroxy-tetrahydro-furan-2-carboxylic acid methylamide. $C_{24}H_{28}ClN_9O_6$ M.W. 574.00. MS 574 (M+H)$^+$.

$^1$H NMR (400 MHz, CD$_3$OD) δ 8.32 (s, 1H); 8.27 (s, 1H); 7.30 (s, 1H); 7.2 (m, 1H); 6.94 (d, 1H, J=8.7 Hz); 6.06 (d, 1H, J=3.9 Hz); 4.93 (s, 2H); 4.82 (bs, 2H); 4.62 (t, 1H, J=4.5 Hz); 4.33 (d, 1H, J=5.7 Hz); 4.13(s, 1H); 3.80 (m, 1H); 3.8 (t, 1H, J=4.5 Hz); 3.76 (bs, 2H); 3.38 (m, 1H); 3.30 (m, 1H); 2.80 (s, 3H).

EXAMPLE 63

(2S,3S,4R,5R)3-Amino-5-{6-[5-chloro-2-(2-oxo-2-piperazin-1-yl-ethoxy)-benzylamino]-purin-9-yl}-4-hydroxy-tetrahydro-furan-2-carboxylic acid methylamide. $C_{24}H_{30}ClN_9O_5$ M.W. 560.01. MS 560 (M+H)$^+$.

$^1$H NMR (400 MHz, CD$_3$OD) δ 8.34 (s, 1H); 8.28 (s, 1H); 7.29 (s, 1H); 7.19 (dd, 1H, J=8.6, 2.6 Hz); 6.92 (d, 1H, J=8.9 Hz); 6.06 (d, 1H, J=4.3 Hz); 4.89 (s, 2H); 4.82 (s, 2H); 4.59 (dd, 1H, J=5.0, 4.5 Hz); 4.30 (d, 1H, J=5.6 Hz); 3.74(d, 1H, J=5.6 Hz); 3.54 (m, 4H); 2.80 (m, 7H).

EXAMPLE 64

(2S,3S,4R,5R)3-Amino-5-(6-{5-chloro-2-[2-(4-ethyl-3-oxo-piperazin-1-yl)-2-oxo-ethoxy]-benzylamino}-purin-9-yl)-4-hydroxy-tetrahydro-furan-2-carboxylic acid methylamide. $C_{26}H_{32}ClN_9O6$ M.W. 602.1. MS 602 (M+H)$^+$.

$^1$H NMR (400 MHz. CD$_3$OD) δ 8.33 (s, 1H); 8.28 (s, 1H); 7.30 (m, 1H); 7.2 (t, 1H, J=6.2 Hz); 6.94 (dd, 1H, J=8.7, 3.9 Hz); 6.06 (d, 1H, J=4.1 Hz); 4.92 (s, 2H); 4.83 (m, 2H); 4.61 (t, 1H, J=4.2 Hz); 4.32 (d, 1H, J=5.7 Hz); 4.22 (s, 1H); 4.13 (s, 1H); 3.8 (m, 3H); 3.46 (m, 4H); 2.81 (s, 3H); 1.12 (q, 3H, J=7.3).

EXAMPLE 65

(2S,3S,4R,5R)3-Amino-5-[6-(5-chloro-2-{2-[4-(2-chlorophenyl)-piperazin-1-yl]-2-oxo-ethoxy}-benzylamino)-purin-9-yl]-4-hydroxy-tetrahydro-furan-2-carboxylic acid methylamide. $C_{30}H_{33}ClN_9O_5$ M.W. 670.55. MS 670 (M+H)$^+$. $^1$H NMR (400 MHz, CD$_3$OD) δ 8.29 (s, 1H); 8.23 (s, 1H); 7.33 (m, 2H); 7.2 (m, 2H); 6.97 (m, 3H); 6.03 (d, 1H, J=4.2 Hz); 4.92 (s, 2H); 4.83 (s, 2H); 4.56 (t, 1H, J=4.6 Hz); 4.28 (d, 1H, J=5.6 Hz); 3.73 (m, 5H); 2.98 (m, 4H); 2.77 (s, 3H).

EXAMPLE 66

(2S,3S,4R,5R)3-Amino-5-{6-[5-chloro-2-(phenethylcarbamoyl-methoxy)-benzylamino]-purin-9-yl}-4-hydroxy-tetrahydro-furan-2-carboxylic acid methylamide. $C_{28}H_{31}ClN_8O_5$ M.W. 595.06. MS 595 (M+H)$^+$.

$^1$H NMR (400 MHz. CD$_3$OD) δ 8.37 (s, 1H); 8.27 (s, 1H); 7.3 (d, 1H, J=2.5 Hz); 7.2–7.02 (m, 6H); 6.83 (d, 1H, J=8.8 Hz); 6.06 (d, 1H, J=4.3 Hz); 4.76 (s, 2H); 4.57 (m, 3H); 4.3 (d, 1H, J=5.7 Hz); 3.74 (t, 1H, 5.6 Hz); 3.5 (t, 4H, 7 Hz); 2.80 (s, 3H); 2.76 (t, 1H, J=7 Hz).

EXAMPLE 67

(2S,3S,4R,5R)3-Amino-5-[6-(5-chloro-2-phenethyloxy-benzylamino)-purin-9-yl]-4-hydroxy-tetrahydro-furan-2-carboxylic acid methylamide. $C_{26}H_{28}ClN_7O_4$. M.W.= 538.01. M.S. 538 (M+H)$^+$. $^1$H NMR (400 MHz, CD$_3$OD) δ 8.35 (s, 1H); 8.27 (s, 1H); 7.3–7.05 (m, 7H); 6.92 (d, 1H, J=8.5 Hz); 6.05 (d, 1H, J=4.2 Hz); 5.45 (s, 2H); 4.65 (bs, 2H); 4.59 (m, 1H); 4.25 (d, 1H, J=5.4 Hz); 4.2 (dd, 2H, J=6.5, 6.0 Hz); 3.74 (m, 1H); 3.02 (dd, 2H, J=6.5, 6.0 Hz); 2.8 (s, 3H).

EXAMPLE 68

(2S,3S,4R,5R)3-Amino-5-(6-{5-chloro-2-[2-(3,5-dimethyl-piperazin-1-yl)-2-oxo-ethoxy]-benzylamino}-purin-9-yl)-4-hydroxy-tetrahydro-furan-2-carboxylic acid methylamide. $C_{26}H_{34}ClN_9O_5$ M.W. 588.1. MS 588 (M+H)$^+$.

$^1$H NMR (400 MHz. CD$_3$OD) δ 8.34 (s, 1H); 8.28 (s, 1H); 7.28 (s, 1H); 7.18 (dd, 1H, J=8.7, 2.6 Hz); 6.92 (d, 1H, J=8.7 Hz); 6.06 (d, 1H, J=4.1 Hz); 4.81 (m, 2H); 4.60 (t, 1H, J=4.8 Hz); 4.4 (d, 1H, J=12 Hz); 4.31 (d, 1H, J=5.6 Hz); 3.83 (d, 1H, 12.9 Hz); 3.76 (m, 1H); 3.13 (m, 1H); 2.81 (s, 3H); 2.72 (m, 2H); 2.51 (s, 2H); 2.27 (t, 1H, J=12 Hz); 1.27 (s, 1H); 1.09 (d, 6H, J=6.4 Hz).

EXAMPLE 69

(2S,3S,4R,5R)3-Amino-5-(6-{5-chloro-2-[2-(4-dimethylamino-piperidin-1-yl)-2-oxo-ethoxy]-benzylamino}-purin-9-yl)-4-hydroxy-tetrahydro-furan-2-carboxylic acid methylamide. $C_{27}H_{36}ClN_9O_5$ M.W. 602.09. MS 602 (M+H)$^+$. $^1$H NMR (400 MHz. CD$_3$OD) δ 8.32 (s, 1H); 8.26 (s, 1H); 7.28 (s, 1H); 7.16 (dd, 1H, J=8.7, 2.4 Hz); 6.90 (dd, 1H, J=8.7, 2.4 Hz); 6.06 (d, 1H, J=4.0 Hz); 4.81 (s, 2H); 4.58 (t, 1H, J=4.8 Hz); 4.55 (d, 1H, J=12.0 Hz); 4.28 (d, 1H, J=5.4 Hz); 4.0 (d, 1H, J=13 Hz); 3.72 (m, 1H); 3.05 (t, 1H, J=5.7 Hz); 2.79 (s, 3H); 2.62 (t, 1H, J=13 Hz); 2.39 (m, 1H); 2.21 (s, 6H); 1.87 (s, 2H); 1.4–1.25 (m, 4H).

EXAMPLE 70

(2S,3S,4R,5R)5-(6-{2-[2-(4-Adamantan-2-yl-piperazin-1-yl)-2-oxo-ethoxy]-5-chloro-benzylamino}-purin-9-yl)-3-amino-4-hydroxy-tetrahydro-furan-2-carboxylic acid methylamide. $C_{34}H_{44}ClN_9O_5$ M.W. 694.24. MS 694 (M+H)$^+$.

$^1$H NMR (400 MHz. CD$_3$OD) δ 8.35 (s, 1H); 8.29 (s, 1H); 7.31 (d, 1H, J=2.1 Hz); 7.2 (dd, 1H, J=8.7, 2.6 Hz); 6.93 (d, 1H, J=8.9 Hz); 6.06 (d, 1H, J=4.3 Hz); 4.83 (m, 2H); 4.58 (t, 1H, J=4.8 Hz); 4.3 (d, 1H, J=5.6 Hz); 3.74 (t, 1H, 5.48 Hz); 3.59 (t, 4H, 4.87 Hz); 2.82 (s, 3H); 2.4 (s, 4H); 2.1–1.27 (m, 17H).

EXAMPLE 71

(2R,3R,4S,5S)1-[(2-{[9-(4-Amino-3-hydroxy-5-methylcarbamoyl-tetrahydro-furan-2-yl)-9H-purin-6-ylamino]-methyl}-4-chloro-phenoxy)-acetyl]-piperidine-4-carboxylic acid amide. $C_{26}H_{32}ClN_9O_6$ M.W. 602.05. MS 602 (M+H)$^+$. $^1$H NMR (400 MHz. CD$_3$OD) δ 8.33 (s, 1H); 8.29 (s, 1H); 7.29 (s, 1H); 7.18 (dd, 1H, J=8.7, 2.6 Hz); 6.93 (d, 1H, J=8.9 Hz); 6.06 (d, 1H, J=4.3 Hz); 4.90 (s, 3H); 4.61 (t, 1H, J=4.3 Hz); 4.4 (d, 1H); 4.3 (d, 1H, J=5.6 Hz); 4.05 (d, 1H); 3.76 (t, 1H); 3.28 (m, 1H); 2.81 (s, 3H); 2.75 (m, 1H); 2.5 (m, 1H); 1.83 (d, 2H); 1.63 (m, 3H).

EXAMPLE 72

(2S,3S,4R,5R)3-Amino-5-(6-{5-chloro-2-[2-(4-cycloheptyl-piperazin-1-yl)-2-oxo-ethoxy]-benzylamino}-purin-9-yl)-4-hydroxy-tetrahydro-furan-2-carboxylic acid methylamide. $C_{31}H_{42}ClN_9O_5$ M.W. 656.19. CIMS 656.1 (M+H)$^+$. $^1$H NMR (400 MHz. CD$_3$OD) δ 8.31 (s, 1H); 8.29 (s, 1H); 7.31 (s, 1H); 7.20 (dd, 1H, J=8.71, 2.69 Hz); 6.94 (d, 1H, J=8.71 Hz); 6.08 (d, 1H, J=3.74 Hz); 4.90 (s, 2H); 4.82 (s, 2H); 4.72 (t, 1H J=4.56 Hz); 4.42 (d, 1H, J=6.02 Hz); 4.03 (t, 1H, J=4.56 Hz); 3.62 (s, 4H); 2.78 (s, 3H); 2.66 (s, 5H); 1.81–1.38 (m, 12H).

EXAMPLE 73

(2S,3S,4R,5R)5-{6-[2-(Adamantan-2-ylcarbamoylmethoxy)-5-chloro-benzylamino]-purin-9-yl}-3-amino-4-hydroxy-tetrahydro-furan-2-carboxylic acid methylamide.

$C_{30}H_{37}ClN_8O_5$ M.W. 625.13. CIMS 625.0 (M+1). $^1$H NMR (400 MHz. CD$_3$OD) δ 8.36 (s, 1H); 8.28 (s, 1H); 7.34 (d, 1H, J=2.49 Hz); 7.24 (dd, 1H, J=8.72, 2.49 Hz); 6.94 (d, 1H, J=8.93 Hz); 6.06 (d, 1H, J=4.15); 4.83 (s, 2H); 4.64 (s, 2H); 4.58 (t, 1H, J=4.77 Hz); 4.30 (d, 1H, J=5.61 Hz); 4.01 (s, 1H); 3.74 (t, 1H, 5.61 Hz); 2.81 (s, 3H); 1.81–1.43 (m, 14H).

EXAMPLE 74

(2S,3S,4R,5R)3-Amino-5-{6-[5-chloro-2-(1-phenyl-ethoxy)-benzylamino]-purin-9-yl}-4-hydroxy-tetrahydro-furan-2-carboxylic acid methylamide. $C_{26}H_{28}ClN_7O_4$. M.W.=538.01. M.S. 538 (M+H)$^+$. $^1$H NMR (400 MHz, CD$_3$OD) δ 8.37 (s, 1H); 8.25 (s, 1H); 7.42–7.08 (m, 6H); 7.0 (d, 1H, J=8.5 Hz); 6.74 (d, 1H, J=8.5 Hz); 6.05 (d, 1H, J=4.2 Hz); 5.4 (q, 1H, J=6.8 Hz); 4.82 (bs, 2H); 4.59 (m, 1H); 4.3 (d, 1H, J=5.5 Hz); 3.73 (m, 1H); 2.8 (s, 3H); 1.58 (bs, 3H).

EXAMPLE 75

(2R,3R,4S,5S)4-[(2-{[9-(4-Amino-3-hydroxy-5-methylcarbamoyl-tetrahydro-furan-2-yl)-9H-purin-6-ylamino]-methyl}-4-chloro-phenoxy)-acetyl]-piperazine-1-carboxylic acid tert-butyl ester. $C_{29}H_{38}ClN_9O_7$ M.W. 660.13. MS 660 (M+H)$^+$. $^1$H NMR (400 MHz, CD$_3$OD) δ 8.33 (s, 1H); 8.28 (bs, 1H); 7.3 (bs, 1H); 7.2 (d, 1H, J=8.9 Hz); 6.93 (d, 1H, J=8.9 Hz); 6.07 (d, 1H, J=3.9 Hz); 4.91 (s, 2H); 4.82 (bs, 2H); 4.6 (t, 1H, J=4.5 Hz); 4.3 (d, 1H, J=5.6 Hz); 3.81 (t, 1H, J=5.0 Hz); 3.6 (m, 4H); 3.42 (m, 4H); 2.8 (s, 3H); 1.42 (s, 9H).

EXAMPLE 76

(2S,3S,4R,5R)3-Amino-5-[6-(5-chloro-2-cyanomethoxy-benzylamino)-purin-9-yl]-4-hydroxy-tetrahydro-furan-2-carboxylic acid methylamide. $C_{20}H_{21}ClN_8O_4$

M.W.472.89. MS 473 (M+H)$^+$.

$^1$H NMR (400 MHz, CD$_3$OD) δ 8.36 (s, 1H); 8.29 (s, 1H); 7.32 (bs, 1H); 7.28 (dd, 1H, J=8.9, 2.5 Hz); 7.08 (d, 1H, J=8.9 Hz); 6.07 (d, 1H, J=4.1 Hz); 5.05 (s, 2H); 4.8 (bs, 2H); 4.6 (t, 1H, J=4.9 Hz); 4.3 (d, 1H, J=5.6 Hz); 3.78 (t, 1H, J=5.5 Hz); 2.8 (s, 3H).

EXAMPLE 77

(2R,3R,4S,5S)(2-{[9-(4-Amino-3-hydroxy-5-methylcarbamoyl-tetrahydro-furan-2-yl)-9H-purin-6-ylamino]-methyl}-4-chloro-phenoxy)-acetic acid methyl ester.

$C_{21}H_{38}ClN_7O_6$ M.W.505.92. MS 506 (M+H)$^+$.

$^1$H NMR (400 MHz, CD$_3$OD) δ 8.35 (s, 1H); 8.29 (s, 1H); 7.3 (bs, 1H); 7.2 (dd, 1H, J=8.9, 2.5 Hz); 6.9 (d, 1H, J=8.9 Hz); 6.04 (d, 1H, J=4.0 Hz); 4.8 (m, 4H); 4.6 (t, 1H, J=4.5 Hz); 4.3 (d, 1H, J=5.6 Hz); 3.78 (m, 4H); 2.8 (s, 3H).

EXAMPLE 78

(2R,3R,4S,5S)(2-{[9-(4-Amino-3-hydroxy-5-methylcarbamoyl-tetrahydro-furan-2-yl)-9H-purin-6-ylamino]-methyl}-4-chloro-phenoxy)-acetic acid ethyl ester.

$C_{22}H_{26}ClN_7O_6$ M.W.519.95. MS 520 (M+H)$^+$.

$^1$H NMR (400 MHz, CD$_3$OD) δ 8.35 (s, 1H); 8.29 (s, 1H); 7.3 (bs, 1H); 7.2 (dd, 1H, J=8.9, 2.5 Hz); 6.9 (d, 1H, J=8.9 Hz); 6.04 (d, 1H, J=4.0 Hz); 4.82 (s, 2H); 4.8 (s, 2H); 4.6 (t, 1H, J=4.5 Hz); 4.3 (d, 1H, J=5.6 Hz); 4.21 (q, 2H, J=7.1 Hz); 3.78 (t, 1H, J=5.4 Hz); 2.8 (s, 3H); 1.22 (t, 3H, J=7.1 Hz).

EXAMPLE 79

(2S,3S,4R,5R)3-Amino-5-{6-[5-chloro-2-(4,5-dihydro-1H-imidazol-2-ylmethoxy)-benzylamino]-purin-9-yl}-4-hydroxy-tetrahydro-furan-2-carboxylic acid methylamide. $C_{22}H_{26}ClN_9O_4$ M.W.515.96. MS 516 (M+H)$^+$.

$^1$H NMR (400 MHz, CD$_3$OD) δ 8.4 (s, 1H); 8.3 (s, 1H); 7.32 (bs, 1H); 7.2 (d, 1H, J=8.9 Hz); 6.97 (d, 1H, J=8.9 Hz); 6.05 (d, 1H, J=3.8 Hz); 4.84 (m, 4H); 4.6 (t, 1H, J=4.5 Hz); 4.3 (d, 1H, J=5.6 Hz); 3.75 (t, 1H, J=5.4 Hz); 3.62 (m, 4H); 2.8 (s, 3H).

EXAMPLE 80

(2S,3S,4R,5R)3-Amino-5-{6-[1-(2-benzyloxy-5-chloro-phenyl)-ethylamino]-purin-9-yl}-4-hydroxy-tetrahydro-furan-2-carboxylic acid methylamide. $C_{26}H_{28}ClN_7O_4$.

M.W.=538.01. M.S. 538 (M+H)$^+$. $^1$H NMR (400 MHz, CD$_3$OD) δ 8.39 (bs, 1H); 8.2 (d, 1H, J=4.5 Hz); 7.5–7.22 (m, 5H); 7.18 (d, 1H, J=8.9 Hz); 7.0 (d, 2H, J=8.6 Hz); 6.05 (d, 1H, J=3.9 Hz); 5.79 (bs, 1H); 5.18 (s, 2H); 4.6 (t, 1H, J=4.5 Hz); 4.3 (d, 1H, J=5.6 Hz); 3.7 (m, 1H); 2.8 (s, 3H); 1.6 (d, 3H, J=6.8 Hz).

EXAMPLE 81

(2S,3S,4R,5R)3-Amino-5-[6-(2-benzyloxy-5-chlorobenzylamino)-2-chloro-purin-9-yl]-4-hydroxy-tetrahydro-furan-2-carboxylic acid methylamide. $C_{25}H_{25}Cl_2N_7O_4$.

M.W.=558.43. M.S. 558 (M+H)$^+$. $^1$H NMR (400 MHz, D6DMSO) δ 8.82 (m, 1H); 8.6 (bs, 1H); 8.2 (bs, 1H); 7.43–7.02 (m, 7H); 5.95 (bs, 2H); 4.62 (bs, 2H); 4.3 (bs, 1H); 4.1 (m, 2H); 3.52 (m, 1H); 3.1 (d, 3H, J=5.0 Hz); 2.42 (bs, 2H); 1.75 (bs, 2H).

EXAMPLE 82

(2S,3S,4R,5R)3-Amino-5-[6-(2-benzylsulfanyl-5-chloro-benzylamino)-purin-9-yl]-4-hydroxy-tetrahydro-furan-2-carboxylic acid methylamide. $C_{25}H_{26}ClN_7O_4S$. M.W.=540.05. M.S. 540 (M+H)$^+$. $^1$H NMR (400 MHz, CD$_3$OD) δ 8.35 (s, 1H); 8.27 (s, 1H); 7.4–7.1 (m, 8H); 6.07 (d, 1H, J=3.9 Hz); 4.8 (bs, 2H); 4.61 (m, 1H); 4.35 (d, 1H, J=5.8 Hz); 4.08 (s, 2H); 3.82 (m, 1H); 2.8 (s, 3H).

EXAMPLE 83

(2S,3S,4R,5R)3-Amino-5-[6-(2-benzyloxy-5-bromo-benzylamino)-purin-9-yl]-4-hydroxy-tetrahydro-furan-2-carboxylic acid methylamide. $C_{25}H_{26}BrN_7O_4$. M.W.=568.43. M.S. 568 (M+H)$^+$. $^1$H NMR (400 MHz, CD$_3$OD) δ 8.35 (s, 1H); 8.25 (s, 1H); 7.42–7.23 (m, 7H); 6.97 (d, 1H, J=9.3 Hz); 6.06 (d, 1H, J=4.1 Hz); 5.13 (s, 2H); 4.8 (bs, 2H); 4.6 (m, 1H); 4.3 (d, 1H, J=5.5 Hz); 3.79 (m, 1H); 2.8 (s, 3H).

EXAMPLE 84

(2S,3S,4R,5R)3-Amino-5-[6-(2-benzyloxy-5-fluoro-benzylamino)purin-9-yl]-4-hydroxy-tetrahydro-furan-2-carboxylic acid methylamide. $C_{25}H_{26}FN_7O_4$. M.W.=507.53. M.S. 508 (M+H)$^+$. $^1$H NMR (400 MHz, CD$_3$OD) δ 8.32 (s, 1H); 8.26 (s, 1H); 7.42–7.22 (m, 4H); 7.16.9 (m, 4H); 6.06 (d, 1H, J=4.2 Hz); 5.13 (s, 2H); 4.8 (bs, 2H); 4.5 (m, 1H); 4.3 (d, 1H, J=5.5 Hz); 3.79 (m, 1H); 2.8 (s, 3H).

EXAMPLE 85

(2S,3S,4R,5R)3-Amino-5-[6-(2-benzyloxy-5-iodo-benzylamino)-purin-9-yl]-4-hydroxy-tetrahydro-furan-2-carboxylic acid methylamide. $C_{25}H_{26}IN_7O_4$. M.W.=615.43. M.S. 490 (M−I)$^+$. $^1$H NMR (400 MHz, CD$_3$OD) δ 8.32 (s, 1H); 8.21 (s, 1H); 7.42–7.18 (m, 5H); 7.02–6.82 (m, 3H); 6.05 (d, 1H, J=4.2 Hz); 5.1 (d, 2H, J=4.9 Hz); 4.83 (bs, 2H); 4.55 (m, 1H); 4.29 (d, 1H, J=5.5 Hz); 3.7 (m, 1H); 2.8 (s, 3H).

EXAMPLE 86

(2S,3S,4R,5R)3-Amino-5-[6-(2-benzyloxy-5-trifluoromethyl-benzylamino)-purin-9-yl]-4-hydroxy-tetrahydro-furan-2-carboxylic acid methylamide. $C_{26}H_{26}F_3N_7O_4$.

M.W.=557.54. M.S. 558 (M+H)$^+$. $^1$H NMR (400 MHz, CD$_3$OD) δ 8.36 (s, 1H); 8.24 (s, 1H); 7.6–7.18 (m, 8H); 6.06 (d, 1H, J=4.1 Hz); 5.21 (s, 2H); 4.83 (bs, 2H); 4.6 (m, 1H); 4.3 (d, 1H, J=5.7 Hz); 3.75 (m, 1H); 2.8 (s, 3H).

EXAMPLE 87

(2S,3S,4R,5R)3-Amino-5-[6-(2-benzyloxy-5-cyano-benzylamino)-purin-9-yl]-4-hydroxy-tetrahydro-furan-2-carboxylic acid methylamide. $C_{26}H_{26}N_8O_4$. M.W.=514.55. M.S. 515 (M+H)$^+$. $^1$H NMR (400 MHz, CD$_3$OD) δ 8.36 (s, 1H); 8.24 (s, 1H); 7.63–7.2 (m, 8H); 6.06 (d, 1H, J=4.1 Hz); 5.24 (s, 2H); 4.83 (bs, 2H); 4.6 (m, 1H); 4.32 (d, 1H, J=5.4 Hz); 3.76 (m, 1H); 2.8 (s, 3H).

EXAMPLE 88

(2S,3S,4R,5R)3-Amino-5-[6-(2-benzyloxy-5-methyl-benzylamino)-purin-9-yl]-4-hydroxy-tetrahydro-furan-2-carboxylic acid methylamide. $C_{26}H_{29}N_7O_4$. M.W.=503.56. M.S. 504 (M+H)$^+$. $^1$H NMR (400 MHz, CD$_3$OD) δ 8.31 (s, 1H); 8.22 (s, 1H); 7.4–6.9 (m, 8H); 6.03 (d, 1H, J=4.3 Hz); 5.04 (s, 2H); 4.8 (bs, 2H); 4.58 (m, 1H); 4.3 (d, 1H, J=5.6 Hz); 3.7 (m, 1H); 2.8 (s, 3H); 2.2 (s, 3H).

EXAMPLE 89

(2S,3S,4R,5R)3-Amino-5-[6-(2-benzyloxy-5-vinyl-benzylamino)-purin-9-yl]-4-hydroxy-tetrahydro-furan-2-carboxylic acid methylamide. $C_{27}H_{29}N_7O_4$. M.W.=515.57. M.S. 516 (M+H)$^+$. $^1$H NMR (400 MHz, CD$_3$OD) δ 8.33 (s, 1H); 8.22 (s, 1H); 7.42–7.2 (m, 7H); 6.98 (d, 1H, J=8.5 Hz); 6.6 (dd, 1H, J=8.2, 6.0 Hz); 6.03 (d, 1H, J=4.2 Hz); 5.58 (d, 1H, J=8.2 Hz); 5.1 (s, 2H); 4.8 (bs, 2H); 4.58 (m, 1H); 4.26 (d, 1H, J=5.5 Hz); 3.72 (m, 1H); 2.8 (s, 3H).

EXAMPLE 90

(2S,3S,4R,5R)3-Amino-5-[6-(2-benzyloxy-5-ethynyl-benzylamino)-purin-9-yl]-4-hydroxy-tetrahydro-furan-2-carboxylic acid methylamide. $C_{27}H_{27}N_7O_4$. M.W.=513.56. M.S. 514 (M+H)$^+$. $^1$H NMR (400 MHz, CD$_3$OD) δ 8.36 (s, 1H); 8.26 (s, 1H); 7.7–7.23 (m, 7H); 7.0 (d, 1H, J=8.5 Hz); 6.06 (d, 1H, J=4.2 Hz); 5.18 (s, 2H); 4.8 (bs, 2H); 4.6 (m, 1H); 4.3 (d, 1H, J=5.5 Hz); 3.75 (m, 1H); 3.3 (s, 1H); 2.8 (s, 3H).

EXAMPLE 91

(2S,3S,4R,5R)3-Amino-5-{6-[5-chloro-2-(2-oxo-2-(4-piperidin-1-yl)piperidin-1-yl-ethoxy)-benzylamino]-purin-9-yl}-4-hydroxy-tetrahydro-furan-2-carboxylic acid methylamide. $C_{30}H_{40}ClN_9O_5$ M.W. 642.18. MS 642 (M+H)$^+$.

$^1$H NMR (400 MHz, CD$_3$OD) δ 8.4 (s, 1H); 8.32 (bs, 1H); 7.35 (bs, 1H); 7.22 (d, 1H, J=8.9 Hz); 6.96 (d, 1H, J=8.9 Hz); 6.07 (d, 1H, J=4.1 Hz); 4.91 (s, 2H); 4.82 (bs, 2H); 4.6 (m, 2H); 4.33 (d, 1H, J=5.6 Hz); 4.2 (bd, 1H, J=10.5 Hz); 3.79 (t, 1H, J=5.4 Hz); 3.18 (m, 1H): 2.82 (s, 3H); 2.6 (m, 6H); 1.9 (m, 2H); 1.65–1.3 (m, 8H).

EXAMPLE 92

(2S,3S,4R,5R)3-Amino-5-(6-{5-chloro-2-[2-(4-methylamino-piperidin-1-yl)-2-oxo-ethoxy]-benzylamino}-purin-9-yl)-4-hydroxy-tetrahydro-furan-2-carboxylic acid methylamide. $C_{26}H_{34}ClN_9O_5$ M.W. 588.07. MS 588 (M+H)$^+$. $^1$H NMR (400 MHz. CD$_3$OD) δ 8.39 (s, 1H); 8.33 (s, 1H); 7.35 (s, 1H); 7.22 (dd, 1H, J=8.7, 2.4 Hz); 6.94 (dd, 1H, J=8.7, 2.4 Hz); 6.06 (d, 1H, J=4.0 Hz); 4.95 (s, 2H); 4.81 (s, 2H); 4.62 (t, 1H, J=4.8 Hz); 4.5 (bd, 1H, J=12.0 Hz); 4.36 (d, 1H, J=5.4 Hz); 4.02 (bd, 1H, J=13 Hz); 3.79 (t, 1H, J=5.7 Hz); 3.2 (m, 1H); 2.82 (s, 3H); 2.79 (t, 1H, J=13 Hz); 2.62 (m, 1H); 2.4 (s, 3H); 1.97 (m, 2H); 1.4–1.15 (m, 2H).

EXAMPLE 93

(2S,3S,4R,5R)3-Amino-5-(6-{5-chloro-2-[2-(4-amino-piperidin-1-yl)-2-oxo-ethoxy]-benzylamino}-purin-9-yl)-4-hydroxy-tetrahydro-furan-2-carboxylic acid methylamide. $C_{25}H_{32}ClN_9O_5$ M.W. 574.04. MS 574 (M+H)$^+$.

$^1$H NMR (400 MHz. CD$_3$OD) δ 8.37 (s, 1H); 8.28 (s, 1H); 7.3 (s, 1H); 7.2 (dd, 1H, J=8.7, 2.4 Hz); 6.92 (dd, 1H, J=8.7, 2.4 Hz); 6.06 (d, 1H, J=4.0 Hz); 4.95 (s, 2H); 4.81 (s, 2H); 4.6 (t, 1H, J=4.8 Hz); 4.4 (bd, 1H, J=12.0 Hz); 4.3 (d, 1H, J=5.4 Hz); 3.95 (bd, 1H, J=13 Hz); 3.75 (t, 1H, J=5.7 Hz); 3.1 (m, 1H); 2.8 (s, 3H); 2.79 (m, 2H); 2.62 (m, 1H); 1.82 (m, 2H); 1.4–1.15 (m, 2H).

Preparation A1

BOC Cleavage (2S,3S,4R,5R)3-Azido-5-{6-[5-chloro-2-(2-oxo-2-piperazin-1-yl-ethoxy)-benzylamino]-purin-9-yl}-4-hydroxy-tetrahydro-furan-2-carboxylic acid methylamide To trifluoroacetic acid (30 mL) was added to (2S,3S,4R,5R)3-azido-5-{6-[5-chloro-2-(2-oxo-2-(4-tert-butyloxycarbonyl)-piperazin-1-yl-ethoxy)-benzylamino]-purin-9-yl}-4-hydroxy-tetrahydro-furan-2-carboxylic acid methylamide (3 g, 4.5 mmol) at ambient temperature. After 1 hour, the mixture was concentrated, and the residue reconcentrated from chloroform three times. The crude product was dissolved in methanol (80 mL) and dichloromethane (100 mL) and neutralized with Amberlite IR 400 (OH) resin. The mixture was filtered and concentrated and the residue was purified by passing through a plug of silica gel (7.5–10% methanol/dichloromethane/0.1% NH$_4$OH) to afford 2.24 g of the title compound as a colorless solid.

In an analogous manner the following compounds, preparations A2–A$_3$, were prepared from the appropriate protected amine using analogous procedures to Preparation A1.

Preparation A2

(2S,3S,4R,5R)3-Azido-5-(6-{5-chloro-2-[2-(4-amino-piperidin-1-yl)-2-oxo-ethoxy]-benzylamino}-purin-9-yl)-4-hydroxy-tetrahydro-furan-2-carboxylic acid methylamide.

Preparation A3

(2S,3S,4R,5R)3-Azido-5-(6-{5-chloro-2-[2-(4-methylamino-piperidin-1-yl)-2-oxo-ethoxy]-benzylamino}-purin-9-yl)-4-hydroxy-tetrahydro-furan-2-carboxylic acid methylamide.

Preparation B1

Amide Coupling (2S,3S,4R,5R)3-Azido-5-(6-{5-chloro-2-[2-oxo-2-(3-oxo-piperazin-1-yl)-ethoxy]-benzylamino}-purin-9-yl)-4-hydroxy-tetrahydro-furan-2-carboxylic acid methylamide EDCI (44 mg, 0.23 mmol), HOBT (30 mg, 0.22 mmol) and DMAP (40 mg) were added to a mixture of (2R,3R,4S,5S)(2-{[9-(4-Azido-3-hydroxy-5-methylcarbamoyl-tetrahydro-furan-2-yl)-9H-purin-6-ylamino]-methyl}-4-chloro-phenoxy)-acetic acid (60 mg, 0.116 mmol) and piperizin-2-one (35 mg, 0.35 mmol) in anhydrous DMF (3 mL). After 20 hours at room temperature, the mixture was concentrated, pre-adsorbed onto silica gel and purified by flash chromatography (6–8% methanol/dichloromethane) to afford the title compound as a colorless solid. MS: 600 (M+H)$^+$.

In an analogous manner the following compounds, preparations B2–B38, were prepared from the appropriate amine using analogous procedures to the Preparation B1.

Preparation B2

(2S,3S,4R,5R)3-Azido-5-{6-[5-chloro-2-(2-oxo-2-piperidin-1-yl-ethoxy)-benzylamino]-purin-9-yl}-4-hydroxy-tetrahydro-furan-2-carboxylic acid methylamide.

Preparation B3

(2S,3S,4R,5R)3-Azido-5-[6-(5-chloro-2-phenylcarbamoylmethoxy-benzylamino)-purin-9-yl]-4-hydroxy-tetrahydro-furan-2-carboxylic acid methylamide.

Preparation B4

(2S,3S,4R,5R)3-Azido-5-[6-(5-chloro-2-dimethylcarbamoylmethoxy-benzylamino)-purin-9-yl]-4-hydroxy-tetrahydro-furan-2-carboxylic acid methylamide

Preparation B5

(2S,3S,4R,5R)3-Azido-5-{6-[2-(benzylcarbamoyl-methoxy)-5-chloro-benzylamino]-purin-9-yl}-4-hydroxy-tetrahydro-furan-2-carboxylic acid methylamide.

Preparation B6

(2S,3S,4R,5R)3-Azido-5-(6-{5-chloro-2-[2-(4-methyl-piperazin-1-yl)-2-oxo-ethoxy]-benzylamino}-purin-9-yl)-4-hydroxy-tetrahydro-furan-2-carboxylic acid methylamide.

Preparation B7

(2S,3S,4R,5R)3-Azido-5-[6-(5-chloro-2-propylcarbamoylmethoxy-benzylamino)-purin-9-yl]-4-hydroxy-tetrahydro-furan-2-carboxylic acid methylamide.

Preparation B8

(2S,3S,4R,5R)3-Azido-5-{6-[5-chloro-2-(2-morpholin-4-yl-2-oxo-ethoxy)-benzylamino]-purin-9-yl}-4-hydroxy-tetrahydro-furan-2-carboxylic acid methylamide.

Preparation B9

(2S,3S,4R,5R)3-Azido-5-{6-[5-chloro-2-(2-oxo-2-pyrrolidin-1-yl-ethoxy)-benzylamino]-purin-9-yl}-4-hydroxy-tetrahydro-furan-2-carboxylic acid methylamide

Preparation B10

(2S,3S,4R,5R)3-Azido-5-[6-(5-chloro-2-dipropylcarbamoylmethoxy-benzylamino)-purin-9-yl]-4-hydroxy-tetrahydro-furan-2-carboxylic acid methylamide

Preparation B11
(2S,3S,4R,5R)3-Azido-5-(6-{5-chloro-2-[(2-methoxy-ethylcarbamoyl)-methoxy]-benzylamino}-purin-9-yl)-4-hydroxy-tetrahydro-furan-2-carboxylic acid methylamide.

Preparation B12
(2S,3S,4R,5R)3-Azido-5-[6-(5-chloro-2-methylcarbamoylmethoxy-benzylamino)-purin-9-yl]-4-hydroxy-tetrahydro-furan-2-carboxylic acid methylamide.

Preparation B13
(2S,3S,4R,5R)3-Azido-5-[6-(5-chloro-2-cyclohexylcarbamoylmethoxy-benzylamino)-purin-9-yl]-4-hydroxy-tetrahydro-furan-2-carboxylic acid methylamide

Preparation B14
(2R,3R,4S,5S)4-[(2-{[9-(4-Azido-3-hydroxy-5-methylcarbamoyl-tetrahydro-furan-2-yl)-9H-purin-6-ylamino]-methyl}-4-chloro-phenoxy)-acetyl]-piperazine-1-carboxylic acid ethyl ester

Preparation B15
(2S,3S,4R,5R)3-Azido-5-{6-[2-(2-azetidin-1-yl-2-oxo-ethoxy)-5-chloro-benzylamino]-purin-9-yl}-4-hydroxy-tetrahydro-furan-2-carboxylic acid methylamide

Preparation B16
(2S,3S,4R,5R)3-Azido-5-(6-{5-chloro-2-[(2-morpholin-4-yl-ethylcarbamoyl)-methoxy]-benzylamino}-purin-9-yl)-4hydroxy-tetrahydro-furan-2-carboxylic acid methylamide

Preparation B17
(2S,3S,4R,5R)3-Azido-5-(6-{5-chloro-2-[2-oxo-2-(4-phenyl-piperazin-1-yl)-ethoxy]-benzylamino}-purin-9-yl)-4-hydroxy-tetrahydro-furan-2-carboxylic acid methylamide

Preparation B18
(2S,3S,4R,5R)3-Azido-5-(6-{5-chloro-2-[2-(4-cyclohexyl-piperazin-1-yl)-2-oxo-ethoxy]-benzylamino}-purin-9-yl)-4-hydroxy-tetrahydro-furan-2-carboxylic acid methylamide

Preparation B19
(2S,3S,4R,5R)3-Azido-5-(6-{5-chloro-2-[2-(4-ethyl-piperazin-1-yl)-2-oxo-ethoxy]-benzylamino}-purin-9-yl)-4-hydroxy-tetrahydro-furan-2-carboxylic acid methylamide.

Preparation B20
(2S,3S,4R,5R)3-Azido-5-[6-(5-chloro-2-cyclopropylcarbamoylmethoxy-benzylamino)-purin-9-yl]-4-hydroxy-tetrahydro-furan-2-carboxylic acid methylamide

Preparation B21
(2S,3S,4R,5R)3-Azido-5-[6-(2-carbamoylmethoxy-5-chloro-benzylamino)-purin-9-yl]-4-hydroxy-tetrahydro-furan-2-carboxylic acid methylamide

Preparation B22
(2S,3S,4R,5R)3-Azido-5-(6-{5-chloro-2-[2-(4-cyclopropyl-piperazin-1-yl)-2-oxo-ethoxy]-benzylamino}-purin-9-yl)-4-hydroxy-tetrahydro-furan-2-carboxylic acid methylamide

Preparation B23
(2S,3S,4R,5R)3-Azido-5-(6-{5-chloro-2-[2-(4-isopropyl-piperazin-1-yl)-2-oxo-ethoxy]-benzylamino}-purin-9-yl)-4-hydroxy-tetrahydro-furan-2-carboxylic acid methylamide

Preparation B24
(2S,3S,4R,5R)3-Azido-5-(6-{5-chloro-2-[2-oxo-2-(4-propyl-piperazin-1-yl)-ethoxy]-benzylamino}-purin-9-yl)-4-hydroxy-tetrahydro-furan-2-carboxylic acid methylamide

Preparation B25
(2S,3S,4R,5R)3-Azido-5-(6-{5-chloro-2-[2-(4-cyclopentyl-piperazin-1-yl)-2-oxo-ethoxy]-benzylamino}-purin-9-yl)-4-hydroxy-tetrahydro-furan-2-carboxylic acid methylamide

Preparation B26
(2S,3S,4R,5R)3-Azido-5-(6-{2-[2-(4-benzyl-piperazin-1-yl)-2-oxo-ethoxy]-5-chloro-benzylamino}-purin-9-yl)-4-hydroxy-tetrahydro-furan-2-carboxylic acid methylamide

Preparation B27
(2S,3S,4R,5R)3-Azido-5-(6-{5-chloro-2-[2-(4-ethyl-3-oxo-piperazin-1-yl)-2-oxo-ethoxy]-benzylamino}-purin-9-yl)-4-hydroxy-tetrahydro-furan-2-carboxylic acid methylamide

Preparation B28
(2S,3S,4R,5R)3-Azido-5-[6-(5-chloro-2-{2-[4-(2-chloro-phenyl)-piperazin-1-yl]-2-oxo-ethoxy}-benzylamino)-purin-9-yl]-4-hydroxy-tetrahydro-furan-2-carboxylic acid methylamide

Preparation B29
(2S,3S,4R,5R)3-Azido-5-{6-[5-chloro-2-phenethylcarbamoyl-methoxy)-benzylamino]-purin-9-yl}-4-hydroxy-tetrahydro-furan-2-carboxylic acid methylamide

Preparation B30
(2S,3S,4R,5R)3-Azido-5-(6-{5-chloro-2-[2-(3,5-dimethyl-piperazin-1-yl)-2-oxo-ethoxy]-benzylamino}-purin-9-yl)-4-hydroxy-tetrahydro-furan-2-carboxylic acid methylamide

Preparation B31
(2S,3S,4R,5R)3-Azido-5-(6-{5-chloro-2-[2-(4-dimethylamino-piperidin-1-yl)-2-oxo-ethoxy]-benzylamino}-purin-9-yl)-4-hydroxy-tetrahydro-furan-2-carboxylic acid methylamide

Preparation B32
(2S,3S,4R,5R)5-(6-{2-[2-(4-Adamantan-2-yl-piperazin-1-yl)-2-oxo-ethoxy]-5-chloro-benzylamino}-purin-9-yl)-3-azido-4-hydroxy-tetrahydro-furan-2-carboxylic acid methylamide

Preparation B33
(2R,3R,4S,5S)1-[(2-{[9-(4-Azido-3-hydroxy-5-methylcarbamoyl-tetrahydro-furan-2-yl)-9H-purin-6-ylamino]-methyl}-4-chloro-phenoxy)-acetyl]-piperidine-4-carboxylic acid amide

Preparation B34
(2S,3S,4R,5R)3-Azido-5-(6-{5-chloro-2-[2-(4-cycloheptyl-piperazin-1-yl)-2-oxo-ethoxy]-benzylamino}-purin-9-yl)-4-hydroxy-tetrahydro-furan-2-carboxylic acid methylamide

Preparation B35
(2S,3S,4R,5R)5-{6-[2-(Adamantan-2-ylcarbamoylmethoxy)-5-chloro-benzylamino]-purin-9-yl}-3-azido-4-hydroxy-tetrahydro-furan-2-carboxylic acid methylamide

Preparation B36
(2S,3S,4R,5R)3-Azido-5-{6-[5-chloro-2-(2-oxo-2-(4-tert-butyloxycarbonyl)-piperazin-1-yl-ethoxy)-benzylamino]-purin-9-yl}-4-hydroxy-tetrahydro-furan-2-carboxylic acid methylamide

Preparation B37
(2S,3S,4R,5R)3-Azido-5-(6-{5-chloro-2-[2-(4-tert-butyloxycarbonylamino-piperidin-1-yl)-2-oxo-ethoxy]- benzylamino}-purin-9-yl)-4-hydroxy-tetrahydro-furan-2-carboxylic acid methylamide.

Preparation B38

(2S,3S,4R,5R)3-Azido-5-(6-{5-chloro-2-[2-(4-tert-butyloxycarbonyl-methylamino-piperidin-1-yl)-2-oxo-ethoxy]-benzylamino}-purin-9-yl)-4-hydroxy-tetrahydro-furan-2-carboxylic acid methylamide.

Preparation C1

Deprotection of t-Butyl Ester (2R,3R,4S,5S)(2-{[9-(4-Azido-3-hydroxy-5-methylcarbamoyl-tetrahydro-furan-2-yl)-9H-purin-6-ylamino]-methyl}-4-chloro-phenoxy)-acetic acid (2R,3R,4S,5S)(2-{[9-(4-Azido-3-hydroxy-5-methylcarbamoyl-tetrahydro-furan-2-yl)-9H-purin-6-ylamino]-methyl}-4-chloro-phenoxy)-acetic acid tert-butyl ester (1 g, 1.9 mmol) was added to trifluoroacetic acid (15 mL) and stirred at room temperature for 3 hours. The mixture was concentrated and the residue was reconcentrated from chloroform three times to afford the title compound as a foam. M.S. 518 (M+H)$^+$. $^1$H NMR (400 MHz, CD$_3$OD) δ 8.5 (m, 2H); 7.38 (bs, 1H); 7.25 (d, 1H, J=8.0 Hz); 6.95 (d, 1H, J=8.0 Hz); 6.0 (d, 1H, J=4.0 Hz); 5.0 (m, 1H); 4.85 (m, 2H); 4.75 (s, 2H); 4.4 (m, 2H); 2.8 (s, 3H).

Preparation D1

Alkylation of Phenol (2R,3R,4S,5S)(2-{[9-(4-Azido-3-hydroxy-5-methylcarbamoyl-tetrahydro-furan-2-yl)-9H-purin-6-ylamino]-methyl}-4-chloro-phenoxy)-acetic acid ethyl ester Sodium hydride (115 mg, 4.8 mmol) was added to a solution of (2S,3S,4R,5R)3-azido-5-{6-[5-chloro-2-hydroxy-benzylamino]-purin-9-yl}-hydroxy-tetrahydro-furan-2-carboxylic acid methylamide (2.06 g, 4.37 mmol) in anhydrous DMF (30 mL) while cooled in an ice bath. After 30 minutes, ethyl bromoacetate (0.58 mL, 5.25 mmol) was added and the reaction was warmed to ambient temperature and stirred overnight. The reaction was quenched with methanol and concentrated. The residue was preadsorbed on silica gel and purified by flash chromatography (2–6% methanol/dichloromethane) to afford 1.7 g product as a colorless solid. MS 546 (M+H)$^+$. $^1$H NMR (400 MHz, CD$_3$OD) δ 8.34 (bs, 1H); 8.3 (s, 1H); 7.32 (bs, 1H); 7.22 (dd, 1H, J=8.9, 2.6 Hz); 6.9 (d, 1H, J=8.9 Hz); 6.02 (d, 1H, J=7.1 Hz); 5.07 (dd, 1H, J=7.1, 4.9 Hz); 4.85 (bs, 2H); 4.8 (s, 2H); 4.42 (m, 2H); 4.25 (q, 2H, J=6.9 Hz); 3.0 (s, 1H); 2.85 (s, 3H); 1.28 (t, 3H, J=6.9 Hz).

In an analogous manner the following compounds, preparations D2–D3, were prepared from the appropriate starting material using analogous procedures to Preparation D1.

Preparation D2

(2R,3R,4S,5S)(2-{[9-(4-Azido-3-hydroxy-5-methylcarbamoyl-tetrahydro-furan-2-yl)-9H-purin-6-ylamino]-methyl}-4-chloro-phenoxy)-acetic acid methyl ester Preparation D3

(2S,3S,4R,5R)3-Azido-5-[6-(5-chloro-2-cyanomethoxy-benzylamino)-purin-9-yl]-4-hydroxy-tetrahydro-furan-2-carboxylic acid methylamide Preparation E1

(2S,3S,4R,5R)3-Azido-5-{6-[5-chloro-2-(2-morpholin-4-yl-ethoxy)-benzylamino]-purin-9-yl}-4-hydroxytetrahydrofuran-2-carboxylic acid methylamide To a mixture of 4-acetoxy-3-azido-5-(6-chloropurin-9-yl) tetrahydrofuran-2-carboxylic acid methyl ester (485 mg, 1.27 mmol) and in anhydrous methanol (20 mL) was added triethylamine (0.51 mL, 3.8 mmol) and the reaction was heated to 50° C. under anhydrous conditions. The reaction was stirred at reflux for 15 hours. Methylamine (3.8 mL, 1.0 M in MeOH) was added to the reaction and the reaction was stirred at room temperature for another 15 hours. The solvent was then removed by rotary evaporation and the product was preadsorbed onto silica gel and purified by flash chromatography (SiO$_2$, 2.5% MeOH, EtOAc) to afford the title compound.

C$_{24}$H$_{29}$ClN$_{10}$O$_5$. MW 573.02. MS 573.1 (M+H)$^+$.

$^1$H NMR (400 MHz, DMSO-d$_6$) δ 8.64 (quart, 1H, J=4.6 Hz); 8.46 (s, 1H); 8.35 (bs, 1H); 8.23 (s, 1H); 7.21 (dd, 1H, J=8.7 Hz, J=2.7 Hz); 7.05 (bs, 1H); 7.01 (d, 1H, J=8.7 Hz); 6.30 (d, 1H, J=5.6 Hz); 5.98 (d, 1H, J=6.2 Hz) 4.98 (quart, 1H, J=5.5 Hz); 4.64 (bs, 2H); 4.50–4.45 (mult, 1H); 4.31 (d, 1H, J=3.1 Hz); 4.12 (t, 2H, J=5.7 Hz); 3.57–3.51 (mult, 4H); 2.72–2.62 (mult, 5H); 2.51–2.45 (mult, 4H).

The following compounds, Preparation E2–E18, were prepared by analogous procedures to Preparation E1 using the appropriate benzyl amine.

Preparation E2

(2S,3S,4R,5R)3-Azido-5-[6-(2-benzyloxy-5-chloro-benzylamino)-purin-9-yl]-4-hydroxytetrahydrofuran-2-carboxylic acid methylamide C$_{25}$H$_{24}$ClN$_9$O$_4$. MW 549.98. MS 550.1 (M+H)$^+$.

$^1$H NMR (400 MHz, DMSO-d$_6$) δ 8.65 (quart, 1H, J=4.6 Hz); 8.47 (s, 1H); 8.42 (bs, 1H); 8.23 (s, 1H); 7.49–7.45 (mult, 2H); 7.40 to 7.35 (mult, 2H); 7.30 (t, 1H, J=7.1 Hz); 7.21 (dd, 1H, J=8.7 Hz, J=2.5 Hz); 7.20 (d, 2H, J=8.9 Hz); 6.31 (d, 1H, J=5.4 Hz); 5.98 (d, 1H, J=6.4 Hz); 5.17 (s, 2H); 4.96 (quart, 1H, J=5.8 Hz); 4.71 (bs, 2H); 4.52–4.45 (mult, 1H); 4.35–4.30 (mult, 1H); 2.66 (d, 3H, J=4.6 Hz).

Preparation E3

(2S,3S,4R,5R)3-Azido-5-[6-(5-chloro-2-cyclobutylmethoxybenzylamino)-purin-9-yl]-4-hydroxytetrahydrofuran-2-carboxylic acid methylamide C$_{23}$H$_{26}$ClN$_9$O$_4$. MW 527.97. MS 527.7 (M+H)$^+$.

$^1$H NMR (400 MHz, DMSO-d$_6$) δ 8.65 (quart, 1H, J=4.6 Hz); 8.47 (s, 1H); 8.35 (bs, 1H); 8.23 (s, 1H); 7.20 (dd, 1H, J=8.7 Hz, J=2.7 Hz); 7.03 (bs, 1H); 6.98 (d, 1H, J=8.7 Hz); 6.31 (d, 1H, J=5.0 Hz); 5.98 (d, 1H, J=6.4 Hz); 4.96 (quart, 1H, J=5.2 Hz); 4.64 (bs, 2H); 4.48 (bs, 1H); 4.30–4.32 (mult, 1H); 3.97 (d, 2H, J=6.2 Hz); 2.71 (bs, 1H); 2.66 (d, 3H, J=4.6 Hz); 2.03 (bs, 2H); 1.86 (bs, 4H).

Preparation E4

(2S,3S,4R,5R)3-Azido-5-{6-[5-chloro-2-(3-methoxy-benzyloxy)-benzylamino]-purin-9-yl}-4-hydroxytetrahydrofuran-2-carboxylic acid methylamide C$_{26}$H$_{26}$ClN$_9$O$_5$. MW 580.01. MS 579.8 (M+H)$^+$.

$^1$H NMR (400 MHz, DMSO-d$_6$) δ 8.65 (quart, 1H, J=4.6 Hz); 8.47 (s, 1H); 8.43 (bs, 1H); 8.24 (s, 1H); 7.28 (t, 1H, J=8.2 Hz); 7.21 (dd, 1H, J=8.6 Hz, J=2.5 Hz); 7.10–7.00 (mult, 4H); 6.86 (d, 1H, J=6.8 Hz); 6.31 (d, 1H, J=5.4 Hz); 5.98 (d, 1H, J=6.4 Hz); 5.15 (s, 2H); 4.96 (quart, 1H, J=5.5 Hz); 4.71 (bs, 2H); 4.50–4.45 (mult, 1H); 4.31 (d, 1H, J=2.9 Hz); 3.72 (s, 3H); 2.66 (d, 3H, J=4.6 Hz).

Preparation E5

(2S,3S,4R,5R)3-Azido-5-{6-[5-chloro-2-(2,5-dimethoxy-benzyloxy)-benzylamino]-purin-9-yl}-4-hydroxytetrahydrofuran-2-carboxylic acid methylamide C$_{27}$H$_{28}$ClN$_9$O$_6$. MW 610.03. MS 609.9 (M+H)$^+$.

$^1$H NMR (400 MHz, DMSO-d$_6$) δ 8.66 (quart, 1H, J=4.8 Hz); 8.47 (s, 1H); 8.41 (bs, 1H); 8.23 (s, 1H); 7.21 (dd, 1H, J=8.7 Hz, J=2.7 Hz); 7.07 (bs, 1H); 7.05–7.00 (mult, 2H);

6.96 (d, 1H, J=8.9 Hz); 6.86 (dd, 1H, J=8.9 Hz, J=3.1 Hz); 6.31 (d, 1H, J=5.4 Hz); 5.98 (d, 1H, J=6.4 Hz); 5.10 (s, 2H); 4.95 (quart, 1H, J=5.8 Hz); 4.69 (bs, 2H); 4.49–4.48 (mult, 1H); 4.31 (d, 1H, J=2.9 Hz); 3.77 (s, 3H); 3.75 (s, 3H); 2.66 (d, 3H, J=4.6 Hz).

Preparation E6

(2S,3S,4R,5R)3-Azido-5-{6-[5-chloro-2-(3-chloro-benzyloxy)-benzylamino]-purin-9-yl}-4-hydroxytetrahydrofuran-2-carboxylic acid methylamide Mp 89.0–95.0° C.

$C_{25}H_{23}Cl_2N_9O_4$. MW 584.43. MS 583.8 (M+H)$^+$.

$^1$H NMR (400 MHz, DMSO-d$_6$) δ 8.63 (quart, 1H, J=4.4 Hz); 8.45 (s, 1H); 8.45 (bs, 1H); 8.23 (s, 1H); 7.52 (s, 1H); 7.45–7.32 (mult, 3H); 7.21 (dd, 1H, J=8.9 Hz, J=2.7 Hz); 7.10 (bs, 1H); 7.02 (d, 1H, J=8.7 Hz); 6.29 (d, 1H, J=5.2 Hz); 5.96 (d, 1H, J=6.4 Hz); 5.17 (s, 2H); 4.98–4.90 (mult, 1H); 4.69 (bs, 2H); 4.48–4.44 (mult, 1H); 4.30 (d, 1H, J=2.9 Hz); 2.64 (d, 3H, J=4.4 Hz).

Preparation E7

(2S,3S,4R,5R)3-Azido-5-{6-[5-chloro-2-(4-chloro-benzyloxy)-benzylamino]-purin-9-yl}-4-hydroxytetrahydrofuran-2-carboxylic acid methylamide Mp 79.0–84.0° C.

$C_{25}H_{23}Cl_2N_9O_4$. MW 584.43. MS 584.1 (M+H)$^+$.

$^1$H NMR (400 MHz, DMSO-d$_6$) δ 8.66 (quart, 1H, J=4.4 Hz); 8.47 (s, 1H); 8.44 (bs, 1H); 8.24 (s, 1H); 7.50 (d, 2H, J=8.3 Hz); 7.47–7.41 (mult, 2H); 7.25–7.20 (mult, 1H); 7.15–7.05 (mult, 2H); 6.32 (d, 1H, J=5.4 Hz); 5.99 (d, 1H, J=7.7 Hz); 5.17 (s, 2H); 4.96 (quart, 1H, J=5.2 Hz); 4.70 (bs, 2H); 4.49 (bs, 1H); 4.32 (d, 1H, J=2.9 Hz); 2.67 (d, 3H, J=4.4 Hz).

Preparation E8

(2S,3S,4R,5R)3-Azido-5-{6-[5-chloro-2-(2-chlorobenzyloxy)-benzylamino]-purin-9-yl}-4-hydroxytetrahydrofuran-2-carboxylic acid methylamide Mp 66.0–70.0° C.

$C_{25}H_{23}Cl_2N_9O_4$. MW 584.43. MS 584.1 (M+H)$^+$.

$^1$H NMR (400 MHz, DMSO-d$_6$) δ 8.66 (quart, 1H, J=4.8 Hz); 8.47 (s, 1H); 8.42 (bs, 1H); 8.22 (s, 1H); 7.67–7.61 (mult, 1H); 7.52–7.48 (mult, 1H); 7.41–7.34 (mult, 2H); 7.27–7.18 (mult, 1H); 7.11 (d, 2H, J=9.1 Hz); 6.32 (d, 1H, J=5.4 Hz); 5.98 (d, 1H, J=6.4 Hz); 5.22 (s, 2H); 4.96 (quart, 1H, J=5.8 Hz); 4.70 (bs, 2H); 4.50–4.45 (mult, 1H); 4.32 (d, 1H, J=3.1 Hz); 2.66 (d, 3H, J=4.8 Hz).

Preparation E9

(2S,3S,4R,5R)3-Azido-5-{6-[5-chloro-2-(tetrahydrofuran-3-ylmethoxy)-benzylamino]-purin-9-yl}-4-hydroxytetrahydrofuran-2-carboxylic acid methylamide $C_{23}H_{26}ClN_9O_5$. MW 543.97. MS 544.1 (M+H)$^+$.

$^1$H NMR (400 MHz, DMSO-d$_6$) δ 8.65 (quart, 1H, J=4.6 Hz); 8.47 (s, 1H); 8.38 (bs, 1H); 8.24 (s, 1H); 7.21 (dd, 1H, J=8.7 Hz, J=2.7 Hz); 7.06 (bs, 1H); 6.99 (d, 1H, J=8.7 Hz); 6.31 (dd, 1H, J=5.4 Hz, J=2.1 Hz); 5.99–5.97 (mult, 1H); 4.97–4.95 (mult, 1H); 4.65 (bs, 2H); 4.50–4.45 (mult, 1H); 4.35–4.29 (mult, 1H); 4.01–3.88 (mult, 2H); 3.83–3.72 (mult, 2H); 3.65–3.60 (mult, 1H); 3.59–3.53 (mult, 1H); 2.70–2.60 (mult, 4H); 2.05–1.95 (mult, 1H); 1.75–1.62 (mult, 1H).

Preparation E10

(2S,3S,4R,5R)3-Azido-5-{6-[5-chloro-2-(4-methyl-benzyloxy)-benzylamino]-purin-9-yl}-4-hydroxytetrahydrofuran-2-carboxylic acid methylamide Mp 88.0–95.0° C.

$C_{26}H_{26}ClN_9O_4$. MW 564.01. MS 564.2 (M+H)$^+$.

$^1$H NMR (400 MHz, DMSO-d$_6$) δ 8.66 (quart, 1H, J=4.8 Hz); 8.47 (s, 1H); 8.42 (bs, 1H); 8.22 (s, 1H); 7.45 (d, 1H, J=7.1 Hz); 7.27–7.16 (mult, 4H); 7.14 (d, 1H, J=8.7 Hz); 7.06 (bs, 1H); 6.32 (d, 1H, J=5.4 Hz); 5.99 (d, 1H, J=6.4 Hz); 5.15 (s, 2H); 4.96 (quart, 1H, J=5.5 Hz); 4.68 (bs, 2H); 4.50–4.45 (mult, 1H); 4.32 (d, 1H, J=2.9 Hz); 2.67 (d, 3H, J=4.8 Hz); 2.34 (s, 3H).

Preparation E11

(2S,3S,4R,5R)3-Azido-5-{6-[5-chloro-2-(2-methyl-benzyloxy)benzylamino]-purin-9-yl}-4-hydroxytetrahydrofuran-2-carboxylic acid methylamide Mp 58.0–62.0° C.

$C_{26}H_{26}ClN_9O_4$. MW 564.01. MS 564.2 (M+H)$^+$.

$^1$H NMR (400 MHz, DMSO-d$_6$) δ 8.66 (quart, 1H, J=4.8 Hz); 8.48 (s, 1H); 8.41 (bs, 1H); 8.24 (s, 1H); 7.35 (d, 1H, J=7.9 Hz); 7.21 (d, 1H, J=8.5 Hz); 7.20–7.15 (mult, 3H); 7.06 (d, 1H, J=8.7 Hz); 6.99 (d, 1H, J=8.7 Hz); 6.32 (d, 1H, J=5.4 Hz); 5.99 (d, 1H, J=6.4 Hz); 5.12 (s, 2H); (quart, 1H, J=5.8 Hz); 4.68 (bs, 2H); 4.50–4.47 (mult, 1H); 4.32 (d, 1H, J=3.1 Hz); 2.67 (d, 3H, J=4.8 Hz); 2.28 (s, 3H).

Preparation E12

(2S,3S,4R,5R)3-Azido-5-{6-[5-chloro-2-(3-methyl-benzyloxy)-benzylamino]-purin-9-yl}-4-hydroxytetrahydrofuran-2-carboxylic acid methylamide Mp 80.0–84.0° C.

$C_{26}H_{26}ClN_9O_4$. MW 564.01. MS 564.2 (M+H)$^+$.

$^1$H NMR (400 MHz, DMSO$_6$) δ 8.66 (quart, 1H, J=4.8 Hz); 8.48 (s, 1H); 8.41 (bs, 1H); 8.24 (s, 1H); 7.28–7.24 (mult, 3H); 7.22 (dd, 1H, J=8.7 Hz, J=2.5 Hz); 7.13–7.05 (mult, 3H); 6.31 (d, 1H, J=5.4 Hz); 5.99 (d, 1H, J=6.4 Hz); 5.13 (s, 2H); 4.96 (quart, 1H, J=5.7 Hz); 4.69 (bs, 2H); 4.50–4.45 (mult, 1H); 4.32 (d, 1H, J=3.1 Hz); 2.67 (d, 3H, J=4.8 Hz); 2.28 (s, 3H).

Preparation E13

(2S,3S,4R,5R)3-Azido-5-{6-[5-chloro-2-(2-methoxybenzyloxy)benzylamino]-purin-9-yl}-4-hydroxytetrahydrofuran-2-carboxylic acid methylamide $C_{26}H_{26}ClN_9O_5$. MW 580.01. MS 580.1 (M+H)$^+$.

$^1$H NMR (400 MHz, DMSO-d$_6$) δ 8.63 (quart, 1H, J=4.8 Hz); 8.45 (s, 1H); 8.36 (bs, 1H); 8.21 (s, 1H); 7.41 (dd, 1H, J=7.7 Hz, J=1.7 Hz); (t, 1H, J=7.2 Hz); 7.19 (dd, 1H, J=8.7 Hz, J=2.7 Hz); 7.05–6.99 (mult, 3H); 6.92 (t, 1H, J=7.5 Hz); 6.28 (d, 1H, J=5.4 Hz); 5.96 (d, 1H, J=6.4 Hz); 5.09 (s, 2H); 4.98–4.90 (mult, 1H); 4.65 (bs, 2H); 4.48–4.42 (mult, 1H); 4.29 (d, 1H, J=3.1 Hz); 3.80 (s, 3H); 2.64 (d, 3H, J=4.8 Hz).

Preparation E14

(2S,3S,4R,5R)3-Azido-5-{6-[5-chloro-2-(furan-3-ylmethoxy)benzylamino]-purin-9-yl}-4-hydroxytetrahydrofuran-2-carboxylic acid methylamide Mp 86.0–90.0° C.

$C_{23}H_{22}ClN_9O_5$. MW 539.94. MS 540.1 (M+H)$^+$.

$^1$H NMR (400 MHz, DMSO-d$_6$) δ 8.66 (quart, 1H, J=4.6 Hz); 8.48 (s, 1H); 8.39 (bs, 1H); 8.24 (s, 1H); 7.80 (s, 1H); 7.66 (s, 1H); 7.22 (dd, 1H, J=8.7 Hz, J=2.5 Hz); 7.11 (d, 1H, J=8.7 Hz); 7.06 (bs, 1H); 6.60 (s, 1H); 6.31 (d, 1H, J=5.4 Hz); 5.99 (d, 1H, J=6.4 Hz); 5.03 (s, 2H); 4.96 (quart, 1H, J=5.6 Hz); 4.64 (bs, 2H); 4.49–4.47 (mult, 1H); 4.32 (d, 1H, J=3.1 Hz); 2.67 (d, 3H, J=4.6 Hz).

Preparation E15
(2S,3S,4R,5R)3-Azido-5-{6-[5-chloro-2-(4-methoxy-benzyloxy)-benzylamino]-purin-9-yl}-4-hydroxy-tetrahydro-furan-2-carboxylic acid methylamide $C_{26}H_{26}ClN_9O_5$. MW 580.01. MS 580.0 (M+H)$^+$.

$^1$H NMR (400 MHz, DMSO-d$_6$) δ 8.63 (quart, 1H, J=4.6 Hz); 8.45 (s, 1H); 8.37 (bs, 1H); 8.21 (s, 1H); 7.37 (d, 2H, J=8.5 Hz); 7.19 (dd, 1H, J=8.5 Hz, J=2.5 Hz); 7.05 (d, 2H, J=8.9 Hz); 6.89 (d, 2H, J=8.7 Hz); 6.28 (d, 1H, J=4.8 Hz); 5.96 (d, 1H, J=6.2 Hz); 5.06 (s, 2H); 4.98–4.90 (mult, 1H); 4.63 (bs, 2H); 4.46–4.42 (mult, 1H); 4.29 (d, 1H, J=2.9 Hz); 3.70 (s, 3H); 2.64 (d, 3H, J=4.6 Hz).

Preparation E16
(2S,3S,4R,5R)3-Azido-5-[6-(5-chloro-2-cyclopentylmethoxybenzylamino)-purin-9-yl]-4-hydroxytetrahydrofuran-2-carboxylic acid methylamide $C_{24}H_{28}ClN_9O_4$. MW 542.00. MS 541.8 (M+H)$^+$.

$^1$H NMR (400 MHz, DMSO-d$_6$) δ 8.64 (quart, 1H, J=4.8 Hz); 8.45 (s, 1H); 8.33 (bs, 1H); 8.21 (s, 1H); 7.17 (dd, 1H, J=8.7 Hz, J=2.9 Hz); 7.00 (bs, 1H); 6.95 (d, 1H, J=8.7 Hz); 6.29 (d, 1H, J=5.6 Hz); 5.96 (d, 1H, J=6.2 Hz); 4.95–4.90 (mult, 1H); 4.62 (bs, 2H); 4.47–4.43 (mult, 1H); 4.29 (d, 1H, J=3.1 Hz); 3.85 (d, 2H, J=6.9 Hz); 2.64 (d, 3H, J=4.8 Hz); 2.32–2.21 (mult, 1H); 1.78–1.66 (mult, 2H); 1.60–1.42 (mult, 4H); 1.37–1.25 (mult, 2H).

Preparation E17
(2S,3S,4R,5R)3-Azido-5-(6-{5-chloro-2-[3-(2-morpholin-4-ylethoxy)-benzyloxy]-benzylamino}-purin-9yl)-4-hydroxytetrahydrofuran-2-carboxylic acid methylamide $C_{31}H_{35}ClN_{10}O_6$. MW 679.14. MS 678.7 (M+H)$^+$.

$^1$H NMR (400 MHz, DMSO-d$_6$) δ 8.62 (quart, 1H, J=5.0 Hz); 8.45 (s, 1H); 8.40 (bs, 1H); 8.22 (s, 1H); 7.27–7.17 (mult, 2H); 7.05–7.03 (mult, 1H); 7.03–6.98 (mult, 3H); 6.84 (d, 1H, J=8.3 Hz); 6.30–6.25 (mult, 1H); 5.99–5.92 (mult, 1H); 5.12 (s, 2H); 4.95–4.88 (mult, 1H); 4.73–4.65 (mult, 2H); 4.45–4.41 (mult, 1H); 4.30–4.26 (mult, 1H); 4.07–4.00 (mult, 2H); 3.55–3.45 (mult, 4H); 2.67–2.60 (mult, 5H); 2.42–2.37 (mult, 4H).

Preparation E18
(2S,3S,4R,5R)3-Azido-5-{6-[5-chloro-2-(2,2,7,7-tetramethyltetrahydro-bis[1,3]dioxolo[4,5-b;4',5'-d]pyran-5-ylmethoxy)benzylamino]purin-9-yl}-4-hydroxytetrahydrofuran-2-carboxylic acid methylamide $C_{30}H_{36}ClN_9O_9$. MW 702.13. MS 702.1 (M+H)$^+$.

$^1$H NMR (400 MHz, DMSO-d$_6$) δ 8.72–8.65 (mult, 1H); 8.47 (s, 1H); 8.38 (bs, 1H); 8.25 (s, 1H); 7.21 (dd, 1H, J=8.5 Hz, J=2.3 Hz); 7.06 (bs, 1H); 7.03 (d, 1H, J=8.5 Hz); 6.38 (bs, 1H); 5.98 (d, 1H, J=6.4 Hz); 5.48 (d, 1H, J=4.8 Hz); 4.95 (t, 1H, J=5.8 Hz); 4.65 (bs, 2H); 4.60 (d, 1H, J=7,9 Hz): 4.51–4.45 (mult, 1H); 4.39–4.35 (mult, 1H); 4.35–4.29 (mult, 2H); 4.21–4.16 (mult, 1H); 4.08–3.99 (mult, 2H); 2.67 (d, 3H, J=4.6 Hz); 1.35 (d, 6H, J=11.4 Hz); 1.25 (s, 6H).

Preparation F1
(5-{6-[5-Chloro-2-(3-methylisoxazol-5-ylmethoxy)benzylamino]purin-9-yl}-4-hydroxy-2-methylcarbamoyltetrahydrofuran-3-yl)carbamic acid tert-butyl ester To a mixture of [5-(6-chloropurin-9-yl)-4-hydroxy-2-methylcarbamoyl-tetrahydrofuran-3-yl]-carbamic acid tert-butyl ester (500 mg, 1.2 mmol) and (3-methylisoxazol-5-ylmethoxy)benzyl amine (1.4 mmol) in anhydrous ethanol (10 mL) was added triethylamine (0.5 mL, 3.6 mmol) and the reaction was heated to 65° C. The reaction was stirred at reflux for 15 hours under anhydrous conditions. The solvent was then removed by rotary evaporation and the product was preadsorbed onto silica gel and purified by flash chromatography to afford the title compound.

Mp 135.0–137.0° C.

$C_{28}H_{33}ClN_8O_7$. MW 629.08. MS 629.2 (M+H)$^+$.

$^1$H NMR (400 MHz, DMSO-d$_6$) δ 8.55 (bs, 1H); 8.41–8.33 (mult, 2H); 8.19 (s, 1H); 7.23 (dd, 1H, J=8.7 Hz, J=2.7 Hz); 7.12 (d, 1H, J=8.7 Hz); 7.07 (bs, 1H); 6.96 (d, 1H, J=6.0 Hz); 6.47 (s, 1H); 5.98 (d, 1H, J=4.6 Hz); 5.91 (bs, 1H); 5.29 (s, 2H); 4.63 (bs, 2H); 4.55–4. 43 (mult, 1H); 4.28–4.17 (mult, 2H); 2.63 (d, 3H, J=4.6 Hz); 2.20 (s, 3H); 1.35 (s, 9H).

Preparation G1
(2R,3R,4S,5S)(2-{[9-(4-Azido-3-hydroxy-5-methylcarbamoyl-tetrahydro-furan-2-yl)-9H-purin-6-ylamino]-methyl}-4-chloro-phenoxy)-acetic acid tert-butyl ester Triethyl amine (0.3 mL, 2.1 mmol) was added to a solution of (2S,3S,4R,5R)3-azido-5-(6-chloro-purin-9-yl)-4-hydroxy-tetrahydro-furan-2-carboxylic acid methylamide (302 mg, 0.9 mmol) and 2-aminomethyl-4-chloro-phenoxy acetic acid tert-butyl ester (290 mg, 1.07 mmol) in ethanol at ambient temperature. The reaction was heated to 70° C. for 2.5 hours, cooled, and the resultant solid was washed with cold ethanol, and dried to afford 420 mg (81%) of the title compound as a colorless solid. Alternatively, the product could be purified by flash chromatography (2–5% methanol/dichloromethane). MS 574 (M+H)$^+$. $^1$H NMR (400 MHz, CD$_3$OD) δ 8.28 (bs, 1H); 8.24 (s, 1H); 7.32 (bs, 1H); 7.18 (dd, 1H, J=8.9, 2.6 Hz); 6.92 (d, 1H, J=8.9 Hz); 5.95 (d, 1H, J=7.1 Hz); 5.03 (dd, 1H, J=7.1, 4.9 Hz); 4.82 (bs, 2H); 4.83 (s, 2H); 4.39 (m, 2H); 3.0 (s, 1H); 2.8 (s, 3H); 1.4 (s, 9H).

In an analogous manner the following compounds, Preparations G2–G30, were prepared from the appropriate starting material using analogous procedures to Preparation G1.

Preparation G2
(2S,3S,4R,5R)3-Azido-5-{6-[5-chloro-2-(3-methylisoxazol-5-ylmethoxy)benzylamino]purin-9-yl}-4-hydroxytetrahydrofuran-2-carboxylic acid methylamide Mp 94.0–98.0° C.; $C_{23}H_{23}ClN_{10}O_5$. MW 554.96. MS 555.1 (M+H)$^+$.

$^1$H NMR (400 MHz, DMSO-d$_6$) δ 8.63 (quart, 1H, J=4.6 Hz); 8.46 (s, 1H); 8.41 (bs, 1H); 8.21 (s, 1H); 7.23 (dd, 1H, J=8.7 Hz, J=2.5 Hz); 7.11 (d, 1H, J=8.7 Hz); 7.06 (bs, 1H); 6.48 (s, 1H); 6.29 (d, 1H, J=5.6 Hz); 5.97 (d, 1H, J=6.4 Hz); 5.29 (s, 2H); 4.94 (quart, 1H, J=5.6 Hz); 4.63 (bs, 2H); 4.48–4.42 (mult, 1H); 4.30 (d, 1H, J=2.7 Hz); 2.64 (d, 3H, J=4.6 Hz); 2.19 (s, 3H).

Preparation G3
(2S,3S,4R,5R)3-Azido-5-{6-[5-chloro-2-(tetrahydrofuran-3-ylmethoxy)-benzylamino]-purin-9-yl}-4-hydroxytetrahydrofuran-2-carboxylic acid methylamide $C_{23}H_{26}ClN_9O_5$. MW 543.97. MS 544.1 (M+H)$^+$.

$^1$H NMR (400 MHz, DMSO-d$_6$) δ 8.65 (quart, 1H, J=4.6 Hz); 8.47 (s, 1H); 8.38 (bs, 1H); 8.24 (s, 1H); 7.21 (dd, 1H, J=8.7 Hz, J=2.7 Hz); 7.06 (bs, 1H); 6.99 (d, 1H, J=8.7 Hz); 6.31 (dd, 1H, J=5.4 Hz, J=2.1 Hz); 5.99–5.97 (mult, 1H); 4.97–4.95 (mult, 1H); 4.65 (bs, 2H); 4.50–4.45 (mult, 1H); 4.35–4.29 (mult, 1H); 4.01–3.88 (mult, 2H); 3.83–3.72 (mult, 2H); 3.65–3.60 (mult, 1H); 3.59–3.53 (mult, 1H); 2.70–2.60 (mult, 4H); 2.05–1.95 (mult, 1H); 1.75–1.62 (mult, 1H).

Preparation G4

(2S,3S,4R,5R)3-Azido-5-{6-[5-chloro-2-(tetrahydrofuran-3-ylmethoxy)-benzylamino]-purin-9-yl}-4-hydroxytetrahydrofuran-2-carboxylic acid methylamide $C_{23}H_{26}ClN_9O_5$. MW 543.97. MS 544.1 (M+H)$^+$.

$^1$H NMR (400 MHz, DMSO-d$_6$) δ 8.65 (quart, 1H, J=4.6 Hz); 8.47 (s, 1H); 8.38 (bs, 1H); 8.24 (s, 1H); 7.21 (dd, 1H, J=8.7 Hz, J=2.7 Hz); 7.06 (bs, 1H); 6.99 (d, 1H, J=8.7 Hz); 6.31 (dd, 1H, J=5.4 Hz, J=2.1 Hz); 5.99–5.97 (mult, 1H); 4.97–4.95 (mult, 1H); 4.65 (bs, 2H); 4.50–4.45 (mult, 1H); 4.35–4.29 (mult, 1H); 4.01–3.88 (mult, 2H); 3.83–3.72 (mult, 2H); 3.65–3.60 (mult, 1H); 3.59–3.53 (mult, 1H); 2.70–2.60 (mult, 4H); 2.05–1.95 (mult, 1H); 1.75–1.62 (mult, 1H).

Preparation G5

(2S,3S,4R,5R)3-Azido-5-{6-[5-chloro-2-(furan-2-ylmethoxy)-benzylamino]-purin-9-yl}-4-hydroxytetrahydrofuran-2-carboxylic acid methylamide Mp 182.0–185.0° C.

$C_{23}H_{22}ClN_9O_5$. MW 539.94. MS 540.1 (M+H)$^+$.

$^1$H NMR (400 MHz, DMSO-d$_6$) δ 8.66 (d, 1H, J=4.6 Hz); 8.47 (s, 1H); 8.38 (bs, 1H); 8.23 (s, 1H); 7.68 (d, 1H, J=1.9 Hz); 7.23 (dd, 1H, J=8.7 Hz, J=2.7 Hz); 7.17 (d, 1H, J=8.7 Hz); 7.03 (bs, 1H); 6.60 (d, 1H, J=3.1 Hz); 6.45 (dd, 1H, J=3.1 Hz, J=1.9 Hz); 6.31 (d, 1H, J=5.4 Hz); 5.98 (d, 1H, J=6.2 Hz); 5.13 (s, 2H); 4.96 (quart, 1H, J=6.0 Hz); 4.60 (bs, 2H); 4.51–4.45 (mult, 1H); 4.31 (d, 1H, J=3.1 Hz); 2.66 (d, 3H, J=4.6 Hz).

Preparation G6

(2S,3S,4R,5R)3-Azido-5-{6-[5-chloro-2-(2,5-dimethylfuran-3-ylmethoxy)benzylamino]purin-9-yl}-4-hydroxytetrahydrofuran-2-carboxylic acid methylamide Mp 85.0–87.0° C.

$C_{25}H_{26}ClN_9O_5$. MW 568.00. MS 568.1 (M+H)$^+$.

$^1$H NMR (400 MHz, DMSO-d$_6$) δ 8.63 (quart, 1H, J=4.6 Hz); 8.45 (s, 1H); 8.33 (bs, 1H); 8.20 (s, 1H); 7.19 (dd, 1H, J=8.7 Hz, J=2.7 Hz); 7.05 (d, 1H, J=8.7 Hz); 7.02 (bs, 1H); 6.28 (d, 1H, J=5.4 Hz); 6.06 (s, 1H); 5.96 (d, 1H, J=6.4 Hz); 4.93 (quart, 1H, J=5.2 Hz); 4.86 (s, 2H); 4.59 (bs, 2H); 4.47–4.42 (mult, 1H); 4.29 (d, 1H, J=3.1 Hz); 2.64 (d, 3H, J=4.6 Hz); 2.21 (s, 3H); 2.14 (s, 3H).

Preparation G7

(2S,3S,4R,5R)3-Azido-5-{6-[5-chloro-2-(5-dimethylaminomethylfuran-2-ylmethoxy)benzylamino]purin-9-yl}-4-hydroxytetrahydrofuran-2-carboxylic acid methylamide $C_{26}H_{29}ClN_{10}O_5$. MW 597.04. MS 597.1 (M+H)$^+$.

$^1$H NMR (400 MHz, DMSO-d$_6$) δ 8.63 (quart, 1H, J=4.6 Hz); 8.45 (s, 1H); 8.34 (bs, 1H); 8.20 (s, 1H); 7.22–7.16 (mult, 1H); 7.13 (d, 1H, J=8.7 Hz); 7.00 (bs, 1H); 6.49 (d, 1H, J=2.7 Hz); 6.29 (bs, 1H); 6.22 (d, 1H, J=3.1 Hz); 5.96 (d, 1H, J=6.0 Hz); 5.06 (s, 2H); 4.92 (bs, 1H); 4.56 (bs, 2H); 4.48–4.41 (mult, 1H); 4.36–4.22 (mult, 1H); 3.28 (bs, 2H); 2.63 (d, 1H, J=4.6 Hz); 2.14–2.04 (mult, 6H).

Preparation G8

(2S,3S,4R,5R)3-Azido-5-{6-[5-chloro-2-(thiazol-2-ylmethoxy)benzylamino]purin-9-yl}-4-hydroxytetrahydrofuran-2-carboxylic acid methylamide Mp 88.0–92.0° C.

$C_{22}H_{21}ClN_{10}O_4S$. MW 556.99. MS 557.1 (M+H)$^+$.

$^1$H NMR (400 MHz, DMSO-d$_6$) δ 8.66 (quart, 1H, J=4.4 Hz); 8.52–8.40 (mult, 2H); 8.24 (s, 1H); 7.84 (d, 1H, J=2.9 Hz); 7.77 (d, 1H, J=2.9 Hz); 7.25 (d, 1H, J=8.5 Hz); 7.15 (d, 1H, J=8.5 Hz); 7.08 (bs, 1H); 6.31 (d, 1H, J=5.4 Hz); 5.98 (d, 1H, J=6.4 Hz); 5.51 (s, 2H); 5.00–4.91 (mult, 1H); 4.72 (bs, 2H); 4.49 (bs, 1H); 4.32 (bs, 1H); 2.66 (d, 3H, J=4.4 Hz).

Preparation G9

(2S,3S,4R,5R)3-Azido-5-{6-[2-(benzothiazol-2-ylmethoxy)-5-chlorobenzylamino]purin-9-yl}-4-hydroxytetrahydrofuran-2-carboxylic acid methylamide Mp 95.0–100.0° C.

$C_{26}H_{23}ClN_{10}O_4S$. MW 607.05. MS 607.0 (M+H)$^+$.

$^1$H NMR (400 MHz, DMSO-d$_6$) δ 8.66 (quart, 1H, J=4.4 Hz); 8.49 (bs, 2H); 8.24 (s, 1H); 8.11 (d, 1H, J=8.1 Hz); 8.01 (d, 1H, J=8.1 Hz); 7.52 (t, 1H, J=7.7 Hz); 7.44 (t, 1H, J=7.7 Hz); 7.26 (d, 1H, J=8.3 Hz); 7.17 (d, 1H, J=8.3 Hz); 7.10 (bs, 1H); 6.32 (d, 1H, J=5.2 Hz); 5.99 (d, 1H, J=6.4 Hz); 5.67 (s, 2H); 5.00–4.96 (mult, 1H); 4.80 (bs, 2H); 4.49 (bs, 1H); 4.32 (bs, 1H); 2.66 (d, 3H, J=4.4 Hz).

Preparation G10

(2S,3S,4R,5R)3-Azido-5-{6-[2-(benzofuran-2-ylmethoxy)-5-chlorobenzylamino]purin-9-yl}-4-hydroxytetrahydrofuran-2-carboxylic acid methylamide Mp 89.0–100.0° C.

$C_{27}H_{24}ClN_9O_5$. MW 590.00. MS 590.1 (M+H)$^+$.

$^1$H NMR (400 MHz, DMSO-d$_6$) δ 8.65 (quart, 1H, J=4.4 Hz); 8.47 (s, 1H); 8.41 (bs, 1H); 8.20 (s, 1H); 7.63 (d, 1H, J=7.9 Hz); 7.57 (d, 1H, J=7.9 Hz); 7.31 (t, 1H, J=7.5 Hz); 7.26–7.20 (mult, 3H); 7.07 (mult, 2H); 6.31 (d, 1H, J=5.2 Hz); 5.98 (d, 1H, J=6.4 Hz); 5.35 (s, 2H); 4.95 (quart, 1H, J=5.8 Hz); 4.66 (bs, 2H); 4.48 (bs, 1H.

Preparation G11

(2S,3S,4R,5R)3-Azido-5-{6-[5-chloro-2-isothiazol-5-ylmethoxy)benzylamino]purin-9-yl}-4-hydroxytetrahydrofuran-2-carboxylic acid methylamide Mp 96.0–99.0° C.

$C_{22}H_{21}ClN_{10}O_4S$. MW 556.99. MS 557.1 (M+H)$^+$.

$^1$H NMR (400 MHz, DMSO-d$_6$) δ 8.63 (quart, 1H, J=4.6 Hz); 8.51 (s, 1H); 8.46 (s, 1H); 8.42 (bs, 1H); 8.22 (s, 1H); 7.45 (s, 1H); 7.24 (dd, 1H, J=8.7 Hz, J=2.5 Hz); 7.12–7.07 (mult, 2H); 6.29 (d, 1H, J=5.4 Hz); 5.97 (d, 1H, J=6.4 Hz); 5.57 (s, 2H); 4.94 (quart, 1H, J=5.8 Hz); 4.67 (bs, 2H); 4.49–4.41 (mult, 1H); 4.30 (d, 1H, J=3.1 Hz); 2.65 (d, 3H, J=4.6 Hz).

Preparation G12

(2S,3S,4R,5R)3-Azido-5-{6-[5-chloro-2-(thiophen-2-ylmethoxy)benzylamino]purin-9-yl}-4-hydroxytetrahydrofuran-2-carboxylic acid methylamide Mp 91.0–112.0° C.

$C_{23}H_{22}ClN_9O_4S$. MW 556.01. MS 556.1 (M+H)$^+$.

$^1$H NMR (400 MHz, DMSO-d$_6$) δ 8.63 (quart, 1H, J=4.6 Hz); 8.46 (s, 1H); 8.42 (bs, 1H); 8.22 (s, 1H); 7.52 (d, 1H, J=5.0 Hz); 7.25–7.18 (mult, 2H); 7.13 (d, 1H, J=8.9 Hz); 7.03 (bs, 1H); 7.01–6.98 (mult, 1H); 6.30 (bs, 1H); 5.97 (d, 1H, J=6.2 Hz); 5.34 (s, 2H); 4.97–4.90 (mult, 1H); 4.62 (bs, 2H); 4.48–4.41 (mult, 1+H); 4.30 (d, 1H, J=3.1 Hz); 2.64 (d, 3H, J=4.6 Hz).

Preparation G13

(2S,3S,4R,5R)3-Azido-5-{6-[5-chloro-2-(quinolin-2-ylmethoxy)benzylamino]purin-9-yl}-4-hydroxytetrahydrofuran-2-carboxylic acid methylamide Mp 117.0–120.0° C.

$C_{28}H_{25}ClN_{10}O_4$. MW 601.03. MS 601.1 (M+H)$^+$.

$^1$H NMR (400 MHz, DMSO-d$_6$) δ 8.64 (quart, 1H, J=4.6 Hz); 8.47 (bs, 1H), 8.46 (s, 1H); 8.37 (d, 1H, J=8.5 Hz); 8.24 (s, 1H); 8.03–7.92 (mult, 2H); 7.80–7.67 mult, 2H); 7.58 (t, 1H, J=7.1 Hz); 7.18 (dd, 1H, J=8.5 Hz, J=2.1 Hz); 7.12 (bs, 1H); 7.07 (d, 1H, J=8.5 Hz); 6.30 (d, 1H, J=5.4 Hz); 5.97 (d, 1H, J=6.4 Hz); 5.42 (s, 2H); 4.95 (quart, 1H, J=5.2 Hz); 4.78 (bs, 2H); 4.51–4.44 (mult, 1H); 4.30 (d, 1H, J=3.1 Hz); 2.64 (d, 3H, J=4.6 Hz).

Preparation G14
(2S,3S,4R,5R)3-Azido-5-{6-[5-chloro-2-(4-methyl-[1,2,3]thiadiazol-5-ylmethoxy)benzylamino]purin-9-yl}-4-hydroxytetrahydrofuran-2-carboxylic acid methylamide
Mp 105.0–107.0° C.
$C_{22}H_{22}ClN_{11}O_4S$. MW 572.01. MS 572.0 (M+H)$^+$.
$^1$H NMR (400 MHz, DMSO-d$_6$) δ 8.63 (quart, 1H, J=4.8 Hz); 8.46 (s, 1H); 8.42 (bs, 1H); 8.20 (s, 1H); 7.27 (dd, 1H, J=8.7 Hz, J=2.7 Hz); 7.16 (d, 1H, J=8.7 Hz); 7.09 (bs, 1H); 6.30 (d, 1H, J=5.4 Hz); 5.96 (d, 1H, J=6.6 Hz); 5.57 (s, 2H); 4.94 (quart, 1H, J=5.2 Hz); 4.63 (bs, 2H); 4.49–4.42 (mult, 1H); 4.30 (d, 1H, J=5.4 Hz); 2.70–2.60 (mult, 6H).

Preparation G15
(2S,3S,4R,5R)3-Azido-5-{6-[5-chloro-2-(naphthalen-1-ylmethoxy)benzylamino]purin-9-yl}-4-hydroxytetrahydrofuran-2-carboxylic acid methylamide
Mp 115.0–119.0° C.
$C_{29}H_{26}ClN_9O_4$. MW 600.04. MS 600.1 (M+H)$^+$.
$^1$H NMR (400 MHz, DMSO-d$_6$) δ 8.63 (quart, 1H, J=4.8 Hz); 8.44 (s, 1H); 8.38 (bs, 1H); 8.19 (s, 1H); 8.14 (d, 1H, J=7.9 Hz); 7.98–7.86 (mult, 2H); 7.70 (d, 1H, J=6.6 Hz); 7.59–7.43 (mult, 3H); 7.32–7.21 (mult, 2H); 7.06 (bs, 1H); 6.29 (d, 1H, J=5.2 Hz); 5.96 (d, 1H, J=6.4 Hz); 5.61 (s, 2H); 4.93 (quart, 1H, J=5.6 Hz); 4.62 (bs, 2H); 4.49–4.42 (mult, 1H); 4.30 (d, 1H, J=2.9 Hz); 2.64 (d, 3H, J=4.8 Hz).

Preparation G16
(2S,3S,4R,5R)3-Azido-5-[6-(5-chloro-2-hydroxybenzylamino)-purin-9-yl]-4-hydroxytetrahydrofuran-2-carboxylic acid methylamide
$^1$H NMR (400 MHz, DMSO-d$_6$) δ 10.04 (bs, 1H); 8.63 (quart, 1H, J=4.6 Hz); 8.45 (s, 1H); 8.40 (bs, 1H); 8.25 (s, 1H); 7.05 (dd, 1H, J=8.5 Hz, J=2.5 Hz); 7.00 (bs, 1H); 6.77 (d, 1H, J=8.5 Hz); 6.30 (d, 1H, J=5.4 Hz); 5.96 (d, 1H, J=6.2 Hz); 4.94 (quart, 1H, J=5.8 Hz); 4.56 (bs, 2H); 4.49–4.43 (mult, 1H); 4.30 (d, 1H, J=2.9 Hz); 2.65 (d, 3H, J=4.6 Hz).

Preparation G17
(2S,3S,4R,5R)3-Azido-5-[6-(2-benzyloxy-5-chloro-benzylamino)-2-chloro-purin-9-yl]-4-hydroxy-tetrahydro-furan-2-carboxylic acid methylamide.

Preparation G18
(2S,3S,4R,5R)3-Azido-5-[6-(5-chloro-2-phenethyloxy-benzylamino)purin-9-yl]-4-hydroxy-tetrahydro-furan-2-carboxylic acid methylamide Preparation G19
(2S,3S,4R,5R)3-Azido-5-{6-[5-chloro-2-(1-phenyl-ethoxy)-benzylamino]-purin-9-yl}-4-hydroxy-tetrahydro-furan-2-carboxylic acid methylamide Preparation G20
(2S,3S,4R,5R)3-Azido-5-{6-[5-chloro-2-(4,5-dihydro-1H-imidazol-2-ylmethoxy)-benzylamino]-purin-9-yl}-4-hydroxy-tetrahydro-furan-2-carboxylic acid methylamide Preparation G21
(2S,3S,4R,5R)3-Azido-5-{6-[1-(2-benzyloxy-5-chloro-phenyl)ethylamino]-purin-9-yl}-4-hydroxy-tetrahydro-furan-2-carboxylic acid methylamide Preparation G22
(2S,3S,4R,5R)3-Azido-5-[6-(2-benzyloxy-5-bromobenzylamino)-purin-9-yl]-4-hydroxy-tetrahydro-furan-2-carboxylic acid methylamide Preparation G23
(2S,3S,4R,5R)3-Azido-5-[6-(2-benzyloxy-5-fluoro-benzylamino)-purin-9-yl]-4-hydroxy-tetrahydro-furan-2-carboxylic acid methylamide Preparation G24
(2S,3S,4R,5R)3-Azido-5-[6-(2-benzyloxy-5-iodo-benzylamino)-purin-9-yl]-4-hydroxy-tetrahydro-furan-2-carboxylic acid methylamide Preparation G25
(2S,3S,4R,5R)3-Azido-5-[6-(2-benzyloxy-5-trifluoromethyl-benzylamino)-purin-9-yl]-4-hydroxy-tetrahydro-furan-2-carboxylic acid methylamide Preparation G26
(2S,3S,4R,5R)3-Azido-5-[6-(2-benzyloxy-5-cyanobenzylamino)-purin-9-yl]-4-hydroxy-tetrahydro-furan-2-carboxylic acid methylamide Preparation G27
(2S,3S,4R,5R)3-Azido-5-[6-(2-benzyloxy-5-methyl-benzylamino)-purin-9-yl]-4-hydroxy-tetrahydro-furan-2-carboxylic acid methylamide Preparation G28
(2S,3S,4R,5R)3-Azido-5-[6-(2-benzyloxy-5-vinyl-benzylamino)-purin-9-yl]-4-hydroxy-tetrahydro-furan-2-carboxylic add methylamide Preparation G29
(2S,3S,4R,5R)3-Azido-5-[6-(2-benzyloxy-5-ethynyl-benzylamino)-purin-9-yl]-4-hydroxy-tetrahydro-furan-2-carboxylic acid methylamide Preparation G30
3-Azido-5-{6-[5-chloro-2-(3,5-dimethylisoxazol-4-ylmethoxy)benzylamino]purin-9-yl}-4-hydroxytetrahydrofuran-2-carboxylic acid methylamide
$C_{24}H_{25}ClN_{10}O_5$. MW 568.98. MS 569.1 (M+H)$^+$.
$^1$H NMR (400 MHz, DMSO$_6$) δ 8.69 (quart, 1H, J=4.8 Hz); 8.40 (s, 1H); 8.35 (bs, 1H); 8.14 (s, 1H); 7.25 (dd, 1H, J=8.7 Hz, J=2.7 Hz); 7.11 (d, 1H, J=8.7 Hz); 7.07 (bs, 1H); 6.28 (d, 1H, J=5.6 Hz); 6.05 (d, 1H, J=6.6 Hz); 4.95 (s, 2H); 4.85–4.77 (mult, 1H); 4.67–4.52 (mult, 2H); 4.49–4.42 (mult, 1H); 4.39–4.32 (mult, 1H); 2.65 (d, 3H, J=4.8 Hz); 2.38 (s, 3H); 2.22 (s, 3H).

Preparation H1
(2S,3S,4R,5R)3-Azido-5-(6-chloro-purin-9-yl)-4-hydroxy-tetrahydro-furan-2-carboxylic acid methylamide
Triethylamine (4.4 mL, 0.032 mL) was added to a solution of (2S,3S,4R,5R)3-azido-5-(6-chloro-purin-9-yl)-4-acetoxy-tetrahydro-furan-2-carboxylic acid methylamide (4 g, 0.011 mmol) in methanol (80 mL). After stirring for 15 hours, the mixture was concentrated and the residue purified by flash chromatography (5% methanol/dichloromethane) to afford 2.7 g (77%) of the title compound as a colorless solid. MS 339 (M+H)$^+$. $^1$H NMR (400 MHz, CDCl3) δ 8.72 (s, 1H); 8.2 (s, 1H); 7.62 (bs, 1H); 5.98 (d, 1H, J=6.7 Hz); 5.07 (t, 1H, J=6.2 Hz); 4.65 (dd, 1H, J=5.4, 2.7 Hz); 4.58 (m, 1H); 4.2 (bs, 1H); 2.88 (d, 1H, J=4.9 Hz); 1.67 (bs, 1H).

Preparation I1

Alternate preparation of (2S,3S,4R,5R)3-Azido-5-(6-chloropurin-9-yl)-4-hydroxytetrahydrofuran-2-carboxylic acid methylamide To a solution of acetic acid 4-azido-2-(6-chloropurin-9-yl)-5-methylcarbamoyl-tetrahydrofuran-3-yl ester (1.1 g, 2.9 mmol) in anhydrous methanol (100 mL), cooled to 0° C., was added methylamine (1.2 mL, 8.6 mmol). The solution was stirred for 2 h at room temperature, under anhydrous conditions. After removal of solvent by rotary evaporation, the resulting solid was purified via flash chromatography (7% MeOH/CH$_2$Cl$_2$) to yield the title compound as a white foam.

$C_{11}H_{11}ClN_8O_3$. MW 338.72. MS 339.1 (M+H)$^+$.

$^1$H NMR (400 MHz, DMSO-d$_6$) δ 9.01 (s, 1H); 8.81 (s, 1H); 8.22 (quart, 1H, J=4.2 Hz); 6.41 (dd, 1H, J=5.2 Hz, J=2.1 Hz); 6.12 (d, 1H, J=5.2 Hz); 5.03 (quart, 1H, J=5.2 Hz); 4.57–4.47 (mult, 1H); 4.41 (d, 1H, J=3.9 Hz); 2.61 (d, 3H, J=4.2 Hz).

Preparation J1

Glycosidation (2S,3S,4R,5R)3-Azido-5-(6-chloro-purin-9-yl)-4-acetoxy-tetrahydro-furan-2-carboxylic acid methylamide 6-Chloropurine (20.4 g, 0.132 mol) was suspended in hexamethyl disilazane (165 mL) and heated at 110° C. After 2 h, the now homogeneous mixture was concentrated and the solid residue reconcentrated from toluene 2× and placed under high vac for 1 hour. The resulting solid was combined with 1,2-bis-O-acetyl-3-azido-3-deoxy-D-ribofuranuronic acid methyl amide (12.7 g, 0.044 mol) and dissolved in anhydrous dichloroethane (350 mL). Powdered 4A molecular sieves (15 g) were added and the mixture stirred for 5 minutes. TMSOTf (16.0 mL, 0.088 mol) was added and the reaction was then heated to 60° C. for two hours, cooled and quenched by the careful addition of saturated sodium bicarbonate solution (200 mL). Ethyl acetate (350 mL) was added and the mixture was filtered through sintered glass. The filtrate was extracted with ethyl acetate (3×) and the combined organic layers were washed with brine, dried (Na$_2$SO$_4$), filtered and concentrated. The residue was purified by flash chromatography (15% then 20% acetone/dichloromethane) to afford the title compound (10.6 g) as an off-white foam. MS 381 (M+H)$^+$. $^1$H NMR (400 MHz, CDCl$_3$) δ 8.8 (s, 1H); 8.2 (s, 1H); 7.6 (bs, 1H); 6.13 (d, 1H, J=7.0 Hz); 5.87 (dd, 1H, J=7.0, 5.6 Hz); 4.85 (dd, 1H, J=5.6, 3.0 Hz); 4.58 (d, 1H, J=3.0 Hz); 2.9 (d, 1H, J=4.9 Hz); 2.11 (s, 3H).

The following compound, Preparation J2, was prepared from the appropriate starting material using analogous procedures to Preparation J1.

Preparation J2

(2S,3S,4R,5R)3-Azido-5-(2,6-dichloro-purin-9-yl)-4-hydroxy-tetrahydro-furan-2-carboxylic acid methylamide

Preparation K1

1,2-bis-O-acetyl-3-azido-3-deoxy-D-ribofuranuronic acid methyl amide

3-Azido-3-deoxy-1,2-O-isopropylidene-α-D-ribofuranuronic acid methyl amide (12 g, 0.05 mmol) was dissolved in acetic acid (150 mL) and acetic anhydride (50 mL). The mixture was cooled in an ice bath and a solution of sulfuric acid (1 mL dissolved in 5 mL acetic acid) was added. The mixture was allowed to warm to room temperature and stirred for 18 hours. The reaction mixture was added dropwise to a saturated solution of sodium bicarbonate (2 L), and then extracted with chloroform (3×). The combined organic layers were washed with water (2×) and sat. NaHCO$_3$ (2×) and brine (1×), dried (Na$_2$SO$_4$) filtered and concentrated to afford a mixture of anomeric acetates as a tan oil.

Preparation L1

3-Azido-3-deoxy-1,2-O-isopropylidene-α-D-ribofuranuronic acid methyl amide

Oxalyl chloride (15 mL) was added to a solution of 3-azido-3-deoxy-α-D-ribofuranuronic acid (30 g) in anhydrous THF (250 mL) at 0° C. DMF (1 mL) was added and the reaction was allowed to warm to room temperature at which time gas evolution commenced. After five hours, the mixture was concentrated and the residue dissolved in dichloromethane (100 mL), cooled to 0° C. A solution of methyl amine in THF (260 mL of a 2M solution) was added slowly. After 30 minutes, the mixture was diluted with water (500 mL) and extracted with chloroform (3×). The combined organic layers were dried (Na$_2$SO$_4$), filtered and concentrated to afford the title compound as a light brown solid. $^1$H NMR (400 MHz, CDCl$_3$) δ 6.39 (bs, 1H); 5.80 (d, 1H, J=3.7 Hz); 4.67 (dd, 1H, J=4.0, 3.7 Hz); 4.42 (d, 1H, J=9.3 Hz); 3.6 (dd, 1H, J=9.3, 4.0 Hz); 2.9 (d, 3H, J=5.0 Hz); 1.54 (s, 3H); 1.34 (s, 3H).

Preparation M1

(2S,3S,4R,5R)4-Acetoxy-3-azido-5-(6-chloropurin-9-yl)tetrahydrofuran-2-carboxylic acid methyl ester A solution of 6-chloropurine (4.96 g, 32 mmol) and hexamethyldisilazane (40 mL) were combined and heated to 100° C. for 3 h under anhydrous conditions. The mixture was allowed to cool to room temperature and was then concentrated to a solid on the rotary evaporator using anhydrous toluene (3×50 mL) to help remove the solvent. The solid was pumped on high vacuum for 15 minutes and then anhydrous acetonitrile (50 mL) was added. 1,2-Bis-O-acetyl-3-Azido-3-deoxy-D-ribofuranuronic acid methyl ester (3.09 g, 10.7 nmol) was dissolved in anhydrous acetonitrile (20 mL) and added to the reaction.

Trimethylsilyltrifluoromethanesulfonate (7.5 mL, 41.4 mmol) was added. The reaction was stirred at 70° C., under anhydrous conditions, for 15 h. The reaction mixture was quenched with saturated aqueous sodium bicarbonate (200 mL). Water (160 mL) was added, and the reaction mixture was extracted with EtOAc (4×100 mL), dried over sodium sulfate, and concentrated to a solid on the rotary evaporator. This solid was purified via flash chromatography (7:3 hexane:EtOAc) to afford 2.88 g of the title compound as a white foam.

Mp 94.0–96.0° C.

$^1$H NMR (400 MHz, CDCl$_3$) δ 8.73 (s, 1H); 8.60 (s, 1H); 6.36 (d, 1H, J=5.4 Hz); 5.83 (t, 1H, J=5.4 Hz); 4.83–4.77 (mult, 1H); 4.65 (d, 1H, J=4.2 Hz); 3.84 (s, 3H); 2.14 (s, 3H).

Preparation N1

1,2-Bis-O-acetyl-3-azido-3-deoxy-D-ribofuranuronic acid methyl ester

3-Azido-3-deoxy-1,2-O-isopropylidene-α-D-ribofuranuronic acid methyl ester (4.85 g, 20 mmol), concentrated H$_2$SO$_4$ (5.5 mL), glacial acetic acid (65 mL), and acetic anhydride (18 mL, 20 mmol) were combined and stirred at room temperature, under anhydrous conditions, for 15 h. The reaction mixture was then taken up in water (500 mL), neutralized with solid sodium hydroxide to pH 7 and extracted with EtOAc (3×250 mL). The combined organic layers were washed with saturated aqueous NaCl (500 mL), dried over sodium sulfate and concentrated on a rotary evaporator to a solid, which was purified via flash chromatography (2:1 hexane:EtOAc) to afford 3.09 g of the title compound as a clear, colorless oil.

$^1$H NMR (400 MHz, CDCl$_3$) δ 6.18 (s, 1H); 5.33 (d, 1H, J=5.0 Hz); 4.53 (d, 1H, J=7.5 Hz); 4.44–4.38 (mult, 1H); 3.83 (s, 3H); 2.17 (s, 3H); 2.08 (s, 3H).

Preparation O1
3-Azido-3-deoxy-1,2-O-isopropylidene-α-D-ribofuranuronic acid methyl ester To a solution of 3-azido-3-deoxy-1,2-isopropylidene-α-D-ribofuranuronic acid (4.23 g, 18 mmol) in DMF (50 mL) was added potassium carbonate (3 g, 22 mmol) and iodomethane (2.3 mL, 37 mmol). The reaction mixture was stirred at room temperature under anhydrous conditions for 15 h. The reaction mixture was then taken up in EtOAc (500 mL) and washed with water (500 mL), saturated aqueous NaHCO (2×500 mL), and saturated aqueous NaCl (500 mL). The combined organic layers were dried over sodium sulfate and concentrated on the rotary evaporator to an oil. The product was purified by flash chromatography (7:3 hexane:EtOAc) to afford 4.45 g of the title compound as a clear, colorless oil.

$^1$H NMR (400 MHz, CDCl$_3$) δ 5.89 (d, 1H, J=3.3 Hz); 4.74–4.68 (mult, 1H); 4.53 (d, 1H, J=9.6 Hz); 3.82 (s, 3H); 3.69–3.63 (mult, 1H); 1.55 (s, 3H); 1.34 (s, 3H).

Preparation P1
3-Azido-3-deoxy-1,2-isopropylidene-α-D-ribofuranuronic acid

A solution of 3-azido-1,2,5,6-bis-O-isopropylidene-3-deoxy-D-allofuranose (451 g, 1.58 mol) in diethyl ether (4.5 L) was treated with periodic acid (540 g, 2.37 mol) at ambient temperature which was maintained with a water bath. After 24 hours, the precipitated salts were filtered and washed with ether. The filtrate was concentrated and the crude aldehyde was added to a mixture of chloroform (2.5 L), acetonitrile (2.5 L) and water (3.4 L). To this vigorously stirred mixture was added sodium periodate (1211 g, 5.67 mol) and ruthenium trichloride hydrate (14.5 g, 0.69 mol) at room temperature maintained with a water bath. After 20 hours, the mixture was diluted with chloroform (4 L) and water (4 L) and the mixture was filtered through Celite® filter aid. The layers were separated and the aqueous phase reextracted with chloroform. The combined organic layers were concentrated in vacuo and the residue partitioned between saturated aqueous sodium bicarbonate (2 L) and ethyl acetate (3 L). The layers were separated and the aqueous layer reextracted with ethyl acetate (2 L). The aqueous layer was acidified with 2N HCl solution and extracted with ethyl acetate (3×3 L). The combined organic layers were dried (Na$_2$SO$_4$), filtered and concentrated to give 208 g of the title compound as an off-white solid pure by tlc and NMR. $^1$H NMR (300 MHz, CDCl$_3$) δ 7.5 (bs, 1H); 5.95 (d, 1H, J=3.7); 4.8 (dd, 1H, J=4.0, 3.7 Hz); 4.6 (d, 1H, J=9.5 Hz); 3.72 (dd, 1H, J=9.5, 4.0 Hz); 1.58 (s, 3H); 1.38 (s, 3H).

Preparation Q1
3-Azido-1,2,5,6-bis-O-isopropylidene-3-deoxy-D-allofuranose.

Triflic anhydride (1500 g, 5.3 mol) was added dropwise to a solution of pyridine (493 g, 6.2 mol) in dichloromethane (7.5 L) at −15° C. After 30 minutes, a solution of 1,2,5,6-bis-O-isopropylidene-D-glucofuranose (735 g, 2.84 mol) was added as a solution in dichloromethane (2.5 L). After 1 hour, the reaction was quenched by the dropwise addition of water (4 L) allowing the reaction temperature to warm to 0° C. The layers were separated and the organic layer dried with sodium sulfate, filtered and concentrated to give a red oil. The triflate was immediately dissolved in DMF (8 L), treated with NaN$_3$ (554 g, 8.5 mol) and warmed to 35° C. After 18 hours, the mixture was poured into water (12 L) and extracted with ethyl acetate (3×4 L). The combined organic layers were washed with water (2×3 L) and brine (1×3 L), dried (Na$_2$SO$_4$), filtered and concentrated. The residue was preadsorbed onto silica gel and purified by flash chromatography (6:1 hex/EtOAc then 4:1 hex/EtOAc) to afford 228 g of the title compound as a colorless oil. $^1$H NMR (400 MHz, CDCl$_3$) δ 5.77 (d, 1H, J=3.7 Hz); 4.7 (dd, 1H, J=4.4, 3.7 Hz); 4.15 (m, 2H); 4.0 (m, 2H); 3.5 (dd, 1H, J=9.1, 4.4 Hz); 1.56 (s, 3H); 1.47 (s, 3H); 1.37 (s, 3H); 1.34 (s, 3H).

Preparation R1
5-Chloro-2-(4,5-dihydro-1H-imidazol-2-ylmethoxy)-benzylamine

A solution of 30% HCl in ether (0.5 mL) was added to a solution of [5-chloro-2-(4,5-dihydro-1H-imidazol-2-ylmethoxy)benzyl]-carbamic acid tert-butyl ester (146 mg, 0.43 mmol) in methanol (5 mL). After stirring overnight, the mixture was concentrated and triturated from ether, filtered, washed with ether and dried to afford 76 mg of the title compound as a colorless solid. $^1$H NMR (400 MHz, CD$_3$OD) δ 7.4 (m, 2H); 7.04 (m, 1H); 4.91 (s, 2H); 4.12 (s, 2H); 4.00 (s, 2H); 3.79 (s, 2H).

Preparation S1
(5-Chloro-2-cyanomethoxy-benzyl)-carbamic acid tert-butyl ester

Di-tert-butyl dicarbonate (0.45 g, 2.03 mmol) was added to a solution of (2-aminomethyl-4-chloro-phenoxy)-acetonitrile (0.2 g, 1.01 mmol) and triethylamine (0.57 mL, 4 mmol) in dry THF (10 mL) at ambient temperature. After 4 hours the mixture was diluted with ethyl acetate (30 mL) washed with 1N HCl solution (1×), sat. sodium bicarbonate solution (1×) and brine (1×), dried (Na$_2$SO$_4$), filtered and concentrated. The residue was purified by flash chromatography (5–20% ethyl acetate/hexanes) to afford 218 mg (74%) of the title compound as a colorless solid.

$^1$H NMR (400 MHz, CDCl$_3$) δ 7.3 (m, 2H); 6.92 (d, 1H, J=8.7 Hz); 4.91 (bs, 1H); 4.78 (s, 2H); 4.28 (s, 2H); 1.41 (s, 9H).

Preparation T1
2-Aminomethyl-4-chloro-phenoxy acetic acid tert-butyl ester.

Raney nickel (~0.5 g) was added to a solution of 2-cyano-4-chlorophenoxy acetic acid-t-butyl ester (560 mg, 0.21 mmol) in methanol (25 mL) containing 1 mL of sat. ammonium hydroxide. The mixture was placed under 40 psi of hydrogen and shaken for two hours. The mixture was filtered and concentrated. The residue was partitioned between 1 N HCl and ether. The layers were separated and the aqueous layer was re-extracted with ether. The aqueous layer was basified to ~pH with K$_2$CO$_3$ solution and extracted with ether (3×). The combined organic layers were dried (MgSO$_4$), filtered and concentrated to afford 360 mg of the title compound as an oil. MS 272 (M+H)$^+$. $^1$H NMR (400 MHz, CDCl$_3$) δ 7.22 (s, 1H); 7.12 (d, 1H, J=8.7 Hz); 6.61 (d, 1H, J=8.7 Hz); 4.5 (s, 2H); 3.85 (s, 2H); 2.62 (bs, 2H); 1.41 (s, 9H).

Preparation U1
2-cyano-4-chlorophenoxy acetic acid-tert-butyl ester

Sodium hydride (96 mg, 4.1 mmol) was added to a solution of 2-cyano-4-chloro phenol (0.5 g, 3.26 mmol) in anhydrous DMF (6 mL) at −10° C. After 15 minutes the mixture became homogeneous and t-butyl bromo acetate was added dropwise. After 2 hours, the mixture was quenched with water and extracted with ethyl acetate (2×). The combined organic layers were washed with water (2×) brine (1×), dried ($Na_2SO_4$), filtered and concentrated. The residue was purified by flash chromatography (10% ethyl acetate/hexanes) to afford 850 mg of the title compound as a colorless syrup (97%). $^1$H NMR (400 MHz, $CDCl_3$) δ 7.53 (d, 1H, J=2.7 Hz); 7.46 (dd, 1H, J=9.1, 2.7 Hz); 6.78 (d, 1H, J=9.1 Hz); 4.63 (s, 3H); 1.46 (s, 9H).

Preparation V1

(−)-5-Chloro-2-(tetrahydrofuran-3-ylmethoxy)benzylamine

After converting 5-chloro-2-(tetrahydrofuran-3-ylmethoxy)benzylamine hydrochloride into its free base, the free base was subjected to chiral HPLC, to yield the title compound.

$[α]_{22}$=−23.57° (c=0.140, MeOH).

$^1$H NMR (400 MHz, DMSO-$d_6$) δ 8.35 (bs, 3H); 7.49 (d, 1H, J=2.7 Hz); 7.37 (dd, 1H, J=8.7 Hz, J=2.7 Hz); 7.07 (d, 1H, J=8.7 Hz); 4.00–3.90 (mult, 4H); 3.80–3.70 (mult, 2H); 3.65–3.60 (mult, 1H); 3.60–3.55 (mult, 1H); 2.75–2.71 (mult, 1H); 2.05–1.95 (mult, 1H); 1.77–1.63 (mult, 1H).

The following compound, Preparation V2, was prepared using analogous procedures to Preparation V1.

Preparation V2

(+)-5-Chloro-2-(tetrahydrofuran-3-ylmethoxy)benzylamine

After converting 5-chloro-2-(tetrahydrofuran-3-ylmethoxy)benzylamine hydrochloride into its free base, the free base was subjected to chiral HPLC, to yield the title compound.

$[α]_{22}$=+16.32° (c=0.190, MeOH).

$^1$H NMR (400 MHz, DMSO-$d_6$) δ 8.35 (bs, 3H); 7.49 (d, 1H, J=2.7 Hz); 7.37 (dd, 1H, J=8.7 Hz, J=2.7 Hz); 7.07 (d, 1H, J=8.7 Hz); 4.00–3.90 (mult, 4H); 3.80–3.70 (mult, 2H); 3.65–3.60 (mult, 1H); 3.60–3.55 (mult, 1H); 2.75–2.71 (mult, 1H); 2.05–1.95 (mult, 1H); 1.77–1.63 (mult, 1H).

Preparation W1

5-Chloro-2-(2-morpholin-4-yl-ethoxy)benzylamine hydrochloride

A solution of 5-chloro-2-(2-morpholin-4-yl-ethoxy) benzonitrile (412 mg, 1.54 mmol) in anhydrous THF (15 mL) was added to a solution of lithium aluminum hydride (3.53 mL, 1.0 M in THF) at room temperature. The reaction was stirred for 15 h at room temperature under anhydrous conditions, whereupon it was cooled to 0° C. and 1 N aqueous NaOH (0.54 mL) was added. The reaction was stirred for ½ h at 0° C. and then the solids were filtered off and rinsed with THF. The filtrate was concentrated by rotary evaporation and the resulting solid was dissolved in 30 mL of absolute ethanol. Aqueous hydrochoride solution (1.0 N, 1.7 mL) was added and the reaction was stirred for 15 min. The solvent was removed by rotary evaporation and the resulting solid was triturated with $Et_2O$ to to yield the title compound.

$C_{13}H_{19}ClN_2O_2$. MW 270.76. MS 271.2 $(M+H)^+$.

$^1$H NMR (400 MHz, $CD_3OD$) δ 7.45–7.40 (mult, 2H); 7.13 (d, 1H, J=5.9); 4.34 (bs, 2H); 4.15 (s, 2H); 3.79 (bs, 4H); 3.35–3.25 (mult, 4H); 3.08 (bs, 2H); 2.83 (bs, 2H).

The following compounds, Preparations W2–W26, were prepared from the appropriate benzonitrile using analogous procedures to Preparation W1.

Preparation W2

2-Benzyloxy-5-chloro-benzylamine hydrochloride

Mp 150.5–152.5° C.

$C_{14}H_{14}ClNO$. MW 247.73. MS 248.1 $(M+H)^+$.

$^1$H NMR (400 MHz, DMSO-$d_6$) δ 8.34 (bs, 3H); 7.49 (d, 1H, J=2.7 Hz); 7.47–7.38 (mult, 2H); 7.43 to 7.33 (mult, 3H) 7.32–7.25 (mult, 1H); 7.10 (d, 1H, J=8.7 Hz); 5.14 (s, 2H); 3.96 (s, 2H).

Preparation W3

5-Chloro-2-cyclobutylmethoxybenzylamine hydrochloride

Mp 168.0–170.0° C.

$C_{12}H_{16}ClNO$. MW 225.72. MS 225.8 $(M+H)^+$.

$^1$H NMR (400 MHz, DMSO-$d_6$) δ 8.36 (bs, 3H); 7.48 (d, 1H, J=2.5 Hz); 7.36 (dd, 1H, J=8.7 Hz, J=2.5 Hz); 7.06 (d, 1H, J=8.7 Hz); 3.97 (d, 2H, J=6.4 Hz); 3.92 (bs, 2H); 2.76–2.71 (mult, 1H); 2.09–1.97 (mult, 2H); 1.97–1.77 (mult, 4H).

Preparation W4

5-Chloro-2-(3-methoxy-benzyloxy)benzylamine hydrochloride.

Mp 159.0–160.0° C.

$C_{15}H_{16}ClNO_2$. MW 277.75. MS 277.9 $(M+H)^+$.

$^1$H NMR (400 MHz. DMSO-$d_6$) δ 8.37 (bs, 3H); 7.51 (d, 1H, J=2.7 Hz); 7.38 (dd, 1H, J=8.7 Hz, J=2.7 Hz); 7.28 (t, 1H, J=8.0 Hz); 7.10 (d, 1H, J=8.9 Hz); 7.06 7.00 (mult, 2H); 6.87 (d, 1H, J=8.3 Hz); 5.13 (s, 2H); 3.99 (s, 2H); 3.74 (s, 3H).

Preparation W5

5-Chloro-2-(2,5-dimethoxy-benzyloxy)benzylamine hydrochloride

Mp 212.0–213.0° C.

$C_{16}H_{18}ClNO_3$. MW 307.78. MS 307.8 $(M+H)^+$.

$^1$H NMR (400 MHz, DMSO-$d_6$) δ 8.30 (bs, 3H); 7.50 (d, 1H, J=2.7 Hz); 7.38 (dd, 1H, J=8.9 Hz, J=2.7 Hz); 7.11 (d, 1H, J=8.9 Hz); 7.02 (d, 1H, J=3.1 Hz); 6.96 (d, 1H, J=8.9 Hz); 6.86 (dd, 1H, J=8.9 Hz, J=3.1 Hz); 5.09 (s, 2H); 3.98 (s, 2H); 3.75 (s, 3H); 3.68 (s, 3H).

Preparation W6

5-Chloro-2-(3-chloro-benzyloxy)benzylamine hydrochloride

Mp 164.0–166.0° C.

$^1$H NMR (400 MHz, DMSO-$d_6$) δ 8.31 (bs, 3H); 7.58 (s 1H); 7.52 (d, 1H, J=2.7 Hz); 7.50–7.37 (mult, 4H); 7.11 (d, 1H, J=8.9 Hz); 5.19 (s, 2H); 4.02 (bs, 2H).

Preparation W7

5-Chloro-2-(2-chloro-benzyloxy)benzylamine hydrochloride $^1$H NMR (400 MHz, DMSO-$d_6$) δ 8.33 (bs, 3H); 7.85–7.80 (mult, 1H); 7.55–7.45 (mult, 2H); 7.45–7.35 (mult, 3H); 7.17 (d, 1H, J=8.7 Hz); 5.22 (s, 2H); 4.00 (d, 2H, J=5.2 Hz).

Preparation W8

5-Chloro-2-(tetrahydrofuran-3-ylmethoxy)benzylamine hydrochloride

Mp 105.5–108.0° C.

$^1$H NMR (400 MHz, DMSO-$d_6$) δ 8.35 (bs, 3H); 7.49 (d, 1H, J=2.7 Hz); 7.37 (dd, 1H, J=8.7 Hz, J=2.7 Hz); 7.07 (d, 1H, J=8.7 Hz); 4.00–3.90 (mult, 4H); 3.80–3.70 (mult, 2H); 3.65–3.60 (mult, 1H); 3.60–3.55 (mult, 1H); 2.75–2.71 (mult, 1H); 2.05–1.95 (mult, 1H); 1.77–1.63 (mult, 1H).

Preparation W9
5-Chloro-2-(4-methyl-benzyloxy)benzylamine hydrochloride

Mp 155.0–157.0° C.

$^1$H NMR (400 MHz, DMSO-d$_6$) δ 8.33 (bs, 3H); 7.50 (d, 1H, J=2.7 Hz); 7.40–7.35 (mult, 3H); 7.17 (d, 2H, J=7.7 Hz); 7.12 (d, 1H, J=8.9 Hz); 5.11 (s, 2H); 3.96 (bs, 2H); 2.28 (s, 3H).

Preparation W10
5-Chloro-2-(2-methyl-benzyloxy)benzylamine hydrochloride

Mp 176.0–178.0° C.

$^1$H NMR (400 MHz, DMSO-d$_6$) δ 8.38 (bs, 3H); 7.53 (d, 1H, J=2.7 Hz); 7.45–7.38 (mult, 2H); 7.25–7.17 (mult, 4H); 5.15 (s, 2H); 3.97 (d, 2H, J=5.4 Hz); 2.31 (s, 3H).

Preparation W11
5-Chloro-2-(3-methyl-benzyloxy)benzylamine hydrochloride

Mp 137.0–140.0° C.

$^1$H NMR (400 MHz, DMSO-d$_6$) δ 8.26 (bs, 3H); 8.49 (d, 1H, J=2.5 Hz); 7.39 (dd, 1H, J=8.7 Hz, J=2.7 Hz); 7.29–7.22 (mult, 3H); 7.12 (d, 2H, J=8.9 Hz); 5.12 (s, 2H); 4.02–3.97 (mult, 2H); 2.30 (s, 3H).

Preparation W12
5-Chloro-2-(2-methoxy-benzyloxy)benzylamine hydrochloride

Mp 199.5–200.5° C.

C$_{15}$H$_{16}$ClNO$_2$. MW 277.75. MS 278.1 (M+H)$^+$.

$^1$H NMR (400 MHz, DMSO-d$_6$) δ 8.37 (bs, 3H); 7.51 (d, 1H, J=2.3 Hz); 7.41 (d, 1H, J=7.5 Hz); 7.37 (dd, 1H, J=8.7 Hz, J=2.5 Hz); 7.33 (dd, 1H, J=8.3 Hz, J=7.5 Hz); 7.12 (d, 1H, J=8.9 Hz); 7.04 (d, 1H, J=8.3 Hz); 6.94 (t, 1H, J=7.5 Hz); 5.12 (s, 2H); 3.97 (bs, 2H); 3.81 (s, 3H).

Preparation W13
5-Chloro-2-(furan-3-ylmethoxy)benzylamine hydrochloride

Mp 137.0–140.0° C.

C$_{12}$H$_{12}$ClNO$_2$. MW 237.7. MS 238.1 (M+H)$^+$.

$^1$H NMR (400 MHz, DMSO-d$_6$) δ 8.33 (bs, 3H); 7.80 (s, 1H); 7.66 (s, 1H); 7.49 (d, 1H, J=2.7 Hz); 7.39 (dd, 1H, J=8.9 Hz, J=2.7 Hz); 7.17 (d, 1H, J=8.7 Hz); 6.62 (s, 1H); 5.03 (s, 2H); 3.92 (quart, 2H, J=5.7 Hz).

Preparation W14
5-Chloro-2-(4-methoxy-benzyloxy)benzylamine

Mp 142.0–147.0° C.

C$_{15}$H$_{16}$ClNO$_2$. MW 277.75. MS 278.1 (M+H)$^+$.

$^1$H NMR (400 MHz, DMSO) δ 8.38 (bs, 2H); 8.25 (bs, 1H); 7.50 (d, 1H, J=2.1 Hz); 7.43–7.36 (mult, 3H); 7.14 (d, 1H, J=8.7 Hz); 6.95–6.90 (mult, 2H); 5.07 (s, 2H); 3.96–3.90 (mult, 2H); 3.73 (s, 3H).

Preparation W15
5-Chloro-2-cyclopentylmethoxybenzylamine

Mp 155.0–157.0° C.

$^1$H NMR (400 MHz, DMSO-d$_6$) δ 8.34 (bs, 3H); 7.47 (d, 1H, J=2.5 Hz); 7.36 (dd, 1H, J=8.9 Hz, J=2.5 Hz); 7.06 (d, 1H, J=8.9 Hz); 3.94 (bs, 2H); 3.88 (d, 2H, J=6.8 Hz); 2.32 (sept, 1H, J=7.5 Hz); 1.80–1.70 (mult, 2H); 1.62–1.45 (mult, 4H); 1.38–1.28 (mult, 2H).

Preparation W16
5-Chloro-2-[3-(2-morpholin-4-ylethoxy)benzyloxy]benzylamine hydrochloride C$_{20}$H$_{25}$ClN$_2$O$_3$. MW 376.89. MS 377.1 (M+H)$^+$.

$^1$H NMR (400 MHz, DMSO-d$_6$) δ 8.39 (bs, 3H); 7.51 (d, 1H, J=2.7 Hz); 7.39 (dd, 1H, J=8.7 Hz, J=2.7 Hz); 7.31 (t, 1H, J=7.9 Hz); 7.12 (d, 2H, J=8.9 Hz); 7.07 (d, 1H, J=7.5 Hz); 6.93 (d, 1H, J=8.5 Hz); 5.14 (s, 2H); 4.47–4.27 (mult, 2H); 4.02–3.98 (mult, 2H); 3.98–3.70 (mult, 4H); 3.59–3.39 (mult, 4H); 3.35–3.25 (mult, 2H).

Preparation W17
5-Chloro-2-(tetrahydrofuran-3-ylmethoxy)benzylamine hydrochloride Mp 105.5–108.0° C.

$^1$H NMR (400 MHz, DMSO-d$_6$) δ 8.35 (bs, 3H); 7.49 (d, 1H, J=2.7 Hz); 7.37 (dd, 1H, J=8.7 Hz, J=2.7 Hz); 7.07 (d, 1H, J=8.7 Hz); 4.00–3.90 (mult, 4H); 3.80–3.70 (mult, 2H); 3.65–3.60 (mult, 1H); 3.60–3.55 (mult, 1H); 2.75–2.71 (mult, 1H); 2.05–1.95 (mult, 1H); 1.77–1.63 (mult, 1H).

Preparation W18
5-Chloro-2-(tetrahydrofuran-3-ylmethoxy)benzylamine hydrochloride Mp 105.5–108.0° C.

$^1$H NMR (400 MHz, DMSO-d$_6$) δ 8.35 (bs, 3H); 7.49 (d, 1H, J=2.7 Hz); 7.37 (dd, 1H, J=8.7 Hz, J=2.7 Hz); 7.07 (d, 1H, J=8.7 Hz); 4.00–3.90 (mult, 4H); 3.80–3.70 (mult, 2H); 3.65–3.60 (mult, 1H); 3.60–3.55 (mult, 1H); 2.75–2.71 (mult, 1H); 2.05–1.95 (mult, 1H); 1.77–1.63 (mult, 1H).

Preparation W19
5-Chloro-2-(furan-2-ylmethoxy)benzylamine hydrochloride

Mp 145.0–150.0° C.

$^1$H NMR (400 MHz, DMSO-d$_6$) δ 8.35 (bs, 3H); 7.69 (s, 1H); 7.50 (d, 1H, J=2.5 Hz); 7.39 (dd, 1H, J=8.9 Hz, J=1.9 Hz); 7.25 (d, 1H, J=8.5 Hz); 6.60 (d, 1H, J=3.1 Hz); 6.46 (bs, 1H); 5.14 (s, 2H); 3.89 (d, 2H, J=4.4 Hz).

Preparation W20
5-Chloro-2-(2,2,7,7-tetramethyltetrahydro-bis[1,3]dioxolo[4,5-b;4',5'-d]pyran-5-ylmethoxy)benzylamine hydrochloride $^1$H NMR (400 MHz, DMSO-d$_6$) δ 8.23 (bs, 3H); 7.48–7.42 (mult, 1H); 7.34 (dd, 1H, J=8.9 Hz, J=2.7 Hz); 7.13 (d, 1H, J=8.9 Hz); 5.43 (d, 1H, J=5.0 Hz); 4.59 (dd, 1H, J=8.1 Hz, J=2.3 Hz); 4.36–4.40 (mult, 2H); 4.01 (s, 2H); 4.05–3.80 (mult, 3H); 1.30 (d, 6H, J=6.6 Hz); 1.23 (d, 6H, J=11.0 Hz).

Preparation W21
5-Chloro-2-(5-dimethylaminomethylfuran-2-ylmethoxy)benzylamine C$_{15}$H$_{19}$ClN$_2$O$_2$. MW 294.78. MS 295.2 (M+H)$^+$.

$^1$H NMR (300 MHz, DMSO-d$_6$) δ 8.49 (bs, 3H); 7.52 (d, 1H, J=2.4 Hz); 7.43 (dd, 1H, J=9.0 Hz, J=2.4 Hz); 7.29 (d, 1H, J=9.0 Hz); 6.77–6.68 (mult, 2H); 5.18 (s, 2H); 4.39–4.34 (mult, 2H); 3.93 (d, 2H, J=5.6 Hz); 2.76–2.61 (mult, 6H).

Preparation W22
5-Chloro-2-(naphthalen-1-ylmethoxy)benzylamine hydrochloride Mp 196.0–198.0° C.

C$_{18}$H$_{16}$ClNO. MW 297.79. MS 297.9 (M+H)$^+$.

$^1$H NMR (300 MHz, DMSO-d$_6$) δ 8.35 (bs, 3H); 8.14 (dd, 1H, J=8.9 Hz, J=2.7 Hz); 8.03–7.92 (mult, 2H); 7.72 (d, 1H, J=6.9 Hz); 7.63–7.41 (mult, 5H); 7.40 (d, 1H, J=8.9 Hz); 5.66 (s, 2H); 3.95 (d, 2H, J=5.6 Hz).

Preparation W23
5-Chloro-2-(4-chloro-benzyloxy)benzylamine hydrochloride $^1$H NMR (400 MHz, DMSO-d$_6$) δ 8.35 (bs, 3H); 7.54–7.47 (mult, 3H); 7.46–7.35 (mult, 3H); 7.10 (d, 1H, J=8.9 Hz); 5.16 (s, 2H); 3.99 (bs, 2H).

Preparation W24
5-Chloro-2-(2,5-dimethylfuran-3-ylmethoxy)benzylamine

Using a modified Preparation W1, wherein instead of making the hydrochloride salt, the title compound was isolated as the free base 5-chloro-2-(2,5-dimethylfuran-3-ylmethoxy)benzonitrile was converted to the title compound. Thus, after the NaOH quench and filter, the solids were washed with THF. The filtrate was concentrated on the rotary evaporator to yield the title compound as a pale yellow oil.

$^1$H NMR (400 MHz, DMSO-d$_6$) δ 7.31 (d, 1H, J=2.7 Hz); 7.15 (dd, 1H, J=8.7 Hz, J=2.7 Hz); 6.98 (d, 1H, J=8.7 Hz); 6.00 (s, 1H); 4.78 (s, 2H); 3.56 (s, 2H); 2.18 (s, 3H); 2.14 (s, 3H); 1.65 (bs, 2H).

Preparation W25
5-Chloro-2-methoxybenzylamine

Using a modified Preparation W1, wherein instead of making the hydrochloride salt, the title compound was isolated as the free base, 5-chloro-2-methoxybenzonitrile and was converted to the title compound. Thus, after the NaOH quench and filter, the solids were washed with THF. The filtrate was concentrated on the rotary evaporator. The resulting viscous oil was then taken up in Et$_2$O (100 mL) and water (100 mL). After separating the layers, the aqueous layer was extracted twice more with Et$_2$O. The combined organic layers were washed with aqueous saturated NaCl, dried over Na$_2$SO$_4$, filtered, and the solvent removed by rotary evaporation to yield the title compound as a pale yellow oil.

$^1$H NMR (400 MHz, DMSO-d$_6$) δ 7.43–7.38 (mult, 1H); 7.25–7.15 (mult, 1H); 6.92 (td, 1H, J=11 Hz, J=8.7 Hz); 3.75 (d, 3H, J=7.2 Hz); 3.65–3.55 (mult, 2H); 1.72 (bs, 2H).

Preparation W26
[3-(2-Morpholin-4-yl-ethoxy)phenyl]methanol

Using a modified Preparation W1, wherein instead of adding the aqueous hydrochloride solution, the title compound was extracted as the alcohol, 3-(2-morpholin-4-yl-ethoxy)benzaldehyde and was converted to the title compound. Thus, after the NaOH quench and filter, the solids were washed with THF. The filtrate was concentrated on the rotary evaporator. The resulting viscous oil was then taken up in Et$_2$O (100 mL) and water (100 mL). After separating the layers, the aqueous layer was extracted twice more with Et$_2$O. The combined organic layers were washed with aqueous saturated NaCl, dried over MgSO$_4$, filtered, and the solvent removed by rotary evaporation to yield the title compound as a pale yellow oil.

$^1$H NMR (400 MHz, DMSO-d$_6$) δ 7.18 (t, 1H, J=7.9 Hz); 6.87–6.81 (mult, 2H); 6.76 (d, 1H, J=8.1 Hz); 5.17–5.09 (mult, 1H); 4.43 (d, 2H, J=5.6 Hz); 4.04 (t, 2H, J=5.6 Hz); 3.59–3.51 (mult, 4H); 2.70–2.62 (mult, 2H); 2.50–2.38 (mult, 4H).

Preparation X1
5-Chloro-2-(3-methylisoxazol-5-ylmethoxy)benzylamine

To a flask containing anhydrous 2-propanol (40 mL), hydrazine hydrate (4 mL, and anhydrous THF (60 mL), at room temperature, was added 2-{5-chloro-2-(3-methylisoxazol-5-ylmethoxy)benzyl}isoindole-1,3-dione (5 g, 13 mmol). The reaction was stirred at 50° C. for 3 h. The solids were filtered and washed with THF. The filtrate was concentrated, dissolved in ether (100 ml) and washed with 1N NaOH (1×) and brine, dried (MgSO$_4$), filtered and concentrated to afford the title product as a solid.

Mp 32.0–35.0° C.; C$_{12}$H$_{13}$ClN$_2$O$_2$. MW 252.70. MS 253.1 (M+H)$^+$.

$^1$H NMR (400 MHz, DMSO-d$_6$) δ 7.37 (d, 1H, J=2.6 Hz); 7.18 (dd, 1H, J=8.8 Hz, J=2.6 Hz); 7.04 (d, 1H, J=8.8 Hz); 6.42 (s, 1H); 5.21 (s, 2H); 3.60 (s, 2H); 2.18 (s, 3H); 1.71 (bs, 2H).

The following compounds, Preparations X1–X6, were prepared from the appropriate phthalimide using analogous procedures to Preparation X1.

Preparation X2
5-Chloro-2-(pyridin-3-ylmethoxy)benzylamine $^1$H NMR (400 MHz, DMSO-d$_6$) δ 8.63 (d, 1H, J=1.5 Hz); 8.50 (dd, 1H, J=4.8 Hz, J=1.5 Hz); 7.83 (dd, 1H, J=6.0 Hz, J=3.1 Hz); 7.42–7.35 (mult, 2H); 7.20 (dd, 1H, J=8.7 Hz, J=2.9 Hz); 7.02 (d, 1H, J=8.7 Hz); 5.13 (s, 2H); 3.67 (s, 2H).

Preparation X3
5-Chloro-2-(thiazol-2-ylmethoxy)benzylamine

Mp 74.0–76.0° C.

C$_{11}$H$_{11}$ClN$_2$OS. MW 254.74. MS 255.1 (M+H)$^+$.

$^1$H NMR (400 MHz, DMSO-d$_6$) δ 7.80 (d, 1H, J=3.3 Hz); 7.74 (d, 1H, J=3.3 Hz); 7.39 (d, 1H, J=2.7 Hz); 7.19 (dd, 1H, J=8.3 Hz, J=2.7 Hz); 7.05 (d, 1H, J=8.7 Hz); 5.41 (s, 2H); 3.68 (s, 2H); 1.78 (bs, 2H).

Preparation X4
2-(Benzothiazol-2-ylmethoxy)-5-chlorobenzylamine

Mp 72.0–79.0.

C$_{15}$H$_{13}$ClN$_2$OS. MW 304.80. MS 305.1 (M+H)$^+$.

$^1$H NMR (400 MHz, DMSO-d$_6$) δ 8.09 (d, 1H, J=7.9 Hz); 7.97 (d, 1H, J=7.9 Hz); 7.49 (dd, 1H, J=8.1 Hz, J=7.3 Hz); 7.44–7.39 (mult, 2H); 7.20 (dd, 1H, J=8.6 Hz, J=2.6 Hz); 7.07 (d, 1H, J=8.6 Hz); 5.57 (s, 2H); 3.75 (s, 2H); 1.83 (bs, 2H).

Preparation X5
2-(Benzofuran-2-ylmethoxy)-5-chlorobenzylamine

Mp 75.5–77.0° C.

C$_{16}$H$_{14}$ClNO$_2$. MW 287.75. MS 288.0 (M+H)$^+$.

$^1$H NMR (400 MHz, DMSO-d$_6$) δ 7.60 (d, 1H, J=7.9 Hz); 7.54 (d, 1H, J=7.9 Hz); 7.36 (d, 1H, J=2.1 Hz); 7.28 (t, 1H, J=7.3 Hz); 7.25–7.16 (mult, 2H); 7.13 (d, 1H, J=8.7 Hz); 6.99 (s, 1H); 5.25 (s, 2H); 3.61 (s, 2H); 1.78 (bs, 2H).

Preparation X6
Chloro-2-(thiophen-2-ylmethoxy)benzylamine

C$_{12}$H$_{12}$ClNOS. MW 253.75. MS 254.0 (M+H)$^+$.

$^1$H NMR (400 MHz, DMSO-d$_6$) δ 7.53 (dd, 1H, J=5.0 Hz, J=1.2 Hz); 7.40–7.36 (mult, 1H); 7.22–7.16 (mult; 2H); 7.07 (dd, 1H, J=8.7 Hz, J=2.3 Hz); 7.04–6.98 (mult, 1H); 5.29 (s, 2H); 3.62 (s, 2H); 1.79 (bs, 2H).

Preparation Y1
5-Chloro-2-(isothiazol-5-ylmethoxy)benzylamine

To a mixture of 2-[5-chloro-2-(isothiazol-5-ylmethoxy)benzyl]isoindole-1,3-dione (464 mg, 1.20 mmol), 2-propanol (20 mL), water (2.5 mL), and THF (25 mL) was added NaBH$_4$ (295 mg, 7.80 mmol). The reaction was stirred at room temperature for 16 h. The organic solvent was then removed by rotary evaporation and the resulting oil was taken up in CH$_2$Cl$_2$ (50 mL). The organic layer was washed with water (50 mL), saturated aqueous NaCl (50 mL), dried over NaSO$_4$, filtered, and concentrated on a rotary evaporator. This material was taken up in 2-propanol (20 mL), glacial acetic acid (1.2 mL), and water (1.0 mL) and the reaction was heated to 80° C. in a sealed tube for 24 h. The organic solvent was then removed by rotary evaporation and the resulting oil was taken up in CH$_2$Cl$_2$ (50 mL). The organic layer was washed with water (50 mL), saturated aqueous NaCl (50 mL), dried over NaSO$_4$, filtered, and concentrated on a rotary evaporator to afford the title compound.

$^1$H NMR (400 MHz, DMSO-d$_6$) δ 8.50 (s, 1H); 7.42–7.38 (mult, 2H); 7.19 (dd, 1H, J=8.7 Hz, J=2.7 Hz); 7.02 (d, 1H, J=8.7 Hz); 5.50 (s, 2H); 3.65 (s, 2H); 1.73 (bs, 2H).

The following compounds, Preparations Y2–Y3, were prepared from the appropriate azide using analogous procedures to Preparation Y1.

Preparation Y2
5-Chloro-2-(quinolin-2-ylmethoxy)benzylamine

C$_{17}$H$_{15}$ClN$_2$O. MW 298.77. MS 299.2 (M+H)$^+$.

$^1$H NMR (400 MHz, DMSO-d$_6$) δ 8.40 (d, 1H, J=8.5 Hz); 8.03–7.96 (mult, 2H); 7.76 (t, 1H, J=6.8 Hz); 7.65 (d, 1H, J=8.3 Hz); 7.60 (t 1H, J=6.8 Hz); 7.42 (s, 1H); 7.18 (d, 1H, J=8.5 Hz); 7.01 (d, 1H, J=8.9 Hz); 5.37 (s, 2H); 3.78 (s, 2H).

Preparation Y3
5-Chloro-2-(4-methyl-[1,2,3]thiadiazol-5-ylmethoxy)benzylamine Mp 64.0–66.0° C.

C$_{11}$H$_{12}$ClN$_3$OS. MW 269.75. MS 270.1 (M+H)$^+$.

$^1$H NMR (400 MHz, DMSO-d$_6$) δ 7.42 (d, 1H, J=2.3 Hz); 7.25 (dd, 1H, J=8.7 Hz, J=2.3 Hz); 7.10 (d, 1H, J=8.7 Hz); 5.53 (s, 2H); 3.65 (s, 2H); 2.66 (s, 3H); 1.84 (bs, 2H).

Preparation Z1
2-Benzyloxy-5-cyano-benzylamine

Triphenylphosphine (1.64 g, 6.24 mmol) was added to a solution of 2-benzyloxy-5-cyano-benzylazide (1.1 g, 4.16 mmol) in anhydrous THF (10 mL) at 0° C. After 1 hour, ammonium hydroxide (0.5 mL) was added and the mixture was warmed to room temperature and stirred overnight. The mixture was concentrated and the residue purified by flash chromatography (3% methanol/dichloromethane) to afford 677 mg (69%) of the title compound as a colorless oil. $^1$H NMR (400 MHz, CDCl$_3$) δ 7.6–7.3 (m, 7H); 6.95 (d, 1H, J=9.1 Hz); 5.18 (s, 2H); 3.9 (s, 2H).

The following compounds, Preparations Z2–Z4, were prepared from the appropriate azide using analogous procedures to Preparation Z1.

Preparation Z2
2-Benzyloxy-5-ethenyl-benzylamine

Preparation Z3
2-Benzyloxy-5-ethynyl-benzylamine

Preparation Z4
(2-Aminomethyl-4-chloro-phenoxy)-acetonitrile

Preparation AA1
2-Benzyloxy-5-trifluoromethyl-benzylamine

LAH (136 mg, 3.58 mmol) was added to a solution of 2-benzyloxy-5-trifluoromethyl-benzylazide (1.1 g, 3.58 mmol) at 0° C. After 1 hour, the reaction was quenched by the sequential addition of water (136 µL), 15% NaOH (136 µL), and water (400 µL), the mixture was diluted with dichloromethane and dried with MgSO$_4$, filtered and concentrated. The residue was purified by flash chromatography (3% methanol/dichloromethane) to afford 825 mg (82%) of the title compound as a colorless oil. MS 282 (M+H)$^+$. $^1$H NMR (400 MHz, CDCl$_3$) δ 7.6–7.3 (m, 7H); 6.92 (d, 1H, J=9.1 Hz); 5.18 (s, 2H); 3.9 (s, 2H); 2.65 (bs, 2H).

The following compounds, Preparations AA2–AA5, were prepared from the appropriate azide using analogous procedures to Preparation AA1.

Preparation AA2
2-Benzyloxy-5-bromo-benzylamine

Preparation AA3
2-Benzyloxy-5-fluoro-benzylamine

Preparation AA4
2-Benzyloxy-5-iodo-benzylamine

Preparation AA5
2-Benzyloxy-5-methyl-benzylamine

Preparation BB1
2-Benzyloxy-5-trifluoromethyl-benzylazide

DBU (1 mL, 6.62 mmol) and diphenyl phosphoryl azide (1.6 mL, 7.5 mmol) were added to a solution of 2-benzyloxy-5-trifluoromethyl-benzyl alcohol (1.24 g, 4.41 mmol) in anhydrous toluene (10 mL) at room temperature. After 3 hours, water was added and the mixture extracted with ethyl acetate (3×). The combined organic layers were washed with 1N HCl (1×), brine (1×), dried (Na$_2$SO$_4$), filtered and concentrated in vacuo. The residue was purified by flash chromatography (3% ethyl acetate/hexanes) to afford 1.14 grams of the title compound as a colorless oil (84%). MS 280 (M−N$_2$)$^+$. $^1$H NMR (400 MHz, CDCl$_3$) δ 7.6–7.3 (m, 7H); 7.01 (d, 1H, J=9.1 Hz); 5.18 (s, 2H); 4.42 (s, 2H).

The following compounds, Preparations BB2–BB7, were prepared from the appropriate alcohol using analogous procedures to Preparation BB1.

Preparation BB2
2-Benzyloxy-5-bromo-benzylazide

Preparation BB3
2-Benzyloxy-5-fluoro-benzylazide

Preparation BB4
2-Benzyloxy-5-methyl-benzylazide

Preparation BB5
2-Benzyloxy-5-cyano-benzylazide

Preparation BB6
2-Benzyloxy-5-iodo-benzylazide

Preparation BB7
(2-Azidomethyl-4-chloro-phenoxy)acetonitrile

Preparation CC1
2-Benzyloxy-5-trifluoromethyl-benzylalcohol

Cesium carbonate (2.24 g, 6.9 mmol) was added to a solution of 2-hydroxy-5-trifluoromethyl-benzyl alcohol (885 mg, 4.6 mmol) and benzyl bromide (547 µL, 4.6 mmol) in anhydrous DMF (8 mL) at room temperature. The reaction was heated to 50° C. for 2 hours, cooled, diluted with ethyl acetate (25 mL) and washed with water (3×25 mL), brine (1×25 mL), and dried (Na$_2$SO$_4$), filtered and concentrated to afford 1.3 g of the title compound as a colorless solid. $^1$H NMR (400 MHz. CDCl$_3$) δ 7.6–7.3 (m, 7H); 7.01 (d, 1H, J=9.1 Hz); 5.18 (s, 2H); 4.79 (s, 2H); 2.8 (bs, 1H).

Preparation DD1
2-Hydroxy-5-trifluoromethyl-benzyl alcohol

Paraformaldehyde (3.4 g, 0.114 mol) was added in 0.5 g portions over a six hour period to a refluxing mixture of 4-trifluoromethyl phenol (2.3 g, 0.0142 mol), phenyl boronic acid (2.1 g, 0.017 mol) and proprionic acid (530 µL, 7 mmol) in benzene with the azeotropic removal of water (Dean-Stark trap). When the addition was complete, the reaction was heated for an additional hour, then cooled with an ice bath, diluted with THF (30 mL) and treated with 5 mL of 30% hydrogen peroxide solution. After stirring for one hour, the mixture was partitioned between water (50 mL) and ethyl acetate (50 mL). The organic layer was washed with $NaHSO_3$ solution (1×50 mL), brine (1×50 mL), dried ($Na_2SO_4$), filtered and concentrated. The residue was purified by flash chromatography (30% ethyl acetate/hexanes) to afford 950 mg (35%) of the title compound as a colorless solid. $^1$H NMR (400 MHz, $CDCl_3$) δ 7.42 (d, 1H, J=9.1 Hz); 7.3 (s, 1H); 6.95 (d, 1H, J=9.1 Hz); 4.89 (s, 2H);

The following compound, Preparation DD2, was prepared from the appropriate phenol using analogous procedures to Preparation DD1.

Preparation DD2
2-Hydroxy-5-cyano-benzyl alcohol

Preparation EE1
2-Benzyloxy-5-fluoro benzyl alcohol

LAH (226 mg, 5.95 mmol) was added to a solution of 2-benzyloxy-5-fluoro-benzoic acid benzyl ester (2 g, 5.95 mmol) at 0° C. The reaction was warmed to room temperature and after 1 hour, the reaction was quenched by the sequential addition of water (226 µL), 15% NaOH (226 µL), and water (760 µL), the mixture was diluted with ethyl acetate and dried with $MgSO_4$, filtered and concentrated. The residue was purified by flash chromatography (10% ethyl acetate/hexanes) to afford 1.13 g (82%) of the title compound as a colorless solid. MS 250 $(M+NH_4)^+$. $^1$H NMR (400 MHz, $CDCl_3$) δ 7.4 (m, 5H); 7.05 (dd, 1H, J=9.1, 4.3 Hz); 6.92 (m, 2H); 5.08 (s, 2H); 4.65 (s, 2H); 2.2 (bs, 1H).

The following compounds, Preparations EE2–EE3, were prepared from the appropriate starting material using analogous procedures to Preparation EE1.

Preparation EE2
2-Benzyloxy-5-iodo-benzyl alcohol

Preparation EE3
2-Benzyloxy-5-methyl-benzyl alcohol

Preparation FF1
2-Benzyloxy-5-ethynyl-benzyl azide and 2-benzyloxy-5-ethenyl-benzyl azide Lithium aluminum hydride (95 mg, 2.49 mmol) was added to a solution of 2-benzyloxy-5-ethynyl-benzoic acid benzyl ester (680 mg, 1.99 mmol) in THF (5 mL) at 0° C. After 15 minutes, the reaction was quenched by the sequential addition of water (100 µL), 15% NaOH (100 µL), and water (300 µL). The mixture was diluted with ethyl acetate (10 mL) and dried ($MgSO_4$), filtered, and concentrated. The residue was purified by flash chromatography (10% ethyl acetate/hexanes) to afford 600 mg of a ~1:1 mixture of 2-benzyloxy-5-ethynyl-benzyl alcohol and 2-benzyloxy-5-ethenyl-benzyl alcohol. This mixture was dissolved in toluene (8 mL) and treated with DBU (0.7 mL, 4.52 mmol) and diphenyl phosphoryl azide (1.1 mL, 5.12 mmol) at room temperature. After 18 hours, water was added and the mixture was extracted with ethyl acetate (3×). The combined organic layers were washed with 1N HCl (1×), brine (1×), dried ($Na_2SO_4$), filtered and concentrated in vacuo. The residue was purified by flash chromatography (3.5% THF/hexanes) and the mixed fractions were rechromatographed with 3% ether/pet ether to afford 206 mg of 2-benzyloxy-5-ethenyl-benzyl azide as the faster eluting fraction. MS 238 $(M-N_2)^+$. $^1$H NMR (400 MHz, $CDCl_3$) δ 7.4 (m, 7H); 6.95 (d, 1H, J=9.1 Hz); 6.62 (dd, 1H, J=17.5, 10.5 Hz); 5.61 (d, 1H, J=17.5 Hz); 5.15 (m, 3H); 4.40 (s, 2H).

Further elution provided 135 mg of 2-benzyloxy-5-ethynyl-benzyl azide. MS 236 $(M-N_2)^+$. $^1$H NMR (400 MHz, $CDCl_3$) δ 7.4 (m, 7H); 7.95 (d, 1H, J=9.1 Hz); 5.1 (s, 2H); 4.39 (s, 2H); 3.0 (s, 1H).

Preparation GG1
2-Benzyloxy-5-ethynyl-benzoic acid benzyl ester

Tetra-butyl ammonium fluoride (2.97 mL of a 1 M solution in THF, 2.97 mmol) was added to a solution of 2-benzyloxy-5-(2-trimethylsilyl-ethynyl)-benzoic acid benzyl ester (1.07 g, 2.58 mmol) in THF (10 mL) at room temperature. After 30 minutes, the mixture was diluted with ether (20 mL) and washed with water (3×30 mL) and brine (1×30 mL), dried ($MgSO_4$), filtered and concentrated. The residue was purified by flash chromatography (5% ethyl acetate/hexanes) to afford 687 mg (78%) product as a light orange oil. $^1$H NMR (400 MHz, $CDCl_3$) δ 7.98 (d, 1H, J=2 Hz); 7.52 (dd, 1H, J=9.1, 1 Hz); 7.38 (m, 10H); 6.95 (d, 1H, J=9.1 Hz); 5.35 (s, 2H); 5.19 (s, 2H); 3.0 (s, 1H).

Preparation HH1
2-Benzyloxy-5-(2-trimethylsilyl-ethynyl)-benzoic acid benzyl ester $Pd(PPh_3)_2Cl_2$ (194 mg, 0.277 mmol), copper iodide (106 mg, 0.554 mmol) and triethylamine (0.8 mL, 5.44 mmol) were added to a solution of 2-benzyloxy-5-iodo-benzoic acid benzyl ester (1.23 g, 2.77 mmol) and trimethylsilyl acetylene (0.5 mL, 3.32 mmol) in anhydrous DMF (15 mL) at room temperature. The flask was covered with aluminum foil and stirred overnight. The mixture was diluted with ethyl acetate (50 mL) and washed with water (3×), 1N HCl (1×) and brine (1×), dried ($Na_2SO_4$), filtered and concentrated. The residue was purified by flash chromatography (5% ethyl acetate/hexanes) to afford 1.07 g (93%) of the title compound as an oil. $^1$H NMR (400 MHz, $CDCl_3$) δ 7.98 (d, 1H, J=2 Hz); 7.52 (dd, 1H, J=9.1, 1 Hz); 7.38 (m, 10H); 6.95 (d, 1H, J=9.1 Hz); 5.31 (s, 2H); 5.17 (s, 2H); 0.1 (s, 9H).

Preparation II1
2-Benzyloxy-5-fluorobenzoic add benzyl ester.

Benzyl bromide (0.86 mL, 7.2 mmol) and cesium carbonate (2.6 g, 8 mmol) were added to a solution of 2-hydroxy-5-fluoro-benzoic acid (0.5 g, 3.2 mmol) in anhydrous DMF (8 mL) at room temperature. The reaction was heated to 80° C. for two hours, cooled and diluted with water (50 mL). The mixture was extracted with ethyl acetate (3×40 mL) and the combined organic layers were washed with water (1×50 mL) and brine (1×50 mL), dried ($Na_2SO_4$), filtered and concentrated to afford 1.02 g of the title compound as a colorless oil (93%). MS: 337 $(M+H)^+$. $^1$H NMR (400 MHz, $CDCl_3$) δ 7.55 (dd, 1H, J=8.7, 3.1 Hz); 7.35 (m, 10H); 7.1 (m, 1H); 6.97 (dd, 1H, J=9.1, 4.3 Hz); 5.3 (s, 2H); 5.1 (s, 2H).

The following compounds, Preparations II2–II3, were prepared from the appropriate starting material using analogous procedures to Preparation II1.

Preparation II2
2-Benzyloxy-5-iodo-benzoic acid benzyl ester.

Preparation II3
2-Benzyloxy-5-methyl-benzoic acid benzyl ester.

Preparation JJ1
2-Benzyloxy-5-bromo-benzyl alcohol.

Sodium borohydride (339 mg, 8.93 mmol) was added to a solution of 2-benzyloxy-5-bromo-benzaldehyde (2.6 g, 8.93 mmol) in anhydrous ethanol (20 mL) at 0° C. The reaction was allowed to warm to room temperature and, after 3 hours, the mixture was concentrated and the residue was dissolved in ethyl acetate (50 mL) and washed with water (1×25 mL), 1N HCl solution (1×25 mL) and brine (1×25 mL). The solution was dried ($Na_2SO_4$), filtered and concentrated. The residue was purified by flash chromatography (8% ethyl acetate/hexane) to afford 2.58 g of the title compound as a colorless oil (98%).

MS 292 (M+H)$^+$. $^1$H NMR (400 MHz, $CDCl_3$) δ 7.39 (m, 7H); 6.9 (d, 1H, J=8.7 Hz); 5.06 (s, 2H); 4.62 (s, 2H); 2.2 (bs, 1H).

Preparation KK1
2-Benzyloxy-5-bromo-benzaldehyde.

Benzyl bromide (18 mL, 14.9 mmol) and cesium carbonate (8.1 g, 24.9 mmol) were added to a solution of 2-hydroxy-5-bromo benzaldehyde 2 g, 9.95 mmol) in anhydrous DMF (25 mL) at room temperature. The reaction was heated to 80° C. for two hours, cooled and diluted with water (50 mL). The mixture was extracted with ethyl acetate (3×40 mL) and the combined organic layers were washed with water (1×50 mL) and brine (1×50 mL), dried ($Na_2SO_4$), filtered and concentrated. The residue was purified by flash chromatography (10% ethyl acetate/hexane) to afford 2.67 g of the title compound as a colorless oil (92%). MS: 291 (M+H)$^+$. $^1$H NMR (400 MHz, $CDCl_3$) δ 7.94 (s, 1H); 7.6 (dd, 1H, J=8.9, 2.7 Hz); 7.39 (m, 6H); 6.92 (d, 1H, J=8.9 Hz); 5.18 (s, 2H).

Preparation LL1
2-[5-Chloro-2-(3-methylisoxazol-5-ylmethoxy)benzyl]isoindole-1,3-dione To a mixture of 2-[5-chloro-2-hydroxy benzyl]isoindole-1,3-dione (800 mg, 2.78 mmol), 5-hydroxymethyl-3-methyl-isoxazole (373 mg, 3.3 mmol), and triphenylphosphine (1.0 g, 4.2 mmol) in anhydrous THF (10 mL) was added diethylazodicarboxylate (0.657 mL, 4.7 mmol). The solution was stirred for 15 h at room temperature under anhydrous conditions. The solvent was then removed by rotary evaporation and the product was preadsorbed onto silica gel and purified by flash chromatography to afford the title compound (555 mg, 52%).

$C_{20}H_{15}ClN_2O_4$. MW 382.81. MS 382.2 (M+H)$^+$.

$^1$H NMR (400 MHz, DMSO-$d_6$) δ 7.85–7.79 (mult, 4H); 7.28 (dd, 1H, J=8.8 Hz, J=2.6 Hz); 7.18 (d, 1H, J=2.6 Hz); 7.16 (d, 1H, J=8.8 Hz); 6.39(s, 1H); 5.25 (s, 2H); 4.67 (s, 2H); 2.17 (s, 3H).

The following compounds, Preparations LL2–LL32, were prepared from the starting material by reaction with the appropriate alcohol using analogous procedures to Preparation LL1.

Preparation LL2
5-Chloro-2-(2-morpholin-4-ylethoxy)benzonitrile

Mp 78.0–80.0° C.

$C_{13}H_{15}ClN_2O_2$. MW 266.73. MS 267.2 (M+H)$^+$.

$^1$H NMR (300 MHz, $CDCl_3$) δ 7.55–7.45 (mult, 2H); 6.92 (d, 1H, J=8.9 Hz); 4.20 (t, 2H, J=5.6 Hz); 3.72 (t, 4H, J=4.6 Hz); 2.86 (t, 2H, J=5.6 Hz); 2.62 (t, 4H, J=4.6 Hz).

Preparation LL3
2-Benzyloxy-5-chlorobenzonitrile

Mp 75.0–76.5° C.

$^1$H NMR (400 MHz, DMSO-$d_6$) δ 7.88 (d, 1H, J=2.7 Hz); 7.68 (dd, 1H, J=9.1 Hz, J=2.7 Hz); 7.45–7.36 (mult, 4H); 7.35–7.28 (mult, 2H); 5.25 (s, 2H).

Preparation LL4
5-Chloro-2-cyclobutylmethoxybenzonitrile $^1$H NMR (400 MHz, DMSO-$d_6$) δ 7.84 (d, 1H, J=2.7 Hz); 7.65 (dd, 1H, J=8.7 Hz, J=2.7 Hz); 7.45 (d, 1H, J=8.7 Hz); 4.06 (d, 2H, J=6.4 Hz); 2.75–2.63 (mult, 1H); 2.05–1.95 (mult, 2H); 1.92–1.75 (mult, 4H).

Preparation LL5
5-Chloro-2-(3-methoxy-benzyloxy)benzonitrile

Mp 90.0–92.0° C.

$^1$H NMR (400 MHz, DMSO-$d_6$) δ 7.91 (d, 1H, J=2.5 Hz); 7.70 (dd, 1H, J=8.9 Hz, J=2.5 Hz); 7.35–7.25 (mult, 2H); 7.05–6.95 (mult, 2H); 6.88 (dd, 1H, J=8.3 Hz, J=2.5 Hz); 5.25 (s, 2H); 3.73 (s, 3H).

Preparation LL6
5-Chloro-2-(2,5-dimethoxy-benzyloxy)benzonitrile

Mp 99.0–102.0° C.

$^1$H NMR (400 MHz, DMSO-$d_6$) δ 7.90 (d, 1H, J=2.7 Hz); 7.69 (dd, 1H, J=8.9 Hz, J=2.7 Hz); 7.33 (d, 1H, J=9.1 Hz); 7.02 (d, 1H, J=3.1 Hz); 6.97 (d, 1H, J=8.9 Hz); 6.87 (dd, 1H, J=8.9 Hz, J=3.1 Hz); 5.17 (s, 2H); 3.75 (s, 3H); 3.68 (s, 3H).

Preparation LL7
5-Chloro-2-(3-chloro-benzyloxy)benzonitrile

Mp 101.0–104.0° C.

$^1$H NMR (400 MHz, DMSO-$d_6$) δ 7.93 (d, 1H, J=2.7 Hz); 7.73 (dd, 1H, J=8.9 Hz, J=2.7 Hz); 7.53 (d, 1H, J=1.5 Hz); 7.47–7.36 (mult, 2H); 7.33 (d, 1H, J=9.1 Hz); 7.25–6.95 (mult, 1H); 5.30 (s, 2H).

Preparation LL8
5-Chloro-2-(4-chloro-benzyloxy)benzonitrile $^1$H NMR (400 MHz, DMSO-$d_6$) δ 7.92 (d, 1H, J=2.7 Hz); 7.71 (dd, 1H, J=9.1 Hz, J=2.7 Hz); 7.46 (s, 4H); 7.33 (d, 1H, J=9.1 Hz); 5.27 (s, 2H).

Preparation LL9
5-Chloro-2-(2-chloro-benzyloxy)benzonitrile $^1$H NMR (400 MHz, DMSO-$d_6$) δ 7.93 (d, 1H, J=2.6 Hz); 7.73 (dd, 1H, J=9.1 Hz, J=2.6 Hz); 7.64–7.59 (mult, 1H); 7.54–7.49 (mult, 1H); 7.45–7.37 (mult, 3H); 5.32 (s, 2H).

Preparation LL10
5-Chloro-2-(tetrahydrofuran-3-ylmethoxy)benzonitrile $^1$H NMR (400 MHz, DMSO-$d_6$) δ 7.89 (d, 1H, J=2.7 Hz); 7.70 (dd, 1H, J=9.1 Hz, J=2.7 Hz); 7.28 (d, 1H, J=9.1 Hz); 4.13–4.00 (mult, 2H); 3.80–3.70 (mult, 2H); 3.65 (dd, 1H, J=7.7 Hz, J=6.6 Hz); 3.55–3.50 (mult, 1H); 2.70–2.60 (mult, 1H); 2.05–1.95 (mult, 1H); 1.70–1.61 (mult, 1H).

Preparation LL11
5-Chloro-2-(4-methyl-benzyloxy)benzonitrile

Mp 106.0–108.0° C.

$^1$H NMR (400 MHz, DMSO-$d_6$) δ 7.89 (d, 1H, J=2.7 Hz); 7.69 (dd, 1H, J=9.1 Hz, J=2.7 Hz); 7.35–7.30 (mult, 3H); 7.19 (d, 2H, J=8.1 Hz); 5.21 (s, 2H); 2.28 (s, 3H).

Preparation LL12
5-Chloro-2-(2-methyl-benzyloxy)benzonitrile $^1$H NMR (400 MHz, DMSO-$d_6$) δ 7.88 (d, 1H, J=2.7 Hz); 7.70 (dd, 1H, J=9.1 Hz, J=2.7 Hz); 7.39 (d, 2H, J=9.1 Hz); 7.25–7.15 (mult, 3H); 5.23 (s, 2H); 2.30 (s, 3H).

Preparation LL13
5-Chloro-2-(3-methyl-benzyloxy)benzonitrile $^1$H NMR (300 MHz, DMSO-$d_6$) δ 7.91 (d, 1H, J=2.5 Hz); 7.71 (dd, 1H, J=9.2 Hz, J=2.5 Hz); 7.40–7.12 (mult, 5H); 5.24 (s, 2H); 2.31 (s, 3H).

Preparation LL14
5-Chloro-2-(2-methoxy-benzyloxy)benzonitrile

Mp 114.0–115.0° C.

$^1$H NMR (400 MHz, DMSO-$d_6$) δ 7.89 (d, 1H, J=2.7 Hz); 7.69 (dd, 1H, J=9.1 Hz, J=2.7 Hz); 7.40 (d, 1H, J=7.5 Hz); 7.39–7.31 (mult, 2H); 7.05 (d, 1H, J=8.3 Hz); 6.97 (t, 1H, J=7.5 Hz); 5.20 (s, 2H); 3.80 (s, 3H).

Preparation LL15
5-Chloro-2-(furan-3-ylmethoxy)benzonitrile

Mp 72.0–74.0° C.

$^1$H NMR (400 MHz, DMSO-$d_6$) δ 7.89 (d, 1H, J=2.7 Hz); 7.81 (s, 1H); 7.73–7.67 (mult, 2H); 7.38 (d, 1H, J=9.1 Hz); 6.56 (s, 1H); 5.13 (s, 2H).

Preparation LL16
5-Chloro-2-(4-methoxy-benzyloxy)benzonitrile

Mp 84.0–85.0° C.

$^1$H NMR (400 MHz, DMSO-$d_6$) δ 7.88 (d, 1H, J=2.7 Hz); 7.69 (dd, 1H, J=9.1 Hz, J=2.7 Hz); 7.41–7.30 (mult, 3H); 6.98–6.92 (mult, 2H); 5.18 (s, 2H); 3.73 (s, 3H).

Preparation LL17
5-Chloro-2-cyclopentylmethoxybenzonitrile.

$^1$H NMR (400 MHz, DMSO-$d_6$) δ 7.86 (d, 1H, J=2.7 Hz); 7.67 (dd, 1H, J=9.1 Hz, J=2.7 Hz); (d, 1H, J=9.1 Hz); 3.99 (d, 2H, J=6.8 Hz); 2.30 (sept, 1H, J=7.4 Hz); 1.80–1.68 (mult, 2H); 1.65–1.48 (mult, 4H); 1.38–1.26 (mult, 2H).

Preparation LL18
3-(2-Morpholin-4-yl-ethoxy)benzaldehyde $C_{13}H_{17}NO_3$. MW 235.29. MS 236.1 (M+H)$^+$.

$^1$H NMR (400 MHz, DMSO-d$_6$) δ 9.94 (s, 1H); 7.51–7.43 (mult, 2H); 7.42 (bs, 1H); 7.29–7.22 (mult, 1H); 4.14 (t, 2H, J=5.6 Hz); 3.55 (t, 4H, J=3.7 Hz); 2.72–2.63 (mult, 2H); 2.50–2.43 (mult, 4H).

Preparation LL19
5-Chloro-2-[3-(2-morpholin-4-yl-ethoxy)benzyloxy]benzonitrile $C_{20}H_{21}ClN_2O_3$. MW 372.86. MS 373.1 (M+H)$^+$.

$^1$H NMR (400 MHz, DMSO-d$_6$) δ 7.89 (d, 1H, J=2.7 Hz); 7.68 (dd, 1H, J=9.1 Hz, J=2.7 Hz); 7.29 (d, 1H, J=9.1 Hz); 7.25 (d, 1H, J=7.7 Hz); 7.00 (bs, 1H); 6.96 (d, 1H, J=7.5 Hz); 6.87 (d, 1H, J=7.5 Hz); 5.21 (s, 2H); 4.04 (t, 2H, J=5.8 Hz); 3.57–3.49 (mult, 4H); 2.67–2.58 (mult, 2H); 2.42–2.38 (mult, 4H).

Preparation LL20
5-Chloro-2-(tetrahydrofuran-3-ylmethoxy)benzonitrile $^1$H NMR (400 MHz, DMSO-d$_6$) δ 7.89 (d, 1H, J=2.7 Hz); 7.70 (dd, 1H, J=9.1 Hz, J=2.7 Hz); 7.28 (d, 1H, J=9.1 Hz); 4.13–4.00 (mult, 2H); 3.80–3.70 (mult, 2H); 3.65 (dd, 1H, J=7.7 Hz, J=6.6 Hz); 3.55–3.50 (mult, 1H); 2.70–2.60 (mult, 1H); 2.05–1.95 (mult, 1H); 1.70–1.61 (mult, 1H).

Preparation LL21
5-Chloro-2-(tetrahydrofuran-3-ylmethoxy)benzonitrile $^1$H NMR (400 MHz, DMSO-d$_6$) δ 7.89 (d, 1H, J=2.7 Hz); 7.70 (dd, 1H, J=9.1 Hz, J=2.7 Hz); 7.28 (d, 1H, J=9.1 Hz); 4.13–4.00 (mult, 2H); 3.80–3.70 (mult, 2H); 3.65 (dd, 1H, J=7.7 Hz, J=6.6 Hz); 3.55–3.50 (mult, 1H); 2.70–2.60 (mult, 1H); 2.05–1.95 (mult, 1H); 1.70–1.61 (mult, 1H).

Preparation LL22
5-Chloro-2-(furan-2-ylmethoxy)benzonitrile

Mp 85.0–88.0° C.

$^1$H NMR (400 MHz, DMSO-d$_6$) δ 7.89 (d, 1H, J=2.7 Hz); 7.78–7.69 (mult, 2H); 7.44 (d, 1H, J=9.1 Hz); 6.64 (d, 1H, J=3.1 Hz); 6.46 (bs, 1H); 5.25 (s, 2H).

Preparation LL23
5-Chloro-2-(2,2,7,7-tetramethyltetrahydro-bis[1,3]dioxolo[4,5b;4',5'-d]pyran-5-ylmethoxy)benzonitrile $^1$H NMR (400 MHz, DMSO-d$_6$) δ 7.88 (d, 1H, J=2.7 Hz); 7.67 (dd, 1H, J=9.1 Hz, J=2.7 Hz); 7.31 (d, 1H, J=9.1 Hz); 5.44 (d, 1H, J=5.0 Hz); 4.64 (dd, 1H, J=7.9 Hz, J=1.9 Hz); 4.37–4.32 (mult, 2H); 4.30 (dd, 1H, J=10.4 Hz, J=4.2 Hz); 4.19–4.11 (mult, 1H); 4.08–4.02 (mult, 1H); 1.34 (d, 6H, J=1.5 Hz); 1.26 (d, 6H, J=10.2 Hz).

Preparation LL24
5-Chloro-2,5-dimethylfuran-3-ylmethoxy)benzonitrile

Mp 103.0–105.0° C.

$^1$H NMR (400 MHz, DMSO-d$_6$) δ 7.87 (d, 1H, J=2.7 Hz); 7.70 (dd, 1H, J=9.1 Hz, J=2.7 Hz); 7.33 (d, 1H, J=9.1 Hz); 6.03 (s, 1H); 5.00 (s, 2H); 2.23 (s, 3H); 2.17 (s, 3H).

Preparation LL25
5-Chloro-2-(5-dimethylaminomethylfuran-2-ylmethoxy)benzonitrile $^1$H NMR (400 MHz, DMSO-d$_6$) δ 7.86 (dd, 1H, J=2.7 Hz, J=1.0 Hz); 7.69 (ddd, 1H, J=9.1 Hz, J=2.7 Hz, J=1.0 Hz); 7.40 (d, 1H, J=9.1 Hz); 6.54 (d, 1H, J=3.1 Hz); 6.23 (d, 1H, J=3.1 Hz); 5.18 (s, 2H); 3.36 (s, 2H); 2.06 (d, 6H, J=1.0 Hz).

Preparation LL26
2-[5-Chloro-2-(thiazol-2-ylmethoxy)benzyl]isoindole-1,3-dione Mp 205.0–205.5

$C_{19}H_{13}ClN_2O_3S$. MW 384.84. MS 385.1 (M+H)$^+$.

$^1$H NMR (400 MHz, DMSO-d$_6$) δ 7.90–7.80 (mult, 4H); 7.78 (d, 1H, J=3.1 Hz); 7.74 (d, 1H, J=3.1 Hz); 7.29 (dd, 1H, J=8.7 Hz, J=2.5 Hz); 7.19 (d, 1H, J=2.5 Hz); 7.16 (d, 1H, J=8.7 Hz); 5.48 (s, 2H); 4.74 (s, 2H).

Preparation LL27
2-[2-(Benzofuran-2-ylmethoxy)-5-chlorobenzyl]isoindole-1,3-dione Mp 155.0–156.0° C.

$^1$H NMR (400 MHz, DMSO-d$_6$) δ 7.83–7.75 (mult, 4H); 7.59 (d, 1H, J=7.5 Hz); 7.37 (d, 1H, J=7.5 Hz); 7.33–7.17 (mult, 5H); 6.98 (s, 1H); 5.29 (s, 2H); 4.69 (s, 2H).

Preparation LL28
2-[5-Chloro-2-(isothiazol-5-ylmethoxy)benzyl]isoindole-1,3-dione $^1$H NMR (400 MHz, DMSO-d$_6$) δ 8.48 (s, 1H); 7.89–7.79 (mult, 4H); 7.42 (s, 1H); 7.30 (dd, 1H, J=8.7 Hz, J=2.5 Hz); 7.20 (d, 1H, J=2.5 Hz); 7.14 (d, 1H, J=8.7 Hz); 5.56 (s, 2H); 4.73 (s, 2H).

Preparation LL29
2-[5-Chloro-2-(thiophen-2-ylmethoxy)benzyl]isoindole-1,3-dione Mp 135.0–137.0° C.

$C_{20}H_{14}ClNO_3S$. MW 383.86. MS 383.1 (M+H)$^+$.

$^1$H NMR (400 MHz, DMSO-d$_6$) δ 7.84–7.78 (mult, 4H); 7.47 (dd, 1H, J=5.0 Hz, J=1.2 Hz); 7.27–7.22 (mult, 1H), 7.19–7.12 (mult, 3H); 6.95 (dd, 1H, J=5.0 Hz, J=3.5 Hz); 5.31 (s, 2H); 4.65 (s, 2H).

Preparation LL30
2-[5-Chloro-2-(quinolin-2-ylmethoxy)benzyl]isoindole-1,3-dione Mp 190.0–192.0° C.

$C_{25}H_{17}ClN_2O_3$. MW 428.89. MS 429.1 (M+H)$^+$.

$^1$H NMR (400 MHz, CDCl$_3$) δ 8.20 (d, 1H, J=8.5 Hz); 8.06 (d, 1H, J=8.5 Hz); 7.90–7.80 (mult, 3H); 7.79–7.67 (mult, 4H); 7.56 (t, 1H, J=7.3. Hz); 7.17–7.08 (mult, 2H); 6.86 (d, 1H, J=8.5 Hz); 5.42 (s, 2H); 5.02 (s, 2H).

Preparation LL31
2-[5-Chloro-2-(4-methyl-[1,2,3]thiadiazol-5-ylmethoxy)benzyl]isoindole-1,3-dione Mp 205.0–208.0° C.

$C_{19}H_{14}ClN_3O_3S$. MW 399.86. MS 400.1 (M+H)$^+$.

$^1$H NMR (400 MHz, DMSO-d$_6$) δ 7.82 (s, 4H); 7.36 (d, 1H, J=8.7 Hz); 7.26 (bs, 1H); 7.19 (d, 1H, J=8.7 Hz); 5.55 (s, 2H); 4.69 (s, 2H); 2.61 (s, 3H).

Preparation LL32
5-Chloro-2-(naphthalen-1-ylmethoxy)benzonitrile

Mp 128.0–130.0° C.

$^1$H NMR (400 MHz, DMSO-d$_6$) δ 8.12–8.05 (mult, 1H); 7.97–7.85 (mult, 3H); 7.74 (dd, 1H, J=9.1 Hz, J=2.7 Hz); 7.68 (d, 1H, J=6.9 Hz); 7.60–7.44 (mult, 4H); 5.71 (s, 2H).

Preparation MM1
2-[5-Chloro-2-(pyridin-3-ylmethoxy)benzyl]isoindole-1,3-dione To a solution of 2-[5-chloro-2-hydroxy benzyl]isoindole-1,3-dione (300 mg, 1.04 mmol), and 3-picolylchloride hydrochloride (171 mg, 1.04 mmol) in anhydrous N,N-dimethylformamide (10 mL), cooled to 0° C., was added a 60% dispersion of sodium hydride in oil (104 mg, 2.6 mmol). The reaction was stirred at room temperature under anhydrous conditions for 15 h. The reaction was quenched by the addition of H$_2$O (5 mL) and then poured into a separatory funnel, and aqueous saturated NaHCO$_3$ solution (50 mL) was added. The aqueous layer was extracted 3×50 mL with CH$_2$Cl$_2$. The organics were combined and washed with saturated aqueous NaCl solution (100 mL), dried over MgSO$_4$, filtered, and concentrated on a rotary evaporator triturated with ether, filtered and dried to yield the title compound.

Mp 173.0–175.0° C.

C$_{21}$H$_{15}$ClN$_2$O$_3$. MW 378.82. MS 379.1 (M+H)$^+$.

$^1$H NMR (400 MHz, DMSO-d$_6$) δ 8.61 (s, 1H); 8.49;(d, 1H, J=5.0 Hz); 7.84–7.78 (mult, 5H); 7.34 (dd, 1H, J=7.9 Hz, J=4.8 Hz); 7.27 (dd, 1H, J=8.7 Hz, J=2.1 Hz); 7.17 (d, 1H, J=1.9 Hz); 7.11 (d, 1H, J=8.7 Hz); 5.15 (s, 2H); 4.70 (s, 2H).

The following compound, preparation MM2, was prepared from the appropriate starting material using analogous procedures to Preparation MM1.

Preparation MM2
2-[2-(Benzothiazol-2-ylmethoxy)-5-chlorobenzyl] isoindole-1,3-dione Mp 209.0–211.0° C.

C$_{23}$H$_{15}$ClN$_2$O$_3$S. MW 434.90. MS 435.1 (M+H)$^+$.

$^1$H NMR (400 MHz, DMSO-d$_6$) δ 8.03 (d, 1H, J=8.0 Hz); 7.93 (d, 1H, J=8.0 Hz); 7.88–7.76 (mult, 4H); 7.49 (td, 1H, J=7.7 Hz, J=1.2 Hz); 7.41 (td, 1H, J=7.7 Hz, J=1.2 Hz); 7.29 (dd, 1H, J=8.7 Hz, J=2.7 Hz); 7.20 (d, 1H, J=2.7 Hz); 7.17 (d, 1H, J=8.7 Hz); 5.63 (s, 2H); 4.80 (s, 2H).

Preparation NN1
4-Methyl-[1,2,3]thiadiazol-5-yl)methanol

To a mixture of 4-methyl-[1,2,3]thiadiazole-5-carboxylic acid methyl ester (923 mg, 5.84 mmol) in anhydrous ethanol (32 mL) was added NaBH$_4$ (992 mg, 26.2 mmol). The reaction was stirred at room temperature for 15 h, under anhydrous conditions. The reaction was then cooled to 0° C. and saturated aqueous NH$_4$Cl (25 mL) was added. The mixture was poured into water (25 mL), extracted with CH$_2$Cl$_2$ (4×40 mL), dried over MgSO$_4$, and concentrated on the rotary evaporator to an oil.

$^1$H NMR (400 MHz, DMSO-d$_6$) δ 6.00 (bs, 1H); 4.78 (s, 2H); 2.51 (s, 3H).

Preparation OO1
4-Methyl-[1,2,3]thiadiazole-5-carboxylic acid methyl ester

4-Methyl-[1,2,3]thiadiazole-5-carboxylic acid (1.0 g, 6.94 mmol), concentrated H$_2$SO$_4$ (866 μL), and methanol (12 mL) were combined and heated to reflux for 15 h. The solvent was reduced by a rotary evaporator and the residue was poured into 15 g of ice. The reaction was neutralized with saturated aqueous NaHCO$_3$. The solution was then extracted with CH$_2$Cl$_2$ (4×35 mL). The combined organics were dried over MgSO$_4$, filtered, and concentrated on the rotary evaporator. The product was preadsorbed onto silica gel and purified by flash chromatography to afford the title compound as a yellow oil.

C$_5$H$_6$N$_2$O$_2$S. MW 158.18. MS 159.0 (M+H)$^+$.

$^1$H NMR (400 MHz, DMSO-d$_6$) δ 3.87 (s, 3H); 2.85 (s, 3H).

Preparation PP1
3-Deoxy-1,2-O-(1-methylethylidene)-3-[(phenylmethyl) amino]-5-O-(triphenylmethyl)-α-D-ribofuranose (3 step procedure)

Step 1:

To a clean and nitrogen purged glass lined reactor, was charged CH$_2$Cl$_2$ (13 gal). To the reactor was added 1,2-O-(1-methylethylidene)-α-D-xylofuranose (7.0 kg, 36.8 mol) followed by pyridine (4.5 L). The reaction was cooled to 10–15° C. and then charged with trityl chloride (10.8 Kg, 38.6 moles; some exotherm noted with this addition). The reaction mixture was then stirred at 20–25° C. for 5 h and judged complete by TLC. The crude reaction mixture was washed with a 5% aqueous acetic acid solution (2×11.5 gal) and with water (22 gal). The organic layer containing 1,2-O-(1-methylethylidene)-5-O-(triphenylmethyl)-α-D-xylofuranose was carried on to Step 2 without drying or isolation.

Step 2:

To the crude containing 1,2-O-(1-methylethylidene)-5-O-(triphenylmethyl)-α-D-xylofuranose in CH$_2$Cl$_2$ was added KBr (877 g, 7.36 mol) at 25–30° C. followed by water (17 gal) and NaHCO$_3$ (15.4 kg). The reactor was cooled to 0–5° C. and 2,2,6,6,-tetramethyl-1-piperidinyloxy free radical (TEMPO) radical (280 g) was added. With 0–5° C. cooling on the jackets of the reactor was charged with high agitation: 14 gallons of Clorox bleach over 4 h (charge is very exothermic, the bleach is added at such a rate to keep the internal temperature between 0–5° C.). The reaction mixture was sampled for completion by $^1$H NMR (CDCl$_3$). When the reaction was judged complete, the mixture was diluted with CH$_2$Cl$_2$ (38 gal) and water (24 gal). The phases were separated and the CH$_2$Cl$_2$ layer was then washed with water (2×30 gal) and brine (16 gal). The organic layer was atmospherically concentrated to 10–15 gal and used directly in Step 3.

Step 3:

To the product of Step 2 in CH$_2$Cl$_2$ was charged acetic acid (1.7 L). To the reactor was added benzylamine (6 L, 56.31 mol) over 30 minutes with a cooling solution of 15° C. on the jacket of the reactor (very exothermic during initial charge, pot kept <30° C.). To the reactor was added NaBH (OAc)$_3$ (11.6 kg, 51.5 mol) over 15 minutes. The reaction was allowed to stir for 12 h and sampled for reaction completion by HPLC. The reaction was diluted with CH$_2$Cl$_2$ (26 gal) and 2N NaOH (26 gal) at a temperature of 4–14° C. over 30 minutes. The phases were separated and the organic layer extracted with water (10 gal) and brine (10 gal). The organic layer was then cloned atmospherically to 15 gal, followed by the addition of methanol (20 gallons) and reconcentrated atmospherically to 17 gal with the final vapor temperature at 65° C. The mixture was cooled to 10–20° C. and granulated overnight. Filtration of the crystalline solids provided 18.4 kg of 3-deoxy-1,2-O-(1-methylethylidene)-3-[(phenylmethyl)amino]-5-O-(triphenylmethyl)-α-D-ribofuranose which was calculated to have 16% by weight methanol content (80% yield corrected for residual solvent over three steps). The material was suitable for transformation in the next step without further drying.

[α]$_D$: +70.75 (c 1, CH$_2$Cl$_2$).

m.p.=116.2–116.3

$^1$H NMR (400 MHz, d$_6$-DMSO): 1.31 (s, 3), 1.47 (s, 3), 2.06 (br s, 1), 2.93 (br s, 1), 3.02 (d, 1, J=5.3, 10.4), 3.27 (d, 1, J=9), 3.61 (br d, 1, J=13.7), 3.76 (m, 1), 3.80 (br d, 1, J=13.5), 4.65 (t, 1, J=4.2), 5.82 (d, 1, J=3.9), 7.16–7.42 (m, 20).

$^{13}$C NMR (100 MHz, d$_6$-DMSO): 26.94, 51.13, 60.60, 63.70, 77.04, 79.12, 86.24, 104.75, 111.32, 127.07, 127.43, 128.07, 128.29, 128.49, 128.78, 140.81, 144.17.

Anal. Calcd for C$_{34}$H$_{35}$NO$_4$: C, 78.28; H, 6.76; N, 2.69. Found: C, 77.89; H, 6.55; N. 2.56.

Preparation QQ1
3-Deoxy-1,2-O-(11-methylethylidene)-3-[(4-nitrobenzoyl) amino]-α-D-ribofuranose (3 step procedure)

Step 1:

To a solution of 3-deoxy-1,2-O-(11-methylethylidene)-3-[(phenylmethyl)amino]-5-O-(triphenylmethyl)-α-D-ribofuranose (200 g, 0.383 mol) in toluene (1000 mL) was added acetic acid (30 mL) followed by 10% Pd/C (48 g). The reaction was hydrogenated on a Parr shaker for 20 h. The reaction still showed 5% starting material by HPLC, so an additional catalyst charge was added (9.6 g) and hydrogenation continued for an additional 20 h. The solution was filtered through celite and the catalyst rinsed with toluene (200 mL). The solution of crude 3-amino-3-deoxy-1,2-O-(1-methylethylidene)-5-O-(triphenylmethyl)-α-D-ribofuranose was used directly in the next reaction.

Step 2:

To the above solution was added water (2 L) and NaHCO$_3$ (128.8 g). While stirring well, p-nitrobenzoyl chloride (71.1 g, 0.383 mol) was added portionwise over 5 min to control foaming. After an additional 5 min, the reaction was complete by HPLC. The phases were separated and the organic layer dried (MgSO$_4$) and filtered to provide crude 3-deoxy-1,2-O-(1-methylethylidene)-3-[(4-nitrobenzoyl)amino]-5-O-(triphenylmethyl)-α-D-ribofuranose which was used directly in the next step.

Step 3:

To the crude 3-deoxy-1,2-O-(1-methylethylidene)-3-[(4-nitrobenzoyl)amino]-5-O-(triphenylmethyl)-α-D-ribofuranose solution from above was added methanol (890 mL) and conc. HCl (0.6 mL). The reaction was monitored by HPLC, and after 3.5 h there was a couple percent starting material as well as several percent of byproducts, and the reaction was quenched by the addition of NaHCO$_3$ (18.5 g). The solution was concentrated with the aid of vacuum to remove all methanol; toward the end the solution was heated under atmospheric pressure to a pot temperature of 60° C. Water (93.5 mL) was added and the solution cooled to rt and allowed to granulate overnight. The solids were filtered off and rinsed with toluene (200 mL) then dried under vacuum at 40–45° C. to provide 117.5 g of 3 deoxy-1,2-O-(1-methylethylidene)-3-[(4-nitrobenzoyl)amino]-α-D-ribofuranose which contained 8.7% ash (NaHCO$_3$ residue). This leads to a corrected yield of 107 g (83%). This material is sufficiently pure for use in further synthetic steps. Analytically pure material can be obtained by a further toluene/water repulp.

[α]$_D$: +53.25 (c 1, CH$_2$Cl$_2$).

m.p.=187.2–187.6

$^1$H NMR (400 MHz, CDCl$_3$): 1.38 (s, 3), 1.58 (s, 3), 3.18 (dd, 1, J=6.6, 7.7), 3.72–3.80 (m, 1), 3.87–3.94 (m, 2), 4.43 (ddd, 5.1, 9.0, 9.0), 4.72 (dd, 1, J=4.0, 4.9), 5.93 (d, 1, J=3.8), 6.77 (d, 1, J=8.1), 7.96 (d, 2, J=8.8), 8.30 (d, 2, J=8.9).

$^{13}$C NMR (75 MHz, CDCl$_3$): 26.38, 26.51, 52.32, 60.77, 78.96, 80.41, 104.24, 112.89, 124.05, 128.40, 138.59, 149.97, 166.08.

M.S. (AP-)=337.2

Anal. Calcd for C$_{15}$H$_{18}$N$_2$O$_7$: C, 53.25; H, 5.36; N, 8.28. Found: C, 53.38; H, 5.62; N, 8.33.

Preparation RR$_1$
1-[3-deoxy-1,2-O-(1-methylethylidene)-3-[(4-nitrobenzoyl) amino]-α-D-ribofuranuronoyl]-piperidine (2 step procedure)

To a mixture of CH$_2$Cl$_2$ (2700 mL) and water (1800 mL) is added 3-deoxy-1,2-O-(1-methylethylidene)-3-[(4-nitrobenzoyl)amino]-α-D-ribofuranose (300 g, 0.887 mol), KBr (21.1 g, 0.177 mol), NaHCO$_3$ (408 g, 4.86 mol), and Et$_4$NCl (12.3 g, 0.044 mol). The solution was cooled to 0–5° C. and TEMPO (6.9 g, 0.044 mol) was added. A solution of commercial Clorox bleach (4400 mL, 5.25% NaOCl) was added via addition funnel over 80 min at such a rate that the internal temperature is maintained below 5° C. After an additional 1 h, the reaction was diluted with water (7500 mL) and warmed to rt. The organic phase was removed and discarded. The pH of the aq. layer was adjusted to pH=2.4 by the addition of conc. HCl (560 mL); EtOAc (4000 mL) was added, and after mixing the phases separated. The aq. layer was extracted again with EtOAc (2000 mL) and the combined EtOAc extracts were dried (MgSO$_4$), filtered, and concentrated to a thin oil (still contains residual EtOAc). This oil was used directly in the next step.

Step 2:

To the crude 3-deoxy-1,2-O-(1-methylethylidene)-3-[(4-nitrobenzoyl)amino]-α-D-ribofuranuronic acid was added CH$_2$Cl$_2$ (3100 mL) and the solution cooled to 0–5° C. To this solution was added NEt$_3$ (310 mL) dropwise, followed by DMF (3.4 mL). To the mixture was slowly added oxalyl chloride (85 mL), causing significant gas evolution. The addition rate was controlled such that the reaction temperature does not rise above 5° C. (addition time=1 h). After an additional 15 min, piperidine (114 mL) was added dropwise to the reaction mixture, at such a rate to maintain internal temperature below 5° C. (addition time=45 min). After an additional 1 h, the reaction was diluted with water (3 L). The phases were separated and the organic layer extracted with aqc. NaHCO$_3$ (1.5 L water, 100 g NaHCO$_3$). The layers were separated and the organic layer dried (MgSO$_4$), filtered, and transferred to a flask equipped for distillation. The majority of the solvent was removed by distillation (3200 mL), followed by the addition of heptane (500 mL) and further heating until the distillate temp. reached 58° C. Additional heptane was added (1 L) and the heating continued until the distillate reached 65° C. An additional 300 mL of distillate was removed with the aid of mild vacuum, followed by cooling and addition of CH$_2$Cl$_2$ (45 mL). This solution was allowed to stir overnight. The solids obtained were still rather sticky, so additional CH$_2$Cl$_2$ (120 mL) was added and the material stirred at rt for 3 h. The solids were filtered, and rinsed with heptane (80 mL) to provide 242 g (65% over 2 steps) 1-[3-deoxy-1,2-O-(1-methylethylidene)-3-[(4-nitrobenzoyl)amino]-α-D-ribofuranuronoyl]piperidine. Estimated repulp solution: 12–14% CH$_2$Cl$_2$ in heptane.

[α]$_D$: +72.1 (c 1, CH$_2$C$_{12}$).

$^1$H NMR (400 MHz, CDCl$_3$): 1.36 (s, 3), 1.57 (s, 3), 1.51–1.68 (m, 6), 3.30–3.45 (m, 2), 3.60–3.74 (m, 2), 4.67 (d, 1, J=8.7), 4.84 (dd, 1, J=3.7, 5.0), 4.90 (ddd, 1, J=5.0, 7.9, 8.3), 5.95 (d, 1, J=3.3), 6.69 (d, 1, J=7.5), 7.94 (d, 2, J=8.7), 8.26 (d, 2, J=9. 1).

$^{13}$C NMR (100 MHz, CDCl$_3$): 24.68, 25.64, 26.57, 26.74, 27.16, 43.79, 46.88, 54.76, 78.79, 105.16, 113.23, 124.00, 128.68, 139.66, 149.90, 165.17, 165.67.

Preparation SS1
1-[1,2-di-O-acetyl-3-deoxy-3-[(4-nitrobenzoyl)amino]-D-ribofuranuronoyl]-piperidine—mix of anomers (2 step procedure):

Step 1:

To a solution of TFA (345 mL) and water (85 mL) was added) 1-[3-deoxy-1,2-O-(1-methylethylidene)-3-[(4-nitrobenzoyl)amino]-α-D-ribofuranuronoyl]-piperidine (150 g, 0.357 mol). The reaction was held at room temperature for 5.5 h, then was slowly added to a quench solution of water (7.5 L) containing NaCl (2250 g), NaHCO$_3$ (450 g), and CH$_2$Cl$_2$ (3.75 L). Once the quench was complete, the mixture was stirred an additional 15 min, and the phases separated. The water layer was extracted with CH$_2$Cl$_2$ (1.5 L) and the combined organic layers were dried (MgSO$_4$), filtered, and this solution used directly in the next step.

Step 2:

To the above solution was added triethylamine (225 mL) followed by acetic anhydride (137 mL, added dropwise to keep temperature below 30° C.). After 45 min, the reaction was confirmed complete by HPLC analysis. To the reaction was slowly added 2N NaOH (1 L) with water cooling to maintain temp at 30° C. Once complete, the phases were separated and the organic layer extracted with water (800 mL) and concentrated to a dark oil. To the residue was added EtOAc (500 mL) and the solution filtered through $SiO_2$ (120 g) and washed with EtOAc (200 mL). The eluents were concentrated to provide 132 g (80% over two steps) of 1-[1,2-di-O-acetyl-3-deoxy-3-[(4-nitrobenzoyl)amino]-D-ribofuranuronoyl]-piperidine as a yellow foam.

Note: ratio of anomers ~3:2. NMR data are listed for the mixture, and for simplicity the integration numbers are approximated as if the ratio were 1:1.

$^1$H NMR (400 MHz, $CDCl_3$): 1.44–1.74 (m, 12), 2.08 (s, 3), 2.09 (s, 3), 2.12 (s, 3), 2.16 (s, 3), 3.22–3.80 (m, 8), 4.84 (d, 1, J=6.8), 5.05 (s, 1), 5.11 (dd, 1, J=6.2, 7.5), 5.45 (d, 1, J=5.35), 5.52–5.60 (m, 2), 6.18 (s, 1), 6.48 (d, 1, J=7.3), 6.60 (d, 1, J=4.5), 6.96 (d, 1, J=7.5), 7.88–7.94 (m, 4), 8.26–8.36 (m, 4).

$^{13}$C NMR (75 MHz, $CDCl_3$): 20.61, 20.93, 21.22, 21.43, 24.57, 24.63, 25.64, 25.80, 26.62, 26.68, 27.15, 43.70, 43.96, 46.87, 46.98, 47.07, 52.20, 52.61, 70.51, 75.92, 78.81, 80.06, 81.51, 94.94, 98.56, 105.17, 124.01, 124.10, 124.34, 128.19, 128.54, 128.64, 139.43, 139.56, 150.00, 150.12, 165.26, 165.39, 165.62, 165.66, 168.59, 168.90, 169.52, 169.55.

Hi Res MS (M+H): calc: 464.1669; found: 464.1674.

Anal. Calcd for $C_{21}H_{25}N_3O_9$: C, 54.42; H. 5.44; N, 9.07. Found: C, 54.21; H, 5.80; N, 9.06.

Preparation TT1

N-[[5-chloro-2-[(3-methyl-5-isoxazolyl)methoxy]phenyl]methyl]-1H-purin-6-amine (2 step procedure)

Step 1:

To a solution of 2-[[5-chloro-2-[(3-methyl-5-isoxazolyl)methoxy]phenyl]methyl]-1H-isoindole-1,3 (2H)-dione (3000.0 g, 7.837 mol) in THF (42 L) and isopropanol (31.5 L) was added 54% aqueous hydrazine (1500 mL). The solution was warmed to 50° C. for 5 h, upon which the reaction was judged complete by HPLC analysis. The solution was cooled to rt, and copious white solids were filtered off and rinsed with THF (2500 mL). The filtrate was concentrated, and to the oily residue was added MTBE (36 L). (Note: the distillate containing excess hydrazine was quenched with bleach). To the MTBE mixture was added 1 N NaOH (35 L) the mixture stirred for 10 min., and the layers separated. The organic phase was extracted with brine (18 L), dried ($Na_2SO_4$), filtered, and conc. to provide an oily residue. The above procedure was repeated, and the crude 5-chloro-2-[(3-methyl-5-isoxazolyl)methoxy]-benzenemethanamine from both runs was combined (theoretical=15.674 mol)

Step 2:

To the above combined oily residue was added isopropanol (79 L), triethylamine (4 L), and 6-chloropurine (2620 g, 16.95 mol). The solution was heated to 75° C. After ~30 min, solid precipitates began to form. After a total reaction time of 22 h, the reaction was judged complete by HPLC analysis. The reaction was cooled to rt, and to the thick slurry was added isopropanol (15 L) to thin the solution. The slurry was filtered and the cake rinsed with ispropanol (2×20 L). The solids were dried under vacuum to provide 4700 g (81% over two steps) of N-[[5-chloro-2-[(3-methyl-5-isoxazolyl)methoxy]phenyl]methyl]-1H-purin-6-amine as an off-white solid.

$^1$H NMR (500 MHz, $d_6$-DMSO): 2.25 (s, 3), 4.68 (br s, 2), 5.35 (s, 2), 6.52 (br s, 1), 7.14 (br s, 1), 7.17 (d, 1, J=8.8), 7.28 (dd, 1, J=2.0, 8.6), 8.17 (br s, 2).

$^{13}$C NMR (125 MHz, $d_6$-DMSO): 11.6, 38.6, 61.7, 105.4, 114.3, 119.3, 125.6, 127.4, 127.8, 131.2, 140.0, 150.7, 153.04, 154.4, 154.7, 160.4, 167.9.

m.p. 264.2–265.8.

Anal. Calcd for $C_{17}H_{15}N_6O_2Cl$: C, 55.07; H, 4.08; N, 22.67; Cl, 9.56. Found: C, 54.98; H, 4.18; N, 22.54; Cl, 9.74.

1-[2-O-acetyl-1-[6-[[[5-chloro-2-[(3-methyl-5-isoxazolyl)methoxy]phenyl]methyl]amino]-9H-purin-9-yl]-1,3-dideoxy-3-[(4-nitrobenzoyl)amino]-β-D-ribofuranuronoyl]-piperidine: To a solution of N-[[5-chloro-2-[(3-methyl-5-isoxazolyl)methoxy]phenyl]methyl]-1H-purin-6-amine (36.54 g, 0.0985 mol) in DME (175 mL) was added trimethylsilyltrifluoromethanesulfonate (TMSOTf) (50.00 g, 0.2250 mol). This solution was heated to 65° C. In a separate flask, 1-[1,2-di-O-acetyl-3-deoxy-3-[(4-nitrobenzoyl)amino]-D-ribofuranuronoyl]-piperidine (crude from previous step, 51.46 g, 0.1110 mol) was dissolved in DME (80 mL). The 1-[1,2-di-O-acetyl-3-deoxy-3-[(4-nitrobenzoyl)amino]-D-ribofuranuronoyl]-piperidine solution was transferred to an addition funnel, and added to the hot N-[[5-chloro-2-[(3-methyl-5-isoxazolyl)methoxy]phenyl]methyl]-1H-purin-6-amine/TMSOTf solution dropwise over 30 min. After an additional 15 min, heating was discontinued and the reaction solution was added to $CH_2Cl_2$ (750 mL) and sat. $NaHCO_3$ (750 mL). The layers were separated and the aq. layer ext. once with $CH_2Cl_2$ (200 mL). The combined organic layers were dried ($MgSO_4$), filtered and concentrated. The residue was dissolved in EtOAc (250 mL), filtered, and rinsed with EtOAc (150 mL). The EtOAc layer (400 mL total volume) was stored at 5° C. overnight, which allowed the slow formation of crystalline pdt. The crystals were filtered and rinsed with cold EtOAc (200 mL). The product retained a slight color, and therefore was repulped in EtOAc (400 mL) for 1 h and refiltered, rinsing with EtOAc (100 mL) to provide 46.76 g (54%) of the title compound as a white solid. This material is ~85% pure by HPLC analysis, and was used without further purification. An analytically pure sample was prepared by chromatography (5% IPA/$CH_2Cl_2$).

$[\alpha]_D$: −51.8 (c 1, $CH_2Cl_2$).

$^1$H NMR (500 MHz, $d_6$-DMSO): 1.40–1.56 (m, 6), 2.02 (s, 3), 2.25 (s, 3), 3.40–3.55 (m, 4), 4.69 (br s, 1 or 2), 5.20 (d, 1, J=5.6), 5.35 (s, 2), 5.35–5.40 (m, 1), 5.93 (app t, 1, J=5.4), 6.52 (br s, 2), 7.15 (br s, 1), 7.17 (d, 1, J=8.8), 7.29 (dd, 1, J=2.5, 8.7), 8.10 (d, 2, J=8.7), 8.24 (s, 1), 8.37 (d, 2, J=8.7), 8.42 (br s, 1), 8.51 (br s, 1), 9.18 (d, 1, J=7.9).

$^{13}$C NMR (125 MHz, $D_6$-DMSO): 10.94, 20.43, 23.83, 25.21, 26.14, 37.94, 42.76, 46.04, 52.42, 61.07, 74.00, 77.81, 86.33, 104.77, 113.77, 119.27, 123.64, 124.97, 126.71, 127.24, 129.05, 130.26, 139.25, 139.49, 148.82, 149.24, 152.92, 153.70, 154.43, 159.71, 165.21, 165.53, 167.22, 169.22.

M.S. (AP+)=774.2.

Anal. Calcd for $C_{36}H_{36}N_9O_9Cl$: C, 55.85; H, 4.69; N, 16.28; Cl, 4.58. Found: C, 55.82; H, 4.77; N, 16.28; Cl, 4.63.

Preparation UU1

3-amino-1-[6-[[[5-chloro-2-[(3-methyl-5-isoxazolyl)methoxy]phenyl]methyl]amino]-9H-purin-9-yl]-1,3-dideoxy-α-D-ribofuranuronic acid: To 1-[2-O-acetyl-1-[6-[[[5-chloro-2-[(3-methyl-5-isoxazolyl)methoxy]phenyl]methyl]amino]-9H-purin-9-yl]-1,3-dideoxy-3-[(4-nitrobenzoyl)-amino]-β-D-ribofuranuronoyl]-piperidine (250.0 g, 0.3229 mol, 88% purity) was added THF (1250 mL, water (650 mL), MeOH (350 mL), and solid KOH (85%, 127.9 g). The solution was heated to 65° C. for 23 h and allowed to cool to rt. To the solution was added water (1250 mL) and MTBE (1250 mL). The phases were separated and the MTBE layer discarded. To the aqueous layer was added conc. HCl to adjust to pH=5.6, forming significant precipitate. After granulating for 2 h, the slurry was filtered. The wet cake was added back to a flask with water (200 mL) and THF (1800 mL) and stirred 1 h. The slurry was refiltered, and the wet cake again added to a flask with water (1 L). To this slurry was added conc. HCl to pH=1.2, THF (2 L) and EtOAc (1 L) were added, followed by additional THF to aid separation (1 L). Due to emulsion, an additional portion of THF was added (500 mL) and the bilayer filtered through celite. The phases were then separated, and the organic phase extracted with water (2×200 mL). All aqueous phases were then combined and 6M NaOH (~100 mL) was added to adjust pH to 5.0. The solids were filtered and rinsed with a solution of 10190 water/THF (1300 mL total). The solids were dried in a vacuum oven to provide 91.02 g (55%) of the title compound as an off-white powder.

Hi. Res. M.S.=516.1390 (M+H). Calculated 516.1398.

$^1$H NMR (500 MHz, $d_6$-DMSO): 2.24 (s, 3), 3.82 (br s, 1), 4.34 (br d, 1, J=5.1). 4.66 (br s, 2), 5.34 (s, 2), 6.14 (d, 1, J=2.9), 6.52 (s, 1), 7.11 (br s, 1), 7.15 (d, 1, J=8.8), 7.27 (dd, 1, J=2.3, 8.7), 8.20 (s, 1), 8.34 (br s, 1), 8.88 (br s, 1).

$^{13}$C NMR (125 MHz, $d_6$-DMSO): 10.94, 37.88, 55.31, 61.05, 73.82, 81.57, 88.61, 104.76, 113.73, 119.34, 124.95, 126.61, 127.16, 130.39, 139.97, 148.70, 152.49, 153.67, 154.33, 159.71, 167.20, 172.06.

Preparation VV1

3-amino-1-[6-[[[5-chloro-2-[(3-methyl-5-isoxazolyl) methoxy]phenyl]methyl]amino]-9H-purin-9-yl]-1,3-dideoxy-N-methyl-β-D-ribofuranuronamide: A solution of HCl/methanol was prepared by adding acetyl chloride (8.5 mL, 0.12 mol) slowly to methanol (1 L). After 10 minutes, 3-amino-1-[6-[[[5-chloro-2-[(3-methyl-5-isoxazolyl) methoxy]phenyl]methyl]amino]-9H-purin-9-yl]-1,3-dideoxy-β-D-ribofuranuronic acid (40.03 g, 0.0776 mol) was added to the HCl/MeOH soln with a methanol rinse (100 mL). The solution was heated at 50° C. for 15 h, upon which conversion of the acid to the methyl ester was confirmed by HPLC. The solution was cooled to 37° C. followed by the addition of methylamine (600 mL of a 2.0M soln in methanol). The reaction was reheated to 50° C. for 5.5 h, and conversion of the ester to methylamide was confirmed by HPLC. The reaction was set up for distillation, and 250 mL of solvent was removed by maintaining the pot temperature between 45–50° C. and using slight vacuum. The solution temperature was then raised to 65° C. at atmospheric pressure, and Darco (6.0 g) and water (10 mL) were added. After 5 min, the solution was filtered through celite while hot, rinsing with methanol (100 mL). The filtrate was allowed to cool to rt while stirring overnight, producing a crystalline product. The crystalline product was filtered and rinsed with methanol (200 mL) to provide 30.73 g (72%) the title compound as the hydrate. HPLC analysis of this material showed greater than 98% purity.

It should be understood that the invention is not limited to the particular embodiments described herein, but that various changes and modifications may be made without departing from the spirit and scope of this novel concept as defined by the following claims.

What is claimed is:

1. A compound having the formula CV

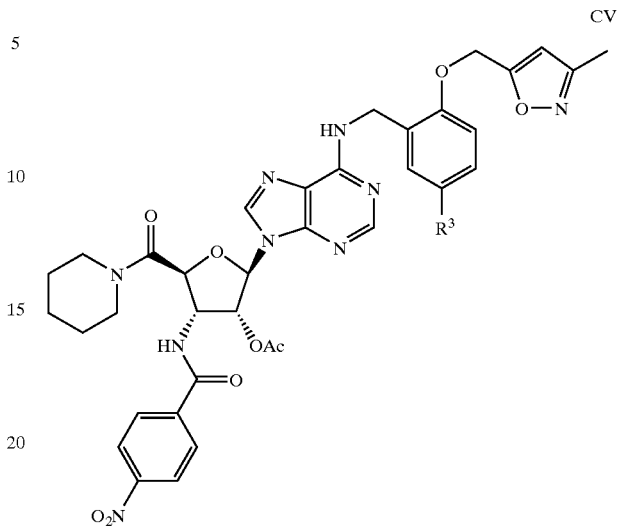

wherein $R^3$ is halo, trifluoromethyl, cyano, ($C_1$–$C_3$)alkyl, ($C_1$–$C_3$)alkoxy, ethenyl or ethynyl.

2. The compound as recited in claim 1 wherein $R_3$ is trifluoromethyl.

3. The compound as recited in claim 1 wherein $R_3$ is fluoro.

4. The compound as recited in claim 1 wherein $R_3$ is chloro.

5. A compound having the Formula CVI

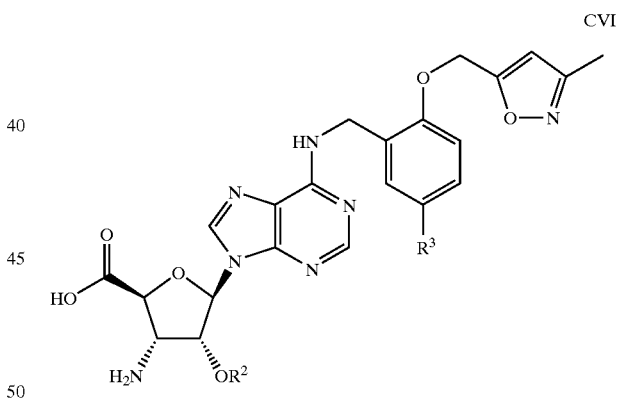

wherein $R_2$ is H, ($C_1$–$C_3$)alkyl or ($C_3$–$C_5$)cycloalkyl; and $R_3$ is halo, trifluoromethyl, cyano, ($C_1$–$C_3$)alkyl, ($C_1$–$C_3$) alkyloxy, ethenyl or ethynyl.

6. The compound as recited in claim 5 wherein $R_2$ is H; and $R_3$ is chloro.

7. The compound as recited in claim 5 wherein $R_2$ is H; and $R^3$ is fluoro.

8. The compound as recited in claim 5 wherein $R_2$ is cyclopropyl; and $R_3$ is fluoro.

* * * * *